US011549119B2

(12) United States Patent
Chatterjee et al.

(10) Patent No.: US 11,549,119 B2
(45) Date of Patent: Jan. 10, 2023

(54) VECTORS FOR CLONING AND EXPRESSION OF PROTEINS, METHODS AND APPLICATIONS THEREOF

(71) Applicant: ZUMUTOR BIOLOGICS, INC., Woburn, MA (US)

(72) Inventors: Sohang Chatterjee, Lexington, MA (US); Kavitha Iyer Rodrigues, Bangalore (IN); Maloy Ghosh, Bangalore (IN); Sunit Maity, Bangalore (IN); Divya Unnikrishnan, Bangalore (IN); Yogendra Manjunath Bangalore Muniraju, Bangalore (IN); Sathyabalan Murugesan, Bangalore (IN); Pavithra Mukunda, Kundapur (IN); Bhargav Prasad, Tamil Nadu (IN); Veeresha Kamanagowda, Bangalore (IN); Sanghamitra Bhattacharjee, Doorvaninagar Bangalore North Bangalore (IN); Pravin Kumar Dakshinamurthy, Tamil Nadu (IN); Vivek Halan, Tamil Nadu (IN); Sankaranarayanan Srinivasan, Bangalore (IN); Anuradha Hora, Uttar Pradesh (IN); Bairavabalakumar Natarajan, Tamil Nadu (IN); Karthika Nair, Karnataka (IN); Aswini Thanigaivel, Tamil Nadu (IN); Amol Maliwalave, Karnataka (IN); Bharath Ravindra Shenoy, Karnataka (IN); Sahana Bhima Rao, Karnataka (IN); Subhra Prakash Chakrabarty, Karnataka (IN); Ashvini Kumar Dubey, Bangalore (IN); Amir Khan, Aligarh (IN); Ankurina Sharma, Bangalore (IN); Rashmi Sharma, Uttarakhand (IN); Anurag Tiwari, Benares (IN); Santosh Kumar, Jharkhand (IN); Shivani Patel, Adhartal Madhya Pradesh (IN); Nikitha M, Karnataka (IN)

(73) Assignee: ZUMUTOR BIOLOGICS, INC., Woburn, MA (US)

( * ) Notice: Subject to any disclaimer, the term of this patent is extended or adjusted under 35 U.S.C. 154(b) by 781 days.

(21) Appl. No.: 16/090,783

(22) PCT Filed: Apr. 6, 2017

(86) PCT No.: PCT/IB2017/051990

§ 371 (c)(1),
(2) Date: Oct. 2, 2018

(87) PCT Pub. No.: WO2017/175176

PCT Pub. Date: Oct. 12, 2017

(65) Prior Publication Data

US 2019/0119691 A1 Apr. 25, 2019

(30) Foreign Application Priority Data

Apr. 6, 2016 (IN) ............................ 201641012164

(51) Int. Cl.
*C12N 15/00* (2006.01)
*C12N 15/81* (2006.01)
(Continued)

(52) U.S. Cl.
CPC .............. *C12N 15/81* (2013.01); *C07K 16/00* (2013.01); *C07K 16/005* (2013.01); *C12N 15/70* (2013.01);
(Continued)

(58) Field of Classification Search
CPC .... C12N 15/81; C12N 15/70; C12N 2810/85; C07K 16/00; C07K 16/005;
(Continued)

(56) References Cited

U.S. PATENT DOCUMENTS

2003/0224408 A1* 12/2003 Hoogenboom .... C12N 15/1082 435/6.16
2004/0235175 A1* 11/2004 Gaudernack ............ A61P 35/00 435/459
2011/0033920 A1* 2/2011 Hartley .................. C12N 15/11 435/320.1

FOREIGN PATENT DOCUMENTS

EP 1054018 A1 11/2000
WO 92/01047 A1 1/1992
(Continued)

OTHER PUBLICATIONS

Liang et al in "Baculovirus expression cassette vectors for rapid production of complete human IgG from phage display selected antibody fragments" (Journal of Immunological Methods vol. 247: 2001, pp. 119-130). (Year: 2001).*
(Continued)

*Primary Examiner* — Catherine S Hibbert
(74) *Attorney, Agent, or Firm* — Hamre, Schumann, Mueller & Larson, P.C.

(57) ABSTRACT

The present disclosure relates to vectors for cloning and expressing genetic material including but not limiting to antibody gene or parts thereof and methods of generating said vectors. Said vectors express the antibody genes in different formats such as Fab or scFv as a part of intertransfer system, intratransfer system or direct cloning and expression in individual display systems. In particular, phage display technology is used to clone and screen potential antibody genes in phagemid which is followed by the transfer of said genes to yeast vector for further screening and identification of lead molecules against antigens. The present vectors have numerous advantages including uniquely designed inserts/expression cassettes resulting in efficient and smooth transfer of clonal population from
(Continued)

phage to yeast vectors resulting in efficient library preparation and identification of lead molecules.

13 Claims, 44 Drawing Sheets

Specification includes a Sequence Listing.

(51) Int. Cl.

| | |
|---|---|
| *C07K 16/00* | (2006.01) |
| *C12N 15/70* | (2006.01) |
| *C40B 40/02* | (2006.01) |

(52) U.S. Cl.
CPC ...... *C07K 2317/10* (2013.01); *C07K 2317/55* (2013.01); *C07K 2317/56* (2013.01); *C07K 2317/622* (2013.01); *C12N 2810/85* (2013.01); *C40B 40/02* (2013.01)

(58) Field of Classification Search
CPC ............ C07K 2317/10; C07K 2317/55; C07K 2317/56; C07K 2317/622; C40B 40/02
See application file for complete search history.

(56) References Cited

FOREIGN PATENT DOCUMENTS

| | | | |
|---|---|---|---|
| WO | 9607754 | A1 | 3/1996 |
| WO | 99/36569 | A1 | 7/1999 |
| WO | 02/088315 | A2 | 11/2002 |
| WO | 2008/143684 | A1 | 11/2008 |
| WO | 2011/060233 | A1 | 5/2011 |
| WO | 2016/125089 | A1 | 8/2016 |

OTHER PUBLICATIONS

International Search Report and Written Opinion, International Patent Application No. PCT/IB2017/051990, dated Aug. 7, 2017 (27 pages).
Christianson et al. "Multifunctional yeast high-copy-number-shuttle vectors", Gene, Elsevier vol. 110, No. 1, pp. 119-122, 1992.
Sikorski et al., "A System of Shuttle Vectors and Yeast Host Strains Designed for Efficient Manipulation of DNA in *Saccharomyces cerevisiae*", Genetics, Genetics Society of America, vol. 122, No. 1, pp. 19-27, May 1, 1989.
Kirsch et al., "Parameters affecting the display of antibodies on phage", Journal of Immunological Methods, Elsevier Science Publishers B.V., vol. 301, No. 1-2, pp. 173-185, Jun. 1, 2005.
Arbabi-Ghahroudi Mehdi et al, "Isolation of monoclonal antibody fragments from phage display libraries", Methods in Molecular Bio, Humana Press, vol. 502, pp. 341-364, Jan. 1, 2009.
Zhao et al., "Rapid isolation of high-affinity human antibodies against the tumor vascular marker Endosialin/TEM1, using a paired yeast-display secretory scFv library platform", Journal of Immunological Methods, vol. 363, No. 2, pp. 221-232, Jan. 5, 2011.
Persic et al., "An integrated vector system for the eukaryotic expression of antibodies or their fragments after selection from phage display libraries", Gene, Elsevier, vol. 187, No. 1, pp. 9-18, Mar. 10, 1997.
"PADL-23c Phagemid, Instruction Manual; Version A1.8", Antibodies Design Laboratories, pp. 1-12, Feb. 1, 2017.
International Preliminary Report on Patentability, International Patent Application No. PCT/IB2017/051990, dated Jun. 35, 2018 (28 pages).

* cited by examiner

| | |
|---|---|
| Lane-1 | GeneRuler 1 kb DNA Ladder (Thermoscientific) |
| Lane-2 | Undigested |
| Lane-3 to 14 | Clones digested with *BamHI* and *EcoRI* |
| Lane-15 | GeneRuler 1 kb DNA Ladder (Thermoscientific) |

| | |
|---|---|
| Lane-1 | GeneRuler 1 kb DNA Ladder (Thermoscientific) |
| Lane-2 | Undigested |
| Lane-3 to 14 | Clones digested with *HindIII* and *NcoI* |
| Lane-15 | GeneRuler 1 kb DNA Ladder (Thermoscientific) |

D.

D.

A.

B.

| | |
|---|---|
| Lane 1 | Undigested |
| Lane 2 to 12 | Clones digested with *PvuII* |
| Lane 13 | GeneRuler 1 kb DNA Ladder (Thermoscientific) |

C.

| | |
|---|---|
| Lane 1 | GeneRuler 1 kb DNA Ladder (Thermoscientific) |
| Lane 2 and4 | Undigested |
| Lane 3 and 5 | Clones digested with *EcoRV* & *KpnI* |

D.

| | |
|---|---|
| Lane 1, 3 and 5 | Undigested |
| Lane 2, 4 and 6 | Clones digested with *NdeI* & *KpnI* |
| Lane 7 | GeneRuler 1 kb DNA Ladder (Thermoscientific) |

E.

A.

B.

| | |
|---|---|
| Lane 1 & 6 | Undigested |
| Lane 2 &7 | Clone digested with *PvuII* |
| Lane 3 & 8 | Clone digested with *NdeI* & *NotI* |
| Lane 5 | GeneRuler 1 kb DNA Ladder (Thermoscientific) |
| Lane 4 & 9 | Clone digested with *NcoI* & *AscI* |

B.

| | |
|---|---|
| Lane 1 | Undigested |
| Lane 2 | Clone digested with *HindIII-HF* |
| Lane 3 | Clone digested with *SpeI-HF* & *SacII* |
| Lane 4 | GeneRuler 1 kb DNA Ladder (Thermoscientific) |
| Lane 5 | Clone digested with *HindIII-HF* |
| Lane 6 | Clone digested with *SpeI-HF* & *SacII* |
| Lane 7 | Undigested |

C

A.

B.

| | |
|---|---|
| Lane 1 | GeneRuler 1 kb DNA Ladder (Thermoscientific) |
| Lane 2 to 4 | Clone digested with *SpeI-HF* & *SacII* |
| Lane 5 | Undigested |
| Lane 6 | GeneRuler 1 kb DNA Ladder (Thermoscientific) |
| Lane 7 to 9 | Clone digested with *HindIII-HF* |
| Lane 10 | Undigested |

B.

| | |
|---|---|
| Lane 1 | GeneRuler 1 kb DNA Ladder (Thermoscientific) |
| Lane 2 | Undigested |
| Lane 3 to Lane 12 | Clones digested with *EcoRV* & *XhoI* |

C

A.

B.

| | |
|---|---|
| Lane-1 | Undigested |
| Lane-2 to 4 | Clones digested with *SpeI-HF* and *XhoI* |
| Lane-5 | GeneRuler 1 kb DNA Ladder (Thermoscientific) |
| Lane-6 to 8 | Clones digested with *SpeI-HF* and *XhoI* |
| Lane 9 | Undigested |

C.

A.

B.

| | |
|---|---|
| Lane-1 | Undigested |
| Lane-2 to 4 | Clones digested with *SpeI-HF* and *XhoI* |
| Lane-5 | GeneRuler 1 kb DNA Ladder (Thermoscientific) |
| Lane-6 to 8 | Clones digested with *SpeI-HF* and *XhoI* |
| Lane 9 | Undigested |

C.

A.

B.

| | |
|---|---|
| Lane-1 | Undigested |
| Lane-2 to 4 | Clones digested with *SpeI-HF* and *XhoI* |
| Lane-5 | GeneRuler 1 kb DNA Ladder (Thermoscientific) |
| Lane-6 to 8 | Clones digested with *SpeI-HF* and *XhoI* |
| Lane-9 | Undigested |

C.

A.

B.

| | |
|---|---|
| Lane-1 | Undigested |
| Lane-2 to 4 | Clones digested with *SpeI-HF* and *HindIII-HF* |
| Lane-5 | GeneRuler 100 bp DNA Ladder (Thermoscientific) |
| Lane 6 | GeneRuler 1 kb DNA Ladder (Thermoscientific) |
| Lane-7 to 9 | Clones digested with *SpeI-HF* and *HindIII-HF* |
| Lane-10 | Undigested |

C

A.

B.

| | |
|---|---|
| Lane-1 | Undigested |
| Lane-2 to 4 | Clones digested with *SpeI-HF* and *HindIII-HF* |
| Lane-5 | GeneRuler 100 bp DNA Ladder (Thermoscientific) |
| Lane 6 | GeneRuler 1 kb DNA Ladder (Thermoscientific) |
| Lane-7 to 9 | Clones digested with *SpeI-HF* and *HindIII-HF* |
| Lane-10 | Undigested |

C.

A.

B.

| | |
|---|---|
| Lane-1 | Undigested |
| Lane-2 to 4 | Clones digested with *SpeI-HF* and *HindIII-HF* |
| Lane-5 | GeneRuler 100 bp DNA Ladder (Thermoscientific) |
| Lane 6 | GeneRuler 1 kb DNA Ladder (Thermoscientific) |
| Lane-7 to 9 | Clones digested with *SpeI-HF* and *HindIII-HF* |
| Lane-10 | Undigested |

C.

| | |
|---|---|
| Lane-1 | Undigested |
| Lane-2 to 6 | Clones digested with *NcoI and XbaI* |
| Lane-7 | GeneRuler 1 kb DNA Ladder (Thermoscientific) |
| Lane-8 to 12 | Clones digested with *NcoI and XbaI* |

| | |
|---|---|
| Lane-1 | Undigested |
| Lane-2 to 6 | Clones digested with *HindIII* and *AscI* |
| Lane-7 | GeneRuler 1 kb DNA Ladder (Thermoscientific) |
| Lane-8 to 12 | Clones digested with *HindIII* and *AscI* |

| | |
|---|---|
| Lane-1 | Undigested |
| Lane-2 to 5 | Clones digested with *HindIII* and *AscI* |
| Lane-6 | GeneRuler 1 kb DNA Ladder (Thermoscientific) |
| Lane-7 to 11 | Clones digested with *HindIII* and *AscI* |
| Lane-12 | Undigested |

| | |
|---|---|
| Lane-1 | Undigested |
| Lane-2 to 5 | Clones digested with *NcoI and XbaI* |
| Lane-6 | GeneRuler 1 kb DNA Ladder (Thermoscientific) |
| Lane-8 to 11 | Clones digested with *NcoI and XbaI* |
| Lane-12 | Undigested |

A.

| | |
|---|---|
| Lane 1 | Undigested |
| Lane 2 to 6 | Digested with *HindIII* and *AscI* |
| Lane 7 | GeneRuler 1 kb DNA Ladder (Thermoscientific) |
| Lane 8 to 12 | Digested with *HindIII* and *AscI* |
| Lane 13 | Undigested |

B.

| | |
|---|---|
| Lane 1 | Undigested |
| Lane 2 to 6 | Digested with *NcoI* and *NotI-HF* |
| Lane 7 | GeneRuler 1 kb DNA Ladder (Thermoscientific) |
| Lane 8 to 12 | Digested with *NcoI* and *NotI-HF* |
| Lane 13 | Undigested |

Flow analysis with Anti c-myc antibody and biotinylated Her2 Antigen

SEQUENCE LISTING

```
<160> NUMBER OF SEQ ID NOS: 43

<210> SEQ ID NO 1
<211> LENGTH: 2205
<212> TYPE: DNA
<213> ORGANISM: Artificial Sequence
<220> FEATURE:
<223> OTHER INFORMATION: pZB001 - Phagemid Kappa Insert
<220> FEATURE:
<221> NAME/KEY: gene
<222> LOCATION: (1)..(2205)
```

<400> SEQUENCE: 1

```
caattcaagg agacagtcat aatgaaatac ctgctgccga ccgctgctgc tggtctgctg      60
ctcctcgctg cccagccggc gatggcccat atgaaaagat ctgcgaagct tgctggcgcg     120
cccggaactg tggctgcacc atctgtcttc atcttcccgc catctgatga gcagttgaaa     180
tctggaactg cctctgttgt gtgcctgctg aataacttct atcccagaga ggccaaagta     240
cagtggaagg tggataacgc cctccaatcg ggtaactccc aggagagtgt cacagagcag     300
gacagcaagg acagcaccta cagcctcagc agcaccctga cgctgtcgaa agcagactac     360
gagaaacaca aagtctacgc ctgcgaagtc acccatcagg gcctgagctc gcccgtcaca     420
aagagcttca acaggggaga gtgtacgcgt gtttaaacat aagccgcgcc aattctattt     480
caaggagaca gtcataaaat gaaatacctg ctgccgaccg ctgctgctgg tctgctgctc     540
ctcgctgccc agccggcgat ggccccatgg acatctagaa aagctagcac agcggccgca     600
gcctccacca agggcccatc ggtcttcccc ctggcaccct cctccaagag cacctctggg     660
ggcacagcgg ccctgggctg cctggtcaag gactacttcc ccgaaccggt gacggtgtcg     720
tggaactcag gcgcgctgac cagcggcgtg cacaccttcc cggctgtcct acagtcatca     780
ggactctact ccctcagcag cgtagtgacc gtgccctcca gcagcttggg cacccagacc     840
tacatctgca acgtgaatca caagcccagc aacaccaagg tggacaagaa agttgagccc     900
aaatcttgtg aattcgacta caaagacgat gacgacaagg gggccgcaga acaaaaactt     960
atttctgaag aggacttgtc ttaggccgaa actgttgaaa gttgtttagc aaaacctcat    1020
acagaaaatt catttactaa cgtctggaaa gacgacaaaa ctttagatcg ttacgctaac    1080
tatgagggct gtctgtggaa tgctacaggc gttgtggttt gtactggtga cgaaactcag    1140
tgttacggta catgggttcc tattgggctt gctatccctg aaaatgaggg tggtggctct    1200
gagggtggcg gttctgaggg tggcggttct gagggtggcg gtactaaacc tcctgagtac    1260
ggtgatacac ctattccggg ctatacttat atcaaccctc tcgacggcac ttatccgcct    1320
ggtactgagc aaaaccccgc taatcctaat ccttctcttg aggagtctca gcctcttaat    1380
actttcatgt ttcagaataa taggttccga aataggcagg gtgcattaac tgtttatacg    1440
ggcactgtta ctcaaggcac tgaccccgtt aaaacttatt accagtacac tcctgtatca    1500
tcaaaagcca tgtatgacgc ttactggaac ggtaaattca gagactgcgc tttccattct    1560
ggctttaatg aggacccatt cgtttgtgaa tatcaaggcc aatcgtctga cctgcctcaa    1620
cctcctgtca atgctggcgg cggctctggt ggtggttctg gtggcggctc tgagggtggc    1680
ggctctgagg gtggcggttc tgagggtggc ggctctgagg gtggcggttc cggtggcggc    1740
tccggttccg gtgattttga ttatgaaaaa atggcaaacg ctaataaggg ggctatgacc    1800
gaaaatgccg atgaaaacgc gctacagtct gacgctaaag gcaaacttga ttctgtcgct    1860
actgattacg gtgctgctat cgatggtttc attggtgacg tttccggcct tgctaatggt    1920
aatggtgcta ctggtgattt tgctggctct aattcccaaa tggctcaagt cggtgacggt    1980
gataattcac ctttaatgaa taatttccgt caatatttac cttctttgcc tcagtcggtt    2040
gaatgtcgcc cttatgtctt tggcgctggt aaaccatatg aattttctat tgattgtgac    2100
aaaataaact tattccgtgg tgtctttgcg tttcttttat atgttgccac ctttatgtat    2160
gtattttcga cgtttgctaa catactgcgt aataaggagt cttaa                    2205
```

<210> SEQ ID NO 2
<211> LENGTH: 4780

<212> TYPE: DNA
<213> ORGANISM: Artificial Sequence
<220> FEATURE:
<223> OTHER INFORMATION: pZB001 - Phagemid Kappa Vector Construct
<220> FEATURE:
<221> NAME/KEY: misc_recomb
<222> LOCATION: (1)..(4780)

<400> SEQUENCE: 2

```
gcacttttcg gggaaatgtg cgcggaaccc ctatttgttt atttttctaa atacattcaa     60

atatgtatcc gctcatgaga caataaccct gataaatgct tcaataatat tgaaaaagga    120

agagtatgag tattcaacat ttccgtgtcg cccttattcc cttttttgcg gcattttgcc    180

ttcctgtttt tgctcaccca gaaacgctgg tgaaagtaaa agatgctgaa gatcagttgg    240

gtgcacgagt gggttacatc gaactggatc tcaacagcgg taagatcctt gagagttttc    300

gccccgaaga acgttttcca atgatgagca cttttaaagt tctgctatgt ggcgcggtat    360

tatcccgtat tgacgccggg caagagcaac tcggtcgccg catacactat tctcagaatg    420

acttggttga gtactcacca gtcacagaaa agcatcttac ggatggcatg acagtaagag    480

aattatgcag tgctgccata accatgagtg ataacactgc ggccaactta cttctgacaa    540

cgatcggagg accgaaggag ctaaccgctt ttttgcacaa catgggggat catgtaactc    600

gccttgatcg ttgggaaccg gagctgaatg aagccatacc aaacgacgag cgtgacacca    660

cgatgcctgt agcaatggca acaacgttgc gcaaactatt aactggcgaa ctacttactc    720

tagcttcccg gcaacaatta atagactgga tggaggcgga taaagttgca ggaccacttc    780

tgcgctcggc gcttccggct ggctggttta ttgctgataa atctggagcc ggtgagcgtg    840

ggtctcgcgg tatcattgca gcactggggc cagatggtaa gccctcccgt atcgtagtta    900

tctacacgac ggggagtcag gcaactatgg atgaacgaaa tagacagatc gctgagatag    960

gtgcctcact gattaagcat tggtaactgt cagaccaagt ttactcatat atactttaga   1020

ttgatttaaa acttcatttt taatttaaaa ggatctaggt gaagatcctt tttgataatc   1080

tcatgaccaa aatcccttaa cgtgagtttt cgttccactg agcgtcagac cccgtagaaa   1140

agatcaaagg atcttcttga gatccttttt ttctgcgcgt aatctgctgc ttgcaaacaa   1200

aaaaaccacc gctaccagcg gtggtttgtt tgccggatca agagctacca actctttttc   1260

cgaaggtaac tggcttcagc agagcgcaga taccaaatac tgttcttcta gtgtagccgt   1320

agttaggcca ccacttcaag aactctgtag caccgcctac atacctcgct ctgctaatcc   1380

tgttaccagt ggctgctgcc agtggcgata agtcgtgtct taccgggttg gactcaagac   1440

gatagttacc ggataaggcg cagcggtcgg gctgaacggg gggttcgtgc acacagccca   1500

gcttggagcg aacgacctac accgaactga gatacctaca gcgtgagcta tgagaaagcg   1560

ccacgcttcc cgaagggaga aaggcggaca ggtatccggt aagcggcagg gtcggaacag   1620

gagagcgcac gagggagctt ccagggggaa acgcctggta tctttatagt cctgtcgggt   1680

ttcgccacct ctgacttgag cgtcgatttt tgtgatgctc gtcagggggg cggagcctat   1740

ggaaaaacgc cagcaacgcg gcctttttac ggttcctggc cttttgctgg ccttttgctc   1800

acatgcgccc aatacgcaaa ccgcctctcc ccgcgcgttg gccgattcat taatgcagct   1860

ggcacgacag gtttcccgac tggaaagcgg gcagtgagcg caacgcaatt aatgtgagtt   1920

agctcactca ttaggcaccc caggctttac actttatgct tccggctcgt atgttgtgtg   1980

gaattgtgag cggataacaa tttcaattca aggagacagt cataatgaaa tacctgctgc   2040

cgaccgctgc tgctggtctg ctgctcctcg ctgcccagcc ggcgatggcc catatgaaaa   2100
```

gatctgcgaa gcttgctggc gcgcccggaa ctgtggctgc accatctgtc ttcatcttcc 2160
cgccatctga tgagcagttg aaatctggaa ctgcctctgt tgtgtgcctg ctgaataact 2220
tctatcccag agaggccaaa gtacagtgga aggtggataa cgccctccaa tcgggtaact 2280
cccaggagag tgtcacagag caggacagca aggacagcac ctacagcctc agcagcaccc 2340
tgacgctgtc gaaagcagac tacgagaaac acaaagtcta cgcctgcgaa gtcacccatc 2400
agggcctgag ctcgcccgtc acaaagagct tcaacagggg agagtgtacg cgtgtttaaa 2460
cataagccgc gccaattcta tttcaaggag acagtcataa aatgaaatac ctgctgccga 2520
ccgctgctgc tggtctgctg ctcctcgctg cccagccggc gatggcccca tggacatcta 2580
gaaaagctag cacagcggcc gcagcctcca ccaagggccc atcggtcttc cccctggcac 2640
cctcctccaa gagcacctct gggggcacag cggccctggg ctgcctggtc aaggactact 2700
tccccgaacc ggtgacggtg tcgtggaact caggcgcgct gaccagcggc gtgcacacct 2760
tcccggctgt cctacagtca tcaggactct actccctcag cagcgtagtg accgtgccct 2820
ccagcagctt gggcacccag acctacatct gcaacgtgaa tcacaagccc agcaacacca 2880
aggtggacaa gaaagttgag cccaaatctt gtgaattcga ctacaaagac gatgacgaca 2940
agggggccgc agaacaaaaa cttatttctg aagaggactt gtcttaggcc gaaactgttg 3000
aaagttgttt agcaaaacct catacagaaa attcatttac taacgtctgg aaagacgaca 3060
aaactttaga tcgttacgct aactatgagg gctgtctgtg gaatgctaca ggcgttgtgg 3120
tttgtactgg tgacgaaact cagtgttacg gtacatgggt tcctattggg cttgctatcc 3180
ctgaaaatga gggtggtggc tctgagggtg gcggttctga gggtggcggt tctgagggtg 3240
gcggtactaa acctcctgag tacggtgata cacctattcc gggctatact tatatcaacc 3300
ctctcgacgg cacttatccg cctggtactg agcaaaaccc cgctaatcct aatccttctc 3360
ttgaggagtc tcagcctctt aatactttca tgtttcagaa taataggttc cgaaataggc 3420
agggtgcatt aactgtttat acgggcactg ttactcaagg cactgacccc gttaaaactt 3480
attaccagta cactcctgta tcatcaaaag ccatgtatga cgcttactgg aacggtaaat 3540
tcagagactg cgctttccat tctggcttta atgaggaccc attcgtttgt gaatatcaag 3600
gccaatcgtc tgacctgcct caacctcctg tcaatgctgg cggcggctct ggtggtggtt 3660
ctggtggcgg ctctgagggt ggcggctctg agggtggcgg ttctgagggt ggcggctctg 3720
agggtggcgg ttccggtggc ggctccggtt ccggtgattt tgattatgaa aaaatggcaa 3780
acgctaataa gggggctatg accgaaaatg ccgatgaaaa cgcgctacag tctgacgcta 3840
aaggcaaact tgattctgtc gctactgatt acggtgctgc tatcgatggt ttcattggtg 3900
acgtttccgg ccttgctaat ggtaatggtg ctactggtga ttttgctggc tctaattccc 3960
aaatggctca agtcggtgac ggtgataatt cacctttaat gaataatttc cgtcaatatt 4020
taccttcttt gcctcagtcg gttgaatgtc gcccttatgt ctttggcgct ggtaaaccat 4080
atgaattttc tattgattgt gacaaaataa acttattccg tggtgtcttt gcgtttcttt 4140
tatatgttgc cacctttatg tatgtatttt cgacgtttgc taacatactg cgtaataagg 4200
agtcttaagc tagctaacag tcctatgaat caactactta gatggtatta gtgacctgta 4260
acagagcatt agcgcaaggt gatttttgtc ttcttgcgct aatttttttgt catcaaacct 4320
gtcgcactcc ttaatatttt gttaaaattc gcgttaaatt tttgttaaat cagctcattt 4380
tttaaccaat aggccgaaat cggcaaaatc ccttataaat caaaagaata gaccgagata 4440
gggttgagtg ttgttccagt ttggaacaag agtccactat taaagaacgt ggactccaac 4500
gtcaaagggc gaaaaaccgt ctatcagggc gatggcccac tacgtgaacc atcaccctaa 4560
tcaagttttt tggggtcgag gtgccgtaaa gcactaaatc ggaaccctaa agggagcccc 4620
cgatttagag cttgacgggg aaagccggcg aacgtggcga gaaaggaagg gaagaaagcg 4680
aaaggagcgg gcgctagggc gctggcaagt gtagcggtca cgctgcgcgt aaccaccaca 4740
cccgccgcgc ttaatgcgcc gctacagggc gcgtcaggtg 4780

<210> SEQ ID NO 3
<211> LENGTH: 2202
<212> TYPE: DNA
<213> ORGANISM: Artificial Sequence
<220> FEATURE:
<223> OTHER INFORMATION: pZB001.1 - Phagemid Lambda Insert
<220> FEATURE:
<221> NAME/KEY: gene
<222> LOCATION: (1)..(2202)

<400> SEQUENCE: 3
caattcaagg agacagtcat aatgaaatac ctgctgccga ccgctgctgc tggtctgctg 60
ctcctcgctg cccagccggc gatggcccat atgaaaagat ctgcgaagct tgctggcgcg 120
cccggtcagc ccaaggccaa ccccactgtc actctgttcc cgccctcctc tgaggagctc 180
caagccaaca aggccacact agtgtgtctg atcagtgact tctacccggg agctgtgaca 240
gtggcctgga aggcagatgg cagccccgtc aaggcgggag tggagaccac caaaccctcc 300
aaacagagca acaacaagta cgcggccagc agctacctga gcctgacgcc cgagcagtgg 360
aagtcccaca gaagctacag ctgccaggtc acgcatgaag ggagcaccgt ggagaagaca 420
gtggccccta cagaatgttc aacgcgtgtt taaacataag ccgcgccaat tctatttcaa 480
ggagacagtc ataaaatgaa atacctgctg ccgaccgctg ctgctggtct gctgctcctc 540
gctgcccagc cggcgatggc cccatggaca tctagaaaag ctagcacagc ggccgcagcc 600
tccaccaagg gcccatcggt cttccccctg gcaccctcct ccaagagcac ctctgggggc 660
acagcggccc tgggctgcct ggtcaaggac tacttccccg aaccggtgac ggtgtcgtgg 720
aactcaggcg cgctgaccag cggcgtgcac accttcccgg ctgtcctaca gtcatcagga 780
ctctactccc tcagcagcgt agtgaccgtg ccctccagca gcttgggcac ccagacctac 840
atctgcaacg tgaatcacaa gcccagcaac accaaggtgg acaagaaagt tgagcccaaa 900
tcttgtgaat tcgactacaa agacgatgac gacaaggggg ccgcagaaca aaaacttatt 960
tctgaagagg acttgtctta ggccgaaact gttgaaagtt gtttagcaaa acctcataca 1020
gaaaattcat ttactaacgt ctggaaagac gacaaaactt tagatcgtta cgctaactat 1080
gagggctgtc tgtggaatgc tacaggcgtt gtggtttgta ctggtgacga aactcagtgt 1140
tacggtacat gggttcctat tgggcttgct atccctgaaa atgagggtgg tggctctgag 1200
ggtggcggtt ctgagggtgg cggttctgag ggtggcggta ctaaacctcc tgagtacggt 1260
gatacaccta ttccgggcta tacttatatc aaccctctcg acggcactta tccgcctggt 1320
actgagcaaa accccgctaa tcctaatcct tctcttgagg agtctcagcc tcttaatact 1380
ttcatgtttc agaataatag gttccgaaat aggcagggtg cattaactgt ttatacgggc 1440
actgttactc aaggcactga ccccgttaaa acttattacc agtacactcc tgtatcatca 1500
aaagccatgt atgacgctta ctggaacggt aaattcagag actgcgcttt ccattctggc 1560
tttaatgagg acccattcgt ttgtgaatat caaggccaat cgtctgacct gcctcaacct 1620

```
cctgtcaatg ctggcggcgg ctctggtggt ggttctggtg gcggctctga gggtggcggc   1680

tctgagggtg gcggttctga gggtggcggc tctgagggtg gcggttccgg tggcggctcc   1740

ggttccggtg attttgatta tgaaaaaatg gcaaacgcta ataagggggc tatgaccgaa   1800

aatgccgatg aaaacgcgct acagtctgac gctaaaggca aacttgattc tgtcgctact   1860

gattacggtg ctgctatcga tggtttcatt ggtgacgttt ccggccttgc taatggtaat   1920

ggtgctactg gtgattttgc tggctctaat tcccaaatgg ctcaagtcgg tgacggtgat   1980

aattcacctt taatgaataa tttccgtcaa tatttacctt ctttgcctca gtcggttgaa   2040

tgtcgccctt atgtctttgg cgctggtaaa ccatatgaat tttctattga ttgtgacaaa   2100

ataaacttat tccgtggtgt ctttgcgttt cttttatatg ttgccacctt tatgtatgta   2160

ttttcgacgt ttgctaacat actgcgtaat aaggagtctt aa                      2202
```

```
<210> SEQ ID NO 4
<211> LENGTH: 4777
<212> TYPE: DNA
<213> ORGANISM: Artificial Sequence
<220> FEATURE:
<223> OTHER INFORMATION: pZB001.1 - Phagemid lambda Vector Construct
<220> FEATURE:
<221> NAME/KEY: misc_recomb
<222> LOCATION: (1)..(4777)

<400> SEQUENCE: 4
```

```
gcacttttcg gggaaatgtg cgcggaaccc ctatttgttt atttttctaa atacattcaa     60

atatgtatcc gctcatgaga caataaccct gataaatgct tcaataatat tgaaaaagga    120

agagtatgag tattcaacat ttccgtgtcg cccttattcc cttttttgcg gcattttgcc    180

ttcctgtttt tgctcaccca gaaacgctgg tgaaagtaaa agatgctgaa gatcagttgg    240

gtgcacgagt gggttacatc gaactggatc tcaacagcgg taagatcctt gagagttttc    300

gccccgaaga acgttttcca atgatgagca cttttaaagt tctgctatgt ggcgcggtat    360

tatcccgtat tgacgccggg caagagcaac tcggtcgccg catacactat tctcagaatg    420

acttggttga gtactcacca gtcacagaaa agcatcttac ggatggcatg acagtaagag    480

aattatgcag tgctgccata accatgagtg ataacactgc ggccaactta cttctgacaa    540

cgatcggagg accgaaggag ctaaccgctt ttttgcacaa catgggggat catgtaactc    600

gccttgatcg ttgggaaccg gagctgaatg aagccatacc aaacgacgag cgtgacacca    660

cgatgcctgt agcaatggca acaacgttgc gcaaactatt aactggcgaa ctacttactc    720

tagcttcccg gcaacaatta atagactgga tggaggcgga taaagttgca ggaccacttc    780

tgcgctcggc gcttccggct ggctggttta ttgctgataa atctggagcc ggtgagcgtg    840

ggtctcgcgg tatcattgca gcactggggc cagatggtaa gccctcccgt atcgtagtta    900

tctacacgac ggggagtcag gcaactatgg atgaacgaaa tagacagatc gctgagatag    960

gtgcctcact gattaagcat tggtaactgt cagaccaagt ttactcatat atactttaga   1020

ttgatttaaa acttcatttt taatttaaaa ggatctaggt gaagatcctt tttgataatc   1080

tcatgaccaa aatcccttaa cgtgagtttt cgttccactg agcgtcagac cccgtagaaa   1140

agatcaaagg atcttcttga gatccttttt ttctgcgcgt aatctgctgc ttgcaaacaa   1200

aaaaaccacc gctaccagcg gtggtttgtt tgccggatca agagctacca actctttttc   1260

cgaaggtaac tggcttcagc agagcgcaga taccaaatac tgttcttcta gtgtagccgt   1320

agttaggcca ccacttcaag aactctgtag caccgcctac atacctcgct ctgctaatcc   1380
```

-continued

```
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccagggggaa acgcctggta tctttatagt cctgtcgggt   1680
ttcgccacct ctgacttgag cgtcgatttt tgtgatgctc gtcagggggg cggagcctat   1740
ggaaaaacgc cagcaacgcg gcctttttac ggttcctggc cttttgctgg ccttttgctc   1800
acatgcgccc aatacgcaaa ccgcctctcc ccgcgcgttg gccgattcat taatgcagct   1860
ggcacgacag gtttcccgac tggaaagcgg gcagtgagcg caacgcaatt aatgtgagtt   1920
agctcactca ttaggcaccc caggctttac actttatgct tccggctcgt atgttgtgtg   1980
gaattgtgag cggataacaa tttcaattca aggagacagt cataatgaaa tacctgctgc   2040
cgaccgctgc tgctggtctg ctgctcctcg ctgcccagcc ggcgatggcc catatgaaaa   2100
gatctgcgaa gcttgctggc gcgcccggtc agcccaaggc caaccccact gtcactctgt   2160
tcccgccctc ctctgaggag ctccaagcca acaaggccac actagtgtgt ctgatcagtg   2220
acttctaccc gggagctgtg acagtggcct ggaaggcaga tggcagcccc gtcaaggcgg   2280
gagtggagac caccaaaccc tccaaacaga gcaacaacaa gtacgcggcc agcagctacc   2340
tgagcctgac gcccgagcag tggaagtccc acagaagcta cagctgccag gtcacgcatg   2400
aagggagcac cgtggagaag acagtggccc ctacagaatg ttcaacgcgt gtttaaacat   2460
aagccgcgcc aattctattt caaggagaca gtcataaaat gaaatacctg ctgccgaccg   2520
ctgctgctgg tctgctgctc ctcgctgccc agccggcgat ggccccatgg acatctagaa   2580
aagctagcac agcggccgca gcctccacca agggcccatc ggtcttcccc ctggcaccct   2640
cctccaagag cacctctggg ggcacagcgg ccctgggctg cctggtcaag gactacttcc   2700
ccgaaccggt gacggtgtcg tggaactcag gcgcgctgac cagcggcgtg cacaccttcc   2760
cggctgtcct acagtcatca ggactctact ccctcagcag cgtagtgacc gtgccctcca   2820
gcagcttggg cacccagacc tacatctgca acgtgaatca caagcccagc aacaccaagg   2880
tggacaagaa agttgagccc aaatcttgtg aattcgacta caaagacgat gacgacaagg   2940
gggccgcaga acaaaaactt atttctgaag aggacttgtc ttaggccgaa actgttgaaa   3000
gttgtttagc aaaacctcat acagaaaatt catttactaa cgtctggaaa gacgacaaaa   3060
ctttagatcg ttacgctaac tatgagggct gtctgtggaa tgctacaggc gttgtggttt   3120
gtactggtga cgaaactcag tgttacggta catgggttcc tattgggctt gctatccctg   3180
aaaatgaggg tggtggctct gagggtggcg gttctgaggg tggcggttct gagggtggcg   3240
gtactaaacc tcctgagtac ggtgatacac ctattccggg ctatacttat atcaaccctc   3300
tcgacggcac ttatccgcct ggtactgagc aaaaccccgc taatcctaat ccttctcttg   3360
aggagtctca gcctcttaat actttcatgt ttcagaataa taggttccga aataggcagg   3420
gtgcattaac tgtttatacg ggcactgtta ctcaaggcac tgaccccgtt aaaacttatt   3480
accagtacac tcctgtatca tcaaaagcca tgtatgacgc ttactggaac ggtaaattca   3540
gagactgcgc tttccattct ggctttaatg aggatccatt cgtttgtgaa tatcaaggcc   3600
aatcgtctga cctgcctcaa cctcctgtca atgctggcgg cggctctggt ggtggttctg   3660
gtggcggctc tgagggtggc ggctctgagg gtggcggttc tgagggtggc ggctctgagg   3720
gtggcggttc cggtggcggc tccggttccg gtgattttga ttatgaaaaa atggcaaacg   3780
```

ctaataaggg ggctatgacc gaaaatgccg atgaaaacgc gctacagtct gacgctaaag 3840
gcaaacttga ttctgtcgct actgattacg gtgctgctat cgatggtttc attggtgacg 3900
tttccggcct tgctaatggt aatggtgcta ctggtgattt tgctggctct aattcccaaa 3960
tggctcaagt cggtgacggt gataattcac ctttaatgaa taatttccgt caatatttac 4020
cttctttgcc tcagtcggtt gaatgtcgcc cttatgtctt tggcgctggt aaaccatatg 4080
aattttctat tgattgtgac aaaataaact tattccgtgg tgtctttgcg tttcttttat 4140
atgttgccac ctttatgtat gtattttcga cgtttgctaa catactgcgt aataaggagt 4200
cttaagctag ctaacagtcc tatgaatcaa ctacttagat ggtattagtg acctgtaaca 4260
gagcattagc gcaaggtgat ttttgtcttc ttgcgctaat tttttgtcat caaacctgtc 4320
gcactcctta atattttgtt aaaattcgcg ttaaattttt gttaaatcag ctcatttttt 4380
aaccaatagg ccgaaatcgg caaaatccct tataaatcaa aagaatagac cgagataggg 4440
ttgagtgttg ttccagtttg gaacaagagt ccactattaa agaacgtgga ctccaacgtc 4500
aaagggcgaa aaaccgtcta tcagggcgat ggcccactac gtgaaccatc accctaatca 4560
agttttttgg ggtcgaggtg ccgtaaagca ctaaatcgga accctaaagg gagcccccga 4620
tttagagctt gacggggaaa gccggcgaac gtggcgagaa aggaagggaa gaaagcgaaa 4680
ggagcgggcg ctagggcgct ggcaagtgta gcggtcacgc tgcgcgtaac caccacaccc 4740
gccgcgctta atgcgccgct acagggcgcg tcaggtg 4777

<210> SEQ ID NO 5
<211> LENGTH: 3940
<212> TYPE: DNA
<213> ORGANISM: Artificial Sequence
<220> FEATURE:
<223> OTHER INFORMATION: pZB004 - Bicistronic Bidirectional Kappa insert
<220> FEATURE:
<221> NAME/KEY: gene
<222> LOCATION: (1)..(3940)

<400> SEQUENCE: 5
gcccatgagg ccagttaatt aagaggtacc tagaattctg ggatcctaag gaggatgttt 60
tggctctggt caatgattac ggcattgata tcgtccaact gcatggagat gagtcgtggc 120
aagaatacca agagttcctc ggtttgccag ttattaaaag actcgtattt ccaaaagact 180
gcaacatact actcagtgca gcttcacaga aacctcattc gtttattccc ttgtttgatt 240
cagaagcagg tgggacaggt gaacttttgg attggaactc gatttctgac tgggttggaa 300
ggcaagagag ccccgaaagc ttacatttta tgttagctgg tggactgacg ccagaaaatg 360
ttggtgatgc gcttagatta aatggcgtta ttggtgttga tgtaagcgga ggtgtggaga 420
caaatggtgt aaaagactct aacaaaatag caaatttcgt caaaaatgct aagaaatagg 480
ttattactga gtagtattta tttaagtatt gtttgtgcac ttgcctgcgg tgtgaaatac 540
cgcacagatg cgtaaggaga aaataccgca tcaggaaatt gtaaacgtta atattttgtt 600
aaaattcgcg ttaaattttt gttaaatcag ctcatttttt aaccaatagg ccgaaatcgg 660
caaaatccct tataaatcaa aagaatagac cgagataggg ttgagtgttg ttccagtttg 720
gaacaagagt ccactattaa agaacgtgga ctccaacgtc aaagggcgaa aaaccgtcta 780
tcagggcgat ggcccactac gtgaaccatc accctaatca agttttttgg ggtcgaggtg 840
ccgtaaagca ctaaatcgga accctaaagg gagcccccga tttagagctt gacggggaaa 900
gccggcgaac gtggcgagaa aggaagggaa gaaagcgaaa ggagcgggcg ctagggcgct 960

```
ggcaagtgta gcggtcacgc tgcgcgtaac caccacaccc gccgcgctta atgcgccgct   1020
acagggcgcg tcgcgccatt cgccattcag gctgcgcaac tgttgggaag ggcgatcggt   1080
gcgggcctct tcgctattac gccagctggc gaagggggga tgtgctgcaa ggcgattaag   1140
ttgggtaacg ccagggtttt cccagtcacg acgttgtaaa acgacggcca gtgaattgta   1200
atacgactca ctatagggcg aattggagct cttaattaat tacatttaca tttacattta   1260
catttacatt tacatttaca tccgcgggcg aattggagct caattctctt aggattcgat   1320
tcacattcat cttttttag ctactaatag gataaattat aggaatttat aacaaattga   1380
aatatggcag gcagcaaaat taaaattgtc ttagtttttt agtgtataga agtgaatagc   1440
tatataaagt atgtgtaaag ttggtaacgg aacgaaaaat agaaaaggat attacatggg   1500
aaaacatgtt gtttacggag aaatgaaaag tatattgtat tttgtacgag ctaaaagtac   1560
agtgggaaca aagtcgattt tgttacatct acactgttgt tatcagattc aatggtgatg   1620
gtgatgatga ccggtacgcg tagaatcgag accgaggaga gggttaggga taggcttacc   1680
gtcgactgta acacgcgtac actctcccct gttgaagctc tttgtgacgg gcgagctcag   1740
gccctgatgg gtgacttcgc aggcgtagac tttgtgtttc tcgtagtctg ctttcgacag   1800
cgtcagggtg ctgctgaggc tgtaggtgct gtccttgctg tcctgctctg tgacactctc   1860
ctgggagtta cccgattgga gggcgttatc caccttccac tgtactttgg cctctctggg   1920
atagaagtta ttcagcaggc acacaacaga ggcagttcca gatttcaact gctcatcaga   1980
tggcgggaag atgaagacag atggtgcagc cacagttccg ggcgcgccag caagcttcgc   2040
agatcttttc atatgagcta atgcggagga tgctgcgaat aaaactgcag taaaaattga   2100
aggaaatctc atggttttca aaaattctta cttttttttt ggatggacgc aaagaagttt   2160
aataatcata ttacatggca ttaccaccat atacatatcc atatacatat ccatatctaa   2220
tcttacttat atgttgtgga aatgtaaaga gccccattat cttagcctaa aaaaaccttc   2280
tctttggaac tttcagtaat acgcttaact gctcattgct atattgaagt acggattaga   2340
agccgccgag cgggtgacag ccctccgaag gaagactctc ctccgtgcgt cctcgtcttc   2400
accggtcgcg ttcctgaaac gcagatgtgc ctcgcgccgc actgctccga acaataaaga   2460
ttctacaata ctagctttta tggttatgaa gaggaaaaat tggcagtaac ctggccccac   2520
aaaccttcaa atgaacgaat caaattaaca accataggat gataatgcga ttagtttttt   2580
agccttattt ctggggtaat taatcagcga agcgatgatt tttgatctat taacagatat   2640
ataaatgcaa aaactgcata accactttaa ctaatacttt caacattttc ggtttgtatt   2700
acttcttatt caaatgtaat aaaagtatca acaaaaaatt gttaatatac ctctatactt   2760
taacgtcaag gagaaaaaac accatgcagt tacttcgctg tttttcaata ttttctgtta   2820
ttgcttcagt tttagcacca tggacatcta gaaaagctag cacagcggcc gcagcctcca   2880
ccaagggccc atcggtcttc cccctggcac cctcctccaa gagcacctct gggggcacag   2940
cggccctggg ctgcctggtc aaggactact tccccgaacc ggtgacggtg tcgtggaact   3000
caggcgcgct gaccagcggc gtgcacacct tcccggctgt cctacagtca tcaggactct   3060
actccctcag cagcgtagtg accgtgccct ccagcagctt gggcacccag acctacatct   3120
gcaacgtgaa tcacaagccc agcaacacca aggtggacaa gaaagttgag cccaaatctt   3180
gtgaattcga acaaaaactt atttctgaag aggacttgga ctacaaagac gatgacgaca   3240
aggaaaacct gtattttcag ggcctgcagg ctagtggtgg aggaggctct ggtggaggcg   3300
```

gtagcggagg cggagggtcg atgactggtc aggaactgac aactatatgc gagcaaatcc 3360
cctcaccaac tttagaatcg acgccgtact ctttgtcaac gactactatt ttggccaacg 3420
ggaaggcaat gcaaggagtt tttgaatatt acaaatcagt aacgtttgtc agtaattgcg 3480
gttctcaccc ctcaacaact agcaaaggca gccccataaa cacacagtat gttttttaat 3540
catgtaatta gttatgtcac gcttacattc acgccctccc cccacatccg ctctaaccga 3600
aaaggaagga gttagacaac ctgaagtcta ggtccctatt tattttttta tagttatgtt 3660
agtattaaga acgttattta tatttcaaat ttttcttttt tttctgtaca gacgcgtgta 3720
cgcatgtaac attatactga aaaccttgct tgagaaggtt ttgggacgct cgaaggcttt 3780
aatttgcact agtatgtaaa tgtaaatgta aatgtaaatg taaatgtaaa tgtaaggcca 3840
tataggccgg tacccagctt ttgttccctt tagtgagggt taattccgag cttgctcgag 3900
cgaagcttta gagctcatgg cgcgcctagg ccttgacggc 3940

<210> SEQ ID NO 6
<211> LENGTH: 7304
<212> TYPE: DNA
<213> ORGANISM: Artificial Sequence
<220> FEATURE:
<223> OTHER INFORMATION: pZB004 - Bicistronic Bidirectional Kappa vector construct
<220> FEATURE:
<221> NAME/KEY: misc_recomb
<222> LOCATION: (1)..(7304)

<400> SEQUENCE: 6
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420
tgagcacgtg agtatacgtg attaagcaca caaaggcagc ttggagtatg tctgttatta 480
atttcacagg tagttctggt ccattggtga aagtttgcgg cttgcagagc acagaggccg 540
cagaatgtgc tctagattcc gatgctgact tgctgggtat tatatgtgtg cccaatagaa 600
agagaacaat tgacccggtt attgcaagga aaatttcaag tcttgtaaaa gcatataaaa 660
atagttcagg cactccgaaa tacttggttg gcgtgtttcg taatcaacct aaggaggatg 720
ttttggctct ggtcaatgat tacggcattg atatcgtcca actgcatgga gatgagtcgt 780
ggcaagaata ccaagagttc ctcggtttgc cagttattaa aagactcgta tttccaaaag 840
actgcaacat actactcagt gcagcttcac agaaacctca ttcgtttatt cccttgtttg 900
attcagaagc aggtgggaca ggtgaacttt tggattggaa ctcgatttct gactgggttg 960
gaaggcaaga gagccccgaa agcttacatt ttatgttagc tggtggactg acgccagaaa 1020
atgttggtga tgcgcttaga ttaaatggcg ttattggtgt tgatgtaagc ggaggtgtgg 1080
agacaaatgg tgtaaaagac tctaacaaaa tagcaaattt cgtcaaaaat gctaagaaat 1140
aggttattac tgagtagtat ttatttaagt attgtttgtg cacttgcctg cggtgtgaaa 1200
taccgcacag atgcgtaagg agaaaatacc gcatcaggaa attgtaaacg ttaatatttt 1260
gttaaaattc gcgttaaatt tttgttaaat cagctcattt tttaaccaat aggccgaaat 1320

```
cggcaaaatc ccttataaat caaaagaata gaccgagata gggttgagtg ttgttccagt   1380
ttggaacaag agtccactat taaagaacgt ggactccaac gtcaaagggc gaaaaaccgt   1440
ctatcagggc gatggcccac tacgtgaacc atcaccctaa tcaagttttt tggggtcgag   1500
gtgccgtaaa gcactaaatc ggaaccctaa agggagcccc cgatttagag cttgacgggg   1560
aaagccggcg aacgtggcga gaaaggaagg gaagaaagcg aaaggagcgg gcgctagggc   1620
gctggcaagt gtagcggtca cgctgcgcgt aaccaccaca cccgccgcgc ttaatgcgcc   1680
gctacagggc gcgtcgcgcc attcgccatt caggctgcgc aactgttggg aagggcgatc   1740
ggtgcgggcc tcttcgctat tacgccagct ggcgaagggg ggatgtgctg caaggcgatt   1800
aagttgggta acgccagggt tttcccagtc acgacgttgt aaaacgacgg ccagtgaatt   1860
gtaatacgac tcactatagg gcgaattgga gctcttaatt aattacattt acatttacat   1920
ttacatttac atttacattt acatccgcgg gcgaattgga gctcaattct cttaggattc   1980
gattcacatt catctttttt tagctactaa taggataaat tataggaatt tataacaaat   2040
tgaaatatgg caggcagcaa aattaaaatt gtcttagttt tttagtgtat agaagtgaat   2100
agctatataa agtatgtgta aagttggtaa cggaacgaaa aatagaaaag gatattacat   2160
gggaaaacat gttgtttacg gagaaatgaa aagtatattg tattttgtac gagctaaaag   2220
tacagtggga acaaagtcga ttttgttaca tctacactgt tgttatcaga ttcaatggtg   2280
atggtgatga tgaccggtac gcgtagaatc gagaccgagg agagggttag ggataggctt   2340
accgtcgact gtaacacgcg tacactctcc cctgttgaag ctctttgtga cgggcgagct   2400
caggccctga tgggtgactt cgcaggcgta gactttgtgt ttctcgtagt ctgctttcga   2460
cagcgtcagg gtgctgctga ggctgtaggt gctgtccttg ctgtcctgct ctgtgacact   2520
ctcctgggag ttacccgatt ggagggcgtt atccaccttc cactgtactt tggcctctct   2580
gggatagaag ttattcagca ggcacacaac agaggcagtt ccagatttca actgctcatc   2640
agatggcggg aagatgaaga cagatggtgc agccacagtt ccgggcgcgc cagcaagctt   2700
cgcagatctt ttcatatgag ctaatgcgga ggatgctgcg aataaaactg cagtaaaaat   2760
tgaaggaaat ctcatggttt tcaaaaattc ttactttttt tttggatgga cgcaaagaag   2820
tttaataatc atattacatg gcattaccac catatacata tccatataca tatccatatc   2880
taatcttact tatatgttgt ggaaatgtaa agagccccat tatcttagcc taaaaaaacc   2940
ttctctttgg aactttcagt aatacgctta actgctcatt gctatattga agtacggatt   3000
agaagccgcc gagcgggtga cagccctccg aaggaagact ctcctccgtg cgtcctcgtc   3060
ttcaccggtc gcgttcctga aacgcagatg tgcctcgcgc cgcactgctc cgaacaataa   3120
agattctaca atactagctt ttatggttat gaagaggaaa aattggcagt aacctggccc   3180
cacaaacctt caaatgaacg aatcaaatta acaaccatag gatgataatg cgattagttt   3240
tttagcctta tttctggggt aattaatcag cgaagcgatg atttttgatc tattaacaga   3300
tatataaatg caaaaactgc ataaccactt taactaatac tttcaacatt ttcggtttgt   3360
attacttctt attcaaatgt aataaaagta tcaacaaaaa attgttaata tacctctata   3420
ctttaacgtc aaggagaaaa aacaccatgc agttacttcg ctgtttttca atattttctg   3480
ttattgcttc agttttagca ccatggacat ctagaaaagc tagcacagcg gccgcagcct   3540
ccaccaaggg cccatcggtc ttccccctgg caccctcctc caagagcacc tctgggggca   3600
cagcggccct gggctgcctg gtcaaggact acttccccga accggtgacg gtgtcgtgga   3660
```

-continued actcaggcgc gctgaccagc ggcgtgcaca ccttcccggc tgtcctacag tcatcaggac 3720
tctactccct cagcagcgta gtgaccgtgc cctccagcag cttgggcacc cagacctaca 3780
tctgcaacgt gaatcacaag cccagcaaca ccaaggtgga caagaaagtt gagcccaaat 3840
cttgtgaatt cgaacaaaaa cttatttctg aagaggactt ggactacaaa gacgatgacg 3900
acaaggaaaa cctgtatttt cagggcctgc aggctagtgg tggaggaggc tctggtggag 3960
gcggtagcgg aggcggaggg tcgatgactg gtcaggaact gacaactata tgcgagcaaa 4020
tcccctcacc aactttagaa tcgacgccgt actctttgtc aacgactact attttggcca 4080
acgggaaggc aatgcaagga gtttttgaat attacaaatc agtaacgttt gtcagtaatt 4140
gcggttctca cccctcaaca actagcaaag gcagccccat aaacacacag tatgtttttt 4200
aatcatgtaa ttagttatgt cacgcttaca ttcacgccct ccccccacat ccgctctaac 4260
cgaaaaggaa ggagttagac aacctgaagt ctaggtccct atttattttt ttatagttat 4320
gttagtatta agaacgttat ttatatttca aatttttctt ttttttctgt acagacgcgt 4380
gtacgcatgt aacattatac tgaaaacctt gcttgagaag gttttgggac gctcgaaggc 4440
tttaatttgc actagtatgt aaatgtaaat gtaaatgtaa atgtaaatgt aaatgtaagg 4500
ccatataggc cggtacccag cttttgttcc ctttagtgag ggttaattcc gagcttggcg 4560
taatcatggt catagctgtt tcctgtgtga aattgttatc cgctcacaat tccacacaac 4620
ataggagccg gaagcataaa gtgtaaagcc tggggtgcct aatgagtgag gtaactcaca 4680
ttaattgcgt tgcgctcact gcccgctttc cagtcgggaa acctgtcgtg ccagctgcat 4740
taatgaatcg gccaacgcgc ggggagaggc ggtttgcgta ttgggcgctc ttccgcttcc 4800
tcgctcactg actcgctgcg ctcggtcgtt cggctgcggc gagcggtatc agctcactca 4860
aaggcggtaa tacggttatc cacagaatca ggggataacg caggaaagaa catgtgagca 4920
aaaggccagc aaaaggccag gaaccgtaaa aaggccgcgt tgctggcgtt tttccatagg 4980
ctcggccccc ctgacgagca tcacaaaaat cgacgctcaa gtcagaggtg gcgaaacccg 5040
acaggactat aaagatacca ggcgttcccc cctggaagct ccctcgtgcg ctctcctgtt 5100
ccgaccctgc cgcttaccgg atacctgtcc gcctttctcc cttcgggaag cgtggcgctt 5160
tctcaatgct cacgctgtag gtatctcagt tcggtgtagg tcgttcgctc caagctgggc 5220
tgtgtgcacg aaccccccgt tcagcccgac cgctgcgcct tatccggtaa ctatcgtctt 5280
gagtccaacc cggtaagaca cgacttatcg ccactggcag cagccactgg taacaggatt 5340
agcagagcga ggtatgtagg cggtgctaca gagttcttga agtggtggcc taactacggc 5400
tacactagaa ggacagtatt tggtatctgc gctctgctga agccagttac cttcggaaaa 5460
agagttggta gctcttgatc cggcaaacaa accaccgctg gtagcggtgg tttttttgtt 5520
tgcaagcagc agattacgcg cagaaaaaaa ggatctcaag aagatccttt gatcttttct 5580
acggggtctg acgctcagtg gaacgaaaac tcacgttaag ggattttggt catgagatta 5640
tcaaaaagga tcttcaccta gatcctttta aattaaaaat gaagttttaa atcaatctaa 5700
agtatatatg agtaaacttg gtctgacagt taccaatgct taatcagtga ggcacctatc 5760
tcagcgatct gtctatttcg ttcatccata gttgcctgac tgcccgtcgt gtagataact 5820
acgatacggg agggcttacc atctggcccc agtgctgcaa tgataccgcg agacccacgc 5880
tcaccggctc cagatttatc agcaataaac cagccagccg gaagggccga gcgcagaagt 5940
ggtcctgcaa ctttatccgc ctccatccag tctattaatt gttgccggga agctagagta 6000
agtagttcgc cagttaatag tttgcgcaac gttgttgcca ttgctacagg catcgtggtg 6060
tcacgctcgt cgtttggtat ggcttcattc agctccggtt cccaacgatc aaggcgagtt 6120
acatgatccc ccatgttgtg aaaaaaagcg gttagctcct tcggtcctcc gatcgttgtc 6180
agaagtaagt tggccgcagt gttatcactc atggttatgg cagcactgca taattctctt 6240
actgtcatgc catccgtaag atgcttttct gtgactggtg agtactcaac caagtcattc 6300
tgagaatagt gtatgcggcg accgagttgc tcttgcccgg cgtcaatacg ggataatacc 6360
gcgccacata gcagaacttt aaaagtgctc atcattggaa aacgttcttc ggggcgaaaa 6420
ctctcaagga tcttaccgct gttgagatcc agttcgatgt aacccactcg tgcacccaac 6480
tgatcttcag catcttttac tttcaccagc gtttctgggt gagcaaaaac aggaaggcaa 6540
aatgccgcaa aaaagggaat aagggcgaca cggaaatgtt gaatactcat actcttcctt 6600
tttcaatatt attgaagcat ttatcagggt tattgtctca tgagcggata catatttgaa 6660
tgtatttaga aaaataaaca aataggggtt ccgcgcacat ttccccgaaa agtgccacct 6720
gggtcctttt catcacgtgc tataaaaata attataattt aaatttttta atataaatat 6780
ataaattaaa aatagaaagt aaaaaaagaa attaaagaaa aaatagtttt tgttttccga 6840
agatgtaaaa gactctaggg ggatcgccaa caaatactac cttttatctt gctcttcctg 6900
ctctcaggta ttaatgccga attgtttcat cttgtctgtg tagaagacca cacacgaaaa 6960
tcctgtgatt ttacatttta cttatcgtta atcgaatgta tatctattta atctgctttt 7020
cttgtctaat aaatatatat gtaaagtacg ctttttgttg aaattttttta aacctttgtt 7080 tattttttttt tcttcattcc gtaactcttc taccttcttt atttactttc taaaatccaa 7140
atacaaaaca taaaaataaa taaacacaga gtaaattccc aaattattcc atcattaaaa 7200
gatacgaggc gcgtgtaagt tacaggcaag cgatccgtcc taagaaacca ttattatcat 7260
gacattaacc tataaaaata ggcgtatcac gaggcccttt cgtc 7304

<210> SEQ ID NO 7
<211> LENGTH: 2509
<212> TYPE: DNA
<213> ORGANISM: Artificial Sequence
<220> FEATURE:
<223> OTHER INFORMATION: pZB004.1 - Bicistronic Bidirectional Lambda insert
<220> FEATURE:
<221> NAME/KEY: gene
<222> LOCATION: (1)..(2509)

<400> SEQUENCE: 7
ccgcgggcga attggagctc aattctctta ggattcgatt cacattcatc tttttttagc 60
tactaatagg ataaattata ggaatttata acaaattgaa atatggcagg cagcaaaatt 120
aaaattgtct tagtttttta gtgtatagaa gtgaatagct atataaagta tgtgtaaagt 180
tggtaacgga acgaaaaata gaaaaggata ttacatggga aaacatgttg tttacggaga 240
aatgaaaagt atattgtatt ttgtacgagc taaaagtaca gtgggaacaa agtcgatttt 300
gttacatcta cactgttgtt atcagattca atggtgatgg tgatgatgac cggtacgcgt 360
agaatcgaga ccgaggagag ggttagggat aggcttaccg tcgactgtaa cacgcgttga 420
acattctgta ggggccactg tcttctccac ggtgctccct tcatgcgtga cctggcagct 480
gtagcttctg tgggacttcc actgctcggg cgtcaggctc aggtagctgc tggccgcgta 540
cttgttgttg ctctgtttgg agggtttggt ggtctccact cccgccttga cggggctgcc 600
atctgccttc caggccactg tcacagctcc cgggtagaag tcactgatca gacacactag 660

```
ggtggccttg ttggcttgga gctcctcaga ggagggcggg aacagagtga cagtggggtt    720

ggccttgggc tgaccgggcg cgccagcaag cttcgcagat cttttcatat gagctaatgc    780

ggaggatgct gcgaataaaa ctgcagtaaa aattgaagga aatctcatgg ttttcaaaaa    840

ttcttacttt tttttggat ggacgcaaag aagtttaata atcatattac atggcattac     900

caccatatac atatccatat acatatccat atctaatctt acttatatgt tgtggaaatg    960

taaagagccc cattatctta gcctaaaaaa accttctctt tggaactttc agtaatacgc   1020

ttaactgctc attgctatat tgaagtacgg attagaagcc gccgagcggg tgacagccct   1080

ccgaaggaag actctcctcc gtgcgtcctc gtcttcaccg gtcgcgttcc tgaaacgcag   1140

atgtgcctcg cgccgcactg ctccgaacaa taaagattct acaatactag cttttatggt   1200

tatgaagagg aaaaattggc agtaacctgg ccccacaaac cttcaaatga acgaatcaaa   1260

ttaacaacca taggatgata atgcgattag tttttagcc ttatttctgg ggtaattaat    1320

cagcgaagcg atgatttttg atctattaac agatatataa atgcaaaaac tgcataacca   1380

ctttaactaa tactttcaac attttcggtt tgtattactt cttattcaaa tgtaataaaa   1440

gtatcaacaa aaaattgtta atatacctct atactttaac gtcaaggaga aaaaacacca   1500

tgcagttact tcgctgtttt tcaatatttt ctgttattgc ttcagtttta gcaccatgga   1560

catctagaaa agctagcaca gcggccgcag cctccaccaa gggcccatcg gtcttccccc   1620

tggcaccctc ctccaagagc acctctgggg gcacagcggc cctgggctgc ctggtcaagg   1680

actacttccc cgaaccggtg acggtgtcgt ggaactcagg cgcgctgacc agcggcgtgc   1740

acaccttccc ggctgtccta cagtcatcag gactctactc cctcagcagc gtagtgaccg   1800

tgccctccag cagcttgggc acccagacct acatctgcaa cgtgaatcac aagcccagca   1860

acaccaaggt ggacaagaaa gttgagccca aatcttgtga attcgaacaa aaacttattt   1920

ctgaagagga cttggactac aaagacgatg acgacaagga aaacctgtat tttcagggcc   1980

tgcaggctag tggtggagga ggctctggtg gaggcggtag cggaggcgga gggtcgatga   2040

ctggtcagga actgacaact atatgcgagc aaatcccctc accaacttta gaatcgacgc   2100

cgtactcttt gtcaacgact actattttgg ccaacgggaa ggcaatgcaa ggagtttttg   2160

aatattacaa atcagtaacg tttgtcagta attgcggttc tcacccctca acaactagca   2220

aaggcagccc cataaacaca cagtatgttt tttaatcatg taattagtta tgtcacgctt   2280

acattcacgc cctcccccca catccgctct aaccgaaaag gaaggagtta gacaacctga   2340

agtctaggtc cctatttatt tttttatagt tatgttagta ttaagaacgt tatttatatt   2400

tcaaattttt cttttttttc tgtacagacg cgtgtacgca tgtaacatta tactgaaaac   2460

cttgcttgag aaggttttgg gacgctcgaa ggctttaatt tgcactagt               2509
```

<210> SEQ ID NO 8
<211> LENGTH: 7301
<212> TYPE: DNA
<213> ORGANISM: Artificial Sequence
<220> FEATURE:
<223> OTHER INFORMATION: pZB004.1 - Bicistronic Bidirectional lambda vector construct
<220> FEATURE:
<221> NAME/KEY: misc_recomb
<222> LOCATION: (1)..(7301)

<400> SEQUENCE: 8

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120
```

```
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct ttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgcctg cggtgtgaaa   1200
taccgcacag atgcgtaagg agaaaatacc gcatcaggaa attgtaaacg ttaatatttt   1260
gttaaaattc gcgttaaatt tttgttaaat cagctcattt tttaaccaat aggccgaaat   1320
cggcaaaatc ccttataaat caaaagaata gaccgagata gggttgagtg ttgttccagt   1380
ttggaacaag agtccactat taaagaacgt ggactccaac gtcaaagggc gaaaaaccgt   1440
ctatcagggc gatggcccac tacgtgaacc atcaccctaa tcaagttttt tggggtcgag   1500
gtgccgtaaa gcactaaatc ggaaccctaa agggagcccc cgatttagag cttgacgggg   1560
aaagccggcg aacgtggcga gaaaggaagg gaagaaagcg aaaggagcgg gcgctagggc   1620
gctggcaagt gtagcggtca cgctgcgcgt aaccaccaca cccgccgcgc ttaatgcgcc   1680
gctacagggc gcgtcgcgcc attcgccatt caggctgcgc aactgttggg aagggcgatc   1740
ggtgcgggcc tcttcgctat tacgccagct ggcgaagggg ggatgtgctg caaggcgatt   1800
aagttgggta acgccagggt tttcccagtc acgacgttgt aaaacgacgg ccagtgaatt   1860
gtaatacgac tcactatagg gcgaattgga gctcttaatt aattacattt acatttacat   1920
ttacatttac atttacattt acatccgcgg gcgaattgga gctcaattct cttaggattc   1980
gattcacatt catctttttt tagctactaa taggataaat tataggaatt tataacaaat   2040
tgaaatatgg caggcagcaa aattaaaatt gtcttagttt tttagtgtat agaagtgaat   2100
agctatataa agtatgtgta aagttggtaa cggaacgaaa aatagaaaag gatattacat   2160
gggaaaacat gttgtttacg gagaaatgaa aagtatattg tattttgtac gagctaaaag   2220
tacagtggga acaaagtcga ttttgttaca tctacactgt tgttatcaga ttcaatggtg   2280
atggtgatga tgaccggtac gcgtagaatc gagaccgagg agagggttag ggataggctt   2340
accgtcgact gtaacacgcg ttgaacattc tgtaggggcc actgtcttct ccacggtgct   2400
cccttcatgc gtgacctggc agctgtagct tctgtgggac ttccactgct cgggcgtcag   2460
```

-continued

```
gctcaggtag ctgctggccg cgtacttgtt gttgctctgt ttggagggtt tggtggtctc   2520
cactcccgcc ttgacggggc tgccatctgc cttccaggcc actgtcacag ctcccgggta   2580
gaagtcactg atcagacaca ctagggtggc cttgttggct tggagctcct cagaggaggg   2640
cgggaacaga gtgacagtgg ggttggcctt gggctgaccg ggcgcgccag caagcttcgc   2700
agatcttttc atatgagcta atgcggagga tgctgcgaat aaaactgcag taaaaattga   2760
aggaaatctc atggttttca aaaattctta cttttttttt ggatggacgc aaagaagttt   2820
aataatcata ttacatggca ttaccaccat atacatatcc atatacatat ccatatctaa   2880
tcttacttat atgttgtgga aatgtaaaga gccccattat cttagcctaa aaaaaccttc   2940
tctttggaac tttcagtaat acgcttaact gctcattgct atattgaagt acggattaga   3000
agccgccgag cgggtgacag ccctccgaag gaagactctc ctccgtgcgt cctcgtcttc   3060
accggtcgcg ttcctgaaac gcagatgtgc ctcgcgccgc actgctccga acaataaaga   3120
ttctacaata ctagctttta tggttatgaa gaggaaaaat tggcagtaac ctggccccac   3180
aaaccttcaa atgaacgaat caaattaaca accataggat gataatgcga ttagtttttt   3240
agccttattt ctggggtaat taatcagcga agcgatgatt tttgatctat taacagatat   3300
ataaatgcaa aaactgcata accactttaa ctaatacttt caacattttc ggtttgtatt   3360
acttcttatt caaatgtaat aaaagtatca acaaaaaatt gttaatatac ctctatactt   3420
taacgtcaag gagaaaaaac accatgcagt tacttcgctg tttttcaata ttttctgtta   3480
ttgcttcagt tttagcacca tggacatcta gaaaagctag cacagcggcc gcagcctcca   3540
ccaagggccc atcggtcttc cccctggcac cctcctccaa gagcacctct gggggcacag   3600
cggccctggg ctgcctggtc aaggactact tccccgaacc ggtgacggtg tcgtggaact   3660
caggcgcgct gaccagcggc gtgcacacct tcccggctgt cctacagtca tcaggactct   3720
actccctcag cagcgtagtg accgtgccct ccagcagctt gggcacccag acctacatct   3780
gcaacgtgaa tcacaagccc agcaacacca aggtggacaa gaaagttgag cccaaatctt   3840
gtgaattcga acaaaaactt atttctgaag aggacttgga ctacaaagac gatgacgaca   3900
aggaaaacct gtattttcag ggcctgcagg ctagtggtgg aggaggctct ggtggaggcg   3960
gtagcggagg cggagggtcg atgactggtc aggaactgac aactatatgc gagcaaatcc   4020
cctcaccaac tttagaatcg acgccgtact ctttgtcaac gactactatt ttggccaacg   4080
ggaaggcaat gcaaggagtt tttgaatatt acaaatcagt aacgtttgtc agtaattgcg   4140
gttctcaccc ctcaacaact agcaaaggca gccccataaa cacacagtat gtttttaat   4200
catgtaatta gttatgtcac gcttacattc acgccctccc cccacatccg ctctaaccga   4260
aaaggaagga gttagacaac ctgaagtcta ggtccctatt tattttttta tagttatgtt   4320
agtattaaga acgttattta tatttcaaat ttttcttttt tttctgtaca gacgcgtgta   4380
cgcatgtaac attatactga aaaccttgct tgagaaggtt ttgggacgct cgaaggcttt   4440
aatttgcact agtatgtaaa tgtaaatgta aatgtaaatg taaatgtaaa tgtaaggcca   4500
tataggccgg tacccagctt ttgttccctt tagtgagggt taattccgag cttggcgtaa   4560
tcatggtcat agctgtttcc tgtgtgaaat tgttatccgc tcacaattcc acacaacata   4620
ggagccggaa gcataaagtg taaagcctgg ggtgcctaat gagtgaggta actcacatta   4680
attgcgttgc gctcactgcc cgctttccag tcgggaaacc tgtcgtgcca gctgcattaa   4740
tgaatcggcc aacgcgcggg gagaggcggt ttgcgtattg ggcgctcttc cgcttcctcg   4800
ctcactgact cgctgcgctc ggtcgttcgg ctgcggcgag cggtatcagc tcactcaaag   4860
```

```
gcggtaatac ggttatccac agaatcaggg gataacgcag gaaagaacat gtgagcaaaa   4920
ggccagcaaa aggccaggaa ccgtaaaaag gccgcgttgc tggcgttttt ccataggctc   4980
ggccccccctg acgagcatca caaaaatcga cgctcaagtc agaggtggcg aaacccgaca   5040
ggactataaa gataccaggc gtttcccccct ggaagctccc tcgtgcgctc tcctgttccg   5100
accctgccgc ttaccggata cctgtccgcc tttctccctt cgggaagcgt ggcgctttct   5160
caatgctcac gctgtaggta tctcagttcg gtgtaggtcg ttcgctccaa gctgggctgt   5220
gtgcacgaac cccccgttca gcccgaccgc tgcgccttat ccggtaacta tcgtcttgag   5280
tccaacccgg taagacacga cttatcgcca ctggcagcag ccactggtaa caggattagc   5340
agagcgaggt atgtaggcgg tgctacagag ttcttgaagt ggtggcctaa ctacggctac   5400
actagaagga cagtatttgg tatctgcgct ctgctgaagc cagttacctt cggaaaaaga   5460
gttggtagct cttgatccgg caaacaaacc accgctggta gcggtggttt ttttgtttgc   5520
aagcagcaga ttacgcgcag aaaaaaagga tctcaagaag atcctttgat cttttctacg   5580
gggtctgacg ctcagtggaa cgaaaactca cgttaaggga ttttggtcat gagattatca   5640
aaaaggatct tcacctagat ccttttaaat taaaaatgaa gttttaaatc aatctaaagt   5700
atatatgagt aaacttggtc tgacagttac caatgcttaa tcagtgaggc acctatctca   5760
gcgatctgtc tatttcgttc atccatagtt gcctgactgc ccgtcgtgta gataactacg   5820
atacgggagg gcttaccatc tggccccagt gctgcaatga taccgcgaga cccacgctca   5880
ccggctccag atttatcagc aataaaccag ccagccggaa gggccgagcg cagaagtggt   5940
cctgcaactt tatccgcctc catccagtct attaattgtt gccgggaagc tagagtaagt   6000
agttcgccag ttaatagttt gcgcaacgtt gttgccattg ctacaggcat cgtggtgtca   6060
cgctcgtcgt ttggtatggc ttcattcagc tccggttccc aacgatcaag gcgagttaca   6120
tgatccccca tgttgtgaaa aaaagcggtt agctccttcg gtcctccgat cgttgtcaga   6180
agtaagttgg ccgcagtgtt atcactcatg gttatggcag cactgcataa ttctcttact   6240
gtcatgccat ccgtaagatg cttttctgtg actggtgagt actcaaccaa gtcattctga   6300
gaatagtgta tgcggcgacc gagttgctct tgcccggcgt caatacggga taataccgcg   6360
ccacatagca gaactttaaa agtgctcatc attggaaaac gttcttcggg gcgaaaactc   6420
tcaaggatct taccgctgtt gagatccagt tcgatgtaac ccactcgtgc acccaactga   6480
tcttcagcat cttttacttt caccagcgtt tctgggtgag caaaaacagg aaggcaaaat   6540
gccgcaaaaa agggaataag ggcgacacgg aaatgttgaa tactcatact cttccttttt   6600
caatattatt gaagcattta tcagggttat tgtctcatga gcggatacat atttgaatgt   6660
atttagaaaa ataaacaaat aggggttccg cgcacatttc cccgaaaagt gccacctggg   6720
tccttttcat cacgtgctat aaaaataatt ataatttaaa ttttttaata taaatatata   6780
aattaaaaat agaaagtaaa aaaagaaatt aaagaaaaaa tagtttttgt tttccgaaga   6840
tgtaaaagac tctaggggga tcgccaacaa atactacctt ttatcttgct cttcctgctc   6900
tcaggtatta atgccgaatt gtttcatctt gtctgtgtag aagaccacac acgaaaatcc   6960
tgtgatttta cattttactt atcgttaatc gaatgtatat ctatttaatc tgcttttctt   7020
gtctaataaa tatatatgta aagtacgctt tttgttgaaa ttttttaaac ctttgtttat   7080
tttttttttct tcattccgta actcttctac cttctttatt tactttctaa aatccaaata   7140
caaaacataa aaataaataa acacagagta aattcccaaa ttattccatc attaaaagat   7200
```

acgaggcgcg tgtaagttac aggcaagcga tccgtcctaa gaaaccatta ttatcatgac 7260
attaacctat aaaaataggc gtatcacgag gccctttcgt c 7301

<210> SEQ ID NO 9
<211> LENGTH: 2951
<212> TYPE: DNA
<213> ORGANISM: Artificial Sequence
<220> FEATURE:
<223> OTHER INFORMATION: pZB004.2 - Bicistronic Unidirectional kappa insert
<220> FEATURE:
<221> NAME/KEY: gene
<222> LOCATION: (1)..(2951)

<400> SEQUENCE: 9
ccgcgggttt tttctccttg acgttaaagt atagaggtat attaacaatt ttttgttgat 60
acttttatta catttgaata agaagtaata caaaccgaaa atgttgaaag tattagttaa 120
agtggttatg cagtttttgc atttatatat ctgttaatag atcaaaaatc atcgcttcgc 180
tgattaatta ccccagaaat aaggctaaaa aactaatcgc attatcatcc tatggttgtt 240
aatttgattc gttcatttga aggtttgtgg ggccaggtta ctgccaattt ttcctcttca 300
taaccataaa agctagtatt gtagaatctt tattgttcgg agcagtgcgg cgcgaggcac 360
atctgcgttt caggaacgcg accggtgaag acgaggacgc acggaggaga gtcttccttc 420
ggagggctgt cacccgctcg gcggcttcta atccgtactt caatatagca atgagcagtt 480
aagcgtatta ctgaaagttc caaagagaag gtttttttag gctaagataa tggggctctt 540
tacatttcca caacatataa gtaagattag atatggatat gtatatggat atgtatatgg 600
tggtaatgcc atgtaatatg attattaaac ttctttgcgt ccatccaaaa aaaaagtaag 660
aatttttgaa aaccatgaga tttccttcaa tttttactgc agttttattc gcagcatcct 720
ccgcattagc tcatatgaaa agatctgcga agcttgctgg cgcgcccgga actgtggctg 780
caccatctgt cttcatcttc ccgccatctg atgagcagtt gaaatctgga actgcctctg 840
ttgtgtgcct gctgaataac ttctatccca gagaggccaa agtacagtgg aaggtggata 900
acgccctcca atcgggtaac tcccaggaga gtgtcacaga gcaggacagc aaggacagca 960
cctacagcct cagcagcacc ctgacgctgt cgaaagcaga ctacgagaaa cacaaagtct 1020
acgcctgcga agtcacccat cagggcctga gctcgcccgt cacaaagagc ttcaacaggg 1080
gagagtgtac gcgtgttaca gtcgacggta agcctatccc taaccctctc ctcggtctcg 1140
attctacgcg taccggtcat catcaccatc accatatctg ataacaacag tgtagatgta 1200
acaaaatcga ctttgttccc actgtacttt tagctcgtac aaaatacaat atacttttca 1260
tttctccgta aacaacatgt ttcccatgt aatatccttt tctattttc gttccgttac 1320 caactttaca catactttat atagctattc acttctatac actaaaaaac taagacaatt 1380
ttaattttgc tgcctgccat atttcaattt gttataaatt cctataattt atcctattag 1440
tagctaaaaa aagatgaatg tgaatcgaat cctaagagaa ttgagctcca attcgccgga 1500
ttagaagccg ccgagcgggt gacagccctc cgaaggaaga ctctcctccg tgcgtcctcg 1560
tcttcaccgg tcgcgttcct gaaacgcaga tgtgcctcgc gccgcactgc tccgaacaat 1620
aaagattcta caatactagc ttttatggtt atgaagagga aaaattggca gtaacctggc 1680
cccacaaacc ttcaaatgaa cgaatcaaat taacaaccat aggatgataa tgcgattagt 1740
tttttagcct tatttctggg gtaattaatc agcgaagcga tgatttttga tctattaaca 1800
gatatataaa tgcaaaaact gcataaccac tttaactaat actttcaaca ttttcggttt 1860

```
gtattacttc ttattcaaat gtaataaaag tatcaacaaa aaattgttaa tatacctcta   1920

tactttaacg tcaaggagac catgcagtta cttcgctgtt tttcaatatt ttctgttatt   1980

gcttcagttt tagcaccatg gacatctaga aaagctagca cagcggccgc agcctccacc   2040

aagggcccat cggtcttccc cctggcaccc tcctccaaga gcacctctgg gggcacagcg   2100

gccctgggct gcctggtcaa ggactacttc cccgaaccgg tgacggtgtc gtggaactca   2160

ggcgcgctga ccagcggcgt gcacaccttc ccggctgtcc tacagtcatc aggactctac   2220

tccctcagca gcgtagtgac cgtgccctcc agcagcttgg gcacccagac ctacatctgc   2280

aacgtgaatc acaagcccag caacaccaag gtggacaaga aagttgagcc caaatcttgt   2340

gaattcgaac aaaaacttat ttctgaagag gacttggact acaaagacga tgacgacaag   2400

gaaaacctgt attttcaggg cctgcaggct agtggtggag gaggctctgg tggaggcggt   2460

agcggaggcg gagggtcgat gactggtcag gaactgacaa ctatatgcga gcaaatcccc   2520

tcaccaactt tagaatcgac gccgtactct ttgtcaacga ctactatttt ggccaacggg   2580

aaggcaatgc aaggagtttt tgaatattac aaatcagtaa cgtttgtcag taattgcggt   2640

tctcacccct caacaactag caaaggcagc cccataaaca cacagtatgt tttttaatca   2700

tgtaattagt tatgtcacgc ttacattcac gccctccccc cacatccgct ctaaccgaaa   2760

aggaaggagt tagacaacct gaagtctagg tccctattta ttttttata gttatgttag   2820

tattaagaac gttatttata tttcaaattt ttcttttttt tctgtacaga cgcgtgtacg   2880

catgtaacat tatactgaaa accttgcttg agaaggtttt gggacgctcg aaggctttaa   2940

tttgcactag t                                                        2951
```

<210> SEQ ID NO 10
<211> LENGTH: 7743
<212> TYPE: DNA
<213> ORGANISM: Artificial Sequence
<220> FEATURE:
<223> OTHER INFORMATION: pZB004.2 - Bicistronic Unidirectional kappa vector construct
<220> FEATURE:
<221> NAME/KEY: misc_recomb
<222> LOCATION: (1)..(7743)

<400> SEQUENCE: 10

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaacg acattactat atatataata taggaagcat ttaatagaca gcatcgtaat    240

atatgtgtac tttgcagtta tgacgccaga tggcagtagt ggaagatatt ctttattgaa    300

aaatagcttg tcaccttacg tacaatcttg atccggagct tttctttttt tgccgattaa    360

gaattaattc ggtcgaaaaa agaaaaggag agggccaaga gggagggcat tggtgactat    420

tgagcacgtg agtatacgtg attaagcaca caaaggcagc ttggagtatg tctgttatta    480

atttcacagg tagttctggt ccattggtga aagtttgcgg cttgcagagc acagaggccg    540

cagaatgtgc tctagattcc gatgctgact tgctgggtat tatatgtgtg cccaatagaa    600

agagaacaat tgacccggtt attgcaagga aaatttcaag tcttgtaaaa gcatataaaa    660

atagttcagg cactccgaaa tacttggttg gcgtgtttcg taatcaacct aaggaggatg    720

ttttggctct ggtcaatgat tacggcattg atatcgtcca actgcatgga gatgagtcgt    780
```

-continued

```
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgcctg cggtgtgaaa   1200
taccgcacag atgcgtaagg agaaaatacc gcatcaggaa attgtaaacg ttaatatttt   1260
gttaaaattc gcgttaaatt tttgttaaat cagctcattt tttaaccaat aggccgaaat   1320
cggcaaaatc ccttataaat caaaagaata gaccgagata gggttgagtg ttgttccagt   1380
ttggaacaag agtccactat taaagaacgt ggactccaac gtcaaagggc gaaaaaccgt   1440
ctatcagggc gatggcccac tacgtgaacc atcaccctaa tcaagttttt tggggtcgag   1500
gtgccgtaaa gcactaaatc ggaaccctaa agggagcccc cgatttagag cttgacgggg   1560
aaagccggcg aacgtggcga gaaaggaagg gaagaaagcg aaaggagcgg gcgctagggc   1620
gctggcaagt gtagcggtca cgctgcgcgt aaccaccaca cccgccgcgc ttaatgcgcc   1680
gctacagggc gcgtcgcgcc attcgccatt caggctgcgc aactgttggg aagggcgatc   1740
ggtgcgggcc tcttcgctat tacgccagct ggcgaagggg ggatgtgctg caaggcgatt   1800
aagttgggta acgccagggt tttcccagtc acgacgttgt aaaacgacgg ccagtgaatt   1860
gtaatacgac tcactatagg gcgaattgga gctcccgcgg atgtaaatgt aaatgtaaat   1920
gtaaatgtaa atgtaaatgt aattaattaa gtttttttctc cttgacgtta aagtatagag   1980
gtatattaac aatttttttgt tgatactttt attacatttg aataagaagt aatacaaacc   2040
gaaaatgttg aaagtattag ttaaagtggt tatgcagttt ttgcatttat atatctgtta   2100
atagatcaaa aatcatcgct tcgctgatta attaccccag aaataaggct aaaaaactaa   2160
tcgcattatc atcctatggt tgttaatttg attcgttcat ttgaaggttt gtggggccag   2220
gttactgcca atttttcctc ttcataacca taaaagctag tattgtagaa tctttattgt   2280
tcggagcagt gcggcgcgag gcacatctgc gtttcaggaa cgcgaccggt gaagacgagg   2340
acgcacggag gagagtcttc cttcggaggg ctgtcacccg ctcggcggct tctaatccgt   2400
acttcaatat agcaatgagc agttaagcgt attactgaaa gttccaaaga gaaggttttt   2460
ttaggctaag ataatggggc tctttacatt tccacaacat ataagtaaga ttagatatgg   2520
atatgtatat ggatatgtat atggtggtaa tgccatgtaa tatgattatt aaacttcttt   2580
gcgtccatcc aaaaaaaaag taagaatttt tgaaaaccat gagatttcct tcaattttta   2640
ctgcagtttt attcgcagca tcctccgcat tagctcatat gaaaagatct gcgaagcttg   2700
ctggcgcgcc cggaactgtg gctgcaccat ctgtcttcat cttcccgcca tctgatgagc   2760
agttgaaatc tggaactgcc tctgttgtgt gcctgctgaa taacttctat cccagagagg   2820
ccaaagtaca gtggaaggtg gataacgccc tccaatcggg taactcccag gagagtgtca   2880
cagagcagga cagcaaggac agcacctaca gcctcagcag caccctgacg ctgtcgaaag   2940
cagactacga gaaacacaaa gtctacgcct gcgaagtcac ccatcagggc ctgagctcgc   3000
ccgtcacaaa gagcttcaac aggggagagt gtacgcgtgt tacagtcgac ggtaagccta   3060
tccctaaccc tctcctcggt ctcgattcta cgcgtaccgg tcatcatcac catcaccata   3120
tctgataaca acagtgtaga tgtaacaaaa tcgactttgt tcccactgta cttttagctc   3180
```

-continued

```
gtacaaaata caatatactt ttcatttctc cgtaaacaac atgttttccc atgtaatatc   3240
cttttctatt tttcgttccg ttaccaactt tacacatact ttatatagct attcacttct   3300
atacactaaa aaactaagac aattttaatt ttgctgcctg ccatatttca atttgttata   3360
aattcctata atttatccta ttagtagcta aaaaaagatg aatgtgaatc gaatcctaag   3420
agaattgagc tccaattcgc cggattagaa gccgccgagc gggtgacagc cctccgaagg   3480
aagactctcc tccgtgcgtc ctcgtcttca ccggtcgcgt tcctgaaacg cagatgtgcc   3540
tcgcgccgca ctgctccgaa caataaagat tctacaatac tagcttttat ggttatgaag   3600
aggaaaaatt ggcagtaacc tggccccaca aaccttcaaa tgaacgaatc aaattaacaa   3660
ccataggatg ataatgcgat tagtttttta gccttatttc tggggtaatt aatcagcgaa   3720
gcgatgattt ttgatctatt aacagatata taaatgcaaa aactgcataa ccactttaac   3780
taatactttc aacattttcg gtttgtatta cttcttattc aaatgtaata aaagtatcaa   3840
caaaaaattg ttaatatacc tctatacttt aacgtcaagg agaccatgca gttacttcgc   3900
tgtttttcaa tattttctgt tattgcttca gttttagcac catggacatc tagaaaagct   3960
agcacagcgg ccgcagcctc caccaagggc ccatcggtct tccccctggc accctcctcc   4020
aagagcacct ctgggggcac agcggccctg ggctgcctgg tcaaggacta cttccccgaa   4080
ccggtgacgg tgtcgtggaa ctcaggcgcg ctgaccagcg gcgtgcacac cttcccggct   4140
gtcctacagt catcaggact ctactccctc agcagcgtag tgaccgtgcc ctccagcagc   4200
ttgggcaccc agacctacat ctgcaacgtg aatcacaagc ccagcaacac caaggtggac   4260
aagaaagttg agcccaaatc ttgtgaattc gaacaaaaac ttatttctga agaggacttg   4320
gactacaaag acgatgacga caaggaaaac ctgtattttc agggcctgca ggctagtggt   4380
ggaggaggct ctggtggagg cggtagcgga ggcggagggt cgatgactgg tcaggaactg   4440
acaactatat gcgagcaaat cccctcacca actttagaat cgacgccgta ctctttgtca   4500
acgactacta ttttggccaa cgggaaggca atgcaaggag tttttgaata ttacaaatca   4560
gtaacgtttg tcagtaattg cggttctcac ccctcaacaa ctagcaaagg cagccccata   4620
aacacacagt atgtttttta atcatgtaat tagttatgtc acgcttacat tcacgccctc   4680
cccccacatc cgctctaacc gaaaaggaag gagttagaca acctgaagtc taggtcccta   4740
tttatttttt tatagttatg ttagtattaa gaacgttatt tatatttcaa atttttcttt   4800
tttttctgta cagacgcgtg tacgcatgta acattatact gaaaaccttg cttgagaagg   4860
ttttgggacg ctcgaaggct ttaatttgca ctagtatgta aatgtaaatg taaatgtaaa   4920
tgtaaatgta aatgtaaggc catataggcc ggtacccagc ttttgttccc tttagtgagg   4980
gttaattccg agcttggcgt aatcatggtc atagctgttt cctgtgtgaa attgttatcc   5040
gctcacaatt ccacacaaca taggagccgg aagcataaag tgtaaagcct ggggtgccta   5100
atgagtgagg taactcacat taattgcgtt gcgctcactg cccgctttcc agtcgggaaa   5160
cctgtcgtgc cagctgcatt aatgaatcgg ccaacgcgcg gggagaggcg gtttgcgtat   5220
tgggcgctct tccgcttcct cgctcactga ctcgctgcgc tcggtcgttc ggctgcggcg   5280
agcggtatca gctcactcaa aggcggtaat acggttatcc acagaatcag gggataacgc   5340
aggaaagaac atgtgagcaa aaggccagca aaaggccagg aaccgtaaaa aggccgcgtt   5400
gctggcgttt ttccataggc tcggcccccc tgacgagcat cacaaaaatc gacgctcaag   5460
tcagaggtgg cgaaacccga caggactata aagataccag gcgttccccc ctggaagctc   5520
```

-continued

```
cctcgtgcgc tctcctgttc cgaccctgcc gcttaccgga tacctgtccg cctttctccc   5580
ttcgggaagc gtggcgcttt ctcaatgctc acgctgtagg tatctcagtt cggtgtaggt   5640
cgttcgctcc aagctgggct gtgtgcacga accccccgtt cagcccgacc gctgcgcctt   5700
atccggtaac tatcgtcttg agtccaaccc ggtaagacac gacttatcgc cactggcagc   5760
agccactggt aacaggatta gcagagcgag gtatgtaggc ggtgctacag agttcttgaa   5820
gtggtggcct aactacggct acactagaag gacagtattt ggtatctgcg ctctgctgaa   5880
gccagttacc ttcggaaaaa gagttggtag ctcttgatcc ggcaaacaaa ccaccgctgg   5940
tagcggtggt ttttttgttt gcaagcagca gattacgcgc agaaaaaaag gatctcaaga   6000
agatcctttg atcttttcta cggggtctga cgctcagtgg aacgaaaact cacgttaagg   6060
gattttggtc atgagattat caaaaaggat cttcacctag atccttttaa attaaaaatg   6120
aagttttaaa tcaatctaaa gtatatatga gtaaacttgg tctgacagtt accaatgctt   6180
aatcagtgag gcacctatct cagcgatctg tctatttcgt tcatccatag ttgcctgact   6240
gcccgtcgtg tagataacta cgatacggga gggcttacca tctggcccca gtgctgcaat   6300
gataccgcga gacccacgct caccggctcc agatttatca gcaataaacc agccagccgg   6360
aagggccgag cgcagaagtg gtcctgcaac tttatccgcc tccatccagt ctattaattg   6420
ttgccgggaa gctagagtaa gtagttcgcc agttaatagt ttgcgcaacg ttgttgccat   6480
tgctacaggc atcgtggtgt cacgctcgtc gtttggtatg gcttcattca gctccggttc   6540
ccaacgatca aggcgagtta catgatcccc catgttgtga aaaaaagcgg ttagctcctt   6600
cggtcctccg atcgttgtca gaagtaagtt ggccgcagtg ttatcactca tggttatggc   6660
agcactgcat aattctctta ctgtcatgcc atccgtaaga tgcttttctg tgactggtga   6720
gtactcaacc aagtcattct gagaatagtg tatgcggcga ccgagttgct cttgcccggc   6780
gtcaatacgg gataataccg cgccacatag cagaacttta aaagtgctca tcattggaaa   6840
acgttcttcg gggcgaaaac tctcaaggat cttaccgctg ttgagatcca gttcgatgta   6900
acccactcgt gcacccaact gatcttcagc atcttttact ttcaccagcg tttctgggtg   6960
agcaaaaaca ggaaggcaaa atgccgcaaa aaagggaata agggcgacac ggaaatgttg   7020
aatactcata ctcttccttt ttcaatatta ttgaagcatt tatcagggtt attgtctcat   7080
gagcggatac atatttgaat gtatttagaa aaataaacaa ataggggttc cgcgcacatt   7140
tccccgaaaa gtgccacctg ggtccttttc atcacgtgct ataaaaataa ttataattta   7200
aatttttaa tataaatata taaattaaaa atagaaagta aaaaaagaaa ttaaagaaaa   7260
aatagtttt gttttccgaa gatgtaaaag actctagggg gatcgccaac aaatactacc   7320
ttttatcttg ctcttcctgc tctcaggtat taatgccgaa ttgtttcatc ttgtctgtgt   7380
agaagaccac acacgaaaat cctgtgattt tacattttac ttatcgttaa tcgaatgtat   7440
atctatttaa tctgcttttc ttgtctaata aatatatatg taaagtacgc tttttgttga   7500
aatttttaa acctttgttt attttttttt cttcattccg taactcttct accttcttta   7560
tttactttct aaaatccaaa tacaaaacat aaaaataaat aaacacagag taaattccca   7620
aattattcca tcattaaaag atacgaggcg cgtgtaagtt acaggcaagc gatccgtcct   7680
aagaaaccat tattatcatg acattaacct ataaaaatag gcgtatcacg aggccctttc   7740
gtc                                                                  7743
```

<210> SEQ ID NO 11
<211> LENGTH: 2948

-continued

<212> TYPE: DNA
<213> ORGANISM: Artificial Sequence
<220> FEATURE:
<223> OTHER INFORMATION: pZB004.3 - Bicistronic Unidirectional lambda insert
<220> FEATURE:
<221> NAME/KEY: gene
<222> LOCATION: (1)..(2948)

<400> SEQUENCE: 11
ccgcgggttt tttctccttg acgttaaagt atagaggtat attaacaatt ttttgttgat 60
acttttatta catttgaata agaagtaata caaaccgaaa atgttgaaag tattagttaa 120
agtggttatg cagtttttgc atttatatat ctgttaatag atcaaaaatc atcgcttcgc 180
tgattaatta ccccagaaat aaggctaaaa aactaatcgc attatcatcc tatggttgtt 240
aatttgattc gttcatttga aggtttgtgg ggccaggtta ctgccaattt ttcctcttca 300
taaccataaa agctagtatt gtagaatctt tattgttcgg agcagtgcgg cgcgaggcac 360
atctgcgttt caggaacgcg accggtgaag acgaggacgc acggaggaga gtcttccttc 420
ggagggctgt cacccgctcg gcggcttcta atccgtactt caatatagca atgagcagtt 480
aagcgtatta ctgaaagttc caaagagaag gtttttttag gctaagataa tggggctctt 540
tacatttcca caacatataa gtaagattag atatggatat gtatatggat atgtatatgg 600
tggtaatgcc atgtaatatg attattaaac ttctttgcgt ccatccaaaa aaaaagtaag 660
aatttttgaa aaccatgaga tttccttcaa tttttactgc agttttattc gcagcatcct 720
ccgcattagc tcatatgaaa agatctgcga agcttgctgg cgcgcccggt cagcccaagg 780
ccaaccccac tgtcactctg ttcccgccct cctctgagga gctccaagcc aacaaggcca 840
ccctagtgtg tctgatcagt gacttctacc cgggagctgt gacagtggcc tggaaggcag 900
atggcagccc cgtcaaggcg ggagtggaga ccaccaaacc ctccaaacag agcaacaaca 960
agtacgcggc cagcagctac ctgagcctga cgcccgagca gtggaagtcc cacagaagct 1020
acagctgcca ggtcacgcat gaagggagca ccgtggagaa gacagtggcc cctacagaat 1080
gttcaacgcg tgttacagtc gacggtaagc ctatccctaa ccctctcctc ggtctcgatt 1140
ctacgcgtac cggtcatcat caccatcacc atatctgata acaacagtgt agatgtaaca 1200
aaatcgactt tgttcccact gtacttttag ctcgtacaaa atacaatata cttttcattt 1260
ctccgtaaac aacatgtttt cccatgtaat atccttttct atttttcgtt ccgttaccaa 1320
ctttacacat actttatata gctattcact tctatacact aaaaaactaa gacaatttta 1380
attttgctgc ctgccatatt tcaatttgtt ataaattcct ataatttatc ctattagtag 1440
ctaaaaaaag atgaatgtga atcgaatcct aagagaattg agctccaatt cgccggatta 1500
gaagccgccg agcgggtgac agccctccga aggaagactc tcctccgtgc gtcctcgtct 1560
tcaccggtcg cgttcctgaa acgcagatgt gcctcgcgcc gcactgctcc gaacaataaa 1620
gattctacaa tactagcttt tatggttatg aagaggaaaa attggcagta acctggcccc 1680
acaaaccttc aaatgaacga atcaaattaa caaccatagg atgataatgc gattagtttt 1740
ttagccttat ttctggggta attaatcagc gaagcgatga tttttgatct attaacagat 1800
atataaatgc aaaaactgca taaccacttt aactaatact ttcaacattt tcggtttgta 1860
ttacttctta ttcaaatgta ataaaagtat caacaaaaaa ttgttaatat acctctatac 1920
tttaacgtca aggagaccat gcagttactt cgctgttttt caatattttc tgttattgct 1980
tcagttttag caccatggac atctagaaaa gctagcacag cggccgcagc ctccaccaag 2040
ggcccatcgg tcttcccct ggcaccctcc tccaagagca cctctggggg cacagcggcc 2100
ctgggctgcc tggtcaagga ctacttcccc gaaccggtga cggtgtcgtg gaactcaggc 2160
gcgctgacca gcggcgtgca caccttcccg gctgtcctac agtcatcagg actctactcc 2220
ctcagcagcg tagtgaccgt gccctccagc agcttgggca cccagaccta catctgcaac 2280
gtgaatcaca agcccagcaa caccaaggtg gacaagaaag ttgagcccaa atcttgtgaa 2340
ttcgaacaaa aacttatttc tgaagaggac ttggactaca aagacgatga cgacaaggaa 2400
aacctgtatt ttcagggcct gcaggctagt ggtggaggag gctctggtgg aggcggtagc 2460
ggaggcggag ggtcgatgac tggtcaggaa ctgacaacta tatgcgagca aatcccctca 2520
ccaactttag aatcgacgcc gtactctttg tcaacgacta ctattttggc caacgggaag 2580
gcaatgcaag gagtttttga atattacaaa tcagtaacgt ttgtcagtaa ttgcggttct 2640
cacccctcaa caactagcaa aggcagcccc ataaacacac agtatgtttt ttaatcatgt 2700
aattagttat gtcacgctta cattcacgcc ctccccccac atccgctcta accgaaaagg 2760
aaggagttag acaacctgaa gtctaggtcc ctatttattt ttttatagtt atgttagtat 2820
taagaacgtt atttatattt caaatttttc tttttttct gtacagacgc gtgtacgcat 2880
gtaacattat actgaaaacc ttgcttgaga aggttttggg acgctcgaag gctttaattt 2940
gcactagt 2948

<210> SEQ ID NO 12
<211> LENGTH: 7740
<212> TYPE: DNA
<213> ORGANISM: Artificial Sequence
<220> FEATURE:
<223> OTHER INFORMATION: pZB004.3 - Bicistronic Unidirectional lambda vector construct
<220> FEATURE:
<221> NAME/KEY: misc_recomb
<222> LOCATION: (1)..(7740)

<400> SEQUENCE: 12
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420
tgagcacgtg agtatacgtg attaagcaca caaaggcagc ttggagtatg tctgttatta 480
atttcacagg tagttctggt ccattggtga aagtttgcgg cttgcagagc acagaggccg 540
cagaatgtgc tctagattcc gatgctgact tgctgggtat tatatgtgtg cccaatagaa 600
agagaacaat tgacccggtt attgcaagga aaatttcaag tcttgtaaaa gcatataaaa 660
atagttcagg cactccgaaa tacttggttg gcgtgtttcg taatcaacct aaggaggatg 720
ttttggctct ggtcaatgat tacggcattg atatcgtcca actgcatgga gatgagtcgt 780
ggcaagaata ccaagagttc ctcggtttgc cagttattaa aagactcgta tttccaaaag 840
actgcaacat actactcagt gcagcttcac agaaacctca ttcgtttatt cccttgtttg 900
attcagaagc aggtgggaca ggtgaacttt tggattggaa ctcgatttct gactgggttg 960
gaaggcaaga gagccccgaa agcttacatt ttatgttagc tggtggactg acgccagaaa 1020
atgttggtga tgcgcttaga ttaaatggcg ttattggtgt tgatgtaagc ggaggtgtgg 1080
agacaaatgg tgtaaaagac tctaacaaaa tagcaaattt cgtcaaaaat gctaagaaat 1140
aggttattac tgagtagtat ttatttaagt attgtttgtg cacttgcctg cggtgtgaaa 1200
taccgcacag atgcgtaagg agaaaatacc gcatcaggaa attgtaaacg ttaatatttt 1260
gttaaaattc gcgttaaatt tttgttaaat cagctcattt tttaaccaat aggccgaaat 1320
cggcaaaatc ccttataaat caaaagaata gaccgagata gggttgagtg ttgttccagt 1380
ttggaacaag agtccactat taaagaacgt ggactccaac gtcaaagggc gaaaaaccgt 1440
ctatcagggc gatggcccac tacgtgaacc atcaccctaa tcaagttttt tggggtcgag 1500
gtgccgtaaa gcactaaatc ggaaccctaa agggagcccc cgatttagag cttgacgggg 1560
aaagccggcg aacgtggcga gaaaggaagg gaagaaagcg aaaggagcgg gcgctagggc 1620
gctggcaagt gtagcggtca cgctgcgcgt aaccaccaca cccgccgcgc ttaatgcgcc 1680
gctacagggc gcgtcgcgcc attcgccatt caggctgcgc aactgttggg aagggcgatc 1740
ggtgcgggcc tcttcgctat tacgccagct ggcgaagggg ggatgtgctg caaggcgatt 1800
aagttgggta acgccagggt tttcccagtc acgacgttgt aaaacgacgg ccagtgaatt 1860
gtaatacgac tcactatagg gcgaattgga gctcttaatt aattacattt acatttacat 1920
ttacatttac atttacattt acatccgcgg gttttttctc cttgacgtta aagtatagag 1980
gtatattaac aatttttttgt tgatactttt attacatttg aataagaagt aatacaaacc 2040
gaaaatgttg aaagtattag ttaaagtggt tatgcagttt ttgcatttat atatctgtta 2100
atagatcaaa aatcatcgct tcgctgatta attaccccag aaataaggct aaaaaactaa 2160
tcgcattatc atcctatggt tgttaatttg attcgttcat ttgaaggttt gtggggccag 2220
gttactgcca atttttcctc ttcataacca taaaagctag tattgtagaa tctttattgt 2280
tcggagcagt gcggcgcgag gcacatctgc gtttcaggaa cgcgaccggt gaagacgagg 2340
acgcacggag gagagtcttc cttcggaggg ctgtcacccg ctcggcggct tctaatccgt 2400
acttcaatat agcaatgagc agttaagcgt attactgaaa gttccaaaga gaaggttttt 2460
ttaggctaag ataatggggc tctttacatt tccacaacat ataagtaaga ttagatatgg 2520
atatgtatat ggatatgtat atggtggtaa tgccatgtaa tatgattatt aaacttcttt 2580
gcgtccatcc aaaaaaaaag taagaatttt tgaaaaccat gagatttcct tcaattttta 2640
ctgcagtttt attcgcagca tcctccgcat tagctcatat gaaaagatct gcgaagcttg 2700
ctggcgcgcc cggtcagccc aaggccaacc ccactgtcac tctgttcccg ccctcctctg 2760
aggagctcca agccaacaag gccaccctag tgtgtctgat cagtgacttc tacccgggag 2820
ctgtgacagt ggcctggaag gcagatggca gccccgtcaa ggcgggagtg gagaccacca 2880
aaccctccaa acagagcaac aacaagtacg cggccagcag ctacctgagc ctgacgcccg 2940
agcagtggaa gtcccacaga agctacagct gccaggtcac gcatgaaggg agcaccgtgg 3000
agaagacagt ggcccctaca gaatgttcaa cgcgtgttac agtcgacggt aagcctatcc 3060
ctaaccctct cctcggtctc gattctacgc gtaccggtca tcatcaccat caccatatct 3120
gataacaaca gtgtagatgt aacaaaatcg actttgttcc cactgtactt ttagctcgta 3180
caaaatacaa tatacttttc atttctccgt aaacaacatg ttttcccatg taatatcctt 3240
ttctattttt cgttccgtta ccaactttac acatacttta tatagctatt cacttctata 3300
cactaaaaaa ctaagacaat ttaattttg ctgcctgcca tatttcaatt tgttataaat 3360

```
tcctataatt tatcctatta gtagctaaaa aaagatgaat gtgaatcgaa tcctaagaga   3420

attgagctcc aattcgccgg attagaagcc gccgagcggg tgacagccct ccgaaggaag   3480

actctcctcc gtgcgtcctc gtcttcaccg gtcgcgttcc tgaaacgcag atgtgcctcg   3540

cgccgcactg ctccgaacaa taaagattct acaatactag cttttatggt tatgaagagg   3600

aaaaattggc agtaacctgg ccccacaaac cttcaaatga acgaatcaaa ttaacaacca   3660

taggatgata atgcgattag ttttttagcc ttatttctgg ggtaattaat cagcgaagcg   3720

atgatttttg atctattaac agatatataa atgcaaaaac tgcataacca ctttaactaa   3780

tactttcaac attttcggtt tgtattactt cttattcaaa tgtaataaaa gtatcaacaa   3840

aaaattgtta atatacctct atactttaac gtcaaggaga ccatgcagtt acttcgctgt   3900

ttttcaatat tttctgttat tgcttcagtt ttagcaccat ggacatctag aaaagctagc   3960

acagcggccg cagcctccac caagggccca tcggtcttcc ccctggcacc ctcctccaag   4020

agcacctctg ggggcacagc ggccctgggc tgcctggtca aggactactt ccccgaaccg   4080

gtgacggtgt cgtggaactc aggcgcgctg accagcggcg tgcacacctt cccggctgtc   4140

ctacagtcat caggactcta ctccctcagc agcgtagtga ccgtgccctc cagcagcttg   4200

ggcacccaga cctacatctg caacgtgaat cacaagccca gcaacaccaa ggtggacaag   4260

aaagttgagc ccaaatcttg tgaattcgaa caaaaactta tttctgaaga ggacttggac   4320

tacaaagacg atgacgacaa ggaaaacctg tattttcagg gcctgcaggc tagtggtgga   4380

ggaggctctg gtggaggcgg tagcggaggc ggagggtcga tgactggtca ggaactgaca   4440

actatatgcg agcaaatccc ctcaccaact ttagaatcga cgccgtactc tttgtcaacg   4500

actactattt tggccaacgg gaaggcaatg caaggagttt ttgaatatta caaatcagta   4560

acgtttgtca gtaattgcgg ttctcacccc tcaacaacta gcaaaggcag ccccataaac   4620

acacagtatg ttttttaatc atgtaattag ttatgtcacg cttacattca cgccctcccc   4680

ccacatccgc tctaaccgaa aaggaaggag ttagacaacc tgaagtctag gtccctattt   4740

atttttttat agttatgtta gtattaagaa cgttatttat atttcaaatt tttctttttt   4800

ttctgtacag acgcgtgtac gcatgtaaca ttatactgaa aaccttgctt gagaaggttt   4860

tgggacgctc gaaggcttta atttgcacta gtatgtaaat gtaaatgtaa atgtaaatgt   4920

aaatgtaaat gtaaggccat ataggccggt acccagcttt tgttcccttt agtgagggtt   4980

aattccgagc ttggcgtaat catggtcata gctgtttcct gtgtgaaatt gttatccgct   5040

cacaattcca cacaacatag gagccggaag cataaagtgt aaagcctggg gtgcctaatg   5100

agtgaggtaa ctcacattaa ttgcgttgcg ctcactgccc gctttccagt cgggaaacct   5160

gtcgtgccag ctgcattaat gaatcggcca acgcgcgggg agaggcggtt tgcgtattgg   5220

gcgctcttcc gcttcctcgc tcactgactc gctgcgctcg gtcgttcggc tgcggcgagc   5280

ggtatcagct cactcaaagg cggtaatacg gttatccaca gaatcagggg ataacgcagg   5340

aaagaacatg tgagcaaaag gccagcaaaa ggccaggaac cgtaaaaagg ccgcgttgct   5400

ggcgtttttc cataggctcg gccccccctga cgagcatcac aaaaatcgac gctcaagtca   5460

gaggtggcga aacccgacag gactataaag ataccaggcg tttccccctg gaagctccct   5520

cgtgcgctct cctgttccga ccctgccgct taccggatac ctgtccgcct ttctcccttc   5580

gggaagcgtg gcgctttctc aatgctcacg ctgtaggtat ctcagttcgg tgtaggtcgt   5640

tcgctccaag ctgggctgtg tgcacgaacc ccccgttcag cccgaccgct gcgccttatc   5700

cggtaactat cgtcttgagt ccaacccggt aagacacgac ttatcgccac tggcagcagc   5760
```

```
cactggtaac aggattagca gagcgaggta tgtaggcggt gctacagagt tcttgaagtg   5820

gtggcctaac tacggctaca ctagaaggac agtatttggt atctgcgctc tgctgaagcc   5880

agttaccttc ggaaaaagag ttggtagctc ttgatccggc aaacaaacca ccgctggtag   5940

cggtggtttt tttgtttgca agcagcagat tacgcgcaga aaaaaaggat ctcaagaaga   6000

tcctttgatc ttttctacgg ggtctgacgc tcagtggaac gaaaactcac gttaagggat   6060

tttggtcatg agattatcaa aaaggatctt cacctagatc cttttaaatt aaaaatgaag   6120

ttttaaatca atctaaagta tatatgagta aacttggtct gacagttacc aatgcttaat   6180

cagtgaggca cctatctcag cgatctgtct atttcgttca tccatagttg cctgactgcc   6240

cgtcgtgtag ataactacga tacgggaggg cttaccatct ggccccagtg ctgcaatgat   6300

accgcgagac ccacgctcac cggctccaga tttatcagca ataaaccagc cagccggaag   6360

ggccgagcgc agaagtggtc ctgcaacttt atccgcctcc atccagtcta ttaattgttg   6420

ccgggaagct agagtaagta gttcgccagt taatagtttg cgcaacgttg ttgccattgc   6480

tacaggcatc gtggtgtcac gctcgtcgtt tggtatggct tcattcagct ccggttccca   6540

acgatcaagg cgagttacat gatcccccat gttgtgaaaa aaagcggtta gctccttcgg   6600

tcctccgatc gttgtcagaa gtaagttggc cgcagtgtta tcactcatgg ttatggcagc   6660

actgcataat tctcttactg tcatgccatc cgtaagatgc ttttctgtga ctggtgagta   6720

ctcaaccaag tcattctgag aatagtgtat gcggcgaccg agttgctctt gcccggcgtc   6780

aatacgggat aataccgcgc cacatagcag aactttaaaa gtgctcatca ttggaaaacg   6840

ttcttcgggg cgaaaactct caaggatctt accgctgttg agatccagtt cgatgtaacc   6900

cactcgtgca cccaactgat cttcagcatc ttttactttc accagcgttt ctgggtgagc   6960

aaaaacagga aggcaaaatg ccgcaaaaaa gggaataagg gcgacacgga aatgttgaat   7020

actcatactc ttcctttttc aatattattg aagcatttat cagggttatt gtctcatgag   7080

cggatacata tttgaatgta tttagaaaaa taaacaaata ggggttccgc gcacatttcc   7140

ccgaaaagtg ccacctgggt ccttttcatc acgtgctata aaaataatta taatttaaat   7200

tttttaatat aaatatataa attaaaaata gaaagtaaaa aaagaaatta aagaaaaaat   7260

agtttttgtt ttccgaagat gtaaaagact ctagggggat cgccaacaaa tactaccttt   7320

tatcttgctc ttcctgctct caggtattaa tgccgaattg tttcatcttg tctgtgtaga   7380

agaccacaca cgaaaatcct gtgattttac attttactta tcgttaatcg aatgtatatc   7440

tatttaatct gcttttcttg tctaataaat atatatgtaa agtacgcttt ttgttgaaat   7500

tttttaaacc tttgtttatt tttttttctt cattccgtaa ctcttctacc ttctttattt   7560

actttctaaa atccaaatac aaaacataaa aataaataaa cacagagtaa attcccaaat   7620

tattccatca ttaaaagata cgaggcgcgt gtaagttaca ggcaagcgat ccgtcctaag   7680

aaaccattat tatcatgaca ttaacctata aaaataggcg tatcacgagg ccctttcgtc   7740
```

<210> SEQ ID NO 13
<211> LENGTH: 1446
<212> TYPE: DNA
<213> ORGANISM: Artificial Sequence
<220> FEATURE:
<223> OTHER INFORMATION: pZB004.4 - Yeast ScFv insert
<220> FEATURE:
<221> NAME/KEY: gene
<222> LOCATION: (1)..(1446)

<400> SEQUENCE: 13

```
ccgcggacgg attagaagcc gccgagcggg tgacagccct ccgaaggaag actctcctcc     60

gtgcgtcctc gtcttcaccg gtcgcgttcc tgaaacgcag atgtgcctcg cgccgcactg    120

ctccgaacaa taaagattct acaatactag cttttatggt tatgaagagg aaaaattggc    180

agtaacctgg ccccacaaac cttcaaatga acgaatcaaa ttaacaacca taggatgata    240

atgcgattag tttttagcc ttatttctgg ggtaattaat cagcgaagcg atgatttttg    300

atctattaac agatatataa atgcaaaaac tgcataacca ctttaactaa tactttcaac    360

attttcggtt tgtattactt cttattcaaa tgtaataaaa gtatcaacaa aaaattgtta    420

atatacctct atactttaac gtcaaggaga aaaaaccccg gatcgaattc cctacttcat    480

acattttcaa ttaagatgca gttacttcgc tgtttttcaa tattttctgt tattgcttca    540

gttttagcac aggaactgac aactatatgc gagcaaatcc cctcaccaac tttagaatcg    600

acgccgtact ctttgtcaac gactactatt ttggccaacg ggaaggcaat gcaaggagtt    660

tttgaatatt acaaatcagt aacgtttgtc agtaattgcg gttctcaccc ctcaacaact    720

agcaaaggca gccccataaa cacacagtat gtttttaagg acaatagctc gacgattgaa    780

ggtagatacc catacgacgt tccagactac gctctgcagg ctagtggtgg aggaggctct    840

ggtggaggcg gtagcggagg cggagggtcg atgactggtg aaaacctgta ttttcagggc    900

gctagcacta gtcatatgaa aagatctgcg aagcttgctg gcgcgcccgg tggttcctct    960

agatcttcct cctctggtgg cggtggctcg ggcggtggtg ggccatggac atctagaaaa   1020

gctagcacag cggccgccct cgagggatcc gaacaaaagc ttatttctga agaggacttg   1080

cgtacccgtg actacaaaga cgatgacgac aagtaataga tctgataaca acagtgtaga   1140

tgtaacaaaa tcgactttgt tcccactgta cttttagctc gtacaaaata caatatactt   1200

ttcatttctc cgtaaacaac atgttttccc atgtaatatc cttttctatt tttcgttccg   1260

ttaccaactt tacacatact ttatatagct attcacttct atacactaaa aaactaagac   1320

aattttaatt ttgctgcctg ccatatttca atttgttata aattcctata atttatccta   1380

ttagtagcta aaaaaagatg aatgtgaatc gaatcctaag agaattgagc tccaattcgc   1440

gggccc                                                               1446
```

```
<210> SEQ ID NO 14
<211> LENGTH: 6135
<212> TYPE: DNA
<213> ORGANISM: Artificial Sequence
<220> FEATURE:
<223> OTHER INFORMATION: pZB004.4 - Yeast ScFv vector construct
<220> FEATURE:
<221> NAME/KEY: misc_recomb
<222> LOCATION: (1)..(6135)

<400> SEQUENCE: 14

gggcccggta cccagctttt gttcccttta gtgagggtta attccgagct tggcgtaatc     60

atggtcatag ctgtttcctg tgtgaaattg ttatccgctc acaattccac acaacatagg    120

agccggaagc ataaagtgta aagcctgggg tgcctaatga gtgaggtaac tcacattaat    180

tgcgttgcgc tcactgcccg ctttccagtc gggaaacctg tcgtgccagc tgcattaatg    240

aatcggccaa cgcgcgggga gaggcggttt gcgtattggg cgctcttccg cttcctcgct    300

cactgactcg ctgcgctcgg tcgttcggct gcggcgagcg gtatcagctc actcaaaggc    360

ggtaatacgg ttatccacag aatcagggga taacgcagga aagaacatgt gagcaaaagg    420

ccagcaaaag gccaggaacc gtaaaaaggc cgcgttgctg gcgtttttcc ataggctcgg    480
```

```
ccccccctgac gagcatcaca aaaatcgacg ctcaagtcag aggtggcgaa acccgacagg    540
actataaaga taccaggcgt ttccccctgg aagctccctc gtgcgctctc ctgttccgac    600
cctgccgctt accggatacc tgtccgcctt tctcccttcg ggaagcgtgg cgctttctca    660
atgctcacgc tgtaggtatc tcagttcggt gtaggtcgtt cgctccaagc tgggctgtgt    720
gcacgaaccc cccgttcagc ccgaccgctg cgccttatcc ggtaactatc gtcttgagtc    780
caacccggta agacacgact tatcgccact ggcagcagcc actggtaaca ggattagcag    840
agcgaggtat gtaggcggtg ctacagagtt cttgaagtgg tggcctaact acggctacac    900
tagaaggaca gtatttggta tctgcgctct gctgaagcca gttaccttcg gaaaaagagt    960
tggtagctct tgatccggca aacaaaccac cgctggtagc ggtggttttt ttgtttgcaa   1020
gcagcagatt acgcgcagaa aaaaaggatc tcaagaagat cctttgatct tttctacggg   1080
gtctgacgct cagtggaacg aaaactcacg ttaagggatt ttggtcatga gattatcaaa   1140
aaggatcttc acctagatcc ttttaaatta aaaatgaagt tttaaatcaa tctaaagtat   1200
atatgagtaa acttggtctg acagttacca atgcttaatc agtgaggcac ctatctcagc   1260
gatctgtcta tttcgttcat ccatagttgc ctgactgccc gtcgtgtaga taactacgat   1320
acgggagggc ttaccatctg gccccagtgc tgcaatgata ccgcgagacc cacgctcacc   1380
ggctccagat ttatcagcaa taaaccagcc agccggaagg gccgagcgca gaagtggtcc   1440
tgcaacttta tccgcctcca tccagtctat taattgttgc cgggaagcta gagtaagtag   1500
ttcgccagtt aatagtttgc gcaacgttgt tgccattgct acaggcatcg tggtgtcacg   1560
ctcgtcgttt ggtatggctt cattcagctc cggttcccaa cgatcaaggc gagttacatg   1620
atcccccatg ttgtgaaaaa aagcggttag ctccttcggt cctccgatcg ttgtcagaag   1680
taagttggcc gcagtgttat cactcatggt tatggcagca ctgcataatt ctcttactgt   1740
catgccatcc gtaagatgct tttctgtgac tggtgagtac tcaaccaagt cattctgaga   1800
atagtgtatg cggcgaccga gttgctcttg cccggcgtca atacgggata ataccgcgcc   1860
acatagcaga actttaaaag tgctcatcat tggaaaacgt tcttcggggc gaaaactctc   1920
aaggatctta ccgctgttga gatccagttc gatgtaaccc actcgtgcac ccaactgatc   1980
ttcagcatct tttactttca ccagcgtttc tgggtgagca aaaacaggaa ggcaaaatgc   2040
cgcaaaaaag ggaataaggg cgacacggaa atgttgaata ctcatactct tcctttttca   2100
atattattga agcatttatc agggttattg tctcatgagc ggatacatat ttgaatgtat   2160
ttagaaaaat aaacaaatag gggttccgcg cacatttccc cgaaaagtgc cacctgggtc   2220
cttttcatca cgtgctataa aaataattat aatttaaatt ttttaatata aatatataaa   2280
ttaaaaatag aaagtaaaaa aagaaattaa agaaaaaata gtttttgttt tccgaagatg   2340
taaaagactc tagggggatc gccaacaaat actacctttt atcttgctct tcctgctctc   2400
aggtattaat gccgaattgt ttcatcttgt ctgtgtagaa gaccacacac gaaaatcctg   2460
tgattttaca ttttacttat cgttaatcga atgtatatct atttaatctg cttttcttgt   2520
ctaataaata tatatgtaaa gtacgctttt tgttgaaatt ttttaaacct ttgtttattt   2580
ttttttcttc attccgtaac tcttctacct tctttattta ctttctaaaa tccaaataca   2640
aaacataaaa ataaataaac acagagtaaa ttcccaaatt attccatcat taaaagatac   2700
gaggcgcgtg taagttacag gcaagcgatc cgtcctaaga aaccattatt atcatgacat   2760
taacctataa aaataggcgt atcacgaggc cctttcgtct cgcgcgtttc ggtgatgacg   2820
```

-continued gtgaaaacct ctgacacatg cagctcccgg agacggtcac agcttgtctg taagcggatg 2880
ccgggagcag acaagcccgt cagggcgcgt cagcgggtgt tggcgggtgt cggggctggc 2940
ttaactatgc ggcatcagag cagattgtac tgagagtgca ccataaacga cattactata 3000
tatataatat aggaagcatt taatagacag catcgtaata tatgtgtact ttgcagttat 3060
gacgccagat ggcagtagtg gaagatattc tttattgaaa aatagcttgt caccttacgt 3120
acaatcttga tccggagctt ttcttttttt gccgattaag aattaattcg gtcgaaaaaa 3180
gaaaaggaga gggccaagag ggagggcatt ggtgactatt gagcacgtga gtatacgtga 3240
ttaagcacac aaaggcagct tggagtatgt ctgttattaa tttcacaggt agttctggtc 3300
cattggtgaa agtttgcggc ttgcagagca cagaggccgc agaatgtgct ctagattccg 3360
atgctgactt gctgggtatt atatgtgtgc ccaatagaaa gagaacaatt gacccggtta 3420
ttgcaaggaa aatttcaagt cttgtaaaag catataaaaa tagttcaggc actccgaaat 3480
acttggttgg cgtgtttcgt aatcaaccta aggaggatgt tttggctctg gtcaatgatt 3540
acggcattga tatcgtccaa ctgcatggag atgagtcgtg gcaagaatac caagagttcc 3600
tcggtttgcc agttattaaa agactcgtat ttccaaaaga ctgcaacata ctactcagtg 3660
cagcttcaca gaaacctcat tcgtttattc ccttgtttga ttcagaagca ggtgggacag 3720
gtgaactttt ggattggaac tcgatttctg actgggttgg aaggcaagag agccccgaaa 3780
gcttacattt tatgttagct ggtggactga cgccagaaaa tgttggtgat gcgcttagat 3840
taaatggcgt tattggtgtt gatgtaagcg gaggtgtgga gacaaatggt gtaaaagact 3900
ctaacaaaat agcaaatttc gtcaaaaatg ctaagaaata ggttattact gagtagtatt 3960
tatttaagta ttgtttgtgc acttgcctgc ggtgtgaaat accgcacaga tgcgtaagga 4020
gaaaataccg catcaggaaa ttgtaaacgt taatattttg ttaaaattcg cgttaaattt 4080
ttgttaaatc agctcatttt ttaaccaata ggccgaaatc ggcaaaatcc cttataaatc 4140
aaaagaatag accgagatag ggttgagtgt tgttccagtt tggaacaaga gtccactatt 4200
aaagaacgtg gactccaacg tcaaagggcg aaaaaccgtc tatcagggcg atggcccact 4260
acgtgaacca tcaccctaat caagtttttt ggggtcgagg tgccgtaaag cactaaatcg 4320
gaaccctaaa gggagccccc gatttagagc ttgacgggga aagccggcga acgtggcgag 4380
aaaggaaggg aagaaagcga aaggagcggg cgctagggcg ctggcaagtg tagcggtcac 4440
gctgcgcgta accaccacac ccgccgcgct taatgcgccg ctacagggcg cgtcgcgcca 4500
ttcgccattc aggctgcgca actgttggga agggcgatcg gtgcgggcct cttcgctatt 4560
acgccagctg gcgaaggggg gatgtgctgc aaggcgatta agttgggtaa cgccagggtt 4620
ttcccagtca cgacgttgta aaacgacggc cagtgaattg taatacgact cactataggg 4680
cgaattggag ctccaccgcg gacggattag aagccgccga gcgggtgaca gccctccgaa 4740
ggaagactct cctccgtgcg tcctcgtctt caccggtcgc gttcctgaaa cgcagatgtg 4800
cctcgcgccg cactgctccg aacaataaag attctacaat actagctttt atggttatga 4860
agaggaaaaa ttggcagtaa cctggcccca caaaccttca aatgaacgaa tcaaattaac 4920
aaccatagga tgataatgcg attagttttt tagccttatt tctggggtaa ttaatcagcg 4980
aagcgatgat ttttgatcta ttaacagata tataaatgca aaaactgcat aaccacttta 5040
actaatactt tcaacatttt cggtttgtat tacttcttat tcaaatgtaa taaaagtatc 5100
aacaaaaaat tgttaatata cctctatact ttaacgtcaa ggagaaaaaa ccccggatcg 5160
aattccctac ttcatacatt ttcaattaag atgcagttac ttcgctgttt ttcaatattt 5220
tctgttattg cttcagtttt agcacaggaa ctgacaacta tatgcgagca aatcccctca 5280
ccaactttag aatcgacgcc gtactctttg tcaacgacta ctattttggc caacgggaag 5340
gcaatgcaag gagtttttga atattacaaa tcagtaacgt ttgtcagtaa ttgcggttct 5400
cacccctcaa caactagcaa aggcagcccc ataaacacac agtatgtttt taaggacaat 5460
agctcgacga ttgaaggtag atacccatac gacgttccag actacgctct gcaggctagt 5520
ggtggaggag gctctggtgg aggcggtagc ggaggcggag ggtcgatgac tggtgaaaac 5580
ctgtattttc agggcgctag cactagtcat atgaaaagat ctgcgaagct tgctggcgcg 5640
cccggtggtt cctctagatc ttcctcctct ggtggcggtg gctcgggcgg tggtgggcca 5700
tggacatcta gaaaagctag cacagcggcc gccctcgagg gatccgaaca aaagcttatt 5760
tctgaagagg acttgcgtac ccgtgactac aaagacgatg acgacaagta atagatctga 5820
taacaacagt gtagatgtaa caaaatcgac tttgttccca ctgtactttt agctcgtaca 5880
aaatacaata tacttttcat ttctccgtaa acaacatgtt ttcccatgta atatcctttt 5940
ctatttttcg ttccgttacc aactttacac atactttata tagctattca cttctataca 6000
ctaaaaaact aagacaattt taattttgct gcctgccata tttcaatttg ttataaattc 6060
ctataattta tcctattagt agctaaaaaa agatgaatgt gaatcgaatc ctaagagaat 6120
tgagctccaa ttcgc 6135

<210> SEQ ID NO 15
<211> LENGTH: 759
<212> TYPE: DNA
<213> ORGANISM: Artificial Sequence
<220> FEATURE:
<223> OTHER INFORMATION: pZB002 - Aga2P Heavy chain Mating Type insert
<220> FEATURE:
<221> NAME/KEY: gene
<222> LOCATION: (1)..(759)

<400> SEQUENCE: 15
actagtatgc agttacttcg ctgtttttca atattttctg ttattgcttc agttttagca 60
ccatggacat ctagaaaagc tagcacagcg gccgcagcct ccaccaaggg cccatcggtc 120
ttccccctgg caccctcctc caagagcacc tctgggggca cagcggccct gggctgcctg 180
gtcaaggact acttccccga accggtgacg gtgtcgtgga actcaggcgc gctgaccagc 240
ggcgtgcaca ccttcccggc tgtcctacag tcatcaggac tctactccct cagcagcgta 300
gtgaccgtgc cctccagcag cttgggcacc cagacctaca tctgcaacgt gaatcacaag 360
cccagcaaca ccaaggtgga caagaaagtt gagcccaaat cttgtgaatt cgaacaaaaa 420
cttatttctg aagaggactt ggactacaaa gacgatgacg acaaggaaaa cctgtatttt 480
cagggcctgc aggctagtgg tggaggaggc tctggtggag gcggtagcgg aggcggaggg 540
tcgcaggaac tgacaactat atgcgagcaa atcccctcac caactttaga atcgacgccg 600
tactctttgt caacgactac tattttggcc aacgggaagg caatgcaagg agtttttgaa 660
tattacaaat cagtaacgtt tgtcagtaat tgcggttctc acccctcaac aactagcaaa 720
ggcagcccca taaacacaca gtatgttttt tgactcgag 759

<210> SEQ ID NO 16
<211> LENGTH: 6169
<212> TYPE: DNA
<213> ORGANISM: Artificial Sequence
<220> FEATURE:
<223> OTHER INFORMATION: pZB002 - Aga2P Heavy chain Mating Type vector construct
<220> FEATURE:
<221> NAME/KEY: misc_recomb
<222> LOCATION: (1)..(6169)

<400> SEQUENCE: 16

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagtca   2160
```

-continued

```
aaaaacatac tgtgtgttta tggggctgcc tttgctagtt gttgaggggt gagaaccgca   2220
attactgaca aacgttactg atttgtaata ttcaaaaact ccttgcattg ccttcccgtt   2280
ggccaaaata gtagtcgttg acaaagagta cggcgtcgat tctaaagttg gtgaggggat   2340
ttgctcgcat atagttgtca gttcctgcga ccctccgcct ccgctaccgc ctccaccaga   2400
gcctcctcca ccactagcct gcaggccctg aaaatacagg ttttccttgt cgtcatcgtc   2460
tttgtagtcc aagtcctctt cagaaataag tttttgttcg aattcacaag atttgggctc   2520
aactttcttg tccaccttgg tgttgctggg cttgtgattc acgttgcaga tgtaggtctg   2580
ggtgcccaag ctgctggagg gcacggtcac tacgctgctg agggagtaga gtcctgatga   2640
ctgtaggaca gccgggaagg tgtgcacgcc gctggtcagc gcgcctgagt tccacgacac   2700
cgtcaccggt tcggggaagt agtccttgac caggcagccc agggccgctg tgcccccaga   2760
ggtgctcttg gaggagggtg ccagggggaa gaccgatggg cccttggtgg aggctgcggc   2820
cgctgtgcta gcttttctag atgtccatgg tgctaaaact gaagcaataa cagaaaatat   2880
tgaaaaacag cgaagtaact gcatactagt tctagatata gtttttctc cttgacgtta   2940
aagtatagag gtatattaac aattttttgt tgatactttt attacatttg aataagaagt   3000
aatacaaacc gaaaatgttg aaagtattag ttaaagtggt tatgcagttt ttgcatttat   3060
atatctgtta atagatcaaa aatcatcgct tcgctgatta attaccccag aaataaggct   3120
aaaaaactaa tcgcattatc atcctatggt tgttaatttg attcgttcat ttgaaggttt   3180
gtggggccag gttactgcca atttttcctc ttcataacca taaaagctag tattgtagaa   3240
tctttattgt tcggagcagt gcggcgcgag gcacatctgc gtttcaggaa cgcgaccggt   3300
gaagacgagg acgcacggag gagagtcttc cttcggaggg ctgtcacccg ctcggcggct   3360
tctaatccgt acttcagagc tccagctttt gttcccttta gtgagggtta attgcgcgct   3420
tggcgtaatc atggtcatag ctgtttcctg tgtgaaattg ttatccgctc acaattccac   3480
acaacatagg agccggaagc ataaagtgta aagcctgggg tgcctaatga gtgaggtaac   3540
tcacattaat tgcgttgcgc tcactgcccg ctttccagtc gggaaacctg tcgtgccagc   3600
tgcattaatg aatcggccaa cgcgcgggga gaggcggttt gcgtattggg cgctcttccg   3660
cttcctcgct cactgactcg ctgcgctcgg tcgttcggct gcggcgagcg gtatcagctc   3720
actcaaaggc ggtaatacgg ttatccacag aatcagggga taacgcagga aagaacatgt   3780
gagcaaaagg ccagcaaaag gccaggaacc gtaaaaaggc cgcgttgctg gcgtttttcc   3840
ataggctccg cccccctgac gagcatcaca aaaatcgacg ctcaagtcag aggtggcgaa   3900
acccgacagg actataaaga taccaggcgt ttccccctgg aagctccctc gtgcgctctc   3960
ctgttccgac cctgccgctt accggatacc tgtccgcctt tctcccttcg ggaagcgtgg   4020
cgctttctca tagctcacgc tgtaggtatc tcagttcggt gtaggtcgtt cgctccaagc   4080
tgggctgtgt gcacgaaccc cccgttcagc ccgaccgctg cgccttatcc ggtaactatc   4140
gtcttgagtc caacccggta agacacgact tatcgccact ggcagcagcc actggtaaca   4200
ggattagcag agcgaggtat gtaggcggtg ctacagagtt cttgaagtgg tggcctaact   4260
acggctacac tagaaggaca gtatttggta tctgcgctct gctgaagcca gttaccttcg   4320
gaaaaagagt tggtagctct tgatccggca aacaaaccac cgctggtagc ggtggttttt   4380
ttgtttgcaa gcagcagatt acgcgcagaa aaaaaggatc tcaagaagat cctttgatct   4440
tttctacggg gtctgacgct cagtggaacg aaaactcacg ttaagggatt ttggtcatga   4500
gattatcaaa aaggatcttc acctagatcc ttttaaatta aaaatgaagt ttaaatcaa   4560
```

tctaaagtat atatgagtaa acttggtctg acagttacca atgcttaatc agtgaggcac 4620
ctatctcagc gatctgtcta tttcgttcat ccatagttgc ctgactcccc gtcgtgtaga 4680
taactacgat acgggagggc ttaccatctg gccccagtgc tgcaatgata ccgcgagacc 4740
cacgctcacc ggctccagat ttatcagcaa taaaccagcc agccggaagg gccgagcgca 4800
gaagtggtcc tgcaacttta tccgcctcca tccagtctat taattgttgc cgggaagcta 4860
gagtaagtag ttcgccagtt aatagtttgc gcaacgttgt tgccattgct acaggcatcg 4920
tggtgtcacg ctcgtcgttt ggtatggctt cattcagctc cggttcccaa cgatcaaggc 4980
gagttacatg atcccccatg ttgtgcaaaa aagcggttag ctccttcggt cctccgatcg 5040
ttgtcagaag taagttggcc gcagtgttat cactcatggt tatggcagca ctgcataatt 5100
ctcttactgt catgccatcc gtaagatgct tttctgtgac tggtgagtac tcaaccaagt 5160
cattctgaga atagtgtatg cggcgaccga gttgctcttg cccggcgtca atacgggata 5220
ataccgcgcc acatagcaga actttaaaag tgctcatcat tggaaaacgt tcttcggggc 5280
gaaaactctc aaggatctta ccgctgttga gatccagttc gatgtaaccc actcgtgcac 5340
ccaactgatc ttcagcatct tttactttca ccagcgtttc tgggtgagca aaaacaggaa 5400
ggcaaaatgc cgcaaaaaag ggaataaggg cgacacggaa atgttgaata ctcatactct 5460
tcctttttca atattattga agcatttatc agggttattg tctcatgagc ggatacatat 5520
ttgaatgtat ttagaaaaat aaacaaatag gggttccgcg cacatttccc cgaaaagtgc 5580
cacctgggtc cttttcatca cgtgctataa aaataattat aatttaaatt ttttaatata 5640
aatatataaa ttaaaaatag aaagtaaaaa aagaaattaa agaaaaaata gtttttgttt 5700
tccgaagatg taaaagactc tagggggatc gccaacaaat actacctttt atcttgctct 5760
tcctgctctc aggtattaat gccgaattgt ttcatcttgt ctgtgtagaa gaccacacac 5820
gaaaatcctg tgattttaca ttttacttat cgttaatcga atgtatatct atttaatctg 5880
cttttcttgt ctaataaata tatatgtaaa gtacgctttt tgttgaaatt ttttaaacct 5940
ttgtttattt ttttttcttc attccgtaac tcttctacct tctttattta ctttctaaaa 6000
tccaaataca aaacataaaa ataaataaac acagagtaaa ttcccaaatt attccatcat 6060
taaaagatac gaggcgcgtg taagttacag gcaagcgatc cgtcctaaga aaccattatt 6120
atcatgacat taacctataa aaataggcgt atcacgaggc cctttcgtc 6169

<210> SEQ ID NO 17
<211> LENGTH: 501
<212> TYPE: DNA
<213> ORGANISM: Artificial Sequence
<220> FEATURE:
<223> OTHER INFORMATION: pZB003 - Light chain (Kappa) ss02 Mating Type insert
<220> FEATURE:
<221> NAME/KEY: gene
<222> LOCATION: (1)..(501)

<400> SEQUENCE: 17
actagtatga gatttccttc aatttttact gcagttttat tcgcagcatc ctccgcatta 60
gctcatatga aaagatctgc gaagcttgct ggcgcgccag gtcagcccaa ggccaacccc 120
actgtcactc tgttcccgcc ctcctctgag gagctccaag ccaacaaggc caccctagtg 180
tgtctgatca gtgacttcta cccgggagct gtgacagtgg cctggaaggc agatggcagc 240
cccgtcaagg cgggagtgga gaccaccaaa ccctccaaac agagcaacaa caagtacgcg 300
gccagcagct acctgagcct gacgcccgag cagtggaagt cccacagaag ctacagctgc 360
caggtcacgc atgaagggag caccgtggag aagacagtgg cccctacaga atgttcagtc 420
gacggtaagc ctatccctaa ccctctcctc ggtctcgatt ctacgcgtac cggtcatcat 480
caccatcacc attgactcga g 501

<210> SEQ ID NO 18
<211> LENGTH: 6021
<212> TYPE: DNA
<213> ORGANISM: Artificial Sequence
<220> FEATURE:
<223> OTHER INFORMATION: pZB003 - Light chain (Kappa) ss02 Mating Type vector construct
<220> FEATURE:
<221> NAME/KEY: misc_recomb
<222> LOCATION: (1)..(6021)

<400> SEQUENCE: 18
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataccac agcttttcaa ttcaattcat cattttttt ttattctttt ttttgatttc 240
ggtttctttg aaattttttt gattcggtaa tctccgaaca gaaggaagaa cgaaggaagg 300
agcacagact tagattggta tatatacgca tatgtagtgt tgaagaaaca tgaaattgcc 360
cagtattctt aacccaactg cacagaacaa aaacctgcag gaaacgaaga taaatcatgt 420
cgaaagctac atataaggaa cgtgctgcta ctcatcctag tcctgttgct gccaagctat 480
ttaatatcat gcacgaaaag caaacaaact tgtgtgcttc attggatgtt cgtaccacca 540
aggaattact ggagttagtt gaagcattag gtcccaaaat ttgtttacta aaaacacatg 600
tggatatctt gactgatttt tccatggagg gcacagttaa gccgctaaag gcattatccg 660
ccaagtacaa tttttactc ttcgaagaca gaaaatttgc tgacattggt aatacagtca 720
aattgcagta ctctgcgggt gtatacagaa tagcagaatg ggcagacatt acgaatgcac 780
acggtgtggt gggcccaggt attgttagcg gtttgaagca ggcggcagaa gaagtaacaa 840
aggaacctag aggccttttg atgttagcag aattgtcatg caagggctcc ctatctactg 900
gagaatatac taagggtact gttgacattg cgaagagcga caaagatttt gttatcggct 960
ttattgctca aagagacatg ggtggaagag atgaaggtta cgattggttg attatgacac 1020
ccggtgtggg tttagatgac aagggagacg cattgggtca acagtataga accgtggatg 1080
atgtggtctc tacaggatct gacattatta ttgttggaag aggactattt gcaaagggaa 1140
gggatgctaa ggtagagggt gaacgttaca gaaaagcagg ctgggaagca tatttgagaa 1200
gatgcggcca gcaaaactaa aaaactgtat tataagtaaa tgcatgtata ctaaactcac 1260
aaattagagc ttcaatttaa ttatatcagt tattacccta tgcggtgtga aataccgcac 1320
agatgcgtaa ggagaaaata ccgcatcagg aaattgtaaa cgttaatatt ttgttaaaat 1380
tcgcgttaaa tttttgttaa atcagctcat tttttaacca ataggccgaa atcggcaaaa 1440
tcccttataa atcaaaagaa tagaccgaga tagggttgag tgttgttcca gtttggaaca 1500
agagtccact attaaagaac gtggactcca acgtcaaagg gcgaaaaacc gtctatcagg 1560
gcgatggccc actacgtgaa ccatcaccct aatcaagttt tttggggtcg aggtgccgta 1620
aagcactaaa tcggaaccct aaagggagcc cccgatttag agcttgacgg ggaaagccgg 1680
cgaacgtggc gagaaaggaa gggaagaaag cgaaaggagc gggcgctagg gcgctggcaa 1740

-continued

```
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagtca atggtgatgg   2280
tgatgatgac cggtacgcgt agaatcgaga ccgaggagag ggttagggat aggcttaccg   2340
tcgactgaac attctgtagg ggccactgtc ttctccacgg tgctcccttc atgcgtgacc   2400
tggcagctgt agcttctgtg ggacttccac tgctcgggcg tcaggctcag gtagctgctg   2460
gccgcgtact tgttgttgct ctgtttggag ggtttggtgg tctccactcc cgccttgacg   2520
gggctgccat ctgccttcca ggccactgtc acagctcccg ggtagaagtc actgatcaga   2580
cacactaggg tggccttgtt ggcttggagc tcctcagagg agggcgggaa cagagtgaca   2640
gtggggttgg ccttgggctg acctggcgcg ccagcaagct tcgcagatct tttcatatga   2700
gctaatgcgg aggatgctgc gaataaaact gcagtaaaaa ttgaaggaaa tctcatacta   2760
gttctagata tagtttttc tccttgacgt taaagtatag aggtatatta acaatttttt   2820
gttgatactt ttattacatt tgaataagaa gtaatacaaa ccgaaaatgt tgaaagtatt   2880
agttaaagtg gttatgcagt ttttgcattt atatatctgt taatagatca aaaatcatcg   2940
cttcgctgat taattacccc agaaataagg ctaaaaaact aatcgcatta tcatcctatg   3000
gttgttaatt tgattcgttc atttgaaggt ttgtggggcc aggttactgc caatttttcc   3060
tcttcataac cataaaagct agtattgtag aatctttatt gttcggagca gtgcggcgcg   3120
aggcacatct gcgtttcagg aacgcgaccg gtgaagacga ggacgcacgg aggagagtct   3180
tccttcggag ggctgtcacc cgctcggcgg cttctaatcc gtacttcaga gctccagctt   3240
ttgttccctt tagtgagggt taattgcgcg cttggcgtaa tcatggtcat agctgtttcc   3300
tgtgtgaaat tgttatccgc tcacaattcc acacaacata ggagccggaa gcataaagtg   3360
taaagcctgg ggtgcctaat gagtgaggta actcacatta attgcgttgc gctcactgcc   3420
cgctttccag tcgggaaacc tgtcgtgcca gctgcattaa tgaatcggcc aacgcgcggg   3480
gagaggcggt ttgcgtattg ggcgctcttc cgcttcctcg ctcactgact cgctgcgctc   3540
ggtcgttcgg ctgcggcgag cggtatcagc tcactcaaag gcggtaatac ggttatccac   3600
agaatcaggg gataacgcag gaaagaacat gtgagcaaaa ggccagcaaa aggccaggaa   3660
ccgtaaaaag gccgcgttgc tggcgttttt ccataggctc cgcccccctg acgagcatca   3720
caaaaatcga cgctcaagtc agaggtggcg aaacccgaca ggactataaa gataccaggc   3780
gtttccccct ggaagctccc tcgtgcgctc tcctgttccg accctgccgc ttaccggata   3840
cctgtccgcc tttctccctt cgggaagcgt ggcgctttct catagctcac gctgtaggta   3900
tctcagttcg gtgtaggtcg ttcgctccaa gctgggctgt gtgcacgaac cccccgttca   3960
gcccgaccgc tgcgccttat ccggtaacta tcgtcttgag tccaacccgg taagacacga   4020
cttatcgcca ctggcagcag ccactggtaa caggattagc agagcgaggt atgtaggcgg   4080
```

tgctacagag ttcttgaagt ggtggcctaa ctacggctac actagaagga cagtatttgg 4140
tatctgcgct ctgctgaagc cagttacctt cggaaaaaga gttggtagct cttgatccgg 4200
caaacaaacc accgctggta gcggtggttt ttttgtttgc aagcagcaga ttacgcgcag 4260
aaaaaaagga tctcaagaag atcctttgat cttttctacg gggtctgacg ctcagtggaa 4320
cgaaaactca cgttaaggga ttttggtcat gagattatca aaaaggatct tcacctagat 4380
ccttttaaat taaaaatgaa gttttaaatc aatctaaagt atatatgagt aaacttggtc 4440
tgacagttac caatgcttaa tcagtgaggc acctatctca gcgatctgtc tatttcgttc 4500
atccatagtt gcctgactcc ccgtcgtgta gataactacg atacgggagg gcttaccatc 4560
tggccccagt gctgcaatga taccgcgaga cccacgctca ccggctccag atttatcagc 4620
aataaaccag ccagccggaa gggccgagcg cagaagtggt cctgcaactt tatccgcctc 4680
catccagtct attaattgtt gccgggaagc tagagtaagt agttcgccag ttaatagttt 4740
gcgcaacgtt gttgccattg ctacaggcat cgtggtgtca cgctcgtcgt ttggtatggc 4800
ttcattcagc tccggttccc aacgatcaag gcgagttaca tgatccccca tgttgtgcaa 4860
aaaagcggtt agctccttcg gtcctccgat cgttgtcaga agtaagttgg ccgcagtgtt 4920
atcactcatg gttatggcag cactgcataa ttctcttact gtcatgccat ccgtaagatg 4980
cttttctgtg actggtgagt actcaaccaa gtcattctga gaatagtgta tgcggcgacc 5040
gagttgctct tgcccggcgt caatacggga taataccgcg ccacatagca gaactttaaa 5100
agtgctcatc attggaaaac gttcttcggg gcgaaaactc tcaaggatct taccgctgtt 5160
gagatccagt tcgatgtaac ccactcgtgc acccaactga tcttcagcat cttttacttt 5220
caccagcgtt tctgggtgag caaaaacagg aaggcaaaat gccgcaaaaa agggaataag 5280
ggcgacacgg aaatgttgaa tactcatact cttccttttt caatattatt gaagcattta 5340
tcagggttat tgtctcatga gcggatacat atttgaatgt atttagaaaa ataaacaaat 5400
aggggttccg cgcacatttc cccgaaaagt gccacctggg tccttttcat cacgtgctat 5460
aaaaataatt ataatttaaa ttttttaata taaatatata aattaaaaat agaaagtaaa 5520
aaaagaaatt aaagaaaaaa tagtttttgt tttccgaaga tgtaaaagac tctaggggga 5580
tcgccaacaa atactacctt ttatcttgct cttcctgctc tcaggtatta atgccgaatt 5640
gtttcatctt gtctgtgtag aagaccacac acgaaaatcc tgtgatttta cattttactt 5700
atcgttaatc gaatgtatat ctatttaatc tgcttttctt gtctaataaa tatatatgta 5760
aagtacgctt tttgttgaaa ttttttaaac ctttgtttat ttttttttct tcattccgta 5820
actcttctac cttctttatt tactttctaa aatccaaata caaaacataa aaataaataa 5880
acacagagta aattcccaaa ttattccatc attaaaagat acgaggcgcg tgtaagttac 5940
aggcaagcga tccgtcctaa gaaaccatta ttatcatgac attaacctat aaaaataggc 6000
gtatcacgag gccctttcgt c 6021

<210> SEQ ID NO 19
<211> LENGTH: 501
<212> TYPE: DNA
<213> ORGANISM: Artificial Sequence
<220> FEATURE:
<223> OTHER INFORMATION: pZB003.1 - Light chain (Lambda)ss01 Mating
Type insert
<220> FEATURE:
<221> NAME/KEY: gene
<222> LOCATION: (1)..(501)

<400> SEQUENCE: 19

```
actagtatga gatttccttc aatttttact gcagttttat tcgcagcatc ctccgcatta     60

gctcatatga aaagatctgc gaagcttgct ggcgcgccaa ctgtggctgc accatctgtc    120

ttcatcttcc cgccatctga tgagcagttg aaatctggaa ctgcctctgt tgtgtgcctg    180

ctgaataact tctatcccag agaggccaaa gtacagtgga aggtggataa cgccctccaa    240

tcgggtaact cccaggagag tgtcacagag caggacagca aggacagcac ctacagcctc    300

agcagcaccc tgacgctgtc gaaagcagac tacgagaaac acaaagtcta cgcctgcgaa    360

gtcacccatc agggcctgag ctcgcccgtc acaaagagct tcaacagggg agagtgtgtc    420

gacggtaagc ctatccctaa ccctctcctc ggtctcgatt ctacgcgtac cggtcatcat    480

caccatcacc attgactcga g                                              501
```

<210> SEQ ID NO 20
<211> LENGTH: 6021
<212> TYPE: DNA
<213> ORGANISM: Artificial Sequence
<220> FEATURE:
<223> OTHER INFORMATION: pZB003.1 - Light chain (Lambda)ss01 Mating Type vector construct
<220> FEATURE:
<221> NAME/KEY: misc_recomb
<222> LOCATION: (1)..(6021)

<400> SEQUENCE: 20

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020

ccggtgtggg tttagatgac aagggagacg cattgggtca acagtataga accgtggatg   1080

atgtggtctc tacaggatct gacattatta ttgttggaag aggactattt gcaaagggaa   1140

gggatgctaa ggtagagggt gaacgttaca gaaaagcagg ctgggaagca tatttgagaa   1200

gatgcggcca gcaaaactaa aaaactgtat tataagtaaa tgcatgtata ctaaactcac   1260

aaattagagc ttcaatttaa ttatatcagt tattacccta tgcggtgtga aataccgcac   1320

agatgcgtaa ggagaaaata ccgcatcagg aaattgtaaa cgttaatatt ttgttaaaat   1380
```

-continued

```
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagtca atggtgatgg   2280
tgatgatgac cggtacgcgt agaatcgaga ccgaggagag ggttagggat aggcttaccg   2340
tcgacacact ctcccctgtt gaagctcttt gtgacgggcg agctcaggcc ctgatgggtg   2400
acttcgcagg cgtagacttt gtgtttctcg tagtctgctt tcgacagcgt cagggtgctg   2460
ctgaggctgt aggtgctgtc cttgctgtcc tgctctgtga cactctcctg ggagttaccc   2520
gattggaggg cgttatccac cttccactgt actttggcct ctctgggata gaagttattc   2580
agcaggcaca caacagaggc agttccagat ttcaactgct catcagatgg cgggaagatg   2640
aagacagatg gtgcagccac agttggcgcg ccagcaagct tcgcagatct tttcatatga   2700
gctaatgcgg aggatgctgc gaataaaact gcagtaaaaa ttgaaggaaa tctcatacta   2760
gttctagata tagtttttc tccttgacgt taaagtatag aggtatatta acaattttt   2820
gttgatactt ttattacatt tgaataagaa gtaatacaaa ccgaaaatgt tgaaagtatt   2880
agttaaagtg gttatgcagt ttttgcattt atatatctgt taatagatca aaaatcatcg   2940
cttcgctgat taattacccc agaaataagg ctaaaaaact aatcgcatta tcatcctatg   3000
gttgttaatt tgattcgttc atttgaaggt ttgtggggcc aggttactgc caatttttcc   3060
tcttcataac cataaaagct agtattgtag aatctttatt gttcggagca gtgcggcgcg   3120
aggcacatct gcgtttcagg aacgcgaccg gtgaagacga ggacgcacgg aggagagtct   3180
tccttcggag ggctgtcacc cgctcggcgg cttctaatcc gtacttcaga gctccagctt   3240
ttgttccctt tagtgagggt taattgcgcg cttggcgtaa tcatggtcat agctgtttcc   3300
tgtgtgaaat tgttatccgc tcacaattcc acacaacata ggagccggaa gcataaagtg   3360
taaagcctgg ggtgcctaat gagtgaggta actcacatta attgcgttgc gctcactgcc   3420
cgctttccag tcgggaaacc tgtcgtgcca gctgcattaa tgaatcggcc aacgcgcggg   3480
gagaggcggt ttgcgtattg ggcgctcttc cgcttcctcg ctcactgact cgctgcgctc   3540
ggtcgttcgg ctgcggcgag cggtatcagc tcactcaaag gcggtaatac ggttatccac   3600
agaatcaggg gataacgcag gaaagaacat gtgagcaaaa ggccagcaaa aggccaggaa   3660
ccgtaaaaag gccgcgttgc tggcgttttt ccataggctc cgcccccctg acgagcatca   3720
caaaaatcga cgctcaagtc agaggtggcg aaacccgaca ggactataaa gataccaggc   3780
```

```
gtttcccccct ggaagctccc tcgtgcgctc tcctgttccg accctgccgc ttaccggata   3840
cctgtccgcc tttctccctt cgggaagcgt ggcgctttct catagctcac gctgtaggta   3900
tctcagttcg gtgtaggtcg ttcgctccaa gctgggctgt gtgcacgaac cccccgttca   3960
gcccgaccgc tgcgccttat ccggtaacta tcgtcttgag tccaacccgg taagacacga   4020
cttatcgcca ctggcagcag ccactggtaa caggattagc agagcgaggt atgtaggcgg   4080
tgctacagag ttcttgaagt ggtggcctaa ctacggctac actagaagga cagtatttgg   4140
tatctgcgct ctgctgaagc cagttacctt cggaaaaaga gttggtagct cttgatccgg   4200
caaacaaacc accgctggta gcggtggttt ttttgtttgc aagcagcaga ttacgcgcag   4260
aaaaaaagga tctcaagaag atcctttgat cttttctacg gggtctgacg ctcagtggaa   4320
cgaaaactca cgttaaggga ttttggtcat gagattatca aaaaggatct tcacctagat   4380
ccttttaaat taaaaatgaa gttttaaatc aatctaaagt atatatgagt aaacttggtc   4440
tgacagttac caatgcttaa tcagtgaggc acctatctca gcgatctgtc tatttcgttc   4500
atccatagtt gcctgactcc ccgtcgtgta gataactacg atacgggagg gcttaccatc   4560
tggccccagt gctgcaatga taccgcgaga cccacgctca ccggctccag atttatcagc   4620
aataaaccag ccagccggaa gggccgagcg cagaagtggt cctgcaactt tatccgcctc   4680
catccagtct attaattgtt gccgggaagc tagagtaagt agttcgccag ttaatagttt   4740
gcgcaacgtt gttgccattg ctacaggcat cgtggtgtca cgctcgtcgt ttggtatggc   4800
ttcattcagc tccggttccc aacgatcaag gcgagttaca tgatccccca tgttgtgcaa   4860
aaaagcggtt agctccttcg gtcctccgat cgttgtcaga agtaagttgg ccgcagtgtt   4920
atcactcatg gttatggcag cactgcataa ttctcttact gtcatgccat ccgtaagatg   4980
cttttctgtg actggtgagt actcaaccaa gtcattctga gaatagtgta tgcggcgacc   5040
gagttgctct tgcccggcgt caatacggga taataccgcg ccacatagca gaactttaaa   5100
agtgctcatc attggaaaac gttcttcggg gcgaaaactc tcaaggatct taccgctgtt   5160
gagatccagt tcgatgtaac ccactcgtgc acccaactga tcttcagcat cttttacttt   5220
caccagcgtt tctgggtgag caaaaacagg aaggcaaaat gccgcaaaaa agggaataag   5280
ggcgacacgg aaatgttgaa tactcatact cttccttttt caatattatt gaagcattta   5340
tcagggttat tgtctcatga gcggatacat atttgaatgt atttagaaaa ataaacaaat   5400
aggggttccg cgcacatttc cccgaaaagt gccacctggg tccttttcat cacgtgctat   5460
aaaaataatt ataatttaaa ttttttaata taaatatata aattaaaaat agaaagtaaa   5520
aaaagaaatt aaagaaaaaa tagtttttgt tttccgaaga tgtaaaagac tctaggggga   5580
tcgccaacaa atactacctt ttatcttgct cttcctgctc tcaggtatta atgccgaatt   5640
gtttcatctt gtctgtgtag aagaccacac acgaaaatcc tgtgatttta cattttactt   5700
atcgttaatc gaatgtatat ctatttaatc tgcttttctt gtctaataaa tatatatgta   5760
aagtacgctt tttgttgaaa ttttttaaac ctttgtttat ttttttttct tcattccgta   5820
actcttctac cttctttatt tactttctaa aatccaaata caaaacataa aaataaataa   5880
acacagagta aattcccaaa ttattccatc attaaaagat acgaggcgcg tgtaagttac   5940
aggcaagcga tccgtcctaa gaaaccatta ttatcatgac attaacctat aaaaataggc   6000
gtatcacgag gccctttcgt c                                            6021
```

<210> SEQ ID NO 21

<211> LENGTH: 711
<212> TYPE: DNA
<213> ORGANISM: Artificial Sequence
<220> FEATURE:
<223> OTHER INFORMATION: pZB003.2 - Light chain (Kappa) ss01 Mating Type insert
<220> FEATURE:
<221> NAME/KEY: gene
<222> LOCATION: (1)..(711)

<400> SEQUENCE: 21

```
actagtatga gatttccttc aatttttact gctgttgttt tcgcagcatc ctccgcatta     60

gctgctccag ctaacactac agctgaagat gaaacggcac aaattccggc tgaagctgtc    120

atcggttact taggtttaga aggggattca gatgttgctg ctttgccatt atccgatagc    180

acaaataacg ggtcattgtc aactaatact actattgcca gcattgctgc taaagaagaa    240

ggggtacaac tcgataaaag agaggctgaa gctcatatga aaagatctgc gaagcttgct    300

ggcgcgccaa ctgtggctgc accatctgtc ttcatcttcc cgccatctga tgagcagttg    360

aaatctggaa ctgcctctgt tgtgtgcctg ctgaataact tctatcccag agaggccaaa    420

gtacagtgga aggtggataa cgccctccaa tcgggtaact cccaggagag tgtcacagag    480

caggacagca aggacagcac ctacagcctc agcagcaccc tgacgctgtc gaaagcagac    540

tacgagaaac acaaagtcta cgcctgcgaa gtcacccatc agggcctgag ctcgcccgtc    600

acaaagagct tcaacagggg agagtgtgtc gacggtaagc ctatccctaa ccctctcctc    660

ggtctcgatt ctacgcgtac cggtcatcat caccatcacc attgactcga g             711
```

<210> SEQ ID NO 22
<211> LENGTH: 6231
<212> TYPE: DNA
<213> ORGANISM: Artificial Sequence
<220> FEATURE:
<223> OTHER INFORMATION: pZB003.2 - Light chain (Kappa) ss01 Mating Type vector construct
<220> FEATURE:
<221> NAME/KEY: misc_recomb
<222> LOCATION: (1)..(6231)

<400> SEQUENCE: 22

```
gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360

tctacacaga caagatgaaa caattcggca ttaatacctg agagcaggaa gagcaagata    420

aaaggtagta tttgttggcg atccccctag agtcttttac atcttcggaa aacaaaaact    480

attttttctt taatttcttt ttttactttc tatttttaat ttatatattt atattaaaaa    540

atttaaatta taattatttt tatagcacgt gatgaaaagg acccaggtgg cacttttcgg    600

ggaaatgtgc gcggaacccc tatttgttta tttttctaaa tacattcaaa tatgtatccg    660

ctcatgagac aataaccctg ataaatgctt caataatatt gaaaaaggaa gagtatgagt    720

attcaacatt tccgtgtcgc ccttattccc ttttttgcgg cattttgcct tcctgttttt    780

gctcacccag aaacgctggt gaaagtaaaa gatgctgaag atcagttggg tgcacgagtg    840

ggttacatcg aactggatct caacagcggt aagatccttg agagttttcg ccccgaagaa    900
```

```
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc cagggggaaa cgcctggtat ctttatagtc ctgtcgggtt tcgccacctc   2280
tgacttgagc gtcgattttt gtgatgctcg tcaggggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gcgcgcaatt   2760
aaccctcact aaagggaaca aaagctggag ctctgaagta cggattagaa gccgccgagc   2820
gggtgacagc cctccgaagg aagactctcc tccgtgcgtc ctcgtcttca ccggtcgcgt   2880
tcctgaaacg cagatgtgcc tcgcgccgca ctgctccgaa caataaagat tctacaatac   2940
tagcttttat ggttatgaag aggaaaaatt ggcagtaacc tggccccaca aaccttcaaa   3000
tgaacgaatc aaattaacaa ccataggatg ataatgcgat tagtttttta gccttatttc   3060
tggggtaatt aatcagcgaa gcgatgattt ttgatctatt aacagatata taaatgcaaa   3120
aactgcataa ccactttaac taatactttc aacattttcg gtttgtatta cttcttattc   3180
aaatgtaata aaagtatcaa caaaaaattg ttaatatacc tctatacttt aacgtcaagg   3240
```

-continued

```
agaaaaaact atatctagaa ctagtatgag atttccttca atttttactg ctgttgtttt   3300
cgcagcatcc tccgcattag ctgctccagc taacactaca gctgaagatg aaacggcaca   3360
aattccggct gaagctgtca tcggttactt aggtttagaa ggggattcag atgttgctgc   3420
tttgccatta tccgatagca caaataacgg gtcattgtca actaatacta ctattgccag   3480
cattgctgct aaagaagaag gggtacaact cgataaaaga gaggctgaag ctcatatgaa   3540
aagatctgcg aagcttgctg gcgcgccaac tgtggctgca ccatctgtct tcatcttccc   3600
gccatctgat gagcagttga aatctggaac tgcctctgtt gtgtgcctgc tgaataactt   3660
ctatcccaga gaggccaaag tacagtggaa ggtggataac gccctccaat cgggtaactc   3720
ccaggagagt gtcacagagc aggacagcaa ggacagcacc tacagcctca gcagcaccct   3780
gacgctgtcg aaagcagact acgagaaaca caaagtctac gcctgcgaag tcacccatca   3840
gggcctgagc tcgcccgtca caaagagctt caacagggga gagtgtgtcg acggtaagcc   3900
tatccctaac cctctcctcg gtctcgattc tacgcgtacc ggtcatcatc accatcacca   3960
ttgactcgag tcatgtaatt agttatgtca cgcttacatt cacgccctcc ccccacatcc   4020
gctctaaccg aaaaggaagg agttagacaa cctgaagtct aggtccctat ttattttttt   4080
atagttatgt tagtattaag aacgttattt atatttcaaa tttttctttt ttttctgtac   4140
agacgcgtgt acgcatgtaa cattatactg aaaaccttgc ttgagaaggt tttgggacgc   4200
tcgaaggctt taatttgcgg ccggtaccca attcgcccta tagtgagtcg tattacgcgc   4260
gctcactggc cgtcgtttta caacgtcgtg actgggaaaa ccctggcgtt acccaactta   4320
atcgccttgc agcacatccc cctttcgcca gctggcgtaa tagcgaagag gcccgcaccg   4380
atcgcccttc ccaacagttg cgcagcctga atggcgaatg gcgcgacgcg ccctgtagcg   4440
gcgcattaag cgcggcgggt gtggtggtta cgcgcagcgt gaccgctaca cttgccagcg   4500
ccctagcgcc cgctcctttc gctttcttcc cttcctttct cgccacgttc gccggctttc   4560
cccgtcaagc tctaaatcgg gggctccctt tagggttccg atttagtgct ttacggcacc   4620
tcgaccccaa aaaacttgat tagggtgatg gttcacgtag tgggccatcg ccctgataga   4680
cggtttttcg ccctttgacg ttggagtcca cgttctttaa tagtggactc ttgttccaaa   4740
ctggaacaac actcaaccct atctcggtct attcttttga tttataaggg attttgccga   4800
tttcggccta ttggttaaaa aatgagctga tttaacaaaa atttaacgcg aattttaaca   4860
aaatattaac gtttacaatt tcctgatgcg gtattttctc cttacgcatc tgtgcggtat   4920
ttcacaccgc atagggtaat aactgatata attaaattga agctctaatt tgtgagttta   4980
gtatacatgc atttacttat aatacagttt tttagttttg ctggccgcat cttctcaaat   5040
atgcttccca gcctgctttt ctgtaacgtt caccctctac cttagcatcc cttccctttg   5100
caaatagtcc tcttccaaca ataataatgt cagatcctgt agagaccaca tcatccacgg   5160
ttctatactg ttgacccaat gcgtctccct tgtcatctaa acccacaccg ggtgtcataa   5220
tcaaccaatc gtaaccttca tctcttccac ccatgtctct ttgagcaata aagccgataa   5280
caaaatcttt gtcgctcttc gcaatgtcaa cagtaccctt agtatattct ccagtagata   5340
gggagccctt gcatgacaat tctgctaaca tcaaaaggcc tctaggttcc tttgttactt   5400
cttctgccgc ctgcttcaaa ccgctaacaa tacctgggcc caccacaccg tgtgcattcg   5460
taatgtctgc ccattctgct attctgtata cacccgcaga gtactgcaat ttgactgtat   5520
taccaatgtc agcaaatttt ctgtcttcga agagtaaaaa attgtacttg gcggataatg   5580
cctttagcgg cttaactgtg ccctccatgg aaaaatcagt caagatatcc acatgtgttt   5640
```

ttagtaaaca aattttggga cctaatgctt caactaactc cagtaattcc ttggtggtac 5700
gaacatccaa tgaagcacac aagtttgttt gcttttcgtg catgatatta aatagcttgg 5760
cagcaacagg actaggatga gtagcagcac gttccttata tgtagctttc gacatgattt 5820
atcttcgttt cctgcaggtt tttgttctgt gcagttgggt taagaatact gggcaatttc 5880
atgtttcttc aacactacat atgcgtatat ataccaatct aagtctgtgc tccttccttc 5940
gttcttcctt ctgttcggag attaccgaat caaaaaaatt tcaaagaaac cgaaatcaaa 6000
aaaaagaata aaaaaaaaat gatgaattga attgaaaagc tgtggtatgg tgcactctca 6060
gtacaatctg ctctgatgcc gcatagttaa gccagccccg acacccgcca acacccgctg 6120
acgcgccctg acgggcttgt ctgctcccgg catccgctta cagacaagct gtgaccgtct 6180
ccgggagctg catgtgtcag aggttttcac cgtcatcacc gaaacgcgcg a 6231

<210> SEQ ID NO 23
<211> LENGTH: 711
<212> TYPE: DNA
<213> ORGANISM: Artificial Sequence
<220> FEATURE:
<223> OTHER INFORMATION: pZB003.3 - Light chain (Kappa) ss03 Mating Type insert
<220> FEATURE:
<221> NAME/KEY: gene
<222> LOCATION: (1)..(711)

<400> SEQUENCE: 23
actagtatga gatttccttc aatttttact gctgttttat tcgcagcatc ctccgcatta 60
gctgctccag ctaacactac aacagaagat gaaacggcac aaattccggc tgaagctgtc 120
atcgattact cagatttaga aggggatttc gatgctgctg ctttgccatt atccaacagc 180
acaaataacg ggttatcatc aactaatact actattgcca gcattgctgc taaagaagaa 240
ggggtacaac tcgataaaag agaggctgaa gctcatatga aaagatctgc gaagcttgct 300
ggcgcgccaa ctgtggctgc accatctgtc ttcatcttcc cgccatctga tgagcagttg 360
aaatctggaa ctgcctctgt tgtgtgcctg ctgaataact tctatcccag agaggccaaa 420
gtacagtgga aggtggataa cgccctccaa tcgggtaact cccaggagag tgtcacagag 480
caggacagca aggacagcac ctacagcctc agcagcaccc tgacgctgtc gaaagcagac 540
tacgagaaac acaaagtcta cgcctgcgaa gtcacccatc agggcctgag ctcgcccgtc 600
acaaagagct tcaacagggg agagtgtgtc gacggtaagc ctatccctaa ccctctcctc 660
ggtctcgatt ctacgcgtac cggtcatcat caccatcacc attgactcga g 711

<210> SEQ ID NO 24
<211> LENGTH: 6231
<212> TYPE: DNA
<213> ORGANISM: Artificial Sequence
<220> FEATURE:
<223> OTHER INFORMATION: pZB003.3 - Light chain (Kappa) ss03 Mating Type vector construct
<220> FEATURE:
<221> NAME/KEY: misc_recomb
<222> LOCATION: (1)..(6231)

<400> SEQUENCE: 24
gacgaaaggg cctcgtgata cgcctatttt tataggttaa tgtcatgata ataatggttt 60
cttaggacgg atcgcttgcc tgtaacttac acgcgcctcg tatcttttaa tgatggaata 120
atttgggaat ttactctgtg tttatttatt tttatgtttt gtatttggat tttagaaagt 180

-continued

```
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atccccctag agtcttttac atcttcggaa aacaaaaact    480
atttttcttt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
gggagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc cagggggaaa cgcctggtat ctttatagtc ctgtcgggtt tcgccacctc   2280
tgacttgagc gtcgattttt gtgatgctcg tcaggggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
```

-continued

```
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gcgcgcaatt   2760
aaccctcact aaagggaaca aaagctggag ctctgaagta cggattagaa gccgccgagc   2820
gggtgacagc cctccgaagg aagactctcc tccgtgcgtc ctcgtcttca ccggtcgcgt   2880
tcctgaaacg cagatgtgcc tcgcgccgca ctgctccgaa caataaagat tctacaatac   2940
tagcttttat ggttatgaag aggaaaaatt ggcagtaacc tggccccaca aaccttcaaa   3000
tgaacgaatc aaattaacaa ccataggatg ataatgcgat tagtttttta gccttatttc   3060
tggggtaatt aatcagcgaa gcgatgattt ttgatctatt aacagatata taaatgcaaa   3120
aactgcataa ccactttaac taatactttc aacattttcg gtttgtatta cttcttattc   3180
aaatgtaata aaagtatcaa caaaaaattg ttaatatacc tctatacttt aacgtcaagg   3240
agaaaaaact atatctagaa ctagtatgag atttccttca atttttactg ctgttttatt   3300
cgcagcatcc tccgcattag ctgctccagc taacactaca acagaagatg aaacggcaca   3360
aattccggct gaagctgtca tcgattactc agatttagaa ggggatttcg atgctgctgc   3420
tttgccatta tccaacagca caaataacgg gttatcatca actaatacta ctattgccag   3480
cattgctgct aaagaagaag gggtacaact cgataaaaga gaggctgaag ctcatatgaa   3540
aagatctgcg aagcttgctg gcgcgccaac tgtggctgca ccatctgtct tcatcttccc   3600
gccatctgat gagcagttga aatctggaac tgcctctgtt gtgtgcctgc tgaataactt   3660
ctatcccaga gaggccaaag tacagtggaa ggtggataac gccctccaat cgggtaactc   3720
ccaggagagt gtcacagagc aggacagcaa ggacagcacc tacagcctca gcagcaccct   3780
gacgctgtcg aaagcagact acgagaaaca caaagtctac gcctgcgaag tcacccatca   3840
gggcctgagc tcgcccgtca caaagagctt caacagggga gagtgtgtcg acggtaagcc   3900
tatccctaac cctctcctcg gtctcgattc tacgcgtacc ggtcatcatc accatcacca   3960
ttgactcgag tcatgtaatt agttatgtca cgcttacatt cacgccctcc ccccacatcc   4020
gctctaaccg aaaaggaagg agttagacaa cctgaagtct aggtccctat ttattttttt   4080
atagttatgt tagtattaag aacgttattt atatttcaaa tttttctttt ttttctgtac   4140
agacgcgtgt acgcatgtaa cattatactg aaaaccttgc ttgagaaggt tttgggacgc   4200
tcgaaggctt taatttgcgg ccggtaccca attcgcccta tagtgagtcg tattacgcgc   4260
gctcactggc cgtcgtttta caacgtcgtg actgggaaaa ccctggcgtt acccaactta   4320
atcgccttgc agcacatccc cctttcgcca gctggcgtaa tagcgaagag gcccgcaccg   4380
atcgcccttc ccaacagttg cgcagcctga atggcgaatg gcgcgacgcg ccctgtagcg   4440
gcgcattaag cgcggcgggt gtggtggtta cgcgcagcgt gaccgctaca cttgccagcg   4500
ccctagcgcc cgctcctttc gctttcttcc cttcctttct cgccacgttc gccggctttc   4560
cccgtcaagc tctaaatcgg gggctccctt tagggttccg atttagtgct ttacggcacc   4620
tcgaccccaa aaaacttgat tagggtgatg gttcacgtag tgggccatcg ccctgataga   4680
cggtttttcg ccctttgacg ttggagtcca cgttctttaa tagtggactc ttgttccaaa   4740
ctggaacaac actcaaccct atctcggtct attcttttga tttataaggg attttgccga   4800
tttcggccta ttggttaaaa aatgagctga tttaacaaaa atttaacgcg aattttaaca   4860
aaatattaac gtttacaatt tcctgatgcg gtattttctc cttacgcatc tgtgcggtat   4920
```

```
ttcacaccgc atagggtaat aactgatata attaaattga agctctaatt tgtgagttta   4980

gtatacatgc atttacttat aatacagttt tttagttttg ctggccgcat cttctcaaat   5040

atgcttccca gcctgctttt ctgtaacgtt caccctctac cttagcatcc cttccctttg   5100

caaatagtcc tcttccaaca ataataatgt cagatcctgt agagaccaca tcatccacgg   5160

ttctatactg ttgacccaat gcgtctccct tgtcatctaa acccacaccg ggtgtcataa   5220

tcaaccaatc gtaaccttca tctcttccac ccatgtctct ttgagcaata aagccgataa   5280

caaaatcttt gtcgctcttc gcaatgtcaa cagtaccctt agtatattct ccagtagata   5340

gggagccctt gcatgacaat tctgctaaca tcaaaaggcc tctaggttcc tttgttactt   5400

cttctgccgc ctgcttcaaa ccgctaacaa tacctgggcc caccacaccg tgtgcattcg   5460

taatgtctgc ccattctgct attctgtata cacccgcaga gtactgcaat ttgactgtat   5520

taccaatgtc agcaaatttt ctgtcttcga agagtaaaaa attgtacttg gcggataatg   5580

cctttagcgg cttaactgtg ccctccatgg aaaaatcagt caagatatcc acatgtgttt   5640

ttagtaaaca aattttggga cctaatgctt caactaactc cagtaattcc ttggtggtac   5700

gaacatccaa tgaagcacac aagtttgttt gcttttcgtg catgatatta aatagcttgg   5760

cagcaacagg actaggatga gtagcagcac gttccttata tgtagctttc gacatgattt   5820

atcttcgttt cctgcaggtt tttgttctgt gcagttgggt taagaatact gggcaatttc   5880

atgtttcttc aacactacat atgcgtatat ataccaatct aagtctgtgc tccttccttc   5940

gttcttcctt ctgttcggag attaccgaat caaaaaaatt tcaaagaaac cgaaatcaaa   6000

aaaaagaata aaaaaaaaat gatgaattga attgaaaagc tgtggtatgg tgcactctca   6060

gtacaatctg ctctgatgcc gcatagttaa gccagccccg acacccgcca acacccgctg   6120

acgcgccctg acgggcttgt ctgctcccgg catccgctta cagacaagct gtgaccgtct   6180

ccgggagctg catgtgtcag aggttttcac cgtcatcacc gaaacgcgcg a            6231
```

```
<210> SEQ ID NO 25
<211> LENGTH: 501
<212> TYPE: DNA
<213> ORGANISM: Artificial Sequence
<220> FEATURE:
<223> OTHER INFORMATION: pZB003.4 - Light chain (Kappa) ss04 Mating Type
      insert
<220> FEATURE:
<221> NAME/KEY: gene
<222> LOCATION: (1)..(501)

<400> SEQUENCE: 25
```

```
actagtatgc ttttgcaagc attccttttc cttttggctg gttttgcagc caaaatatct     60

gcacatatga aaagatctgc gaagcttgct ggcgcgccaa ctgtggctgc accatctgtc    120

ttcatcttcc cgccatctga tgagcagttg aaatctggaa ctgcctctgt tgtgtgcctg    180

ctgaataact tctatcccag agaggccaaa gtacagtgga aggtggataa cgccctccaa    240

tcgggtaact cccaggagag tgtcacagag caggacagca aggacagcac ctacagcctc    300

agcagcaccc tgacgctgtc gaaagcagac tacgagaaac acaaagtcta cgcctgcgaa    360

gtcacccatc agggcctgag ctcgcccgtc acaaagagct tcaacagggg agagtgtgtc    420

gacggtaagc ctatccctaa ccctctcctc ggtctcgatt ctacgcgtac cggtcatcat    480

caccatcacc attgactcga g                                              501
```

```
<210> SEQ ID NO 26
<211> LENGTH: 6021
```

-continued

```
<212> TYPE: DNA
<213> ORGANISM: Artificial Sequence
<220> FEATURE:
<223> OTHER INFORMATION: pZB003.4 - Light chain (Kappa) ss04 Mating Type
      vector construct
<220> FEATURE:
<221> NAME/KEY: misc_recomb
<222> LOCATION: (1)..(6021)

<400> SEQUENCE: 26

gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360

tctacacaga caagatgaaa caattcggca ttaatacctg agagcaggaa gagcaagata    420

aaaggtagta tttgttggcg atccccctag agtcttttac atcttcggaa aacaaaaact    480

atttttttctt taatttcttt ttttacttttc tatttttaat ttatatattt atattaaaaa    540

atttaaatta taattatttt tatagcacgt gatgaaaagg acccaggtgg cacttttcgg    600

ggaaatgtgc gcggaacccc tatttgttta tttttctaaa tacattcaaa tatgtatccg    660

ctcatgagac aataaccctg ataaatgctt caataatatt gaaaaaggaa gagtatgagt    720

attcaacatt tccgtgtcgc ccttattccc ttttttgcgg cattttgcct tcctgttttt    780

gctcacccag aaacgctggt gaaagtaaaa gatgctgaag atcagttggg tgcacgagtg    840

ggttacatcg aactggatct caacagcggt aagatccttg agagttttcg ccccgaagaa    900

cgttttccaa tgatgagcac ttttaaagtt ctgctatgtg gcgcggtatt atcccgtatt    960

gacgccgggc aagagcaact cggtcgccgc atacactatt ctcagaatga cttggttgag   1020

tactcaccag tcacagaaaa gcatcttacg gatggcatga cagtaagaga attatgcagt   1080

gctgccataa ccatgagtga taacactgcg gccaacttac ttctgacaac gatcggagga   1140

ccgaaggagc taaccgcttt tttgcacaac atgggggatc atgtaactcg ccttgatcgt   1200

tgggaaccgg agctgaatga agccatacca aacgacgagc gtgacaccac gatgcctgta   1260

gcaatggcaa caacgttgcg caaactatta actggcgaac tacttactct agcttcccgg   1320

caacaattaa tagactggat ggaggcggat aaagttgcag gaccacttct gcgctcggcc   1380

cttccggctg gctggtttat tgctgataaa tctggagccg gtgagcgtgg gtctcgcggt   1440

atcattgcag cactggggcc agatggtaag ccctcccgta tcgtagttat ctacacgacg   1500

gggagtcagg caactatgga tgaacgaaat agacagatcg ctgagatagg tgcctcactg   1560

attaagcatt ggtaactgtc agaccaagtt tactcatata tactttagat tgatttaaaa   1620

cttcattttt aatttaaaag gatctaggtg aagatccttt ttgataatct catgaccaaa   1680

atcccttaac gtgagttttc gttccactga gcgtcagacc ccgtagaaaa gatcaaagga   1740

tcttcttgag atcctttttt tctgcgcgta atctgctgct tgcaaacaaa aaaaccaccg   1800

ctaccagcgg tggtttgttt gccggatcaa gagctaccaa ctctttttcc gaaggtaact   1860

ggcttcagca gagcgcagat accaaatact gtccttctag tgtagccgta gttaggccac   1920

cacttcaaga actctgtagc accgcctaca tacctcgctc tgctaatcct gttaccagtg   1980

gctgctgcca gtggcgataa gtcgtgtctt accgggttgg actcaagacg atagttaccg   2040
```

-continued

```
gataaggcgc agcggtcggg ctgaacgggg ggttcgtgca cacagcccag cttggagcga   2100
acgacctaca ccgaactgag atacctacag cgtgagctat gagaaagcgc cacgcttccc   2160
gaagggagaa aggcggacag gtatccggta agcggcaggg tcggaacagg agagcgcacg   2220
agggagcttc caggggggaaa cgcctggtat ctttatagtc ctgtcgggtt tcgccacctc   2280
tgacttgagc gtcgattttt gtgatgctcg tcaggggggc ggagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gcgcgcaatt   2760
aaccctcact aaagggaaca aaagctggag ctctgaagta cggattagaa gccgccgagc   2820
gggtgacagc cctccgaagg aagactctcc tccgtgcgtc ctcgtcttca ccggtcgcgt   2880
tcctgaaacg cagatgtgcc tcgcgccgca ctgctccgaa caataaagat tctacaatac   2940
tagcttttat ggttatgaag aggaaaaatt ggcagtaacc tggccccaca aaccttcaaa   3000
tgaacgaatc aaattaacaa ccataggatg ataatgcgat tagtttttta gccttatttc   3060
tggggtaatt aatcagcgaa gcgatgattt ttgatctatt aacagatata taaatgcaaa   3120
aactgcataa ccactttaac taatactttc aacattttcg gtttgtatta cttcttattc   3180
aaatgtaata aaagtatcaa caaaaaattg ttaatatacc tctatacttt aacgtcaagg   3240
agaaaaaact atatctagaa ctagtatgct tttgcaagca ttccttttcc ttttggctgg   3300
ttttgcagcc aaaatatctg cacatatgaa aagatctgcg aagcttgctg gcgcgccaac   3360
tgtggctgca ccatctgtct tcatcttccc gccatctgat gagcagttga aatctggaac   3420
tgcctctgtt gtgtgcctgc tgaataactt ctatcccaga gaggccaaag tacagtggaa   3480
ggtggataac gccctccaat cgggtaactc ccaggagagt gtcacagagc aggacagcaa   3540
ggacagcacc tacagcctca gcagcaccct gacgctgtcg aaagcagact acgagaaaca   3600
caaagtctac gcctgcgaag tcacccatca gggcctgagc tcgcccgtca caaagagctt   3660
caacagggga gagtgtgtcg acggtaagcc tatccctaac cctctcctcg gtctcgattc   3720
tacgcgtacc ggtcatcatc accatcacca ttgactcgag tcatgtaatt agttatgtca   3780
cgcttacatt cacgccctcc ccccacatcc gctctaaccg aaaaggaagg agttagacaa   3840
cctgaagtct aggtccctat ttattttttt atagttatgt tagtattaag aacgttattt   3900
atatttcaaa tttttctttt ttttctgtac agacgcgtgt acgcatgtaa cattatactg   3960
aaaaccttgc ttgagaaggt tttgggacgc tcgaaggctt taatttgcgg ccggtaccca   4020
attcgcccta tagtgagtcg tattacgcgc gctcactggc cgtcgtttta caacgtcgtg   4080
actgggaaaa ccctggcgtt acccaactta atcgccttgc agcacatccc cctttcgcca   4140
gctggcgtaa tagcgaagag gcccgcaccg atcgcccttc ccaacagttg cgcagcctga   4200
atggcgaatg gcgcgacgcg ccctgtagcg gcgcattaag cgcggcgggt gtggtggtta   4260
cgcgcagcgt gaccgctaca cttgccagcg ccctagcgcc cgctcctttc gctttcttcc   4320
cttcctttct cgccacgttc gccggctttc cccgtcaagc tctaaatcgg gggctccctt   4380
tagggttccg atttagtgct ttacggcacc tcgaccccaa aaaacttgat tagggtgatg   4440
```

gttcacgtag tgggccatcg ccctgataga cggtttttcg ccctttgacg ttggagtcca 4500
cgttctttaa tagtggactc ttgttccaaa ctggaacaac actcaaccct atctcggtct 4560
attcttttga tttataaggg attttgccga tttcggccta ttggttaaaa aatgagctga 4620
tttaacaaaa atttaacgcg aattttaaca aaatattaac gtttacaatt tcctgatgcg 4680
gtattttctc cttacgcatc tgtgcggtat ttcacaccgc atagggtaat aactgatata 4740
attaaattga agctctaatt tgtgagttta gtatacatgc atttacttat aatacagttt 4800
tttagttttg ctggccgcat cttctcaaat atgcttccca gcctgctttt ctgtaacgtt 4860
caccctctac cttagcatcc cttccctttg caaatagtcc tcttccaaca ataataatgt 4920
cagatcctgt agagaccaca tcatccacgg ttctatactg ttgacccaat gcgtctccct 4980
tgtcatctaa acccacaccg ggtgtcataa tcaaccaatc gtaaccttca tctcttccac 5040
ccatgtctct ttgagcaata aagccgataa caaaatcttt gtcgctcttc gcaatgtcaa 5100
cagtaccctt agtatattct ccagtagata gggagccctt gcatgacaat tctgctaaca 5160
tcaaaaggcc tctaggttcc tttgttactt cttctgccgc ctgcttcaaa ccgctaacaa 5220
tacctgggcc caccacaccg tgtgcattcg taatgtctgc ccattctgct attctgtata 5280
cacccgcaga gtactgcaat ttgactgtat taccaatgtc agcaaatttt ctgtcttcga 5340
agagtaaaaa attgtacttg gcggataatg cctttagcgg cttaactgtg ccctccatgg 5400
aaaaatcagt caagatatcc acatgtgttt ttagtaaaca aattttggga cctaatgctt 5460
caactaactc cagtaattcc ttggtggtac gaacatccaa tgaagcacac aagtttgttt 5520
gcttttcgtg catgatatta aatagcttgg cagcaacagg actaggatga gtagcagcac 5580
gttccttata tgtagctttc gacatgattt atcttcgttt cctgcaggtt tttgttctgt 5640
gcagttgggt taagaatact gggcaatttc atgtttcttc aacactacat atgcgtatat 5700
ataccaatct aagtctgtgc tccttccttc gttcttcctt ctgttcggag attaccgaat 5760
caaaaaaatt tcaaagaaac cgaaatcaaa aaaaagaata aaaaaaaaat gatgaattga 5820
attgaaaagc tgtggtatgg tgcactctca gtacaatctg ctctgatgcc gcatagttaa 5880
gccagccccg acacccgcca acacccgctg acgcgccctg acgggcttgt ctgctcccgg 5940
catccgctta cagacaagct gtgaccgtct ccgggagctg catgtgtcag aggttttcac 6000
cgtcatcacc gaaacgcgcg a 6021

<210> SEQ ID NO 27
<211> LENGTH: 309
<212> TYPE: DNA
<213> ORGANISM: Artificial Sequence
<220> FEATURE:
<223> OTHER INFORMATION: CH1 - Modified CH1 domain
<220> FEATURE:
<221> NAME/KEY: gene
<222> LOCATION: (1)..(309)

<400> SEQUENCE: 27
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgcgctgac cagcggcgtg cacaccttcc cggctgtcct acagtcatca 180
ggactctact ccctcagcag cgtagtgacc gtgccctcca gcagcttggg cacccagacc 240
tacatctgca acgtgaatca caagcccagc aacaccaagg tggacaagaa agttgagccc 300
aaatcttgt 309

<210> SEQ ID NO 28
<211> LENGTH: 321
<212> TYPE: DNA
<213> ORGANISM: Artificial Sequence
<220> FEATURE:
<223> OTHER INFORMATION: Ck - Modified Ck domain
<220> FEATURE:
<221> NAME/KEY: misc_recomb
<222> LOCATION: (1)..(321)
<220> FEATURE:
<221> NAME/KEY: gene
<222> LOCATION: (1)..(321)

<400> SEQUENCE: 28
ggaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgtcgaaagc agactacgag 240
aaacacaaag tctacgcctg cgaagtcacc catcagggcc tgagctcgcc cgtcacaaag 300
agcttcaaca ggggagagtg t 321

<210> SEQ ID NO 29
<211> LENGTH: 332
<212> TYPE: DNA
<213> ORGANISM: Artificial Sequence
<220> FEATURE:
<223> OTHER INFORMATION: CL - Modified CL domain
<220> FEATURE:
<221> NAME/KEY: gene
<222> LOCATION: (1)..(332)

<400> SEQUENCE: 29
gtcagcccaa ggccaacccc actgtcactc tgttcccgcc ctcctctgag gagctccaag 60
ccaacaaggc caccctagtg tgtctgatca gtgacttcta cccgggagct gtgacagtgg 120
cctggaaggc agatggcagc cccgtcaagg cgggagtgga gaccaccaaa ccctccaaac 180
agagcaacaa caagtacgcg gccagcagct acctgagcct gacgcccgag cagtggaagt 240
cccacagaag ctacagctgc caggtcacgc atgaagggag caccgtggag aagacagtgg 300
cccctacaga atgttcaacg cgtgttacag tc 332

<210> SEQ ID NO 30
<211> LENGTH: 3960
<212> TYPE: DNA
<213> ORGANISM: Artificial Sequence
<220> FEATURE:
<223> OTHER INFORMATION: pADL23c - Phagemid vector backbone
<220> FEATURE:
<221> NAME/KEY: old_sequence
<222> LOCATION: (1)..(3960)

<400> SEQUENCE: 30
gcacttttcg gggaaatgtg cgcggaaccc ctatttgttt atttttctaa atacattcaa 60
atatgtatcc gctcatgaga caataaccct gataaatgct tcaataatat tgaaaaagga 120
agagtatgag tattcaacat ttccgtgtcg cccttattcc cttttttgcg gcattttgcc 180
ttcctgtttt tgctcaccca gaaacgctgg tgaaagtaaa agatgctgaa gatcagttgg 240
gtgcacgagt gggttacatc gaactggatc tcaacagcgg taagatcctt gagagttttc 300
gccccgaaga acgttttcca atgatgagca cttttaaagt tctgctatgt ggcgcggtat 360

```
tatcccgtat tgacgccggg caagagcaac tcggtcgccg catacactat tctcagaatg    420
acttggttga gtactcacca gtcacagaaa agcatcttac ggatggcatg acagtaagag    480
aattatgcag tgctgccata accatgagtg ataacactgc ggccaactta cttctgacaa    540
cgatcggagg accgaaggag ctaaccgctt ttttgcacaa catgggggat catgtaactc    600
gccttgatcg ttgggaaccg gagctgaatg aagccatacc aaacgacgag cgtgacacca    660
cgatgcctgt agcaatggca acaacgttgc gcaaactatt aactggcgaa ctacttactc    720
tagcttcccg gcaacaatta atagactgga tggaggcgga taaagttgca ggaccacttc    780
tgcgctcggc gcttccggct ggctggttta ttgctgataa atctggagcc ggtgagcgtg    840
ggtctcgcgg tatcattgca gcactggggc cagatggtaa gccctcccgt atcgtagtta    900
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgttcttcta gtgtagccgt   1320
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccagggggaa acgcctggta tctttatagt cctgtcgggt   1680
ttcgccacct ctgacttgag cgtcgatttt tgtgatgctc gtcagggggg cggagcctat   1740
ggaaaaacgc cagcaacgcg gcctttttac ggttcctggc cttttgctgg ccttttgctc   1800
acatgcgccc aatacgcaaa ccgcctctcc ccgcgcgttg gccgattcat taatgcagct   1860
ggcacgacag gtttcccgac tggaaagcgg gcagtgagcg caacgcaatt aatgtgagtt   1920
agctcactca ttaggcaccc caggctttac actttatgct tccggctcgt atgttgtgtg   1980
gaattgtgag cggataacaa tttgaattca aggagacagt cataatgaaa tacctattgc   2040
ctacggcggc cgctggattg ttattactcg cggcccagcc ggcctaacta gtggcccggg   2100
aggccaacac catcaccacc atcatggcgc agaacaaaaa ctcatctcag aagaggatct   2160
gtcttaggcc gaaactgttg aaagttgttt agcaaaacct catacagaaa attcatttac   2220
taacgtctgg aaagacgaca aaactttaga tcgttacgct aactatgagg gctgtctgtg   2280
gaatgctaca ggcgttgtgg tttgtactgg tgacgaaact cagtgttacg gtacatgggt   2340
tcctattggg cttgctatcc ctgaaaatga gggtggtggc tctgagggtg gcggttctga   2400
gggtggcggt tctgagggtg gcggtactaa acctcctgag tacggtgata cacctattcc   2460
gggctatact tatatcaacc ctctcgacgg cacttatccg cctggtactg agcaaaaccc   2520
cgctaatcct aatccttctc ttgaggagtc tcagcctctt aatactttca tgtttcagaa   2580
taataggttc cgaaataggc agggtgcatt aactgtttat acgggcactg ttactcaagg   2640
cactgacccc gttaaaactt attaccagta cactcctgta tcatcaaaag ccatgtatga   2700
cgcttactgg aacggtaaat tcagagactg cgctttccat tctggcttta atgaggatcc   2760
```

attcgtttgt gaatatcaag gccaatcgtc tgacctgcct caacctcctg tcaatgctgg 2820
cggcggctct ggtggtggtt ctggtggcgg ctctgagggt ggcggctctg agggtggcgg 2880
ttctgagggt ggcggctctg agggtggcgg ttccggtggc ggctccggtt ccggtgattt 2940
tgattatgaa aaaatggcaa acgctaataa gggggctatg accgaaaatg ccgatgaaaa 3000
cgcgctacag tctgacgcta aaggcaaact tgattctgtc gctactgatt acggtgctgc 3060
tatcgatggt ttcattggtg acgtttccgg ccttgctaat ggtaatggtg ctactggtga 3120
ttttgctggc tctaattccc aaatggctca agtcggtgac ggtgataatt cacctttaat 3180
gaataatttc cgtcaatatt taccttcttt gcctcagtcg gttgaatgtc gcccttatgt 3240
ctttggcgct ggtaaaccat atgaattttc tattgattgt gacaaaataa acttattccg 3300
tggtgtcttt gcgtttcttt tatatgttgc cacctttatg tatgtatttt cgacgtttgc 3360
taacatactg cgtaataagg agtcttaagc tagctaacag tcctatgaat caactactta 3420
gatggtatta gtgacctgta acagagcatt agcgcaaggt gatttttgtc ttcttgcgct 3480 aatttttgt catcaaacct gtcgcactcc ttaatatttt gttaaaattc gcgttaaatt 3540
tttgttaaat cagctcattt tttaaccaat aggccgaaat cggcaaaatc ccttataaat 3600
caaaagaata gaccgagata gggttgagtg ttgttccagt ttggaacaag agtccactat 3660
taaagaacgt ggactccaac gtcaaagggc gaaaaaccgt ctatcagggc gatggcccac 3720
tacgtgaacc atcaccctaa tcaagttttt tggggtcgag gtgccgtaaa gcactaaatc 3780
ggaaccctaa agggagcccc cgatttagag cttgacgggg aaagccggcg aacgtggcga 3840
gaaaggaagg gaagaaagcg aaaggagcgg gcgctagggc gctggcaagt gtagcggtca 3900
cgctgcgcgt aaccaccaca cccgccgcgc ttaatgcgcc gctacagggc gcgtcaggtg 3960

<210> SEQ ID NO 31
<211> LENGTH: 4783
<212> TYPE: DNA
<213> ORGANISM: Artificial Sequence
<220> FEATURE:
<223> OTHER INFORMATION: pRS314 - Yeast Bicistronic bidirectional, Uni directional and ScFv vector backbone
<220> FEATURE:
<221> NAME/KEY: old_sequence
<222> LOCATION: (1)..(4783)

<400> SEQUENCE: 31
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240
atatgtgtac tttgcagtta tgacgccaga tggcagtagt ggaagatatt ctttattgaa 300
aaatagcttg tcaccttacg tacaatcttg atccggagct tttctttttt tgccgattaa 360
gaattaattc ggtcgaaaaa agaaaaggag agggccaaga gggagggcat tggtgactat 420
tgagcacgtg agtatacgtg attaagcaca caaaggcagc ttggagtatg tctgttatta 480
atttcacagg tagttctggt ccattggtga aagtttgcgg cttgcagagc acagaggccg 540
cagaatgtgc tctagattcc gatgctgact tgctgggtat tatatgtgtg cccaatagaa 600
agagaacaat tgacccggtt attgcaagga aaatttcaag tcttgtaaaa gcatataaaa 660
atagttcagg cactccgaaa tacttggttg gcgtgtttcg taatcaacct aaggaggatg 720

-continued

```
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgcctg cggtgtgaaa   1200
taccgcacag atgcgtaagg agaaaatacc gcatcaggaa attgtaaacg ttaatatttt   1260
gttaaaattc gcgttaaatt tttgttaaat cagctcattt tttaaccaat aggccgaaat   1320
cggcaaaatc ccttataaat caaaagaata gaccgagata gggttgagtg ttgttccagt   1380
ttggaacaag agtccactat taaagaacgt ggactccaac gtcaaagggc gaaaaaccgt   1440
ctatcagggc gatggcccac tacgtgaacc atcaccctaa tcaagttttt tggggtcgag   1500
gtgccgtaaa gcactaaatc ggaaccctaa agggagcccc cgatttagag cttgacgggg   1560
aaagccggcg aacgtggcga gaaaggaagg gaagaaagcg aaaggagcgg gcgctagggc   1620
gctggcaagt gtagcggtca cgctgcgcgt aaccaccaca cccgccgcgc ttaatgcgcc   1680
gctacagggc gcgtcgcgcc attcgccatt caggctgcgc aactgttggg aagggcgatc   1740
ggtgcgggcc tcttcgctat tacgccagct ggcgaagggg ggatgtgctg caaggcgatt   1800
aagttgggta acgccagggt tttcccagtc acgacgttgt aaaacgacgg ccagtgaatt   1860
gtaatacgac tcactatagg gcgaattgga gctccaccgc ggtggcggcc gctctagaac   1920
tagtggatcc cccgggctgc aggaattcga tatcaagctt atcgataccg tcgacctcga   1980
ggggggggcc cggtacccagc ttttgttccc tttagtgagg gttaattccg agcttggcgt   2040
aatcatggtc atagctgttt cctgtgtgaa attgttatcc gctcacaatt ccacacaaca   2100
taggagccgg aagcataaag tgtaaagcct ggggtgccta atgagtgagg taactcacat   2160
taattgcgtt gcgctcactg cccgctttcc agtcgggaaa cctgtcgtgc cagctgcatt   2220
aatgaatcgg ccaacgcgcg gggagaggcg gtttgcgtat tgggcgctct tccgcttcct   2280
cgctcactga ctcgctgcgc tcggtcgttc ggctgcggcg agcggtatca gctcactcaa   2340
aggcggtaat acggttatcc acagaatcag gggataacgc aggaaagaac atgtgagcaa   2400
aaggccagca aaaggccagg aaccgtaaaa aggccgcgtt gctggcgttt ttccataggc   2460
tcggcccccc tgacgagcat cacaaaaatc gacgctcaag tcagaggtgg cgaaacccga   2520
caggactata aagataccag gcgtttcccc ctggaagctc cctcgtgcgc tctcctgttc   2580
cgaccctgcc gcttaccgga tacctgtccg cctttctccc ttcgggaagc gtggcgcttt   2640
ctcaatgctc acgctgtagg tatctcagtt cggtgtaggt cgttcgctcc aagctgggct   2700
gtgtgcacga accccccgtt cagcccgacc gctgcgcctt atccggtaac tatcgtcttg   2760
agtccaaccc ggtaagacac gacttatcgc cactggcagc agccactggt aacaggatta   2820
gcagagcgag gtatgtaggc ggtgctacag agttcttgaa gtggtggcct aactacggct   2880
acactagaag gacagtattt ggtatctgcg ctctgctgaa gccagttacc ttcggaaaaa   2940
gagttggtag ctcttgatcc ggcaaacaaa ccaccgctgg tagcggtggt ttttttgttt   3000
gcaagcagca gattacgcgc agaaaaaaag gatctcaaga agatcctttg atcttttcta   3060
cggggtctga cgctcagtgg aacgaaaact cacgttaagg gattttggtc atgagattat   3120
```

caaaaaggat cttcacctag atccttttaa attaaaaatg aagttttaaa tcaatctaaa 3180
gtatatatga gtaaacttgg tctgacagtt accaatgctt aatcagtgag gcacctatct 3240
cagcgatctg tctatttcgt tcatccatag ttgcctgact gcccgtcgtg tagataacta 3300
cgatacggga gggcttacca tctggcccca gtgctgcaat gataccgcga gacccacgct 3360
caccggctcc agatttatca gcaataaacc agccagccgg aagggccgag cgcagaagtg 3420
gtcctgcaac tttatccgcc tccatccagt ctattaattg ttgccgggaa gctagagtaa 3480
gtagttcgcc agttaatagt ttgcgcaacg ttgttgccat tgctacaggc atcgtggtgt 3540
cacgctcgtc gtttggtatg gcttcattca gctccggttc ccaacgatca aggcgagtta 3600
catgatcccc catgttgtga aaaaaagcgg ttagctcctt cggtcctccg atcgttgtca 3660
gaagtaagtt ggccgcagtg ttatcactca tggttatggc agcactgcat aattctctta 3720
ctgtcatgcc atccgtaaga tgcttttctg tgactggtga gtactcaacc aagtcattct 3780
gagaatagtg tatgcggcga ccgagttgct cttgcccggc gtcaatacgg gataataccg 3840
cgccacatag cagaacttta aaagtgctca tcattggaaa acgttcttcg gggcgaaaac 3900
tctcaaggat cttaccgctg ttgagatcca gttcgatgta acccactcgt gcacccaact 3960
gatcttcagc atcttttact ttcaccagcg tttctgggtg agcaaaaaca ggaaggcaaa 4020
atgccgcaaa aaagggaata agggcgacac ggaaatgttg aatactcata ctcttccttt 4080
ttcaatatta ttgaagcatt tatcagggtt attgtctcat gagcggatac atatttgaat 4140
gtatttagaa aaataaacaa ataggggttc cgcgcacatt tccccgaaaa gtgccacctg 4200
ggtccttttc atcacgtgct ataaaaataa ttataattta aattttttaa tataaatata 4260
taaattaaaa atagaaagta aaaaaagaaa ttaaagaaaa aatagttttt gttttccgaa 4320
gatgtaaaag actctagggg gatcgccaac aaatactacc ttttatcttg ctcttcctgc 4380
tctcaggtat taatgccgaa ttgtttcatc ttgtctgtgt agaagaccac acacgaaaat 4440
cctgtgattt tacattttac ttatcgttaa tcgaatgtat atctatttaa tctgcttttc 4500
ttgtctaata aatatatatg taaagtacgc tttttgttga aattttttaa acctttgttt 4560
attttttttt cttcattccg taactcttct accttcttta tttactttct aaaatccaaa 4620
tacaaaacat aaaaataaat aaacacagag taaattccca aattattcca tcattaaaag 4680
atacgaggcg cgtgtaagtt acaggcaagc gatccgtcct aagaaaccat tattatcatg 4740
acattaacct ataaaaatag gcgtatcacg aggccctttc gtc 4783

<210> SEQ ID NO 32
<211> LENGTH: 5473
<212> TYPE: DNA
<213> ORGANISM: Artificial Sequence
<220> FEATURE:
<223> OTHER INFORMATION: p414Gal1 - Vector backbone for Mating Type Heavy Chain
<220> FEATURE:
<221> NAME/KEY: old_sequence
<222> LOCATION: (1)..(5473)

<400> SEQUENCE: 32
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accataaacg acattactat atatataata taggaagcat ttaatagaca gcatcgtaat 240

-continued

```
atatgtgtac tttgcagtta tgacgccaga tggcagtagt ggaagatatt ctttattgaa    300
aaatagcttg tcaccttacg tacaatcttg atccggagct ttcttttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga aagtttgcgg cttgcagagc acagaggccg    540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacggtatcg ataagcttga tatcgaattc ctgcagcccg ggggatccac tagttctaga   2220
tatagttttt tctccttgac gttaaagtat agaggtatat taacaatttt ttgttgatac   2280
ttttattaca tttgaataag aagtaataca aaccgaaaat gttgaaagta ttagttaaag   2340
tggttatgca gtttttgcat ttatatatct gttaatagat caaaaatcat cgcttcgctg   2400
attaattacc ccagaaataa ggctaaaaaa ctaatcgcat tatcatccta tggttgttaa   2460
tttgattcgt tcatttgaag gtttgtgggg ccaggttact gccaattttt cctcttcata   2520
accataaaag ctagtattgt agaatcttta ttgttcggag cagtgcggcg cgaggcacat   2580
ctgcgtttca ggaacgcgac cggtgaagac gaggacgcac ggaggagagt cttccttcgg   2640
```

```
agggctgtca cccgctcggc ggcttctaat ccgtacttca gagctccagc ttttgttccc   2700
tttagtgagg gttaattgcg cgcttggcgt aatcatggtc atagctgttt cctgtgtgaa   2760
attgttatcc gctcacaatt ccacacaaca taggagccgg aagcataaag tgtaaagcct   2820
ggggtgccta atgagtgagg taactcacat taattgcgtt gcgctcactg cccgctttcc   2880
agtcgggaaa cctgtcgtgc cagctgcatt aatgaatcgg ccaacgcgcg gggagaggcg   2940
gtttgcgtat tgggcgctct tccgcttcct cgctcactga ctcgctgcgc tcggtcgttc   3000
ggctgcggcg agcggtatca gctcactcaa aggcggtaat acggttatcc acagaatcag   3060
gggataacgc aggaaagaac atgtgagcaa aaggccagca aaaggccagg aaccgtaaaa   3120
aggccgcgtt gctggcgttt ttccataggc tccgcccccc tgacgagcat cacaaaaatc   3180
gacgctcaag tcagaggtgg cgaaacccga caggactata aagataccag gcgtttcccc   3240
ctggaagctc cctcgtgcgc tctcctgttc cgaccctgcc gcttaccgga tacctgtccg   3300
cctttctccc ttcgggaagc gtggcgcttt ctcatagctc acgctgtagg tatctcagtt   3360
cggtgtaggt cgttcgctcc aagctgggct gtgtgcacga accccccgtt cagcccgacc   3420
gctgcgcctt atccggtaac tatcgtcttg agtccaaccc ggtaagacac gacttatcgc   3480
cactggcagc agccactggt aacaggatta gcagagcgag gtatgtaggc ggtgctacag   3540
agttcttgaa gtggtggcct aactacggct acactagaag gacagtattt ggtatctgcg   3600
ctctgctgaa gccagttacc ttcggaaaaa gagttggtag ctcttgatcc ggcaaacaaa   3660
ccaccgctgg tagcggtggt ttttttgttt gcaagcagca gattacgcgc agaaaaaaag   3720
gatctcaaga agatcctttg atcttttcta cggggtctga cgctcagtgg aacgaaaact   3780
cacgttaagg gattttggtc atgagattat caaaaaggat cttcacctag atccttttaa   3840
attaaaaatg aagttttaaa tcaatctaaa gtatatatga gtaaacttgg tctgacagtt   3900
accaatgctt aatcagtgag gcacctatct cagcgatctg tctatttcgt tcatccatag   3960
ttgcctgact ccccgtcgtg tagataacta cgatacggga gggcttacca tctggcccca   4020
gtgctgcaat gataccgcga gacccacgct caccggctcc agatttatca gcaataaacc   4080
agccagccgg aagggccgag cgcagaagtg gtcctgcaac tttatccgcc tccatccagt   4140
ctattaattg ttgccgggaa gctagagtaa gtagttcgcc agttaatagt ttgcgcaacg   4200
ttgttgccat tgctacaggc atcgtggtgt cacgctcgtc gtttggtatg gcttcattca   4260
gctccggttc ccaacgatca aggcgagtta catgatcccc catgttgtgc aaaaaagcgg   4320
ttagctcctt cggtcctccg atcgttgtca gaagtaagtt ggccgcagtg ttatcactca   4380
tggttatggc agcactgcat aattctctta ctgtcatgcc atccgtaaga tgcttttctg   4440
tgactggtga gtactcaacc aagtcattct gagaatagtg tatgcggcga ccgagttgct   4500
cttgcccggc gtcaatacgg gataataccg cgccacatag cagaacttta aaagtgctca   4560
tcattggaaa acgttcttcg gggcgaaaac tctcaaggat cttaccgctg ttgagatcca   4620
gttcgatgta acccactcgt gcacccaact gatcttcagc atcttttact ttcaccagcg   4680
tttctgggtg agcaaaaaca ggaaggcaaa atgccgcaaa aaagggaata agggcgacac   4740
ggaaatgttg aatactcata ctcttccttt ttcaatatta ttgaagcatt tatcagggtt   4800
attgtctcat gagcggatac atatttgaat gtatttagaa aaataaacaa ataggggttc   4860
cgcgcacatt tccccgaaaa gtgccacctg ggtccttttc atcacgtgct ataaaaataa   4920
ttataattta aattttttaa tataaatata taaattaaaa atagaaagta aaaaaagaaa   4980
```

```
ttaaagaaaa aatagttttt gttttccgaa gatgtaaaag actctagggg gatcgccaac   5040

aaatactacc ttttatcttg ctcttcctgc tctcaggtat taatgccgaa ttgtttcatc   5100

ttgtctgtgt agaagaccac acacgaaaat cctgtgattt tacattttac ttatcgttaa   5160

tcgaatgtat atctatttaa tctgcttttc ttgtctaata aatatatatg taaagtacgc   5220

tttttgttga aatttttaa acctttgttt attttttttt cttcattccg taactcttct   5280

accttcttta tttactttct aaaatccaaa tacaaaacat aaaaataaat aaacacagag   5340

taaattccca aattattcca tcattaaaag atacgaggcg cgtgtaagtt acaggcaagc   5400

gatccgtcct aagaaaccat tattatcatg acattaacct ataaaaatag gcgtatcacg   5460

aggccctttc gtc                                                      5473
```

<210> SEQ ID NO 33
<211> LENGTH: 5583
<212> TYPE: DNA
<213> ORGANISM: Artificial Sequence
<220> FEATURE:
<223> OTHER INFORMATION: p416Gal1 - Vector backbone for Mating Type Light Chain
<220> FEATURE:
<221> NAME/KEY: old_sequence
<222> LOCATION: (1)..(5583)

<400> SEQUENCE: 33

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat cattttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540

aggaattact ggagttagtt gaagcattag gtcccaaaat ttgtttacta aaaacacatg    600

tggatatctt gactgatttt tccatggagg gcacagttaa gccgctaaag gcattatccg    660

ccaagtacaa tttttactc ttcgaagaca gaaaatttgc tgacattggt aatacagtca    720

aattgcagta ctctgcgggt gtatacagaa tagcagaatg ggcagacatt acgaatgcac    780

acggtgtggt gggcccaggt attgttagcg gtttgaagca ggcggcagaa gaagtaacaa    840

aggaacctag aggccttttg atgttagcag aattgtcatg caagggctcc ctatctactg    900

gagaatatac taagggtact gttgacattg cgaagagcga caaagatttt gttatcggct    960

ttattgctca aagagacatg ggtggaagag atgaaggtta cgattggttg attatgacac   1020

ccggtgtggg tttagatgac aagggagacg cattgggtca acagtataga accgtggatg   1080

atgtggtctc tacaggatct gacattatta ttgttggaag aggactattt gcaaagggaa   1140

gggatgctaa ggtagagggt gaacgttaca gaaaagcagg ctgggaagca tatttgagaa   1200

gatgcggcca gcaaaactaa aaaactgtat tataagtaaa tgcatgtata ctaaactcac   1260

aaattagagc ttcaatttaa ttatatcagt tattacccta tgcggtgtga aataccgcac   1320

agatgcgtaa ggagaaaata ccgcatcagg aaattgtaaa cgttaatatt ttgttaaaat   1380

tcgcgttaaa tttttgttaa atcagctcat tttttaacca ataggccgaa atcggcaaaa   1440
```

```
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccgcaaatt aaagccttcg agcgtcccaa   2040
aaccttctca agcaaggttt tcagtataat gttacatgcg tacacgcgtc tgtacagaaa   2100
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgaggtc gacggtatcg   2280
ataagcttga tatcgaattc ctgcagcccg ggggatccac tagttctaga tatagttttt   2340
tctccttgac gttaaagtat agaggtatat taacaatttt ttgttgatac ttttattaca   2400
tttgaataag aagtaataca aaccgaaaat gttgaaagta ttagttaaag tggttatgca   2460
gtttttgcat ttatatatct gttaatagat caaaaatcat cgcttcgctg attaattacc   2520
ccagaaataa ggctaaaaaa ctaatcgcat tatcatccta tggttgttaa tttgattcgt   2580
tcatttgaag gtttgtgggg ccaggttact gccaattttt cctcttcata accataaaag   2640
ctagtattgt agaatcttta ttgttcggag cagtgcggcg cgaggcacat ctgcgtttca   2700
ggaacgcgac cggtgaagac gaggacgcac ggaggagagt cttccttcgg agggctgtca   2760
cccgctcggc ggcttctaat ccgtacttca gagctccagc ttttgttccc tttagtgagg   2820
gttaattgcg cgcttggcgt aatcatggtc atagctgttt cctgtgtgaa attgttatcc   2880
gctcacaatt ccacacaaca taggagccgg aagcataaag tgtaaagcct ggggtgccta   2940
atgagtgagg taactcacat taattgcgtt gcgctcactg cccgctttcc agtcgggaaa   3000
cctgtcgtgc cagctgcatt aatgaatcgg ccaacgcgcg gggagaggcg gtttgcgtat   3060
tgggcgctct tccgcttcct cgctcactga ctcgctgcgc tcggtcgttc ggctgcggcg   3120
agcggtatca gctcactcaa aggcggtaat acggttatcc acagaatcag gggataacgc   3180
aggaaagaac atgtgagcaa aaggccagca aaaggccagg aaccgtaaaa aggccgcgtt   3240
gctggcgttt ttccataggc tccgcccccc tgacgagcat cacaaaaatc gacgctcaag   3300
tcagaggtgg cgaaacccga caggactata aagataccag gcgtttcccc ctggaagctc   3360
cctcgtgcgc tctcctgttc cgaccctgcc gcttaccgga tacctgtccg cctttctccc   3420
ttcgggaagc gtggcgcttt ctcatagctc acgctgtagg tatctcagtt cggtgtaggt   3480
cgttcgctcc aagctgggct gtgtgcacga accccccgtt cagcccgacc gctgcgcctt   3540
atccggtaac tatcgtcttg agtccaaccc ggtaagacac gacttatcgc cactggcagc   3600
agccactggt aacaggatta gcagagcgag gtatgtaggc ggtgctacag agttcttgaa   3660
gtggtggcct aactacggct acactagaag gacagtattt ggtatctgcg ctctgctgaa   3720
gccagttacc ttcggaaaaa gagttggtag ctcttgatcc ggcaaacaaa ccaccgctgg   3780
```

tagcggtggt ttttttgttt gcaagcagca gattacgcgc agaaaaaaag gatctcaaga 3840
agatcctttg atcttttcta cggggtctga cgctcagtgg aacgaaaact cacgttaagg 3900
gattttggtc atgagattat caaaaaggat cttcacctag atccttttaa attaaaaatg 3960
aagttttaaa tcaatctaaa gtatatatga gtaaacttgg tctgacagtt accaatgctt 4020
aatcagtgag gcacctatct cagcgatctg tctatttcgt tcatccatag ttgcctgact 4080
ccccgtcgtg tagataacta cgatacggga gggcttacca tctggcccca gtgctgcaat 4140
gataccgcga gacccacgct caccggctcc agatttatca gcaataaacc agccagccgg 4200
aagggccgag cgcagaagtg gtcctgcaac tttatccgcc tccatccagt ctattaattg 4260
ttgccgggaa gctagagtaa gtagttcgcc agttaatagt ttgcgcaacg ttgttgccat 4320
tgctacaggc atcgtggtgt cacgctcgtc gtttggtatg gcttcattca gctccggttc 4380
ccaacgatca aggcgagtta catgatcccc catgttgtgc aaaaaagcgg ttagctcctt 4440
cggtcctccg atcgttgtca gaagtaagtt ggccgcagtg ttatcactca tggttatggc 4500
agcactgcat aattctctta ctgtcatgcc atccgtaaga tgcttttctg tgactggtga 4560
gtactcaacc aagtcattct gagaatagtg tatgcggcga ccgagttgct cttgcccggc 4620
gtcaatacgg gataataccg cgccacatag cagaacttta aaagtgctca tcattggaaa 4680
acgttcttcg gggcgaaaac tctcaaggat cttaccgctg ttgagatcca gttcgatgta 4740
acccactcgt gcacccaact gatcttcagc atcttttact ttcaccagcg tttctgggtg 4800
agcaaaaaca ggaaggcaaa atgccgcaaa aaagggaata agggcgacac ggaaatgttg 4860
aatactcata ctcttccttt ttcaatatta ttgaagcatt tatcagggtt attgtctcat 4920
gagcggatac atatttgaat gtatttagaa aaataaacaa ataggggttc cgcgcacatt 4980
tccccgaaaa gtgccacctg ggtccttttc atcacgtgct ataaaaataa ttataattta 5040
aattttttaa tataaatata taaattaaaa atagaaagta aaaaaagaaa ttaaagaaaa 5100
aatagttttt gttttccgaa gatgtaaaag actctagggg gatcgccaac aaatactacc 5160
ttttatcttg ctcttcctgc tctcaggtat taatgccgaa ttgtttcatc ttgtctgtgt 5220
agaagaccac acacgaaaat cctgtgattt tacattttac ttatcgttaa tcgaatgtat 5280
atctatttaa tctgcttttc ttgtctaata aatatatatg taaagtacgc tttttgttga 5340
aattttttaa acctttgttt attttttttt cttcattccg taactcttct accttcttta 5400
tttactttct aaaatccaaa tacaaaacat aaaaataaat aaacacagag taaattccca 5460
aattattcca tcattaaaag atacgaggcg cgtgtaagtt acaggcaagc gatccgtcct 5520
aagaaaccat tattatcatg acattaacct ataaaaatag gcgtatcacg aggccctttc 5580
gtc 5583

<210> SEQ ID NO 34
<211> LENGTH: 13
<212> TYPE: DNA
<213> ORGANISM: Artificial Sequence
<220> FEATURE:
<223> OTHER INFORMATION: BamHI restriction site
<220> FEATURE:
<221> NAME/KEY: gene
<222> LOCATION: (1)..(13)

<400> SEQUENCE: 34
atgaggatcc att 13

<210> SEQ ID NO 35

<211> LENGTH: 59
<212> TYPE: DNA
<213> ORGANISM: Artificial Sequence
<220> FEATURE:
<223> OTHER INFORMATION: Removed region of pADL23c vector
<220> FEATURE:
<221> NAME/KEY: misc_feature
<222> LOCATION: (1)..(59)

<400> SEQUENCE: 35
caacaccatc accaccatca tggcgcagaa caaaaactca tctcagaaga ggatctgtc 59

<210> SEQ ID NO 36
<211> LENGTH: 13
<212> TYPE: DNA
<213> ORGANISM: Artificial Sequence
<220> FEATURE:
<223> OTHER INFORMATION: NotI and EagI restriction sites
<220> FEATURE:
<221> NAME/KEY: gene
<222> LOCATION: (1)..(13)

<400> SEQUENCE: 36
acggcggccg ctg 13

<210> SEQ ID NO 37
<211> LENGTH: 10
<212> TYPE: DNA
<213> ORGANISM: Artificial Sequence
<220> FEATURE:
<223> OTHER INFORMATION: XmaI and SmaI restrictions sites
<220> FEATURE:
<221> NAME/KEY: gene
<222> LOCATION: (1)..(10)

<400> SEQUENCE: 37
ggcccgggag 10

<210> SEQ ID NO 38
<211> LENGTH: 15
<212> TYPE: DNA
<213> ORGANISM: Artificial Sequence
<220> FEATURE:
<223> OTHER INFORMATION: SfiI restriction site
<220> FEATURE:
<221> NAME/KEY: gene
<222> LOCATION: (1)..(15)

<400> SEQUENCE: 38
cggcccagcc ggcct 15

<210> SEQ ID NO 39
<211> LENGTH: 14
<212> TYPE: DNA
<213> ORGANISM: Artificial Sequence
<220> FEATURE:
<223> OTHER INFORMATION: BstXI restriction site
<220> FEATURE:
<221> NAME/KEY: gene
<222> LOCATION: (1)..(14)

<400> SEQUENCE: 39
accaccatca tggc 14

<210> SEQ ID NO 40
<211> LENGTH: 15
<212> TYPE: DNA
<213> ORGANISM: Artificial Sequence
<220> FEATURE:

-continued

```
<223> OTHER INFORMATION: EcoRI restriction site
<220> FEATURE:
<221> NAME/KEY: gene
<222> LOCATION: (1)..(15)

<400> SEQUENCE: 40

aatttgaatt caagg                                                    15


<210> SEQ ID NO 41
<211> LENGTH: 11
<212> TYPE: DNA
<213> ORGANISM: Artificial Sequence
<220> FEATURE:
<223> OTHER INFORMATION: SacII restriction site
<220> FEATURE:
<221> NAME/KEY: gene
<222> LOCATION: (1)..(11)

<400> SEQUENCE: 41

caccgcggtg g                                                        11


<210> SEQ ID NO 42
<211> LENGTH: 11
<212> TYPE: DNA
<213> ORGANISM: Artificial Sequence
<220> FEATURE:
<223> OTHER INFORMATION: EagI and NotI restriction sites
<220> FEATURE:
<221> NAME/KEY: gene
<222> LOCATION: (1)..(11)

<400> SEQUENCE: 42

tggcggccgc t                                                        11


<210> SEQ ID NO 43
<211> LENGTH: 51
<212> TYPE: DNA
<213> ORGANISM: Artificial Sequence
<220> FEATURE:
<223> OTHER INFORMATION: BamHI, SmaI, TspMI, XmaI, PstI, EcoRI, HindIII,
      BspDI, ClaI, SalI and HincII restriction sites
<220> FEATURE:
<221> NAME/KEY: gene
<222> LOCATION: (1)..(51)

<400> SEQUENCE: 43

ggatcccccg ggctgcagga attcgatatc aagcttatcg ataccgtcga c            51
```

VECTORS FOR CLONING AND EXPRESSION OF PROTEINS, METHODS AND APPLICATIONS THEREOF

SEQUENCE LISTING

In accordance with 37 CFR § 1.52(e)(5), the present specification makes reference to a Sequence Listing (SEQ ID NOs: 1-43) provided in electronic form as an ASCII.txt file named "Substitute_Sequence_Listing 1118" that was generated on Jun. 11, 2021, and is 173,192 bytes in size. The entire contents of the Sequence Listing are herein incorporated by reference.

TECHNICAL FIELD

The present disclosure relates to the field of biotechnology, genetic engineering and immunology. Particularly, the present disclosure relates to vectors for cloning and expressing genetic material, and methods of generating said vectors. Any genetic material including but not limiting to genetic material obtained from naturally occurring antibody genes or parts thereof, artificially designed synthetic antibody genes or parts thereof, or a combination of both can be employed for cloning and expression using the vectors of the present disclosure.

BACKGROUND OF THE DISCLOSURE

Cell surface display is a technique that allows the target protein to be expressed on the cell exterior by fusing it to a carrier protein, which is typically a cell membrane associated protein or its subunit. Surface display technology is employed as library screening tool for protein engineering, directed evolution, and drug discovery. However, said display technology is associated with it's own merits and demerits.

For instance, the ribosome display method is technically more challenging due to relative instability of the RNA and the ribosomal complex. Another limitation of this technique is the inability to display a single chain protein such as ScFv. Intracellular selection methods, such as yeast-two-hybrid system or protein complementation assay directly rely on intracellular expression of the target protein. However, they come with several limitations including propensity to aggregate in intracellular scenario, low cellular half-life and most importantly the whole system needs to be tailored for a specific application depending on the type of antigen against which the screening is intended. Further, though phage display is widely accepted method, there are limitations on proper protein folding due to being a prokaryotic expression system and lack of post translational modifications of the displayed proteins. To overcome these limitations, yeast display platform, a eukaryotic display system can be employed. However, major challenge in case of yeast display system and similarly all other eukaryotic cell surface systems is the limited transformation efficiency setting limits on the library size that can be achieved which makes the entire process less efficient.

Success of a protein/antibody library, in terms of screening against an antigen, lies in its independent representation of vast size without compromising on the diversity and functional size of the library along with secretion efficiency, processing efficiency and post translation efficiency amongst other factors. In this regard, the flexibility of display systems, such as phage and/or yeast display platforms, is an absolute essential criterion to achieve such an objective. The flexibility of display systems is contingent on the kind of expression vectors being used and whether compatibility exists between them. Further, the compatibility and complementarity of vectors signify the transfer of diversity from phage to yeast display system either via combinatorial or batch transfer approaches. Said compatibility and complementarity features are lacking in the presently employed synthetic constructs/vectors of phage and yeast display systems.

The instant disclosure is directed towards addressing the above limitations of the current technologies and therefore aims at providing vectors which accommodate and cross-transfer large and diverse protein gene libraries via a combinatorial process which thereby improves the potential of identifying, transferring, preserving and generating proteins with varied affinities and specificities.

STATEMENT OF THE DISCLOSURE

This section contains a copy of independent claims. The present disclosure relates to a vector construct designed to clone antibody or a fragment thereof, said vector construct containing an expression cassette which comprises:

at least one leader sequence, at least one cloning region for receiving a gene encoding a peptide or protein that selectively binds to a biologically active ligand, at least one nucleotide sequence encoding constant region immunoglobulin heavy chain or constant region immunoglobulin light chain, or fragments thereof, wherein said constant region comprises at least one mutation with respect to constant region of a native immunoglobulin or fragments thereof, and at least one recombinant tag sequence or selection coding nucleic acid sequence, wherein, the at least one cloning region of the expression cassette contains restriction sites selected from a group comprising NdeI, BglII, BmtI, HindIII, AscI, NcoI, XbaI, NheI, NotI and combinations thereof;

a vector construct designed to clone antibody or a fragment thereof, or, to transfer or receive an antibody or a fragment thereof from the vector construct as claimed in claim 1, said vector construct containing an expression cassette which comprises:

a promoter sequence, a leader sequence, a nucleotide sequence encoding a product that enables display of a peptide or protein on the surface of a protein expression system, a first enzyme cleavage site, a first recombinant tag sequence or selection coding nucleic acid sequence, a first linker sequence, a second enzyme cleavage site, a first cloning region operably linked to a second cloning region in presence of a second linker sequence, wherein the cloning regions receive gene encoding a peptide or protein that selectively binds to a biologically active ligand, a second recombinant tag sequence(s) or selection coding nucleic acid sequence(s), and a terminator sequence, wherein, the first cloning region or the second cloning region of the expression cassette contains restriction sites selected from a group comprising NdeI, BglII, HindIII, AscI, NcoI, XbaI, NheI, NotI and combinations thereof;

a method of preparing the vector construct as described above, said method comprising steps of:

a) synthesis of the expression cassette, b) linearization of a destination vector, and c) inserting the expression cassette into the linearized destination vector to obtain the vector construct; a method of preparing library of vector constructs, said method comprising steps of: a) preparing the vector construct by the method as described above, b) cloning nucleotide sequences encoding for regions selected from a group comprising kappa variable region (Vk) of the immunoglobulin light chain, lambda variable region (VL) of the immunoglobulin light chain or fragments thereof, variable region of the immunoglobulin heavy chain or a fragment thereof (VH) and combinations thereof, into the cloning region of the vector construct to obtain the library, or, transferring the nucleotide sequences encoding regions selected from a group comprising kappa variable region (Vk) of the immunoglobulin light chain, lambda variable region (VL) of the immunoglobulin light chain or fragments thereof, variable region of the immunoglobulin heavy chain or a fragment thereof (VH) and combinations thereof, from the cloning region of one vector construct to the cloning region of another vector construct to obtain the library;

a method of screening and identifying antibody or a fragment thereof having desired functional characteristic(s), comprising steps of: (a) preparing the library of vector constructs by the method as described above and transforming said vector constructs into bacterial host cells, yeast host cells or a combination thereof, and (b) selecting the bacterial or yeast host cells expressing the antibody or fragment thereof having the desired functional characteristic(s);

a bacterial or yeast host cell, or a phage library or a yeast library thereof comprising the vector construct(s) as described above; and an expression cassette provided by the vector construct(s) as described above wherein said expression cassette has a nucleic acid sequence selected from a group comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23 and SEQ ID No. 25.

BRIEF DESCRIPTION OF THE ACCOMPANYING FIGURES

The features of the present disclosure will become fully apparent from the following description taken in conjunction with the accompanying figures. With the understanding that the figures depict only several embodiments in accordance with the disclosure and are not to be considered limiting of its scope, the disclosure will be described further through use of the accompanying figures.

B) Analysis of independent clones from pZB001 construct using BamHI and EcoRI enzymes C) Analysis of independent clones from pZB001 construct using HindIII and NcoI enzymes D) Schematic depiction of the pZB001 vector comprising the insert/expression cassette designed to clone antibody library genes comprising variable antibody heavy chain and antibody light chain (kappa) in respective cloning sites.

Figure 3:
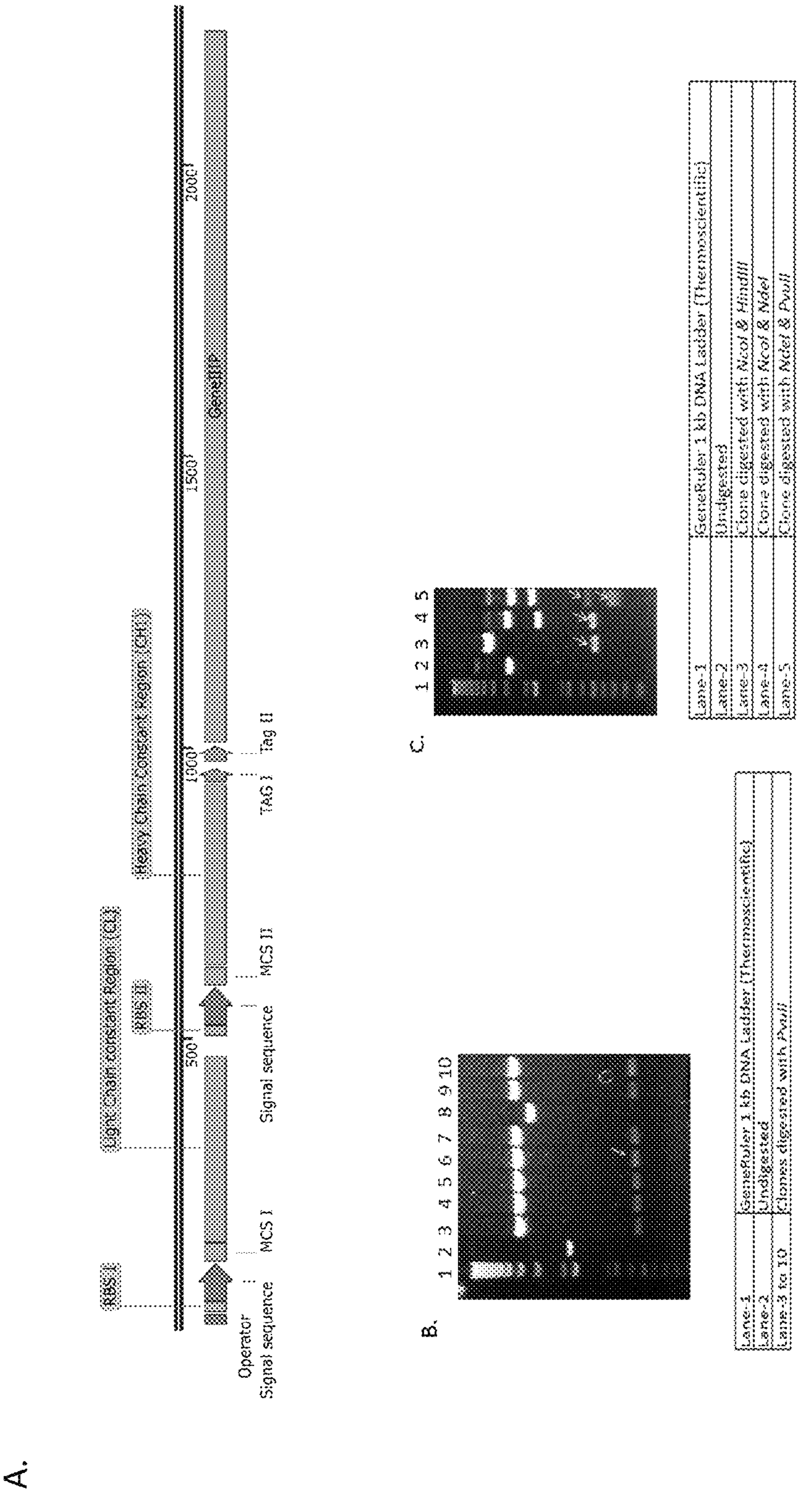
Figure 3:
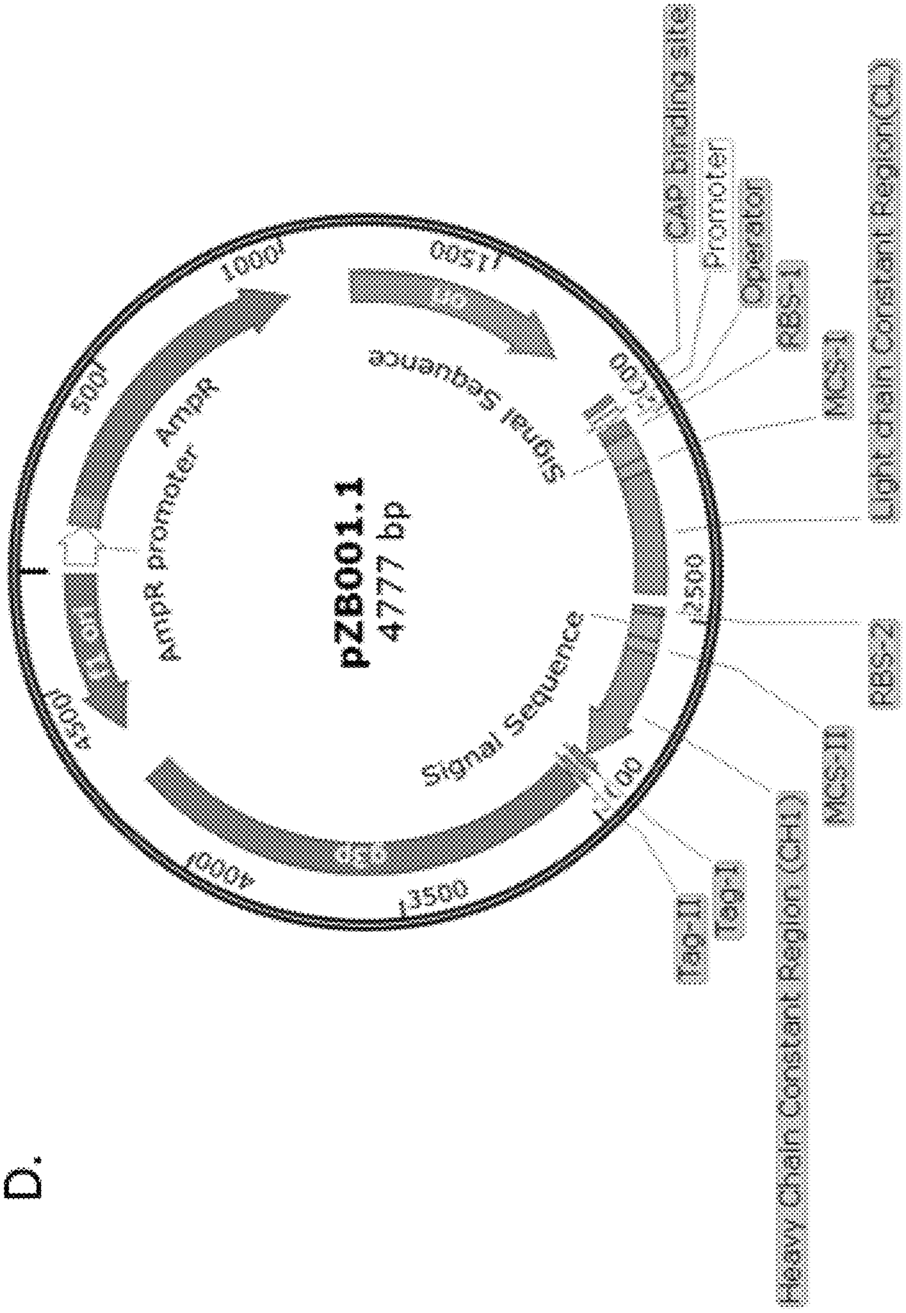

FIG. 3 illustrates generation of pZB001.1—phagemid vector with lambda light chain constant region.

A) Schematic depiction of designed insert/expression cassette containing heavy chain CH1 domain and Lambda constant light chain (CL) domain.

B) Analysis of independent clones from pZB001.1 construct using PvuII enzyme.

C) Analysis of independent clones from pZB001.1 construct using NcoI and HindIII enzymes.

D) Schematic depiction of pZB001.1 vector construct comprising the insert/expression cassette designed to clone antibody library genes comprising variable antibody heavy chain and antibody light chain (lambda) in respective cloning sites.

Figure 4:
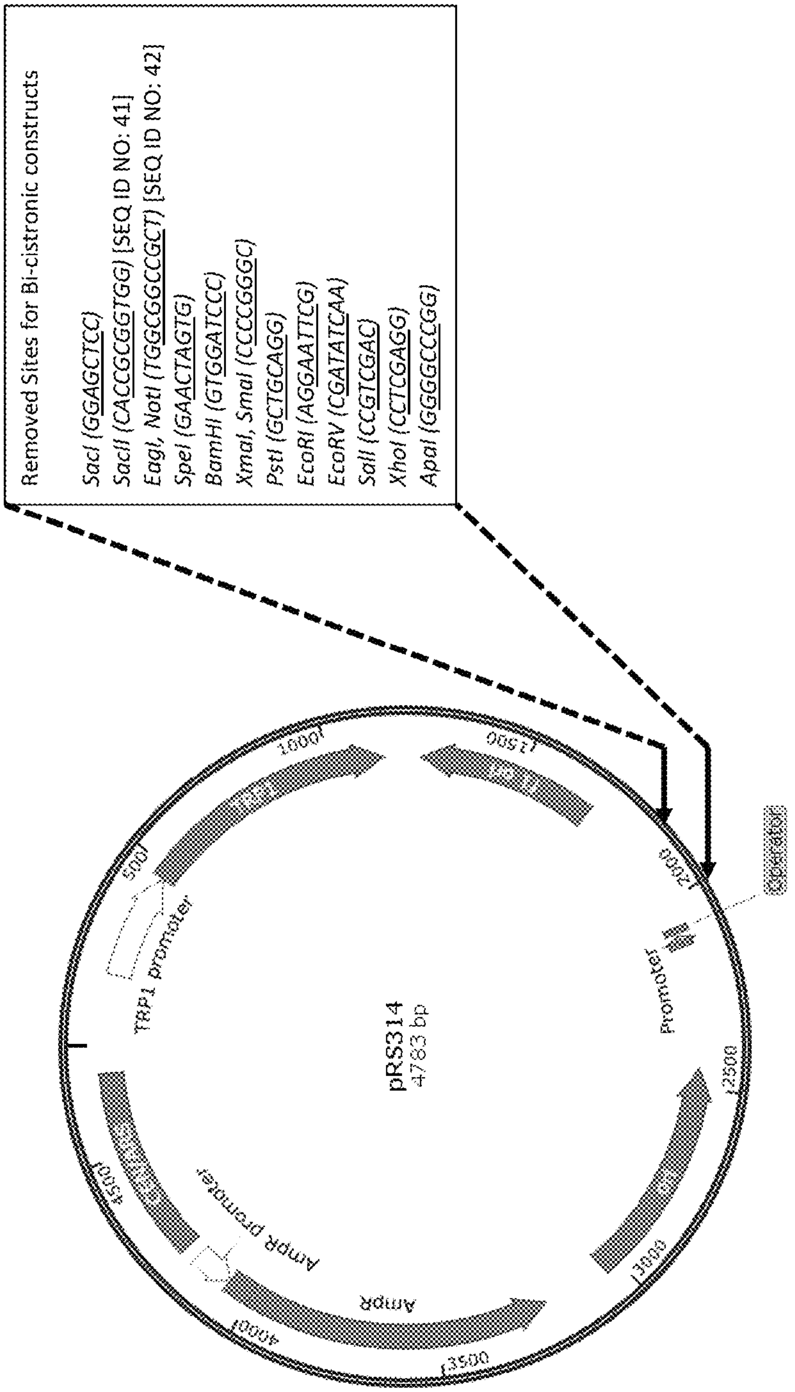

FIG. 4 illustrates modification of pRS314 vector. Multiple restriction sites were modified as described in the figure.

Figure 5:
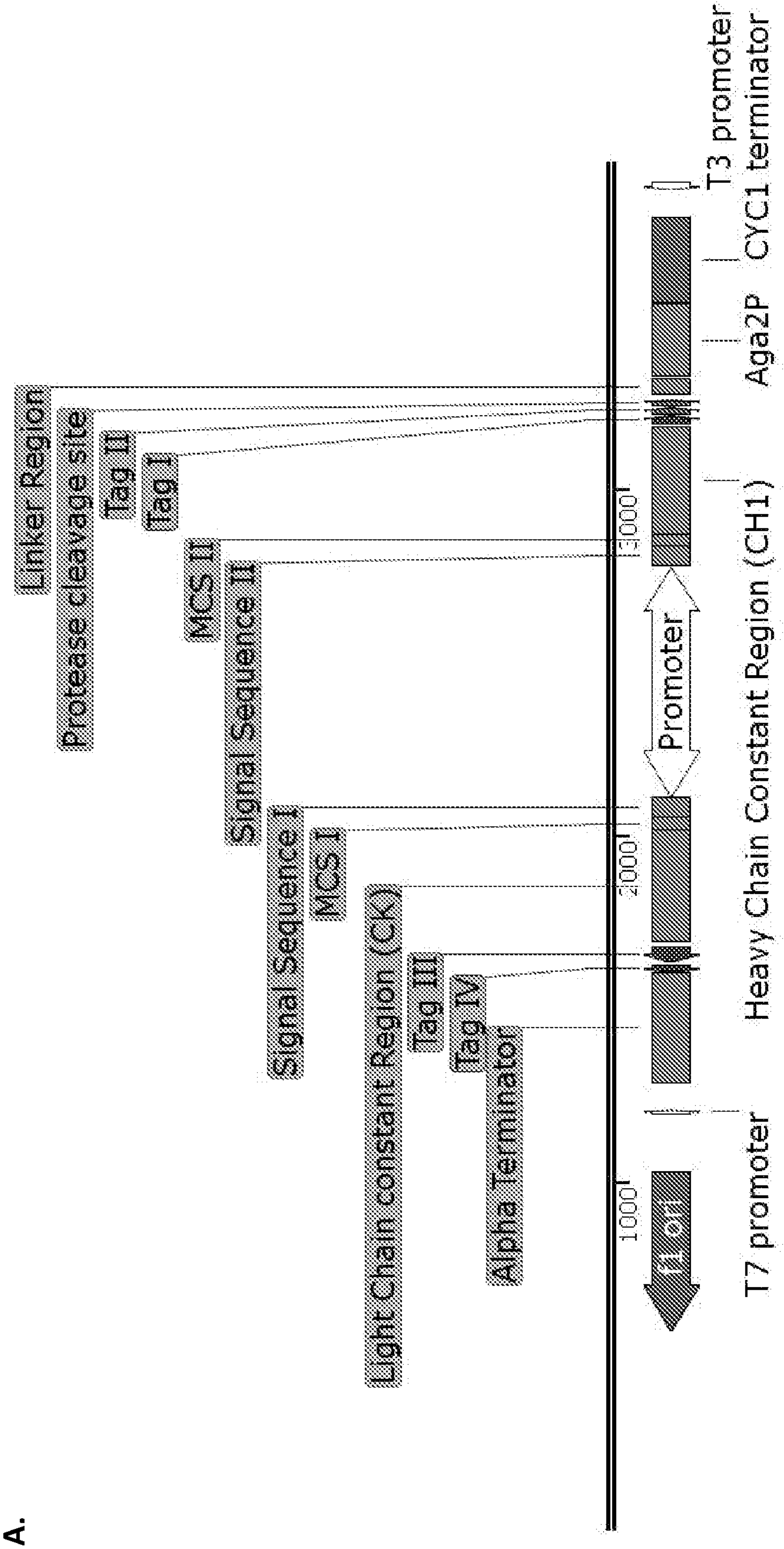
Figure 5:
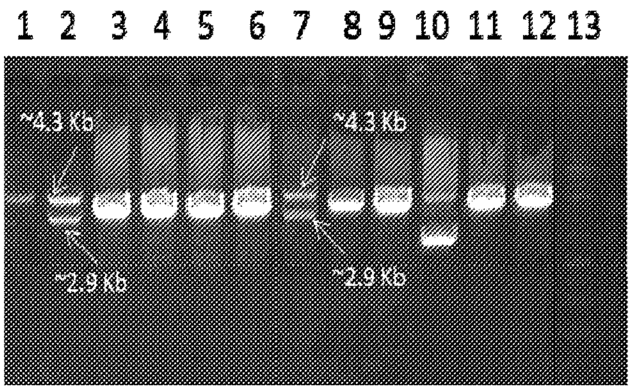
Figure 5:
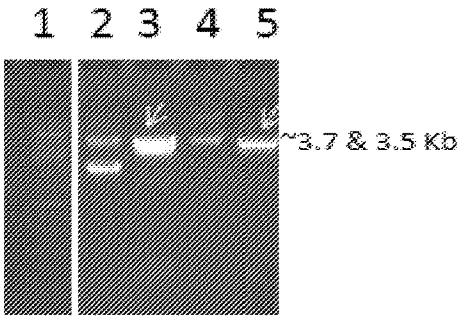
Figure 5:
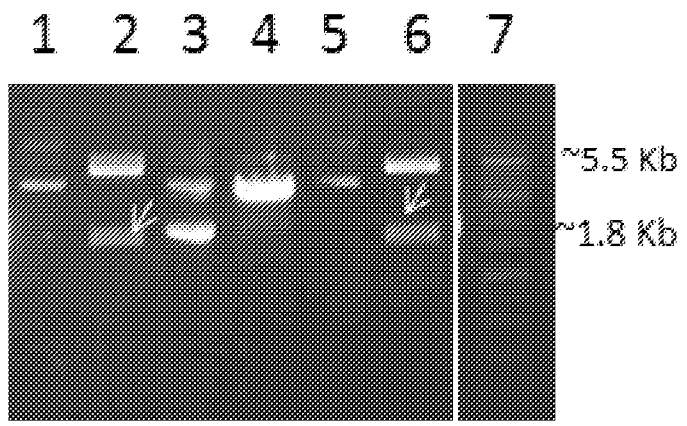
Figure 5:
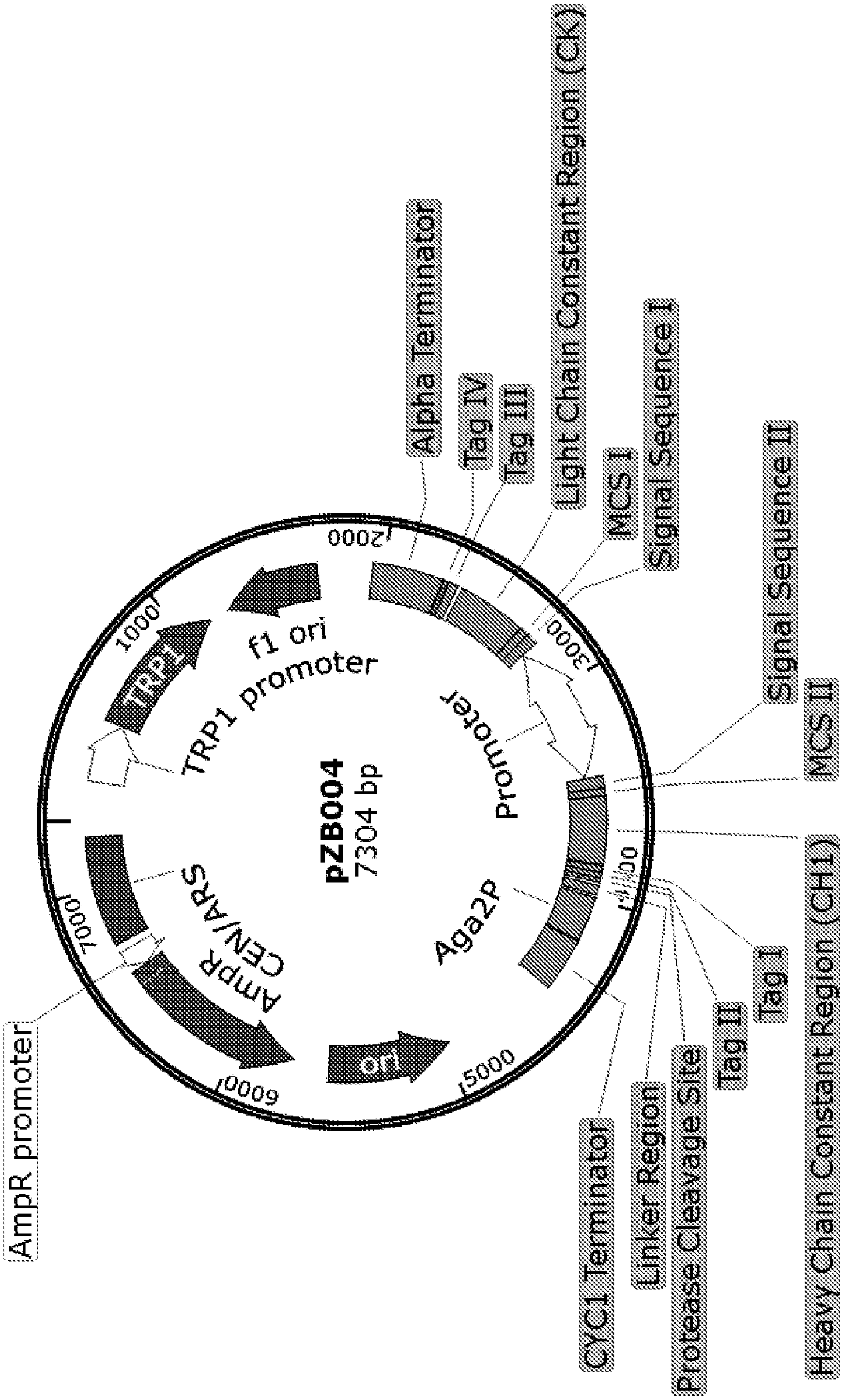

FIG. 5 illustrates generation of pZB004—yeast bidirectional vector with antibody kappa light chain constant region.

A) Schematic depiction of designed insert/expression cassette containing heavy chain CH1 domain and kappa light chain (CK) constant domain.

B) Analysis of independent clones from pZB004 construct using PvuII enzyme.

C) Analysis of independent clones from pZB004 construct using EcoRV and KpnI enzymes.

D) Analysis of independent clones from pZB004 construct using NdeI and KpnI enzymes.

E) Schematic depiction of pZB004 construct designed to clone antibody library genes comprising antibody variable heavy chain and antibody light chain (kappa) in respective cloning sites.

Figure 6:
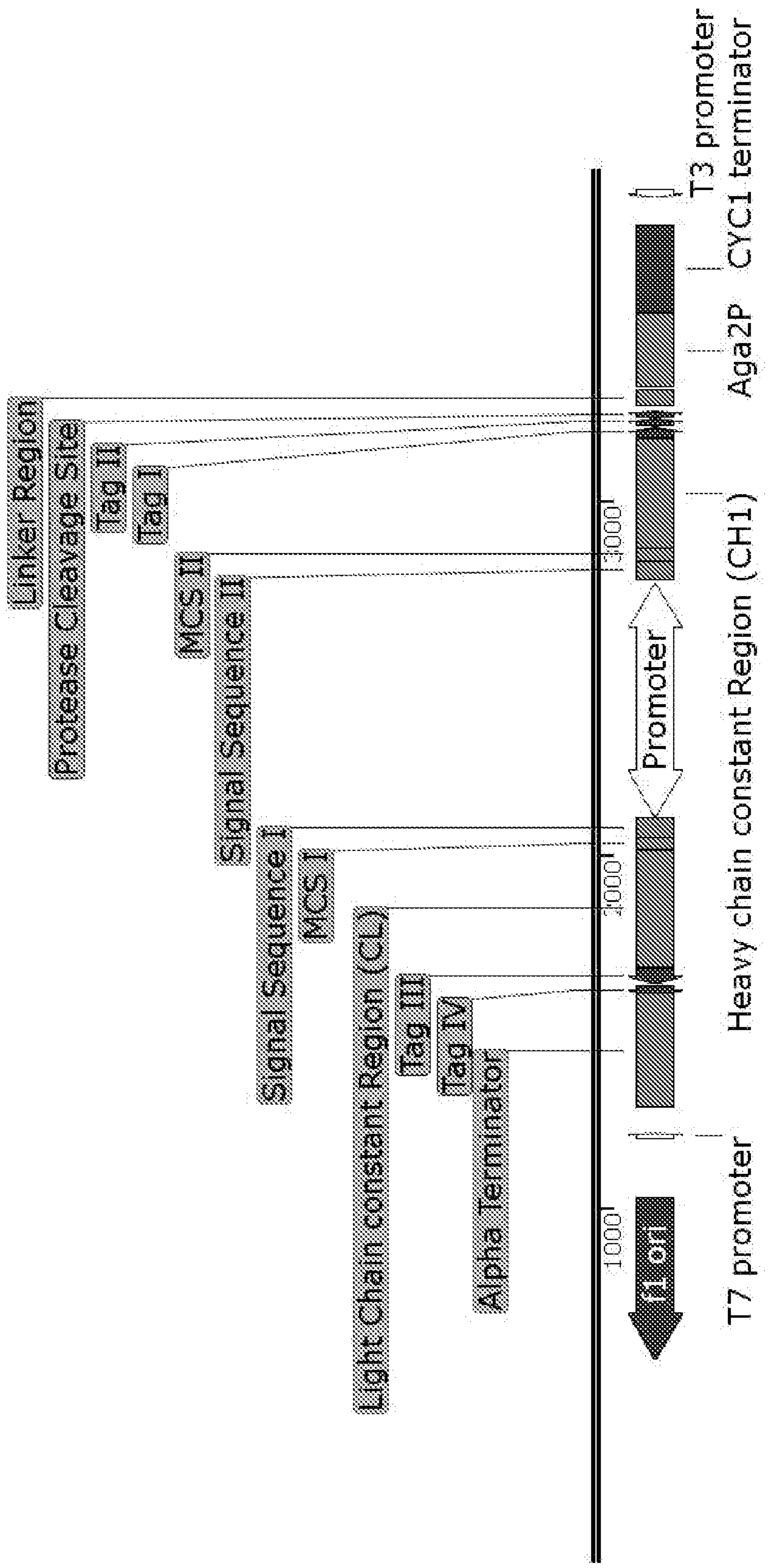
Figure 6:
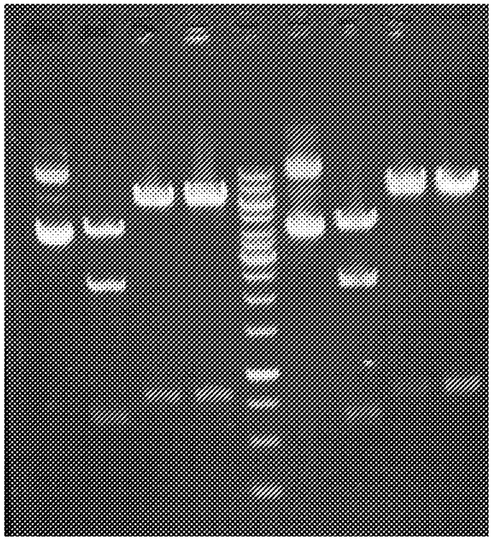
Figure 6:
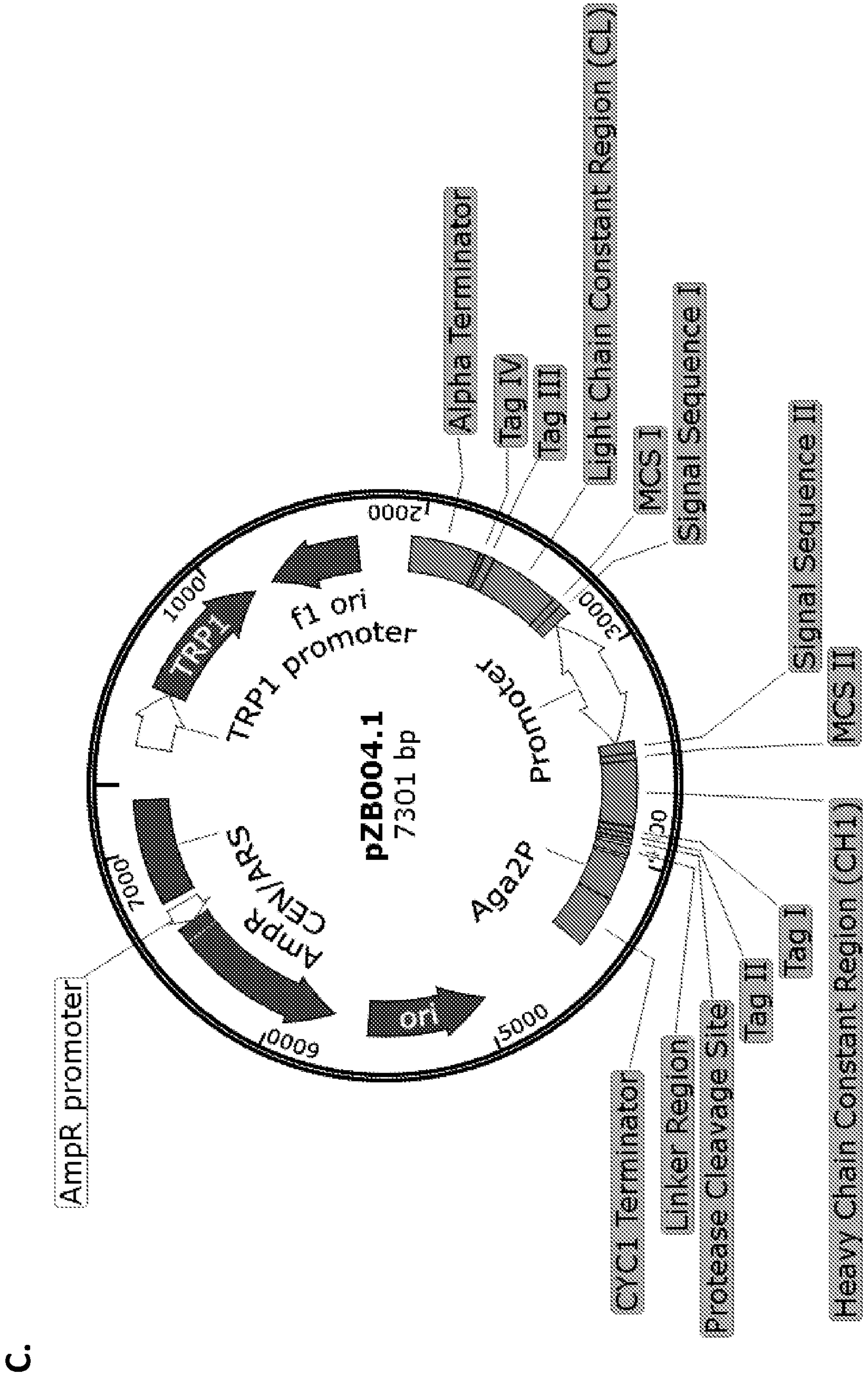

FIG. 6 illustrates generation of pZB004.1—yeast bidirectional vector with antibody lambda light chain constant region.

A) Schematic depiction of designed insert/expression cassette containing heavy chain CH1 domain and lambda light chain CL domain.

B) Analysis of independent clones from pZB004.1 construct using PvuII, NdeI & NotI and NcoI & AscI enzymes in respective combinations.

C) Schematic depiction of pZB004.1 construct designed to clone antibody library genes comprising antibody variable heavy chain and light chain (lambda) in respective cloning sites.

Figure 7:
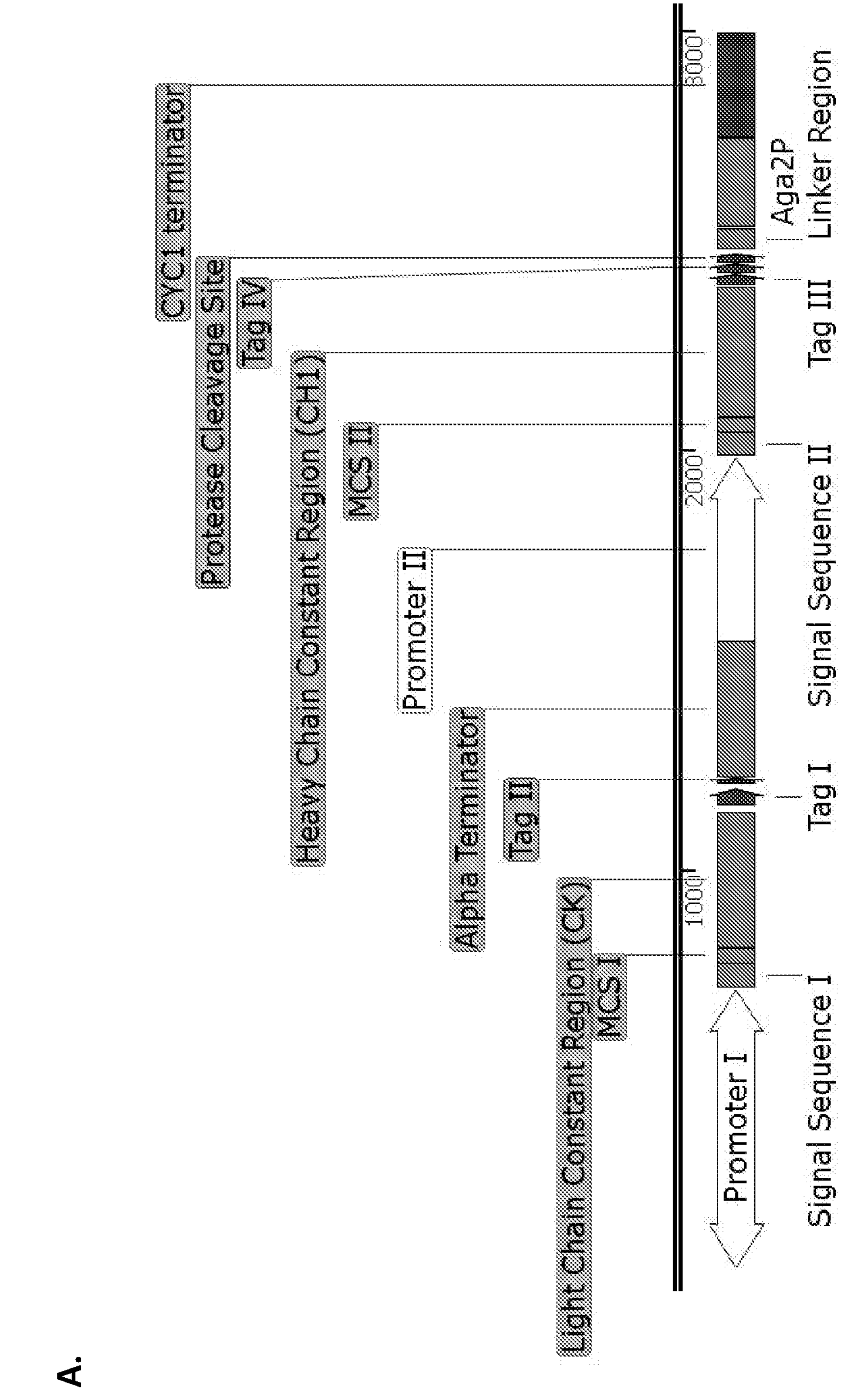
Figure 7:
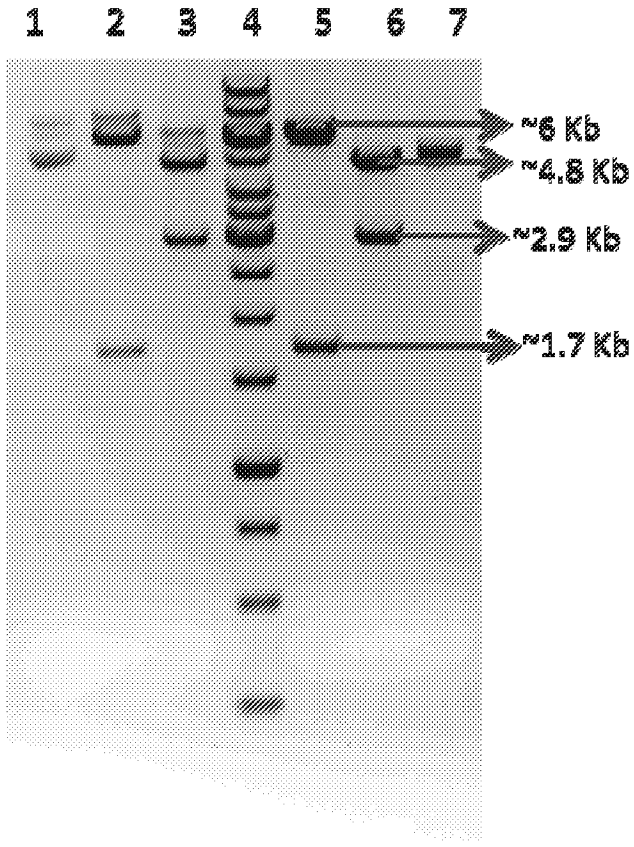
Figure 7:
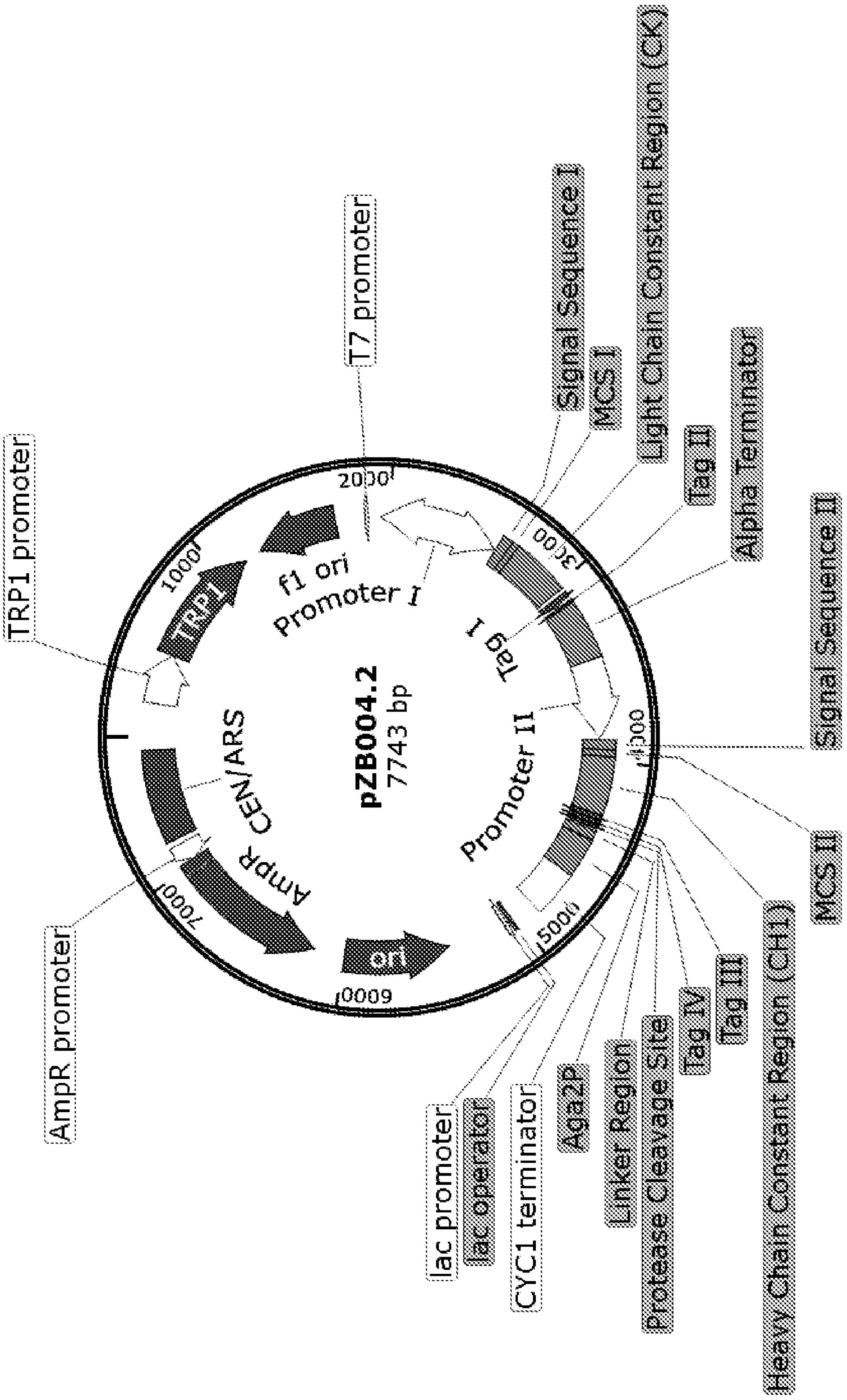

FIG. 7 illustrates generation of pZB004.2—yeast unidirectional vector with antibody kappa light chain constant region.

A) Schematic depiction of designed insert containing heavy chain CH1 domain and kappa light chain CK domain.

B) Analysis of independent clones from pZB004.2 construct using HindIII, SpeI & SacII enzymes in respective combinations.

C) Schematic depiction of pZB004.2 vector construct designed to clone antibody library genes comprising antibody variable heavy chain and light chain (kappa) in respective cloning sites.

Figure 8:
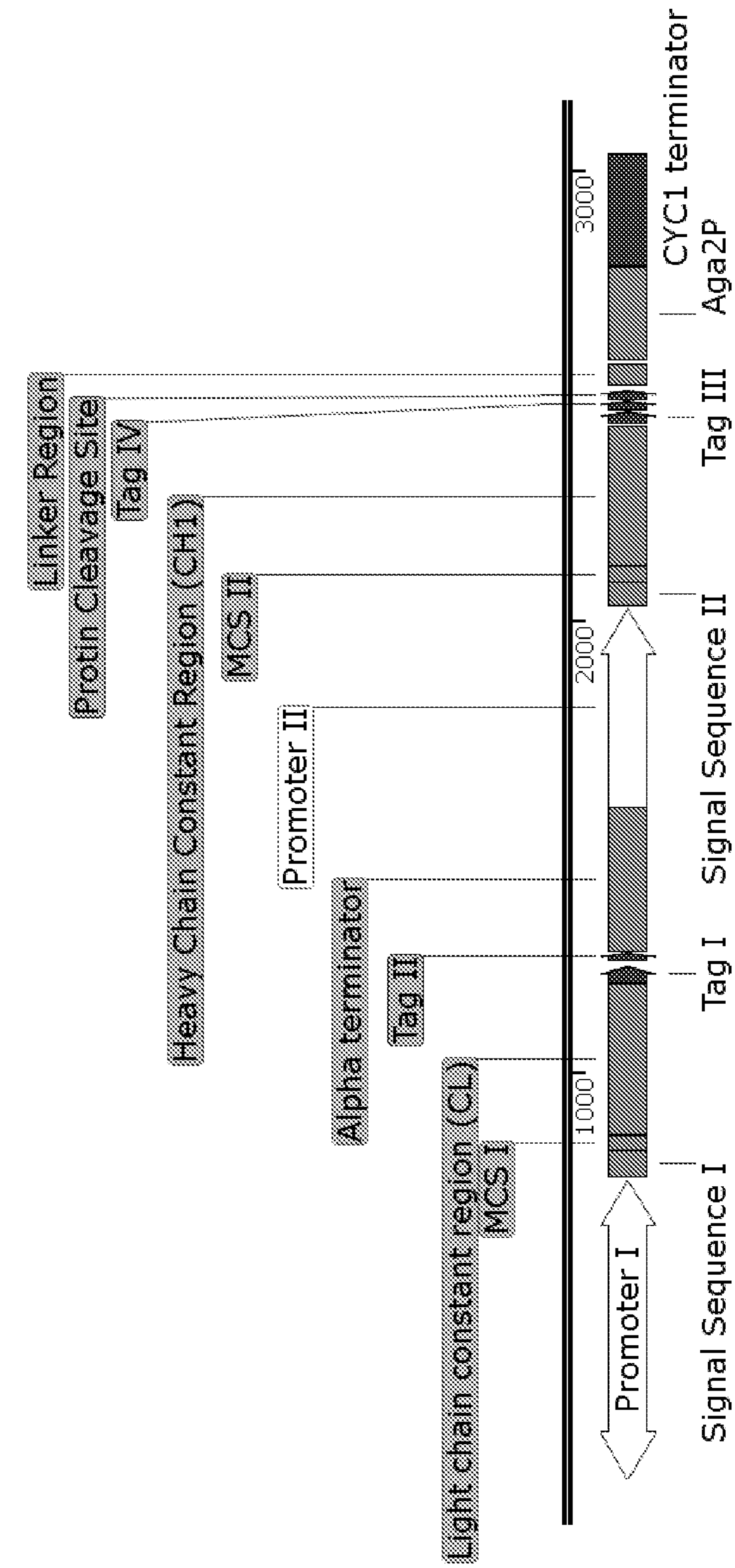
Figure 8:
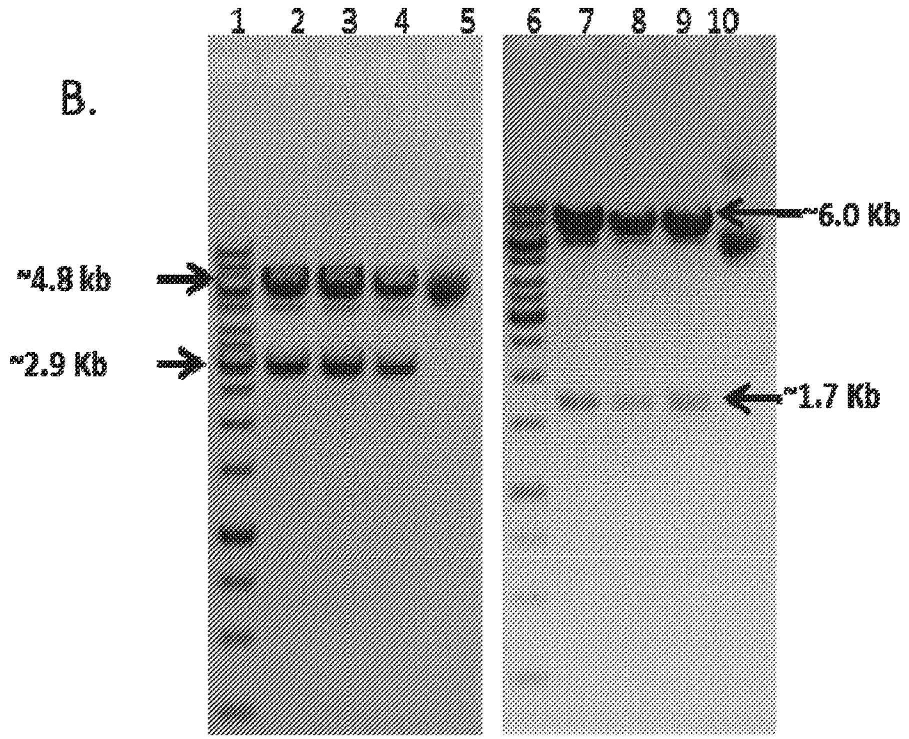
Figure 8:
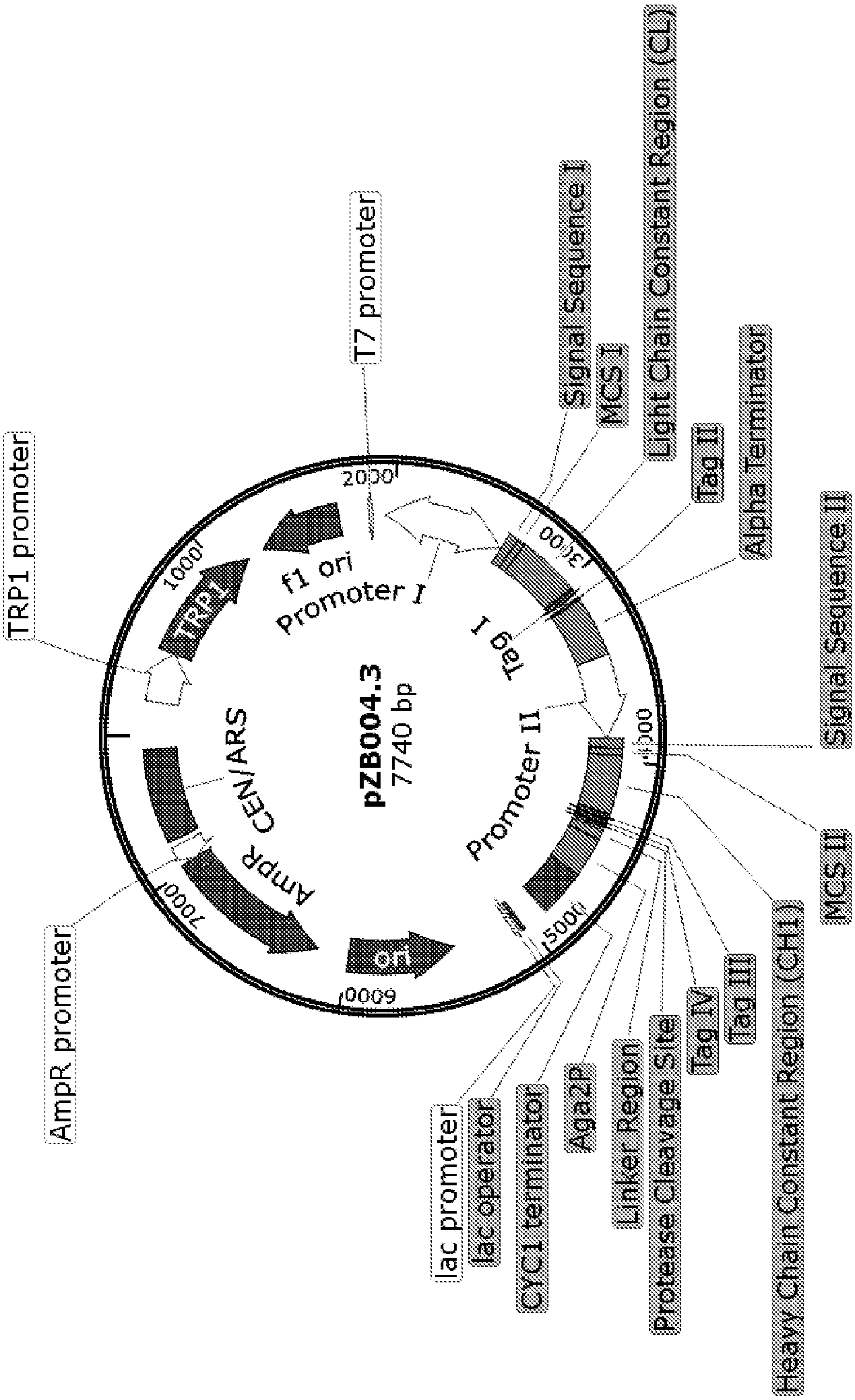

FIG. 8 illustrates generation of pZB004.3—yeast unidirectional vector with antibody lambda light chain constant region.

A) Schematic depiction of designed insert/expression cassette containing heavy chain CH1 domain and lambda light chain CL domain.

B) Analysis of independent clones from pZB004.3 construct using HindIII, SpeI & SacII enzymes in respective combinations.

C) Schematic depiction of pZB004.3 vector construct designed to clone antibody library genes comprising antibody variable heavy chain and light chain (lambda) in respective cloning sites.

Figure 9:
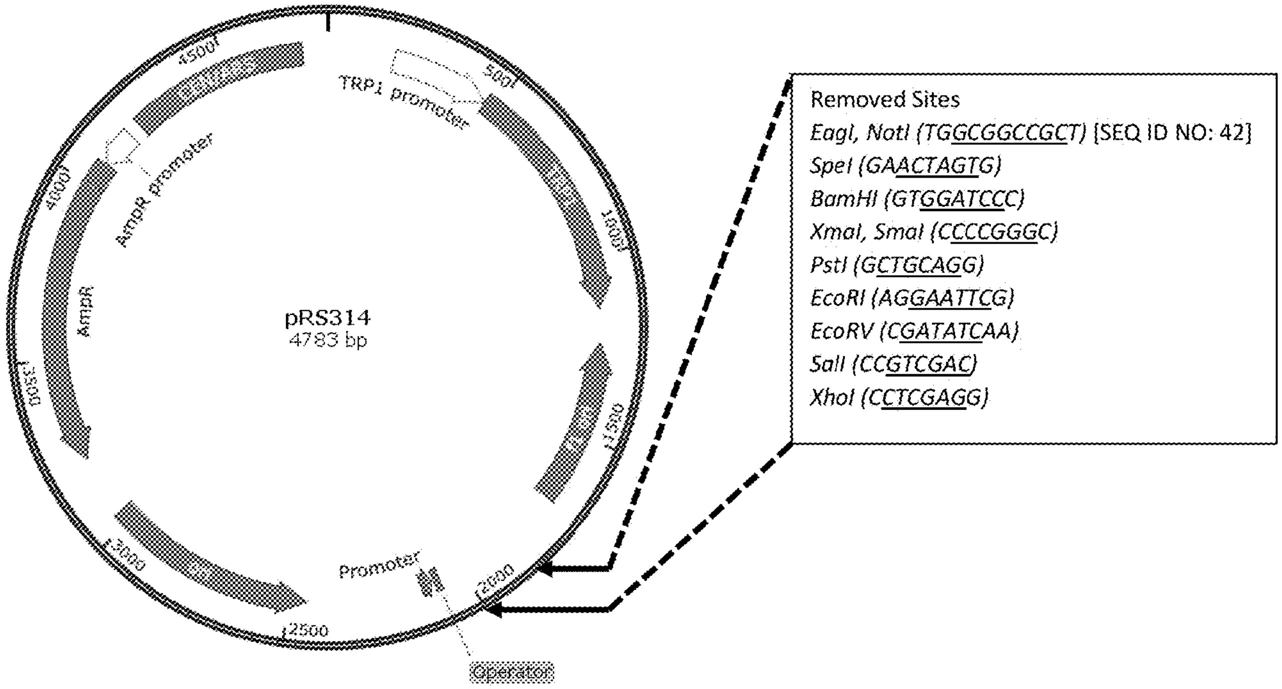

FIG. 9 illustrates modification of pRS314 vector. Multiple restriction sites were modified as described in the figure.

Figure 10:
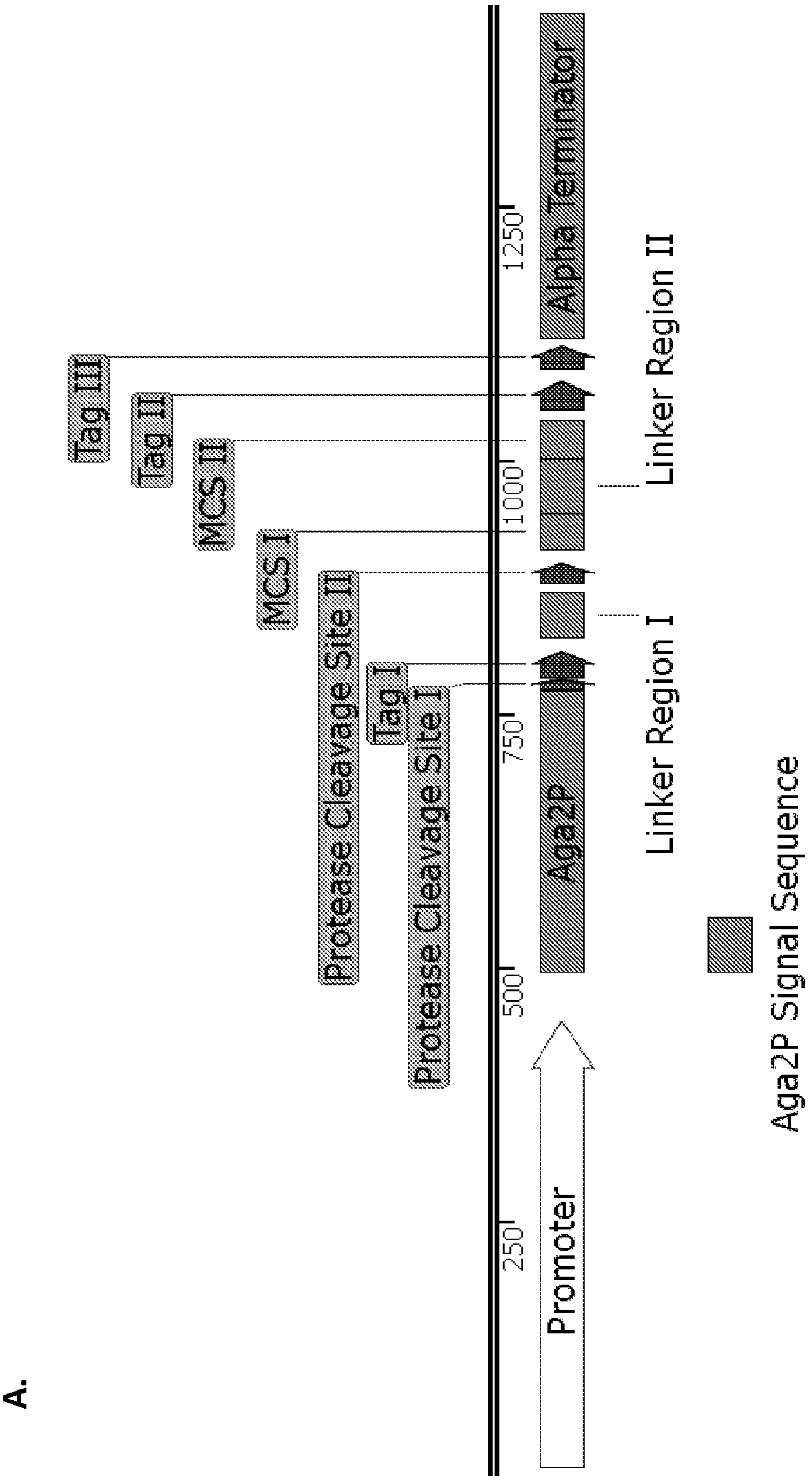
Figure 10:
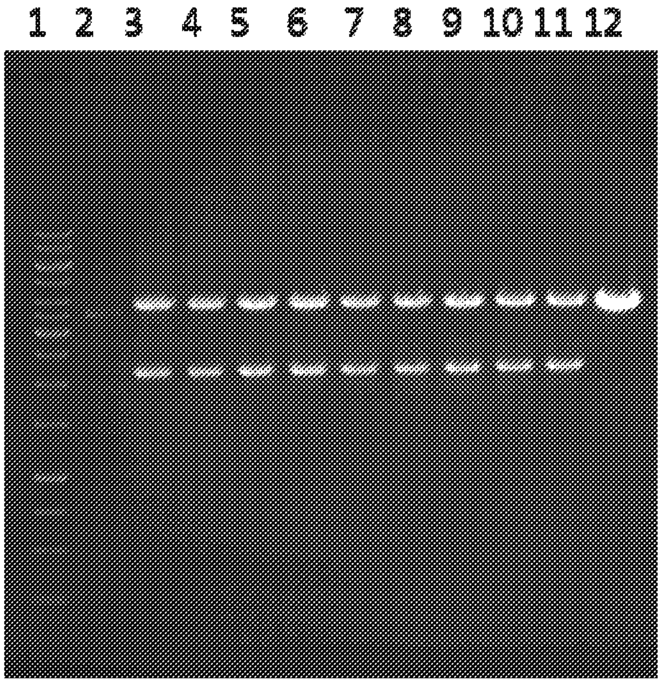
Figure 10:
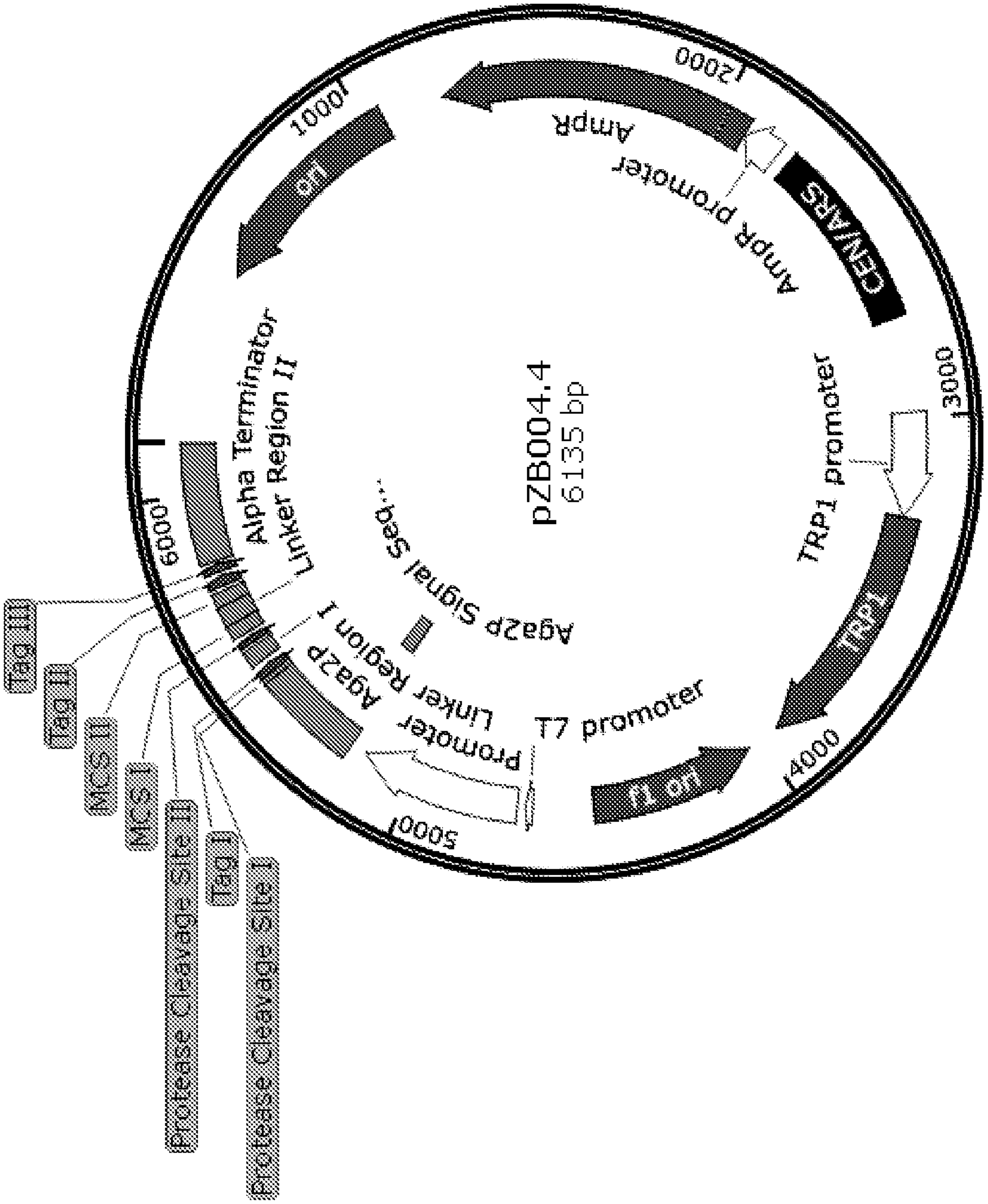

FIG. 10 illustrates generation of pZB004.4—yeast scFv vector.

A) Schematic depiction of designed insert/expression cassette containing cloning regions (MCS I and MCS II) for antibody heavy chain variable domain and antibody light chain variable domain respectively.

B) Analysis of independent clones from pZB004.4 construct using EcoRV & XhoI enzymes.

C) Schematic depiction of pZB004.4 vector construct designed to clone antibody library genes comprising antibody heavy chain variable region and light chain variable region at respective cloning sites.

Figure 11:
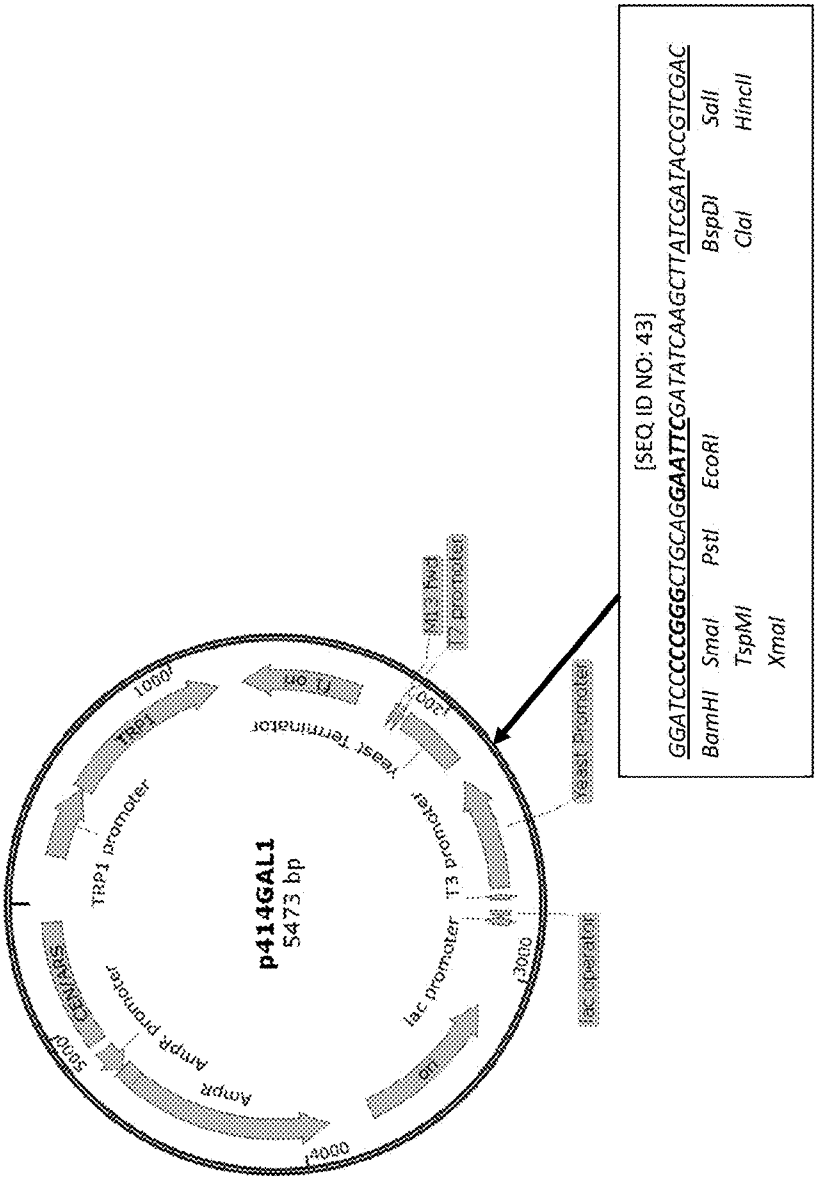

FIG. 11 illustrates modification of p414GAL1 vector. Multiple restriction sites were modified as described in the figure.

Figure 12:
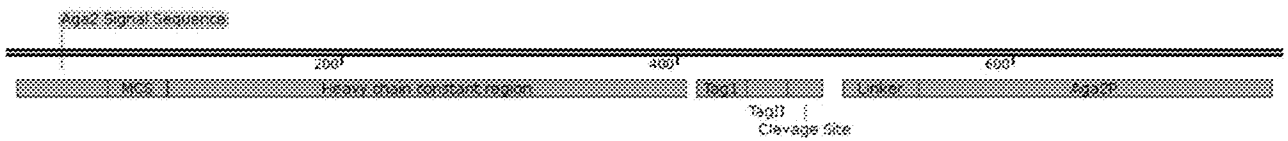
Figure 12:
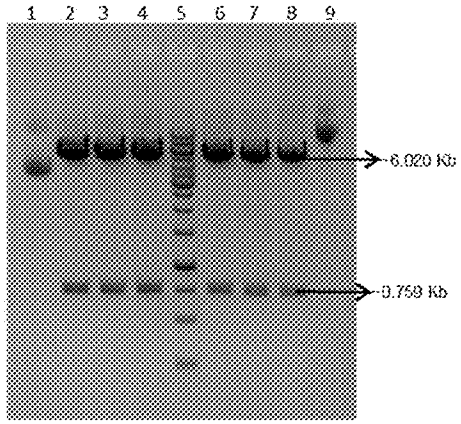
Figure 12:
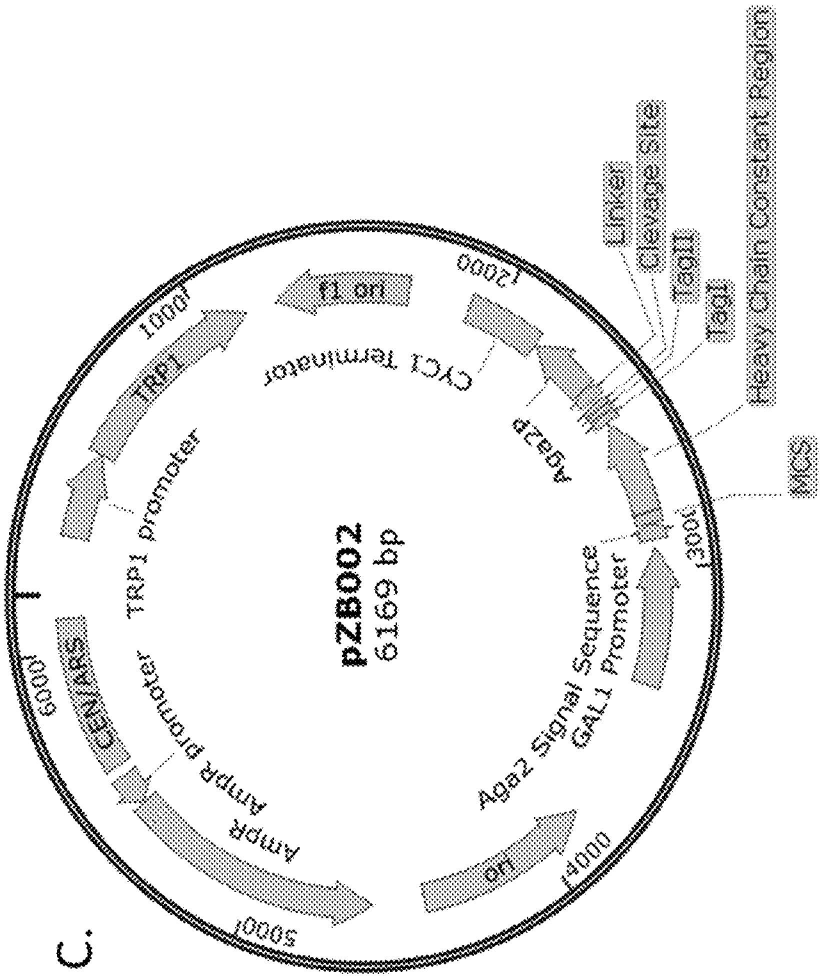

FIG. 12 illustrates generation of pZB002 construct yeast mating vector with heavy chain constant region A) Schematic depiction of designed insert containing heavy chain CH1 domain B) Analysis of independent clones from pZB002 construct using SpeI-HF and XhoI enzymes B) Schematic depiction of pZB002 construct designed to clone antibody library genes comprising antibody heavy chain in respective cloning site.

Figure 13:
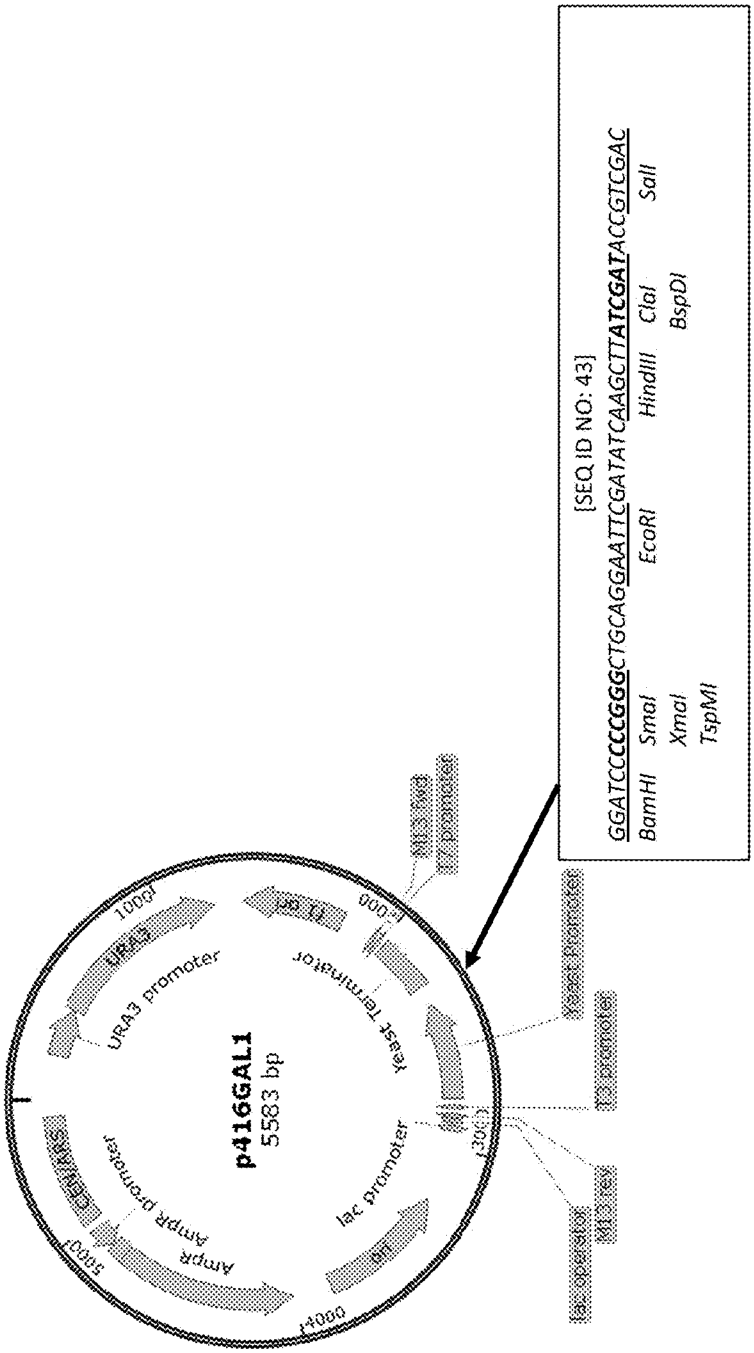

FIG. 13 illustrates modification of p416 GAL1 vector. Multiple restriction sites were modified as described in the figure.

Figure 14:
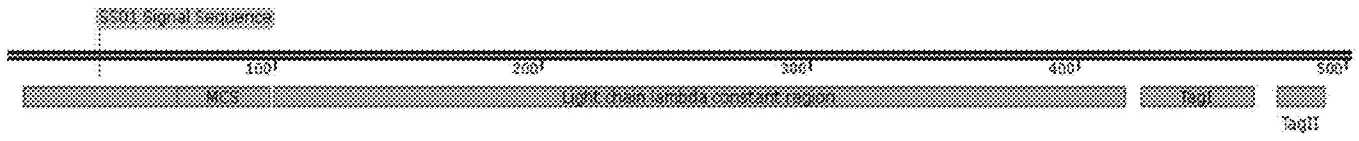
Figure 14:
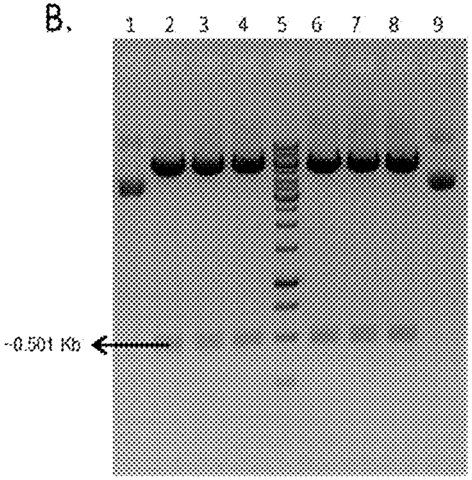
Figure 14:
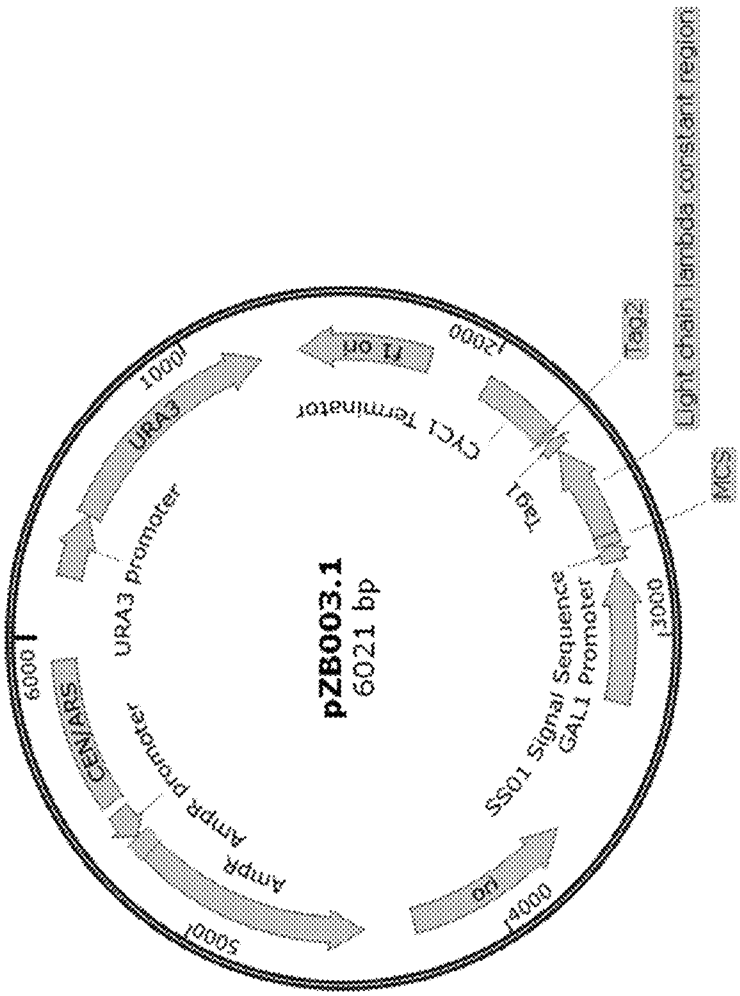
Figure 15:
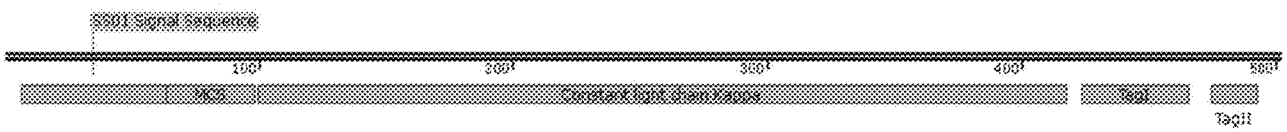
Figure 15:
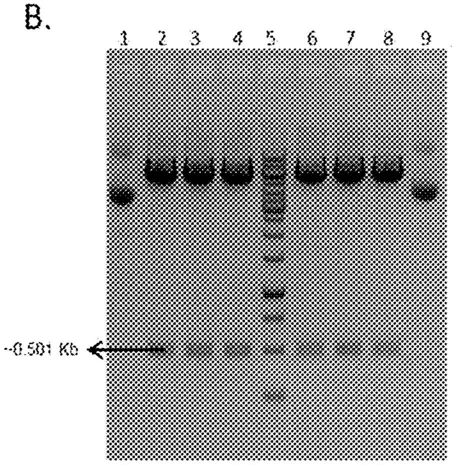
Figure 15:
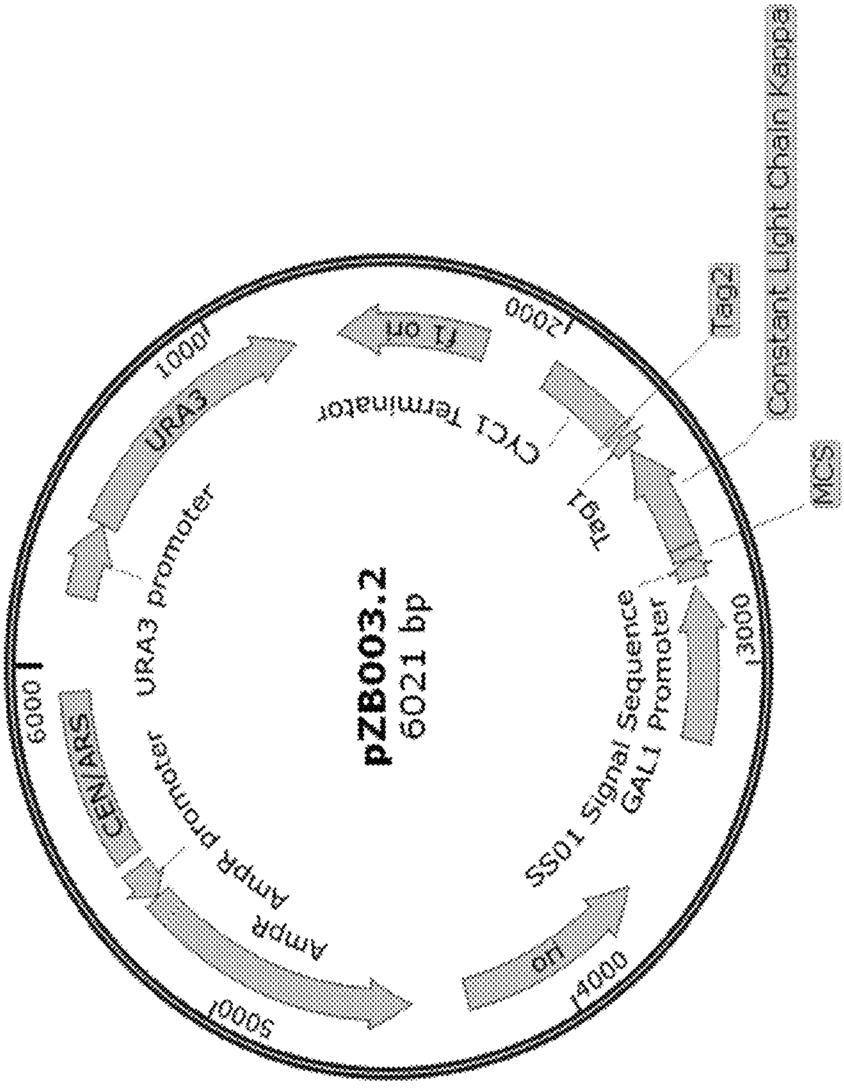
Figure 16:
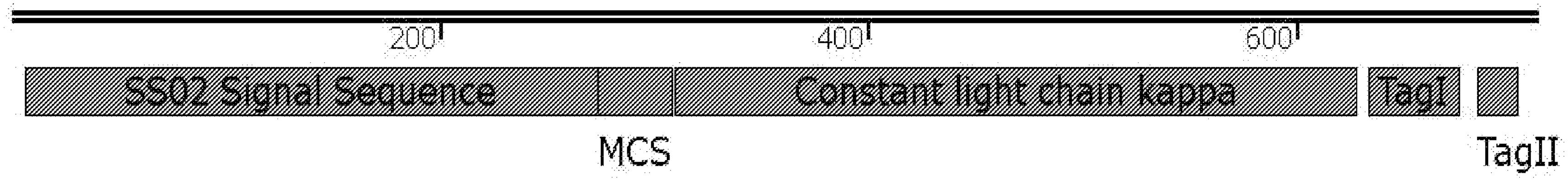
Figure 16:
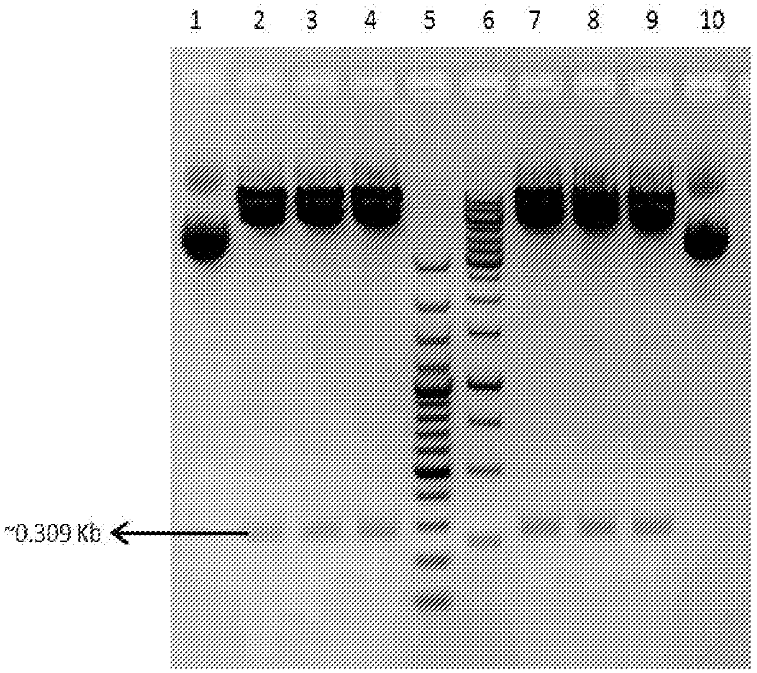
Figure 16:
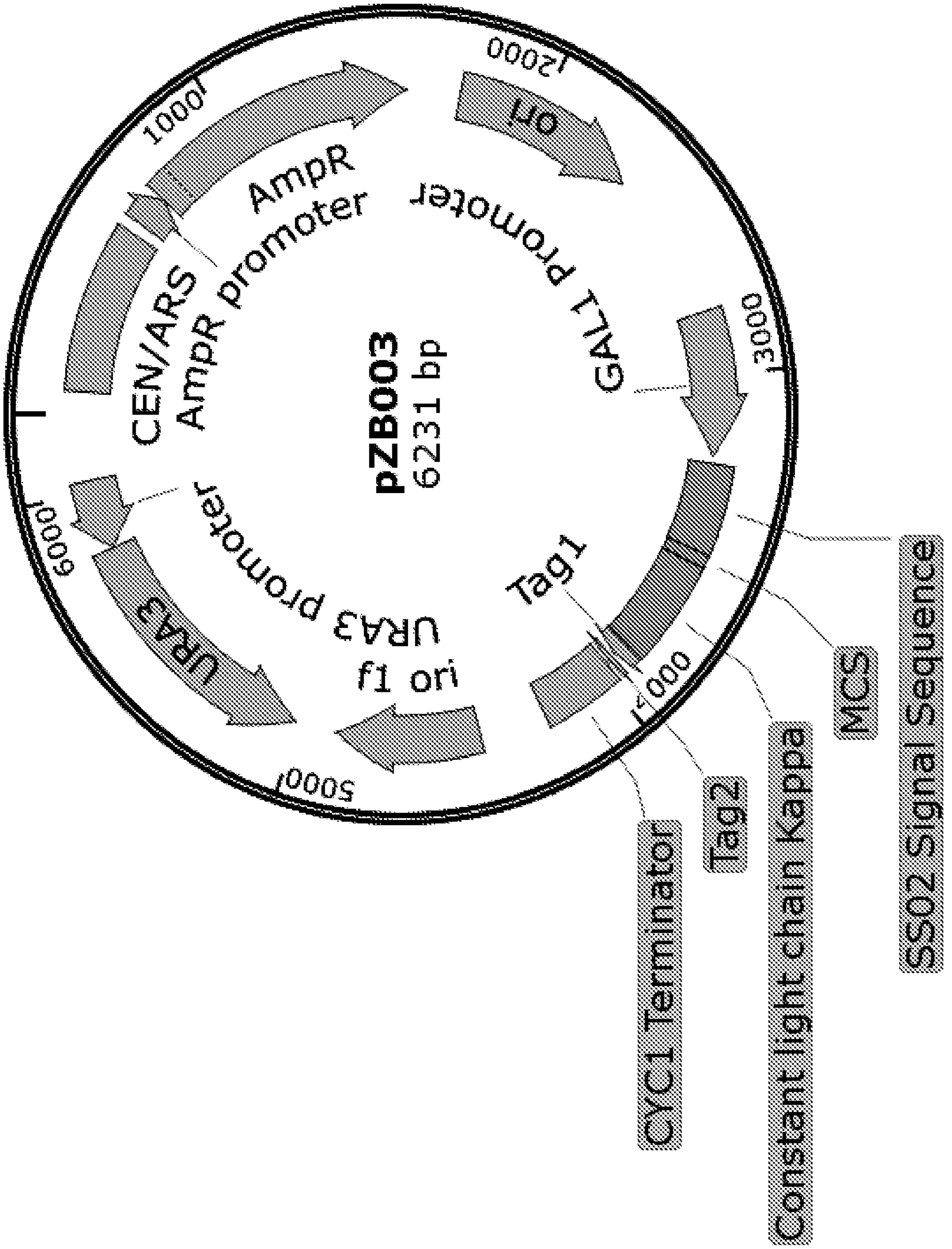

FIG. 14 illustrates generation of pZB003.1 construct yeast mating vector with Light chain lambda constant region A) Schematic depiction of designed insert containing Lambda light chain CL domain with SS01 signal sequence B) Analysis of independent clones from pZB003.1 construct using SpeI-HF and XhoI enzymes C) Schematic depiction of pZB003.1 construct designed to clone antibody library genes comprising antibody light chain (Lambda) in respective cloning site FIG. 15 illustrates generation of pZB003.2 construct yeast mating vector with Light chain kappa constant region A) Schematic depiction of designed insert containing Kappa light chain CK domain with SS01 signal sequence B) Analysis of independent clones from pZB003.2 construct using SpeI-HF and XhoI enzymes C) Schematic depiction of pZB003.2 construct designed to clone antibody library genes comprising antibody light chain (kappa) in respective cloning site FIG. 16 illustrates generation of pZB003 construct yeast mating vector with Light chain kappa constant region containing SS02 signal sequence A) Schematic depiction of designed insert containing Kappa light chain CK domain with SS02 signal sequence B) Analysis of independent clones from pZB003 construct using SpeI-HF and HindIII-HF enzymes C) Schematic depiction of pZB003 construct with SS02 signal sequence designed to clone antibody library genes comprising antibody light chain (kappa) at respective cloning site.

Figure 17:
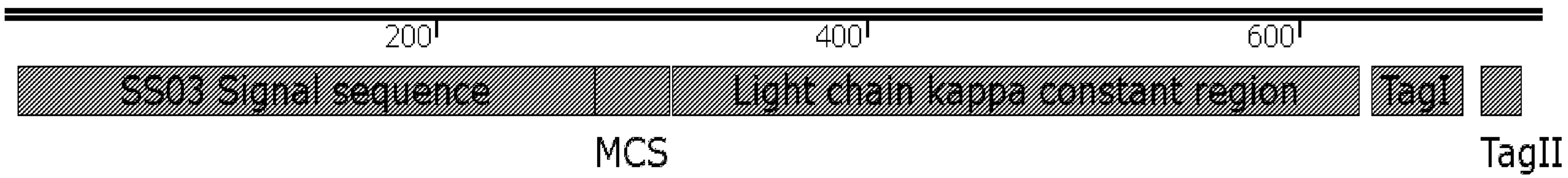
Figure 17:
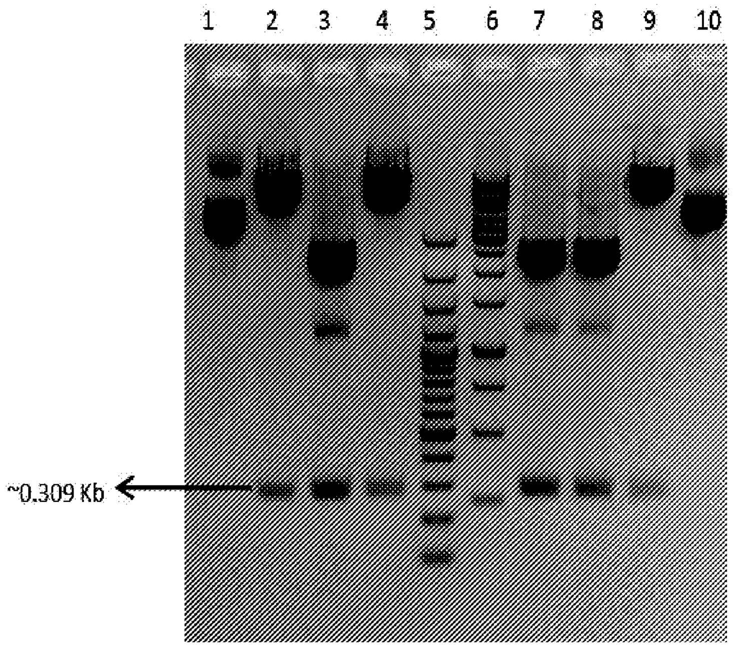
Figure 17:
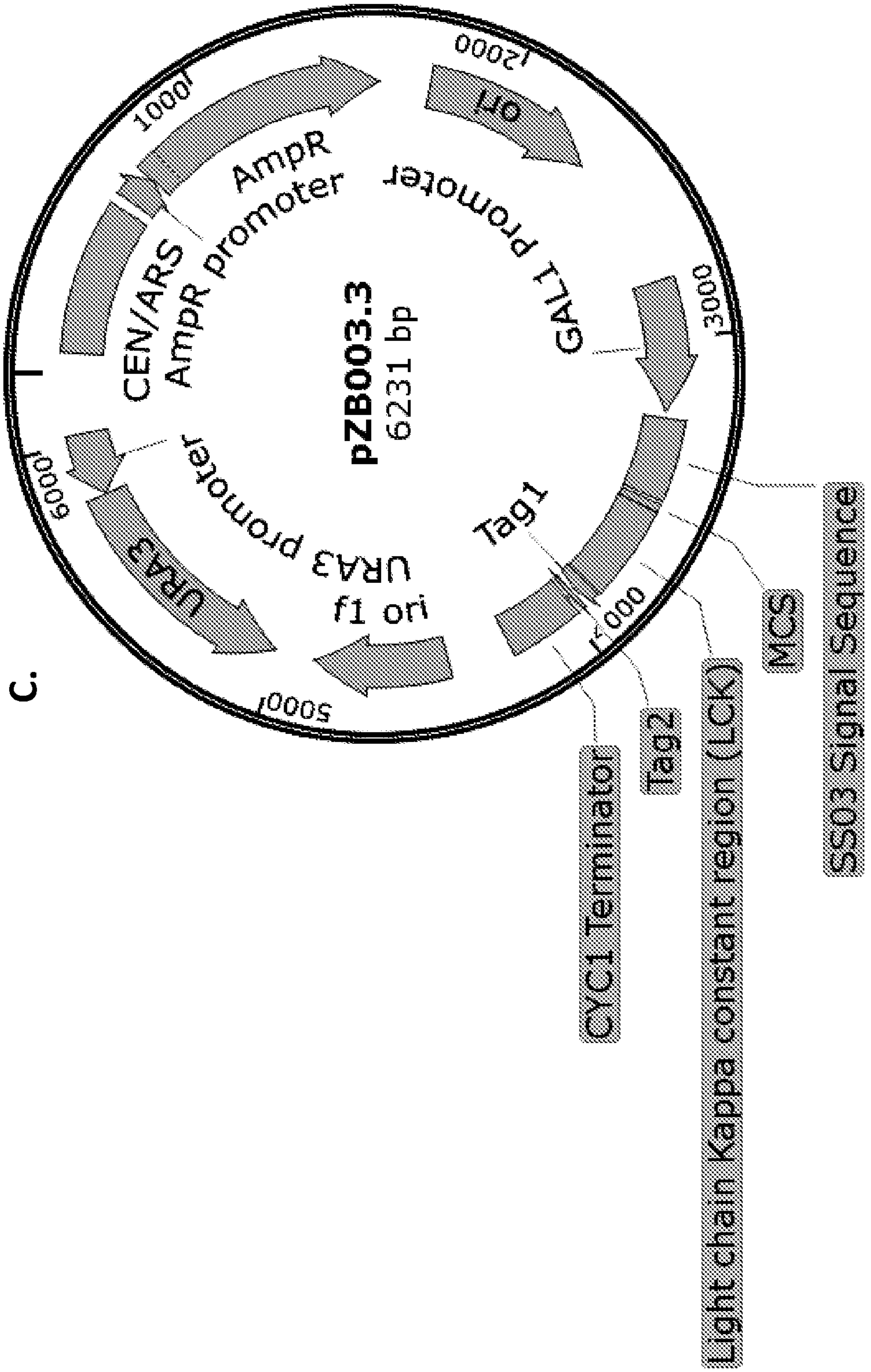

FIG. 17 illustrates generation of pZB003.3 construct yeast mating vector with Light chain kappa constant region containing SS03 signal sequence A) Schematic depiction of designed insert containing Kappa light chain CK domain with SS03 signal sequence B) Analysis of independent clones from pZB003.3 construct using SpeI-HF and HindII-HF enzymes C) Schematic depiction of pZB003.3 construct with SS03 signal sequence designed to clone antibody library genes comprising antibody light chain (kappa) at respective cloning site.

Figure 18:
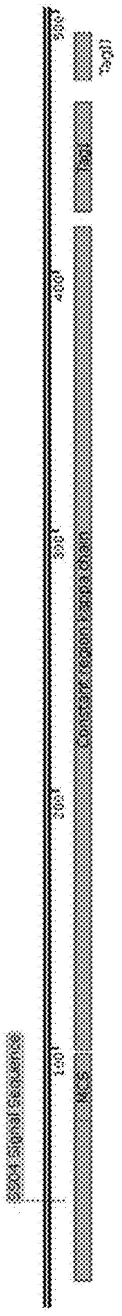
Figure 18:
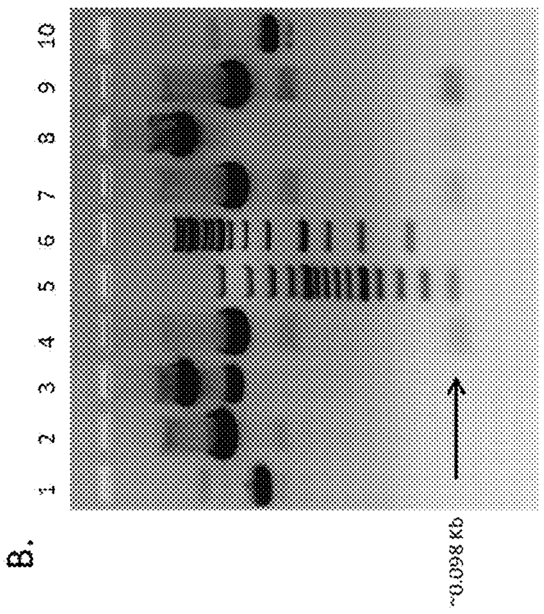
Figure 18:
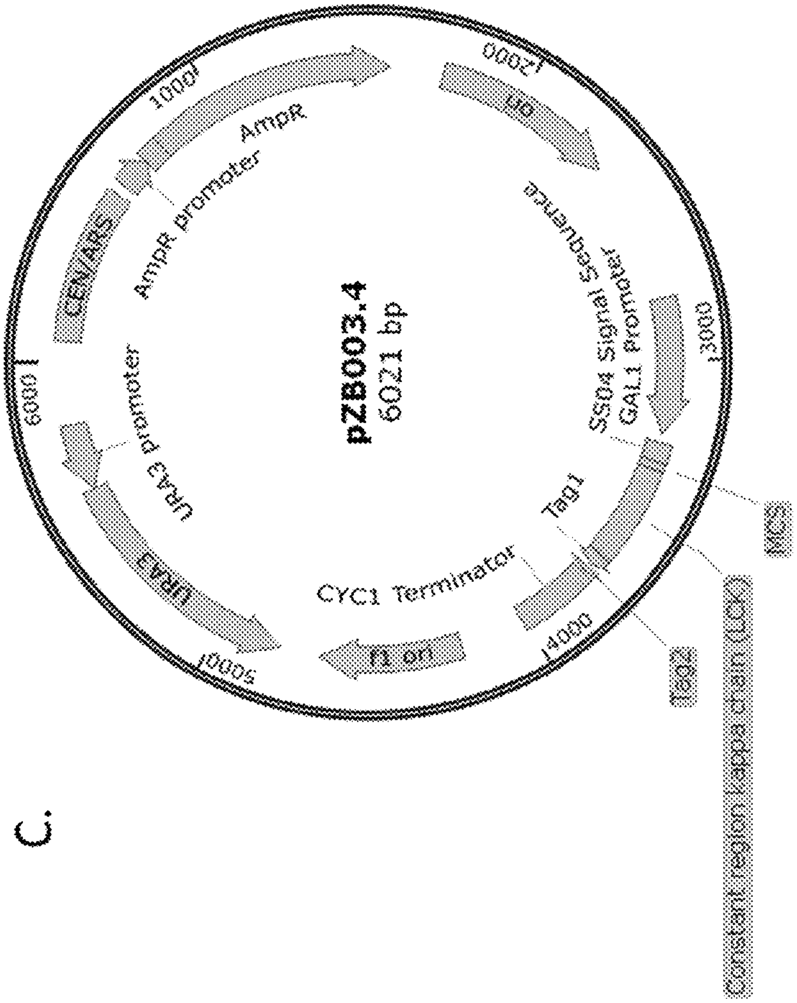

FIG. 18 illustrates generation of pZB003.4 construct yeast mating vector with Light chain kappa constant region containing SS04 signal sequence A) Schematic depiction of designed insert containing Kappa light chain CK domain with SS04 signal sequence B) Analysis of independent clones from pZB003.4 construct using SpeI-HF and HindIII-HF enzymes C) Schematic depiction of pZB003.4 construct with SS04 signal sequence designed to clone antibody library genes comprising antibody light chain (kappa) at respective cloning site.

Figure 19:
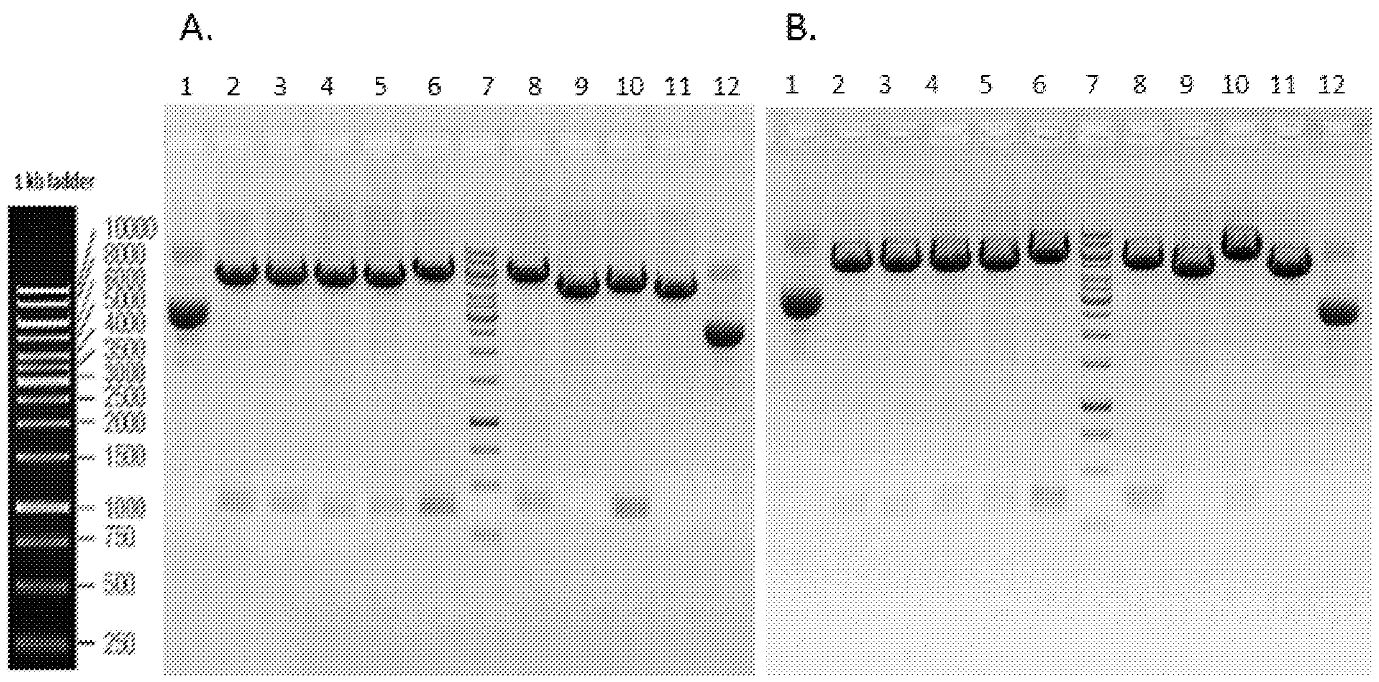

FIG. 19 illustrates restriction digestion analysis of antibody genes cloned in pZB001.

Figure 20:
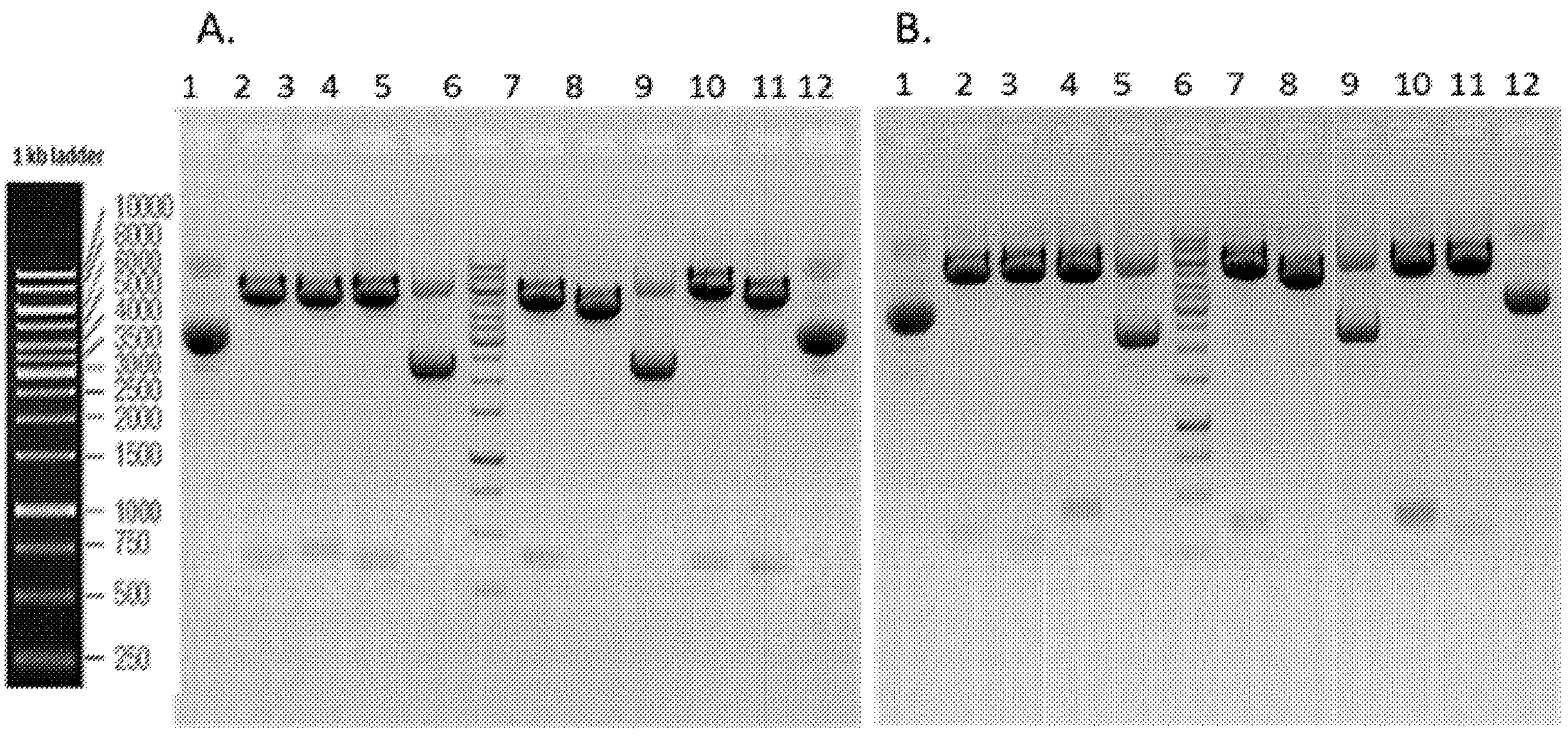

A. Digestion with HindIII and AscI to confirm antibody Light chain Kappa insert, B. Digestion with NcoI and XbaI to confirm antibody Heavy chain insert FIG. 20 illustrates restriction digestion analysis of antibody genes cloned in pZB001.1

Figure 21:
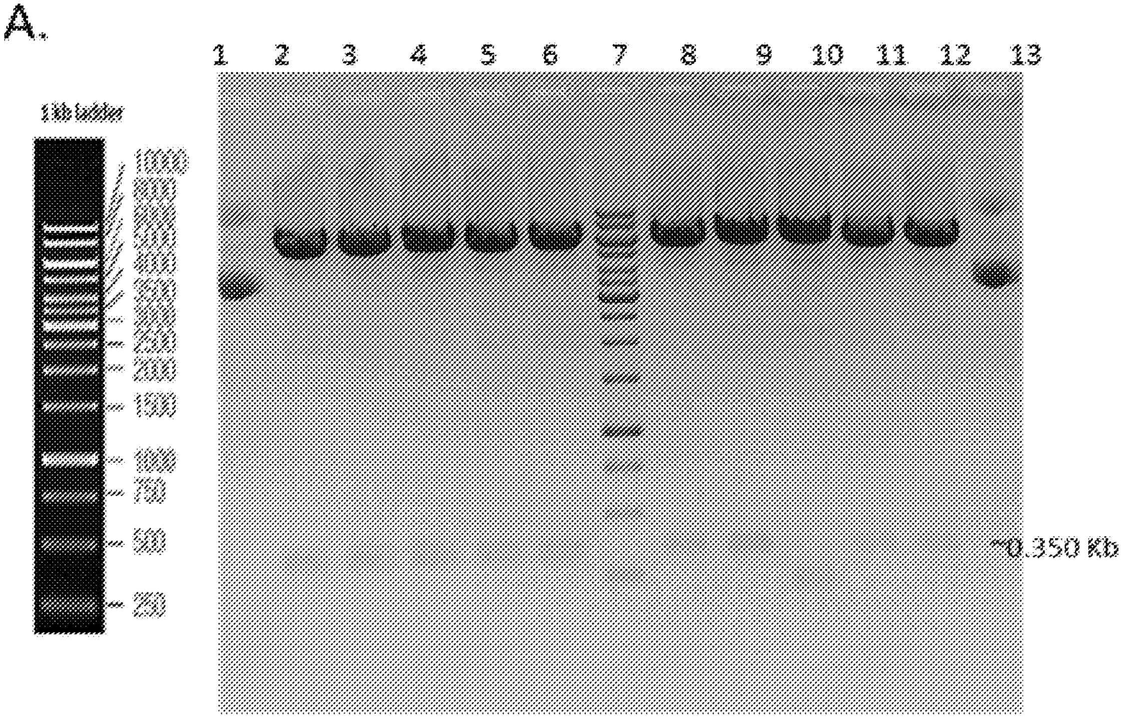
Figure 21:
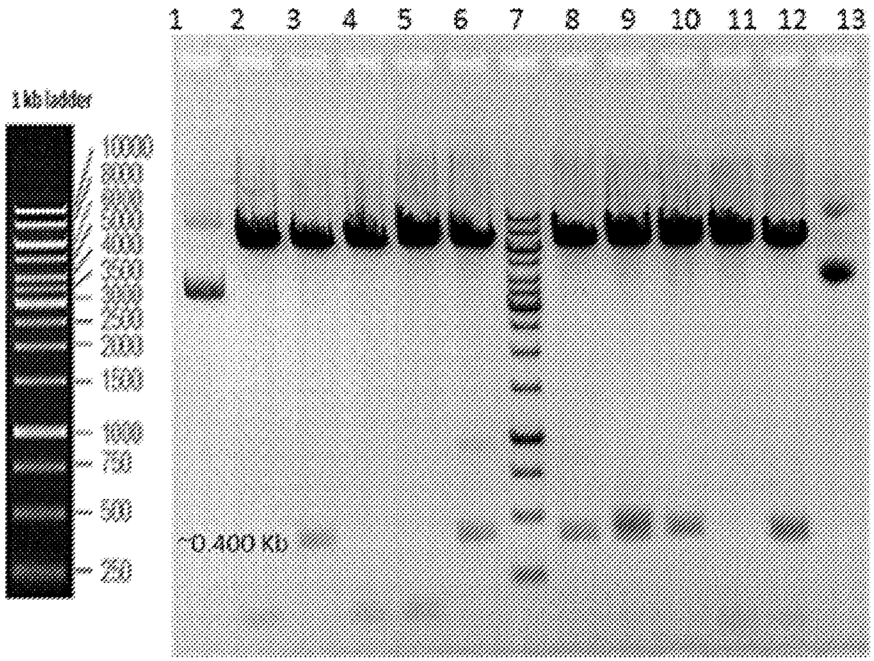

A. Digestion with HindIII and AscI to confirm antibody Light chain Lambda insert, B. Digestion with NcoI and XbaI to confirm antibody Heavy chain insert FIG. 21 illustrates restriction digestion analysis of antibody genes cloned in yeast mating type vectors.

A. Restriction enzyme digestion of antibody light chain genes (Kappa) cloned in pZB003.2 using HindIII & AscI.

B. Restriction enzyme digestion of antibody heavy chain genes cloned in pZB002 using NcoI & NotI.

Figure 22:
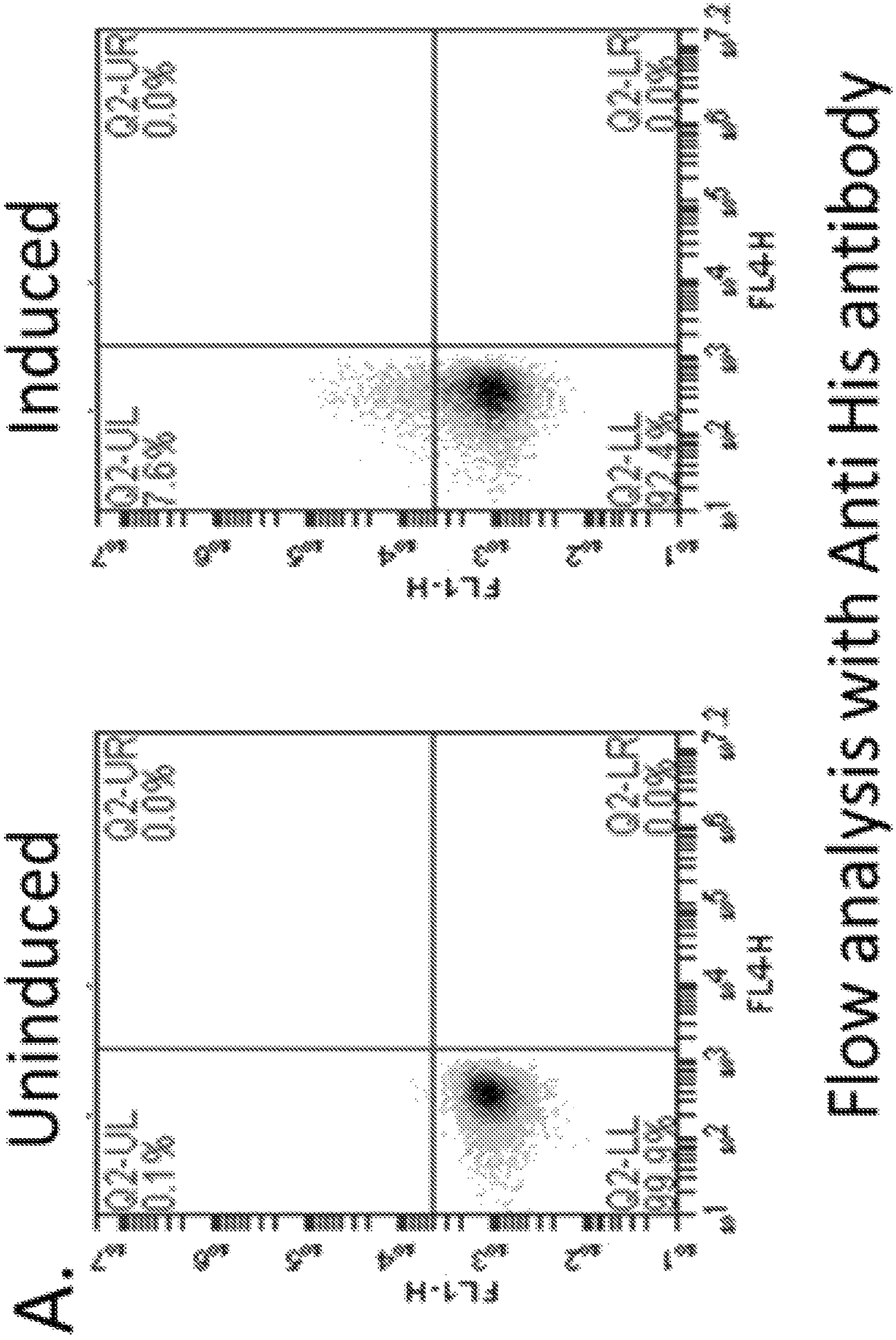
Figure 22:
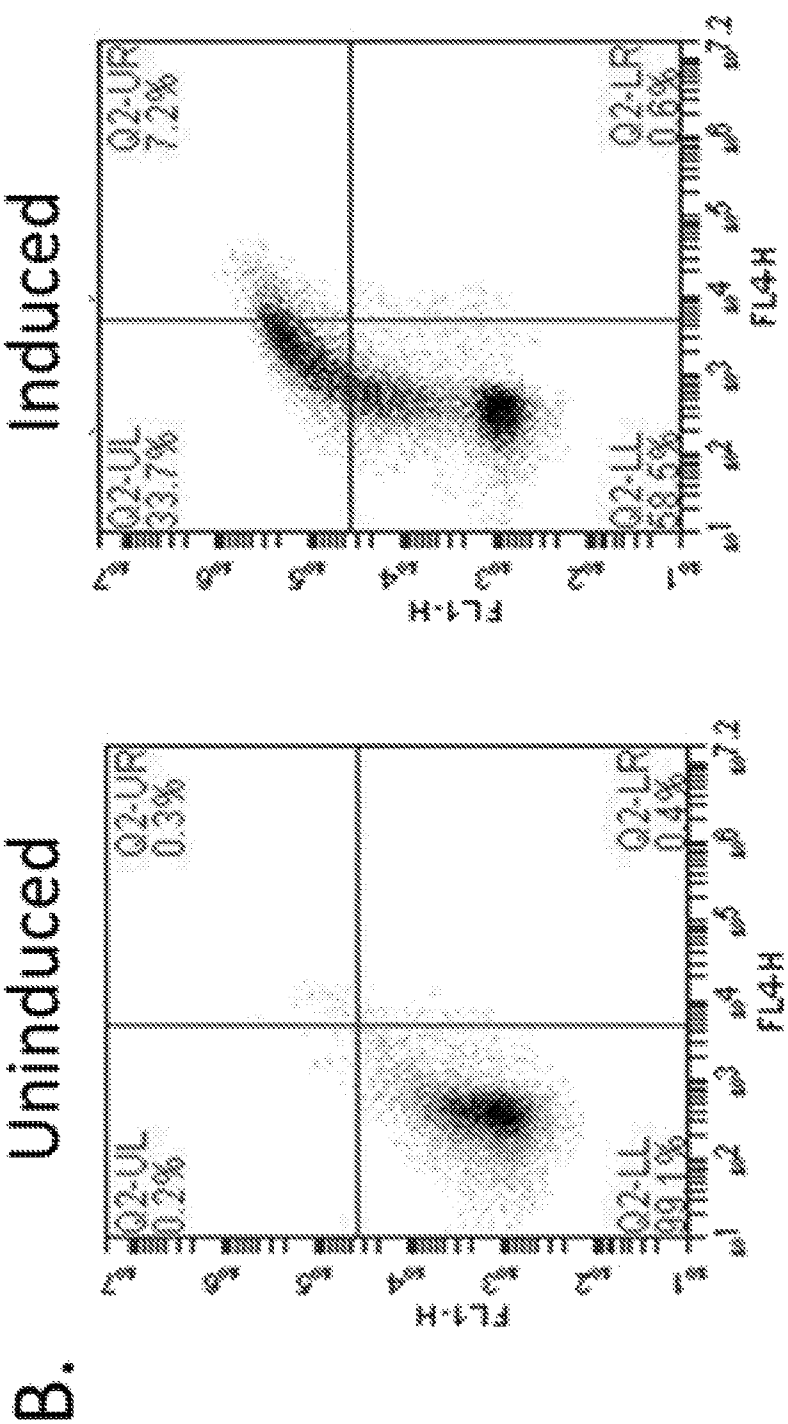

FIG. 22 illustrates flow cytometry analysis to confirm antibody Fab expression.

A. Flow analysis with Anti His antibody.

B. Flow analysis with Anti c-myc antibody and biotinylated Her2 Antigen.

Figure 23:
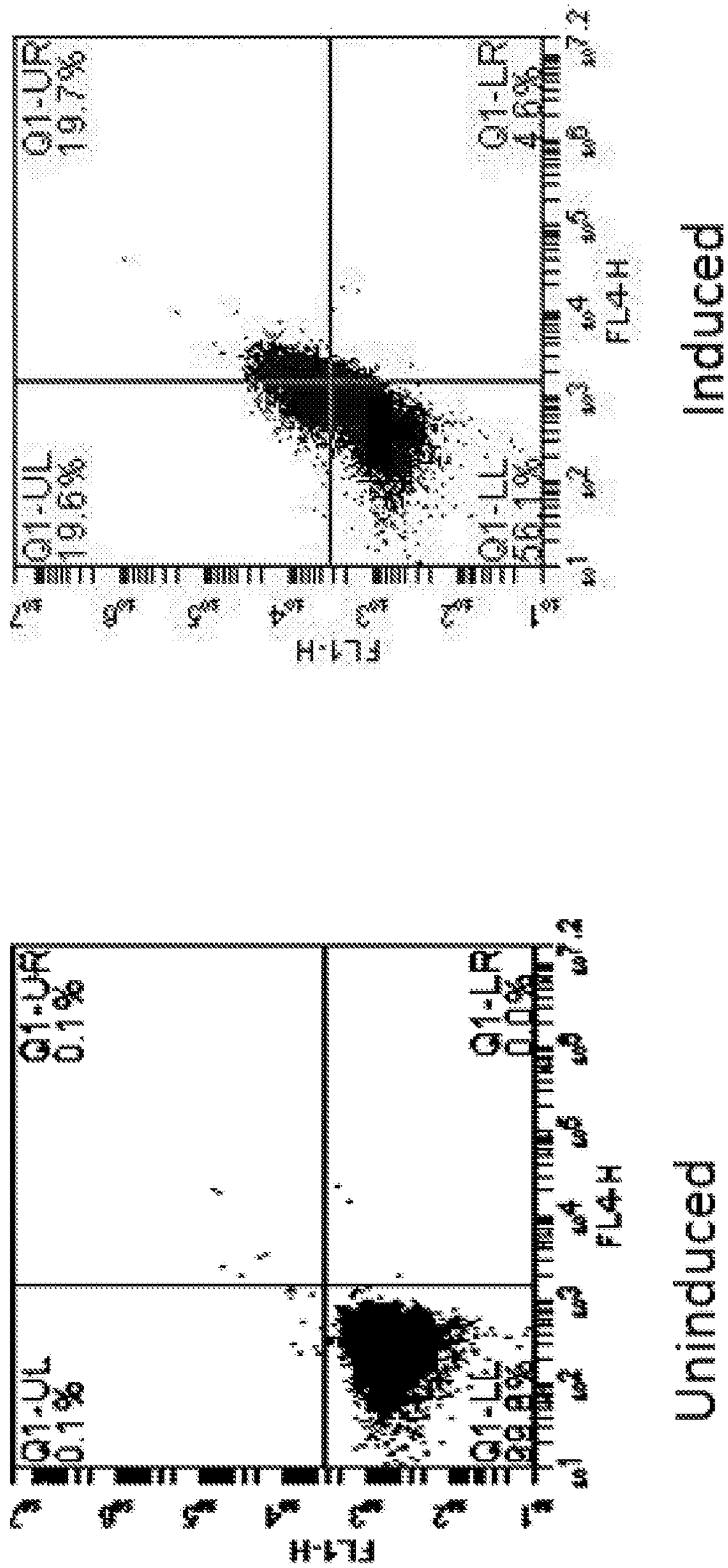

FIG. 23 illustrates flow cytometry analysis to confirm antibody ScFv expression on surface of yeast after transformation with pZB004.4 containing anti-Her2 ScFv sequences.

DETAILED DESCRIPTION OF THE DISCLOSURE

This section starts with a copy of our entire claim set.

The present disclosure relates to a vector construct designed to clone antibody or a fragment thereof, said vector construct containing an expression cassette which comprises:

at least one leader sequence, at least one cloning region for receiving a gene encoding a peptide or protein that selectively binds to a biologically active ligand, at least one nucleotide sequence encoding constant region immunoglobulin heavy chain or constant region immunoglobulin light chain, or fragments thereof, wherein said constant region comprises at least one mutation with respect to constant region of a native immunoglobulin or fragments thereof, and at least one recombinant tag sequence or selection coding nucleic acid sequence, wherein, the at least one cloning region of the expression cassette contains restriction sites selected from a group comprising NdeI, BglII, BmtI, HindIII, AscI, NcoI, XbaI, NheI, NotI and combinations thereof.

In an embodiment of the present disclosure, the vector construct as described above is designed to receive antibody or a fragment thereof from a phagemid comprising at least one cloning region or from a yeast vector comprising at least one cloning region, or, to transfer antibody or a fragment thereof to a yeast vector comprising at least one cloning region; and wherein the at least one cloning region of the expression cassette, the phagemid and the yeast vector comprises one or more common restriction sites selected from a group comprising NdeI, BglII, BmtI, HindIII, AscI, NcoI, XbaI, NheI, NotI and combinations thereof.

In another embodiment of the present disclosure, the expression cassette as described above comprises at least one terminator sequence lacking or comprising at upstream an enzyme cleavage site fused with a nucleotide sequence encoding a product that enables display of a peptide or protein on the surface of a protein expression system; or, a nucleotide sequence encoding phage coat protein comprising at upstream at least one ribosomal binding site.

In yet another embodiment of the present disclosure, the expression cassette as described above contains or lacks one or more promoter sequence, operator sequence or a combination thereof; the vector construct as described above is capable of expressing the antibody or a fragment thereof in a bacterial cell or a yeast cell; the restriction sites in the cloning region of the expression cassette as described above, the phagemid and the yeast vector is selected from combinations comprising HindIII and AscI; NdeI, BglII, HindIII and AscI; NcoI and XbaI; NcoI and NotI; XbaI, NheI and NotI; the promoter sequence is selected from a group comprising Gal 1, Gal 1/10 and a combination thereof; the leader sequence is selected from a group comprising pelB sequence, alpha leader sequence, Aga2P leader sequence, alpha mating factor 1 secretory signal sequence (SS01), engineered alpha factor (aapS4) signal sequence (SS02), engineered alpha factor (aap8) signal sequence (SS03), engineered alpha factor (aap8), signal sequence (SS04) and combinations thereof; the recombinant tag sequence or selection coding nucleic acid sequence is selected from a group comprising FLAG, c-Myc, V5, His and combinations thereof; the terminator sequence is selected from a group comprising alpha terminator, CYC1 terminator, and combinations thereof; the enzyme cleavage site is TEV protease cleavage site; the nucleotide sequence encoding a product that enables display of a peptide or protein on the surface of a protein expression system is Aga2P protein; and the phage coat protein is selected from a group comprising pill protein, G8P and a combination thereof.

In still another embodiment of the present disclosure, the nucleotide sequence encoding constant region immunoglobulin heavy chain or constant region immunoglobulin light chain having at least one mutation is selected from a group comprising first constant domain (CH1) of the immunoglobulin heavy chain or a fragment thereof, kappa constant region (Ck) of the immunoglobulin light chain or a fragment thereof and lambda constant region (CL) of the immunoglobulin light chain or a fragment thereof; and wherein the gene of the cloning region is selected from a group comprising kappa variable region (Vk) of the immunoglobulin light chain or a fragment thereof, lambda variable region (VL) of the immunoglobulin light chain or a fragment thereof and variable region of the immunoglobulin heavy chain (VH) or a fragment thereof.

In still another embodiment of the present disclosure, the vector construct as described above is selected from a group comprising yeast bicistronic bidirectional vector, yeast bicistronic unidirectional vector, yeast mating type heavy chain expressing vector, yeast mating type light chain expressing vector and phagemid; and wherein the expression cassette is selected from a group comprising:

(a) sequentially, a promoter sequence;

a leader sequence;

a cloning region capable of receiving a gene encoding variable region of the immunoglobulin heavy chain or a fragment thereof and comprising restriction sites selected from a group comprising NcoI, BmtI, NheI, NotI and combinations thereof;

a nucleotide sequence encoding first constant domain (CH1) of the IgG1 immunoglobulin heavy chain, wherein said constant domain comprises at least one mutation with respect to heavy chain constant domain of native immunoglobulin or fragment thereof;

recombinant tag sequences or selection coding nucleic acid sequences; and a terminator sequence comprising at upstream a protease cleavage site fused with a nucleotide sequence encoding Aga2P protein via a linker sequence, (b) sequentially, a promoter sequence;

a leader sequence;

a cloning region capable of receiving a gene encoding variable region of the immunoglobulin light chain or a fragment thereof and comprising restriction sites selected from a group comprising NdeI, BglII, HindIII, AscI and combinations thereof;

a nucleotide sequence encoding kappa constant region (Ck) of the immunoglobulin light chain or lambda constant region (CL) of the immunoglobulin light chain, or fragments thereof, wherein said constant region comprises at least one mutation with respect to light chain constant region of a native immunoglobulin or fragment thereof;

recombinant tag sequences or selection coding nucleic acid sequences; and a terminator sequence, (c) sequentially, a first terminator sequence;

a first set of recombinant tag sequences or selection coding nucleic acid sequences;

a first nucleotide sequence encoding kappa constant region (Ck) of the immunoglobulin light chain or lambda constant region (CL) of the immunoglobulin light chain, or fragments thereof, wherein said constant region comprises at least one mutation with respect to light chain constant region of a native immunoglobulin or fragment thereof;

a first cloning region capable of receiving a gene encoding variable region of the immunoglobulin light chain or a fragment thereof and comprising restriction sites selected from a group comprising NdeI, BglII, HindIII, AscI and combinations thereof;

a first leader sequence, a promoter sequence;

a second leader sequence;

a second cloning region capable of receiving a gene encoding variable region of the immunoglobulin heavy chain or a fragment thereof and comprising restriction sites selected from a group comprising NcoI, XbaI, NheI, NotI and combinations thereof;

a second nucleotide sequence encoding first constant domain (CH1) of the IgG1 immunoglobulin heavy chain, wherein said constant region comprises at least one mutation with respect to heavy chain constant region of a native immunoglobulin or fragment thereof;

a second set of recombinant tag sequences or selection coding nucleic acid sequences; and a second terminator sequence comprising at upstream a protease cleavage site fused with a nucleotide sequence encoding Aga2P protein via a linker sequence, (d) sequentially, a first promoter sequence;

a first leader sequence.

a first cloning region capable of receiving a gene encoding variable region of the immunoglobulin light chain or a fragment thereof and comprising restriction sites selected from a group comprising NdeI, BglII, HindIII, AscI and combinations thereof;

a first nucleotide sequence encoding kappa constant region (Ck) of the immunoglobulin light chain or lambda constant region (CL) of the immunoglobulin light chain, or fragments thereof, wherein said constant domain comprises at least one mutation with respect to light chain constant domain of native immunoglobulin or fragment thereof;

a first set of recombinant tag sequences or selection coding nucleic acid sequences;

a first terminator sequence;

a second promoter sequence;

a second leader sequence;

a second cloning region capable of receiving a gene encoding variable region of the immunoglobulin heavy chain or a fragment thereof and comprising restriction sites selected from a group comprising NcoI, XbaI NheI, NotI and combinations thereof;

a second nucleotide sequence encoding first constant domain (CH1) of the IgG1 immunoglobulin heavy chain, wherein said constant domain comprises at least one mutation with respect to heavy chain constant domain of native immunoglobulin or fragment thereof;

a second set of recombinant tag sequences or selection coding nucleic acid sequences; and a second terminator sequence comprising at upstream a protease cleavage site fused with a nucleotide sequence encoding Aga2P protein via a linker sequence, and (e) sequentially, a promoter sequence;

a operator sequence;

a first ribosomal binding site;

a first leader sequence;

a first cloning region capable of receiving a gene encoding variable region of the immunoglobulin light chain or a fragment thereof and comprising restriction sites selected from a group comprising NdeI, BglII, HindIII, AscI and combinations thereof;

a first nucleotide sequence encoding kappa constant region (Ck) of the immunoglobulin light chain or lambda constant region (CL) of the immunoglobulin light chain, or fragments thereof, wherein said constant domain comprises at least one mutation with respect to light chain constant domain of native immunoglobulin or fragment thereof;

a second ribosomal binding site;

a second leader sequence;

a second cloning region capable of receiving a gene encoding variable region of the immunoglobulin heavy chain or a fragment thereof and comprising restriction sites selected from a group comprising NcoI, XbaI NheI, NotI and combinations thereof;

a second nucleotide sequence encoding first constant domain (CH1) of the IgG1 immunoglobulin heavy chain, wherein said constant domain comprises at least one mutation with respect to heavy chain constant domain of native immunoglobulin or fragment thereof;

a recombinant tag sequence(s) or selection coding nucleic acid sequence(s); and a nucleotide sequence encoding phage coat protein.

The present disclosure further relates to a vector construct designed to clone antibody or a fragment thereof, or, to transfer or receive an antibody or a fragment thereof from the vector construct as claimed in claim 1, said vector construct containing an expression cassette which comprises:

a promoter sequence, a leader sequence, a nucleotide sequence encoding a product that enables display of a peptide or protein on the surface of a protein expression system, a first enzyme cleavage site, a first recombinant tag sequence or selection coding nucleic acid sequence, a first linker sequence, a second enzyme cleavage site, a first cloning region operably linked to a second cloning region in presence of a second linker sequence, wherein the cloning regions receive gene encoding a peptide or protein that selectively binds to a biologically active ligand, a second recombinant tag sequence(s) or selection coding nucleic acid sequence(s), and a terminator sequence, wherein, the first cloning region or the second cloning region of the expression cassette contains restriction sites selected from a group comprising NdeI, BglII, HindIII, AscI, NcoI, XbaI, NheI, NotI and combinations thereof. In an embodiment of the present disclosure, this vector construct is a scFv vector and is capable of expressing single-chain variable fragment (scFv) or a fragment thereof in yeast cell; wherein the cloning region of the expression cassette of said scFv vector and the vector construct further as described above comprises one or more common restriction sites selected from a group comprising NdeI, BglII, HindIII AscI, NcoI, XbaI, NheI, NotI and combinations thereof; and wherein the promoter sequence is Gal 1; the nucleotide sequence encoding a product that enables display of a peptide or protein on the surface of a protein expression system is Aga2P protein; the enzyme cleavage sites are protease cleavage sites selected from a group comprising Factor Xa cleavage site, TEV protease cleavage site and a combination thereof; the recombinant tag sequences or selection coding nucleic acid sequences are selected from a group comprising HA tag, c-Myc tag, FLAG and combinations thereof; the linker sequence is G4S sequence; the gene of the first cloning region is selected from a group comprising kappa variable region (Vk) of the immunoglobulin light chain or a fragment thereof, lambda variable region (VL) of the immunoglobulin light chain or a fragment thereof and a combination thereof; the gene of the second cloning region is variable region of the immunoglobulin heavy chain (VH) or a fragment thereof; and the terminator sequence is selected from a group comprising alpha terminator, CYC1 terminator and a combination thereof.

In another embodiment of the present disclosure, the vector constructs as described above have a nucleic acid sequence selected from a group comprising SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24 and SEQ ID No. 26.

In yet another embodiment of the present disclosure, the vector constructs as described above further comprises regions selected from a group comprising origin of replication (Ori), antibiotic resistant marker, f1 origin of replication, promoter and combinations thereof and combinations thereof; and wherein the vector constructs are capable of expressing or displaying an antibody or a fragment thereof in a prokaryotic expression system, yeast expression system or a combination thereof.

In still another embodiment of the present disclosure, the CH1 region has a nucleic acid sequence of SEQ ID No. 27, the Ck region has a nucleic acid sequence of SEQ ID No. 28, and the CL region has a nucleic acid sequence of SEQ ID No. 29; and wherein the Vk, VL and VH sequences are derived from naïve antibody repertoire, synthetic antibody repertoire, or a combination thereof.

The present disclosure further relates to a method of preparing the vector construct as described above, said method comprising steps of: a) synthesis of the expression cassette, b) linearization of a destination vector, and c) inserting the expression cassette into the linearized destination vector to obtain the vector construct.

In an embodiment of the present disclosure, the method of preparing the vector construct as described above comprises confirming error-free vector clones by sequencing technique; the destination vector is selected from a group comprising pADL23c, pRS314, p414Gal1, p416Gal1 and combinations thereof; the linearization is carried out by digestion with restriction enzyme(s); and inserting the expression cassette into the linearized destination vector is carried out by techniques selected from a group comprising homologous recombination, restriction digestion followed by ligation and a combination thereof.

The present disclosure further relates to a method of preparing library of vector constructs, said method comprising steps of: a) preparing the vector construct by the method as described above, b) cloning nucleotide sequences encoding for regions selected from a group comprising kappa variable region (Vk) of the immunoglobulin light chain, lambda variable region (VL) of the immunoglobulin light chain or fragments thereof, variable region of the immunoglobulin heavy chain or a fragment thereof (VH) and combinations thereof, into the cloning region of the vector construct to obtain the library, or, transferring the nucleotide sequences encoding regions selected from a group comprising kappa variable region (Vk) of the immunoglobulin light chain, lambda variable region (VL) of the immunoglobulin light chain or fragments thereof, variable region of the immunoglobulin heavy chain or a fragment thereof (VH) and combinations thereof, from the cloning region of one vector construct to the cloning region of another vector construct to obtain the library.

In an embodiment of the above method of preparing library of vector constructs, the vector construct is selected from a group comprising phagemid, yeast mating type heavy chain expressing vector, yeast mating type light chain expressing vector, yeast bicistronic bidirectional vector, yeast bicistronic unidirectional vector and single-chain variable fragment (scFv) vector; the Vk, VL and VH regions are derived from naïve antibody, synthetic antibody or a combination thereof; the library of vector constructs is a synthetic library, naïve library or a combination thereof; and wherein the transfer of the nucleotide sequence is carried out between the phagemid vector construct to the yeast vector construct or between yeast vector constructs.

The present disclosure further relates to a method of screening and identifying antibody or a fragment thereof having desired functional characteristic(s), comprising steps of: (a) preparing the library of vector constructs by the method as described above and transforming said vector constructs into bacterial host cells, yeast host cells or a combination thereof, and (b) selecting the bacterial or yeast host cells expressing the antibody or fragment thereof having the desired functional characteristic(s).

In an embodiment of the present disclosure, the screening and identification is carried out by phage display in bacterial host cells, yeast display in yeast host cells or sequentially by phage display and yeast display; and wherein the desired functional characteristic(s) is selected from a group comprising affinity, specificity, antigenicity, manufacturability, generation of new epitopes, thermal stability, solubility, aggregation and catalytic activity and combinations thereof.

In another embodiment of the present disclosure, the screening and identification as described above is carried out by sequential phage display and yeast display comprising steps of:

(i) transforming the library of phagemid constructs into bacterial host cells to obtain phage antibody library;

(ii) screening the displayed antibody or fragment thereof against antigen(s) to obtain panned phage antibody library comprising selected clones;

(iii) transferring the antibody or fragment thereof from the selected clones into yeast vector followed by transformation into yeast host cells for expression and display of said antibody or fragment thereof;

(iv) screening the yeast displayed antibody or fragment thereof against antigen(s) to identify the antibody or fragment thereof having desired functional characteristic(s).

In yet another embodiment of the above described method of screening and identifying antibody or a fragment thereof, the antibody or a fragment thereof is in Fab or Scfv format for cloning into phage or yeast vector; and wherein transformation efficiency into the phage vector is in the range of about $10^9$ to about $10^{11}$; and transferring or transformation efficiency into the yeast vector is in the range of about $10^6$ to about $10^8$.

The present disclosure further relates to a bacterial or yeast host cell, or a phage library or a yeast library thereof comprising the vector construct(s) as described above.

The present disclosure further relates to an expression cassette provided by the vector construct(s) as described above wherein said expression cassette has a nucleic acid sequence selected from a group comprising SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23 and SEQ ID No. 25.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of biotechnology, immunology, molecular and cellular biology, recombinant DNA technology described herein are those well-known and commonly used in the art. Certain references cited herein are expressly incorporated herein by reference. In case of conflict, the present specification, including definitions, will control. The materials, methods, figures and examples are illustrative only and not intended to be limiting.

Furthermore, the methods and preparation of the various phagemid and yeast expression vectors disclosed employ, unless otherwise indicated, techniques in molecular biology, biochemistry, computational chemistry, cell culture, recombinant DNA technology, Polymerase Chain Reaction (PCR) and related fields. These techniques, their principles, and requirements are explained in the literature and are known.

Before the expression vectors and the nucleic acid sequences which constitutes these vectors and other embodiments/methods of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, the term 'vector' refers to a DNA molecule used as a vehicle to artificially carry foreign genetic material into another cell, where it can be replicated and/or expressed. The vector of the present disclosure is capable of replicating and/or expressing in prokaryotic cell, eukaryotic cell, or a combination thereof.

As used herein, the term "Antigen" refers to any foreign substance which induces an immune response in the body.

As used herein, the term "antibody" or "a fragment thereof" refers to an immunoglobulin which may be derived from natural sources or synthetically produced, in whole or in part. The terms "antibody" and "immunoglobulin" are used synonymously throughout the specification unless indicated otherwise. Further, as used herein, the term "antibody" includes both polyclonal and monoclonal antibody preparations and also includes the following: Chimeric antibody molecules, F(ab')2 and F(ab) fragments. Fv molecules, single chain Fv molecules (ScFv), dimeric and trimeric antibody fragments, minibodies, humanized monoclonal antibody molecules, human antibodies, fusion proteins comprising Fc region of antibody and any functional fragments arising out of these molecules, where derivative molecules retain immunological functionality of the parent antibody molecule.

As used herein, the term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

As used herein, "antibody fragment" is a portion of a whole antibody which retains the ability to exhibit antigen binding activity. The terms Fab or ScFv are used as antibody fragments with specific mention wherein the former being associated exclusively with heavy chain constant domain (CH1) and light chain constant region for either kappa or lambda (Ck or Cλ).

As used herein, "Antibody display library" refers to a platform(s) expressing antibodies on the surface of cell or cell-free suited for a screening methodology against target antigens. Herein, phage display library and yeast display library are used with accurate specification unless indicated otherwise.

As used herein, the terms "signal peptide" and "leader peptide" are used interchangeably.

As used herein, the terms "cloning region", "multiple cloning site" and "MCS" are used interchangeably.

The present disclosure relates to vectors for cloning and expressing genetic material. In particular, the disclosure relates to generation of vectors to clone and express genetic material, including but not limiting to genetic material obtained from naturally occurring antibody genes, artificially designed synthetic antibody genes or parts of it, or a combination thereof.

The present disclosure provides phagemid and yeast vectors. In an embodiment, the vectors of the present disclose include but are not limited to phagemid, yeast bicistronic bidirectional vector, yeast bicistronic unidirectional vector, yeast mating type heavy chain expressing vector, yeast mating type light chain expressing vector and scFv vector. The vectors are designed for cloning of large library of genes, and at the same time are flexible for transferring the cloned library between different vectors. In an exemplary embodiment, the vectors of the present disclosure are flexible for transferring the cloned library from phagemid to yeast vector(s) i.e. inter-transfer. The vectors of the present disclosure are equipped with multiple expression tags and genetic elements to ensure proper expression and screening of expressed gene products through high throughput screening platforms. In another exemplary embodiment, the vectors of the present disclosure are flexible for transferring the cloned library between different yeast vectors i.e. intra-transfer.

In a non-limiting embodiment of the present disclosure, the phagemid vector comprises an expression cassette which includes homologous recombination sequences, ribosome binding sites, promoter, signal peptide/leader peptide, tags, multiple cloning sites (MCS), constant regions of heavy chain [constant region of IgG1 heavy chain (CH1)] and light chain [constant region of kappa light chain (Ck) or lambda light chain (CL)] or fragments thereof; and geneIIIP phage coat protein. In an embodiment, the constant regions of heavy chain and/or light chain is derived from naïve antibody or synthetic antibody. Additionally, the phagemid also comprises but not limiting to origin of replication (Ori), antibiotic resistant marker and f1 origin of replication.

Figure 2:
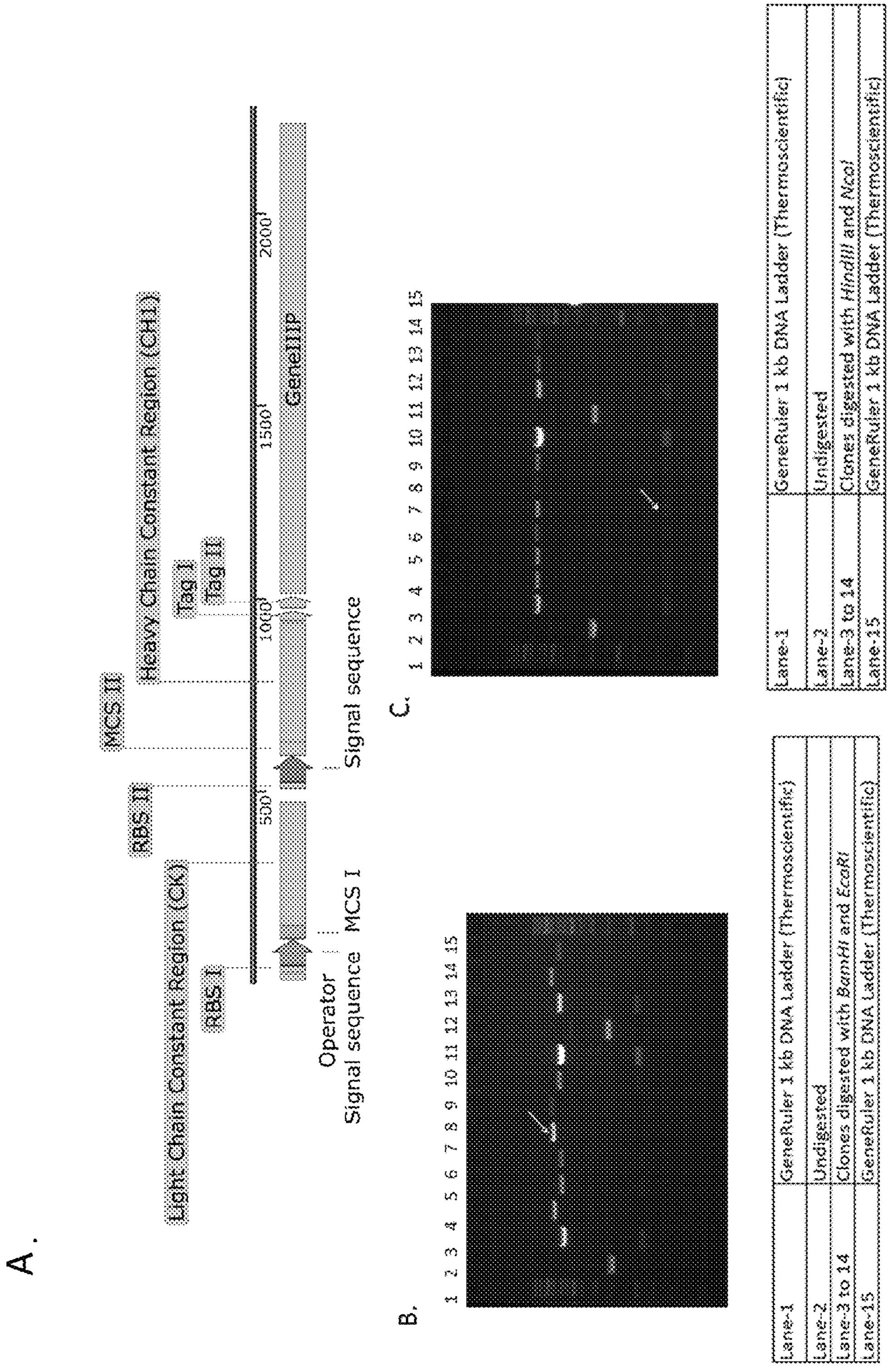
FIG. 2 illustrates generation of pZB001—phagemid vector with kappa light chain constant region A) Schematic depiction of designed insert/expression cassette containing heavy chain CH1 domain and kappa constant light chain (CK) domain.
Figure 2:
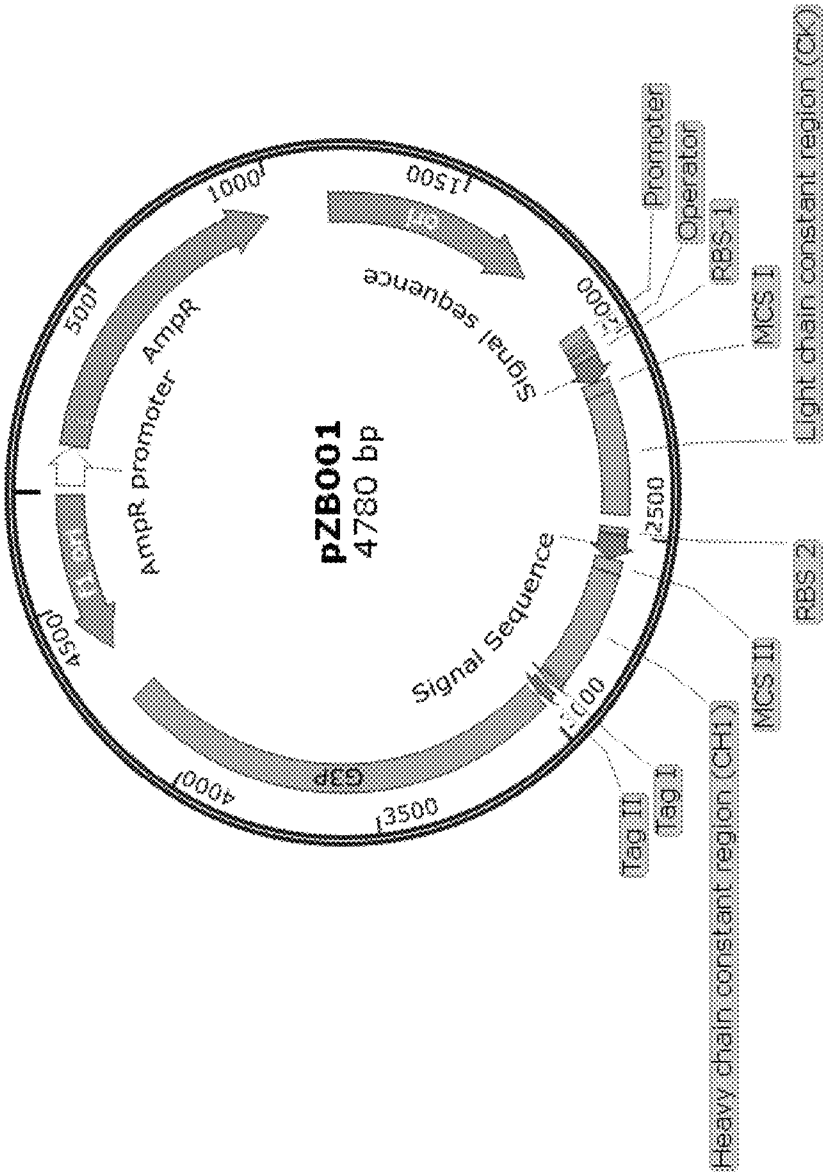

In an embodiment of the present disclosure, the expression cassettes for phagemids are provided in FIGS. 2A and 3A respectively. In another embodiment of the present disclosure, the expression cassette has a nucleic acid sequence selected from a group comprising SEQ ID No. 1 and SEQ ID No. 3.

In an embodiment of the present disclosure, the phagemid vector map is depicted in FIGS. 2D and 3D respectively. In another embodiment of the present disclosure, the phagemid vector has a nucleic acid sequence selected from a group comprising SEQ ID No. 2 and SEQ ID No. 4.

In another non-limiting embodiment of the present disclosure, the yeast vector is selected from a group comprising mating type heavy chain expressing vector, mating type light chain expressing vector, bi-directional bi-cistronic vector, unidirectional bi-cistronic vector and mono-cistronic ScFv display vector.

In yet another non-limiting embodiment of the present disclosure, the yeast vector comprises an expression cassette which includes promoter, signal peptide, tag, multiple cloning sites (MCS), enzyme cleavage sites, transcription terminator and optionally, constant regions of heavy chain [constant region of IgG1 heavy chain (CH1)] and light chain [constant region of kappa light chain (Ck) or lambda light chain (CL)] or fragments thereof, and linker sequence. In an embodiment, the constant regions of heavy chain and/or light chain is derived from naïve antibody or synthetic antibody. In an exemplary embodiment, the yeast vector comprises constant regions of heavy chain [constant region of IgG heavy chain (CH1)] and light chain [constant region of kappa light chain (Ck) or lambda light chain (CL)] or fragments thereof when the antibody is to be displayed in Fab format. In a preferred embodiment, such yeast vector displaying Fab format is selected from mating type heavy chain expressing vector, mating type light chain expressing vector, bi-directional bi-cistronic vector and unidirectional bi-cistronic vector and mono-cistronic ScFv display vector. In another exemplary embodiment, the yeast vector lacks constant regions of heavy chain [constant region of IgG1 heavy chain (CH1)] and light chain [constant region of kappa light chain (Ck) or lambda light chain (CL)] or fragments thereof when the antibody is to be displayed in scFv format. In a preferred embodiment, such yeast vector displaying scFv format is scFv vector. Additionally, the yeast vectors also comprise regions including but not limiting to origin of replication, f1 origin of replication, antibiotic resistant marker, auxotrophic marker and centromere fused autonomously replicating sequence.

In an embodiment of the present disclosure, the yeast vectors are depicted in FIGS. 5E, 6C, 7C, 8C, 10C, 12C, 14C, 15C, 16C, 17C and 18C respectively. In another embodiment of the present disclosure, the yeast vector has a nucleic acid sequence selected from a group comprising SEQ ID No. 6. SEQ ID No. 8, SEQ ID No. 10, SEQ ID No. 12, SEQ ID No. 14, SEQ ID No. 16, SEQ ID No. 20, SEQ ID No. 22, SEQ ID No. 18, SEQ ID No. 24 and SEQ ID No. 26.

The present disclosure further provides expression cassette/insert for expression of antibody or a fragment thereof. In an exemplary embodiment of the present disclosure, the expression cassette is provided for expressing the antibody in Fab format, scFv format or a combination thereof. In another exemplary embodiment, the expression cassette is designed to form a part of phagemid vector, yeast vector, or a combination thereof. In an embodiment, the expression cassette is designed for phagemid vector to express antibody in Fab format. In another embodiment, the expression cassette is designed for yeast vector to express antibody in Fab format, scFv format, or a combination thereof. In an embodiment of the present disclosure, the representative expression cassettes for yeast vectors are provided in 5A, 6A, 7A, 8A, 10A, 12A, 14A, 15A, 16A, 17A and 18A respectively. In another embodiment of the present disclosure, the yeast expression cassette has a nucleic acid sequence selected from a group comprising SEQ ID No. 5, SEQ ID No. 7, SEQ ID No. 9, SEQ ID No. 11, SEQ ID No. 13, SEQ ID No. 15, SEQ ID No. 19, SEQ ID No. 21, SEQ ID No. 17, SEQ ID No. 23 and SEQ ID No. 25.

The present disclosure further relates to generation of expression cassettes and vectors for cloning and expressing genetic material. In a non-limiting embodiment, said vector is a phagemid, yeast expression vector, or a combination thereof, as described above.

In an embodiment, the method of generating phagemid comprises synthesizing expression cassette/insert region and incorporating the said region into a linearized vector backbone (destination vector) to obtain the phagemid.

In an exemplary embodiment, the method of generating phagemid comprises steps of:

1. designing and syntheses of expression cassette comprising signal sequences, ribosomal binding sites (RBS), MCSs, tags, phage coat protein, respective constant region of light chain and heavy chain to align with Fab display format, and optionally along with homologous nucleotide length against destination vector to aid insertion of the expression cassette;
2. linearization of a destination vector such as pADL23c with restriction enzymes;
3. purification of respective fragments and set up of enzyme-mediated homologous recombination to insert the synthesized expression cassette into the linearized vector to generate the phagemid.

In another embodiment, confirmation of error-free phagemid clones is carried out by sequencing, and the variable region of heavy chain (VH) and light chain (Vk or VL) repertoire are cloned to destined location (MCS) by employing designated restriction enzymes in the of the generated phagemid vectors. In an embodiment, said variable region of heavy chain or light chain are derived from naïve antibodies or synthetically generated antibodies. In another embodiment, naïve repertoire or synthetic consensus pool of VH, Vk and VL are cloned into respective MCS of specific location in vectors to generate library constructs. Further, synthetic diversity is introduced into CDR regions of framework constructs to develop synthetic antibody gene library of phagemids.

In an exemplary embodiment, the synthesized nucleotide sequence (expression cassette) of above step (1) is a large DNA segment of ~2 Kb size comprising two segments wherein segment 1 comprises of homologous region, operator, promoter, ribosome binding sites (RBS) 1, multiple cloning site (MCS) I, light chain constant region [kappa (Ck) or lambda (CL)] while segment 2 comprises RBS 2, MCS II, heavy chain constant region (CH1) followed by a phage protein GeneIIIp as fusion protein and homologous region. The synthesized expression cassette is incorporated into the linearized pADL23c vector backbone via an efficient, productive and ligation-free infusion cloning methodology which is a homologous recombination based cloning method. Light chain and heavy chain variables from naïve and/or synthetic antibody repertoire are cloned into MCS I of segment 1 and MCS II of segment 2 of phagemid, respectively. Therefore, two designated phagemids solely based on kappa or lambda constant regions are generated, thus accommodating respective variable regions of kappa and lambda light chain pools into respective destination phagemid vectors (FIGS. 2D & 3D). For synthetic library, these phagemids are used to generate multiple clones in possible combinations of consensus heavy and light chain variable regions retaining the phagemid categorization/expression cassettes based on the constant regions of light chains. Further, synthetic diversity is introduced to designated restriction enzyme boundaries in CDR regions of Vh, Vk and Vλ chains. On the other hand, naïve repertoire with differentiation in kappa and lambda light chains is cloned directly into designated phagemids.

In another embodiment of the present disclosure, the method of generating yeast vector comprises designing the expression cassette, linearization of the destination vector followed by homologous recombination for insertion of the cassette or using restriction digestion followed by ligation of the cassette into the linearized vector to generate the yeast vector. Further, variable heavy chain and light chain repertoire is cloned to the destined location within the respective vector.

In an exemplary embodiment, the method of generating yeast vector comprises steps of:

1. designing and syntheses of expression cassette with desired promoters, terminators, signal sequences, MCSs, tags, restriction sites against destination vector to aid insertion, optional elements including linker, homologous recombination sequence, fusion protein for display, and optionally, respective constant region of heavy and light chains to align with Fab display format or lack of said constant region of heavy and light chains if the antibody is to be displayed in ScFv format;
2. linearization of destination vector such as pRS314, p414GAL1, or p416GAL1 with restriction enzymes;
3. purification of respective fragments and set up of enzyme-mediated homologous recombination for insertion of synthesized expression cassette into linearized destination vector; or setting up restriction digestions and ligations to incorporate synthesized cassette into linearized vector to generate the yeast vector.

In another embodiment, confirmation of error-free yeast vector clones is performed by sequencing, and variable regions heavy chain (VH) and light chain (Vk or VL) repertoire are cloned into destined MCS location with designated restriction enzymes in the respective yeast vectors. In an embodiment, said variable region of heavy chain or light chain are derived from naïve antibodies or synthetically generated antibodies. In another embodiment, naïve pool and/or synthetic pool of Vh, Vk and Vλ, are transferred from phagemids to yeast vectors or these regions are directly cloned into respective MCS of yeast vectors to generate eukaryotic antibody gene library of constructs.

In another exemplary embodiment, the representative yeast vectors are depicted under FIGS. 5E, 6C, 7C, 8C, 10C, 12C, 14C, 15C, 16C, 17C and 18C respectively. Apart from restriction sites and related compatibility factors, other characteristics such as display format have been featured in yeast vectors, as exemplified by Fab and ScFv format, while Fab format is further projected via expression systems: 1) mating type yeast vector, comprising genes encoding the two different heavy and light chains on different vectors in different yeast strains yielding a larger library size in Fab format; 2) bi-cistronic yeast vector wherein single yeast display vector is constructed comprising two expression cassettes driven by identical or different inducible promoters. This bi-cistronic yeast vector format lead to the production of stoichiometric amounts of separate light chain and heavy chain proteins and thus optimize the yield of functional Fab antibodies; and 3) ScFv vector for cloning ScFv fragment of antibody gene with a specific length linker separating the $V_H$ and $V_L$ regions.

In a non-limiting embodiment, the yeast vectors of the present disclosure have suitable fusion tags for fluorescence based detection and separation. The protein tags are placed as both N-terminal and C-terminal tags as applicable. The utility of these tags are multiple, including but not limiting to detection, isolation, purification and assay development.

There are several inherent features of surface display technology via using a suitably designed vector that would make it a seemly protein/antibody library screening tool against a specific antigen/protein. First, the display of a combinatorial protein library on the cell surface establishes a physical link between DNA and protein, conveniently and efficiently allowing the use of high throughput methods such as ELISA or fluorescence-activated cell sorting (FACS) in a quantitative manner. Second, the target substrates or ligands/receptors are directly accessible to proteins displayed on the surface without the need of crossing the cell membrane barrier, thus avoiding any labor-intensive protein purification steps being required. Third, cell attachment stabilizes proteins displayed on the surface. Owing to the design of display system and their inter-connectivity, it is necessary to make sure that there is no loss of molecules while being transferred to another system, which should be again be error free. The same is successfully achieved in the present disclosure which provide vectors for smooth and error-free transfer of genes from prokaryotic/phage display system to eukaryotic/yeast display system.

In an embodiment of the present disclosure, the commercially available vectors pADL23c, pRS314 and p414GAL1 & p416GAL1 were employed for designing the vectors for phage and yeast display platforms, respectively. For efficient cloning of variable heavy chains and light chains from naïve or synthetic antibody repertoire in respective display systems and transfer across display systems, restriction enzymes sites were carefully provided in such a way so that they are absent in the vector backbone, constant regions of heavy & light chains, tags, display proteins such as GeneIIIp or G3P for phage vector and Aga2P for yeast vector, leader and terminator sequences. Moreover, said uniquely designed and placed restrictions sites should not be present in the designed consensus sequence of variable regions—VH (7 families), Vk (4 families) and VL (3 families) chains. In addition, boundary enzymes selected for incorporation of synthetic diversity across all CDRs are unique and non-existent in any of the vectors carrying synthetic antibody gene repertoire.

Accordingly, the vectors of the present disclosure are uniquely designed to comprise specific restriction sites for inter-transfer (i.e. transfer of antibody genes from a vector of one expression system to another) as well as intra-transfer (i.e. transfer within the vectors of the same expression system). In an embodiment, the vectors of the present disclosure are capable of intersystem transfer viz. transfer of antibody genes from phage system to yeast expression system. In another embodiment, the vectors of the present disclosure are capable of intra-system transfer i.e., altering display format from Fab to ScFv or vice versa, or same format but different expression vector such as transferring from mating type yeast vectors to bi-cistronic yeast vector via respective set of MCS enzymes. In an embodiment, the cloning regions (MCS) of the vectors i.e. phagemid and yeast vectors comprise uniform restriction sites selected from a group comprising NdeI, BglII, BmtI. HindIII, AscI. NcoI, XbaI. NheI, Nod, and combinations thereof. In an exemplary embodiment, the MCS I/MCS region of phagemid vector and yeast vectors (yeast bicistronic bidirectional vector, yeast bicistronic unidirectional vector, yeast mating type heavy chain expressing vector, yeast mating type light chain expressing vector and scFv vector) for cloning variable light chain sequence comprises restriction sites selected from NdeI, BglII, HindIII, AscI and any combination thereof. In another exemplary embodiment, the MCS II/MCS region of phagemid vector and yeast vectors (yeast bicistronic bidirectional vector, yeast bicistronic unidirectional vector, yeast mating type heavy chain expressing vector, yeast mating type light chain expressing vector and scFv vector) for cloning variable heavy chain sequence comprises restriction sites selected from NcoI, XbaI, NheI, NotI and any combination thereof. In a preferred embodiment, the cloning region for variable light chain (MCS I/MCS) comprises combination of restriction sites selected from HindIII and AscI, and NdeI and AscI. In another preferred embodiment, the cloning region for variable heavy chain (MCS I/MCS) comprises combination of restriction sites selected from NcoI and XbaI, and NcoI and NotI.

The present disclosure further relates to the application of instant vectors in constructing a protein library. In an embodiment, the protein library is an antibody library. In another embodiment, the antibody library includes but is not limited to synthetic antibody gene expression library, naïve antibody library, or a combination thereof.

In the present disclosure, the vectors as described above are employed in a method of generating antibody gene expression library including but not limiting to synthetic antibody gene expression library, naïve antibody gene expression library or a combination thereof wherein said method comprises screening procedure for specific antigen(s), by employing combinatorial tools.

In an exemplary embodiment, the combinatorial tools include phage display technology and yeast display technology. In another embodiment, the method employs screening by phage display technology alone, yeast display technology alone, or a combination of phage and yeast display technology to create antibody gene expression library. In a preferred embodiment, the method employs screening by phage display technology sequentially followed by yeast display technology to create antibody gene expression library.

In a non-limiting embodiment of the present disclosure, the synthetic antibody gene expression library allows isolation of unique antibody molecules with desired functional properties for a specific therapeutic target i.e., antigen, with enhanced affinity and specificity.

In another non-limiting embodiment of the present disclosure, the desired functional properties of the antibodies are selected from a group comprising, but not limiting to affinity, specificity, manufacturability, generation of new epitopes, thermal stability, antigenicity, solubility, aggregation and catalytic activity, or any combination thereof and any other properties related to successful product commercialization.

In yet another non-limiting embodiment of the present disclosure, the method of generating antibody gene expression library includes sequentially exploring phage display technology and yeast display technology which allows in harnessing larger set of antibody gene diversity, a character of phage based library. The antibody clones are thereafter screened through yeast display system. Use of yeast system for antibody gene expression is advantageous because of eukaryotic protein translation, processing and proper folding of the antibody products on cell surface. Further, yeast expression allows proper interaction with antigenic targets with high specificity. Information obtained using these two complementary systems generate "lead molecules" (i.e., antibodies specific to an antigen) with higher success rate in terms of commercialization potential. The vectors of the present disclosure successfully aid in generating antibody gene expression library by the sequential phage display technology and yeast display technology due to the various features of the vectors as described above.

The phagemid and yeast vectors of the present disclosure accommodate and cross-transfer large and diverse antibody gene libraries via an error-free process which thereby improves the potential of identifying, transferring, preserving and generating unique/lead molecules against multitude of antigens with varied affinities and specificities.

In a non-limiting embodiment of the present disclosure, the prokaryotic phage display surface expression system is employed in the present disclosure to accommodate large antibody gene library about $10^9$ to about $10^{11}$ and preferably $>10^{11}$ in such a way that the widespread diversity inherent in such library is maintained. At the same time, since using a prokaryotic screening system may not be best for identifying superior functionality of antibody molecule, the phage display system is therefore integrated with eukaryotic yeast display platform that allows post translational modifications for superior functionality. To achieve this feat, the phagemid vectors for cloning and expression of highly diversified antibody gene library ($>10^{11}$ clones) are designed and employed in the present disclosure. These gene libraries are gathered either from artificially designed and chemically synthesized oligonucleotides or from naturally occurring antibody gene sequences. All sets of vectors are designed with genetic elements as described in the above paragraphs which ensure high level of expression of antibody genes as fusion proteins as well as multiple protein tags which allow efficient isolation and purification of targeted antibody genes.

In a specific embodiment of the disclosure, the strategy is to first screen a large antibody gene library through phage display technology, wherein the selected clones thereafter are re-cloned in yeast display vectors to represent the antibody gene formats including but not limiting to ScFv or Fab or other antibody formats. Therefore, the phagemid vectors of the present disclosure are designed in such a way that preliminary screening of antibody genes are completed through phagemid and then the clones are transferred to various yeast expression vectors to express different antibody gene formats including but not limiting to ScFv, Fab or other antibody formats. The phagemid vectors of the present disclosure are compatible for transferring the cloned genes to multiple types of yeast display vectors. The present yeast expression vectors are also unique in terms of cloning and expression of different formats of antibody genes including but not limiting to ScFv, Fab and other formats. Further, the present yeast expression vectors are used either for transferring the partially screened clones from phage display system to yeast display system or to directly generate naïve or synthetic library in the yeast systems either combinatorially or non-combinatorially, wherein the later strategy preserves a specific combination of heavy chain and light chain being transferred directly from phage display system. Transfer of clones preferably takes place preferably via restriction digestion based methods into yeast strains. Restriction sites for gene transferring or new cloning are carefully and uniquely designed to render the gene transfer compatible between different vectors. The yeast expression plasmids contain multiple fusion protein tags and cleavage sites to ensure expression of full length proteins and designed to be isolated and purified through high throughput methodologies. Multiple variants of signal sequences were used to optimize the secretion of various antibody formats once expressed inside yeast. In an embodiment, high throughput methodology includes but is not limited to ELISA, fluorescence-activated cell sorting (FACS), high throughput bead based selection methods, cell separation technologies, automated high throughput microscopy, magnetic separation technology and combinations thereof. The selected clonal populations are also useful in rapid purification of antibody gene product using strategically positioned protein cleavage sites.

Thus, the present vectors and methods tap both diverse and unique antibody repertoire of antibody gene library based on unique design and exclusive screening/selection criteria. The vector design, expression profiling and screening strategies adopted herein enables efficient transition between phage to yeast display platforms, or between various vectors themselves. The designing also accommodates the non-combinatorial transfer of clones obtained from phage display screening to yeast display system. The phage display accommodates the library size (>$10^{11}$) for primary screening which is focused on stringency and specificity of antibody-antigen interaction in a high-throughput format and the screened molecules again go through a randomization process to mimic native display via yeast platform. The unique set of restriction enzymes/sites used in both phagemids and yeast vectors of the present disclosure enables the transfer of heavy and light variable chains without an introduction of any amplification based methodologies such as PCR, thereby preserving the existing screened diversity of the library. Such an approach is very important/critical for successful generation of antibody gene libraries and screening for lead antibody molecules/products. Thus, each kind of vectors (vectors for phage display and vectors for yeast display) contribute combinatorially to the pipeline of developing functionally specific yet structurally varied antibody moieties/lead molecules. The expression procedure also ensures a unique display of Fab moiety or such type of antibody fragments on phage while Fab and scFv fragments or similar antibody fragments display on yeast surface. In addition, the yeast display platform has a provision of selecting vectors with bicistronic and mating type approach to display Fab or similar antibody fragments. This particular strategy, especially mating type, is adopted to circumvent the issue of poor transformation efficiency generally observed in yeast cells when compared with *E. coli* transformation efficiency, thereby screening more number of clones. The overall process with multiple rounds of selection on an antigen or on antigen-expressing cells via two different display systems is extremely valuable to positively or negatively select a range of desired antibody properties, such as affinity, specificity, manufacturability and catalytic activity.

The strategic design and combinatorial use of the vectors of the present disclosure enables to preserve diversity in the antibody gene library that is capable of identifying unique molecules against varied antigenic targets. The present vectors and their employment as a part of two different display systems thus helps in the generation of antibody gene libraries including but not limiting to naïve or synthetic libraries of human antibodies with high diversity which serve as a tremendous resource for new and functionally improved antibody identification and further commercial development.

Taken together, in phage display technology, the phagemid vectors of the present disclosure are used to clone and screen potential antibody genes with high to moderate affinity towards specific antigen. These genes are then transferred to the yeast display vectors of the present disclosure for further screening and identifying lead molecules. Use of these two technologies by employing the present vectors is beneficial as phage display technology allows cloning and expression of large diversified antibody libraries while yeast display technology is superior in terms of eukaryotic expression system and proper protein folding. Therefore, yeast display technology helps in mimicking antibody structural motifs for better antigen recognition when expressed on surface of yeast cell.

Thus, combining these two complementary technologies by employing the prokaryotic and eukaryotic vectors of the present disclosure is advantageous in screening highly diverse antibody libraries and developing new antibody molecules against specific antigens. The lead molecules identified have higher potential for productization as the present strategy accounts for higher antibody library diversification, screening through eukaryotic systems and incorporation of rational designing.

In an embodiment of the disclosure, the unique/critical features of the vectors of the present invention are further summarized in table 1.

TABLE 1

Features of the present vectors

| Phagemid of the present invention | Yeast vector - ScFv display of the present invention | Yeast Vector (Bi-Directional bi-cistronic) of the present invention | Yeast Vector (Uni-Directional bi-cistronic) of the present invention | Yeast vector - Mating Type of the present invention |
|---|---|---|---|---|
| Designed for antibody Fab library development | Designed for antibody ScFv development | Designed for antibody Fab development | Designed for antibody Fab and ScFv library development | Accommodates Heavy Chain/Light Chain independently to display final antibody Fab format |
| Designed for stable and High copy number | Designed for high expression. Maintains copy number in yeast | Designed for high expression. Maintains copy number in yeast | Designed for high expression. Maintains copy number in yeast | Designed for high expression. Maintains copy number in yeast |
| Independent and individual representation of Fab on surface | Introduced an exclusive recombination based transformation. | Introduced an exclusive recombination based transformation. | Introduced an exclusive recombination based transformation. | Introduced an exclusive recombination based transformation. |
| Unique restriction enzyme sites and design of expression cassette to accommodate antibody repertoire | Uniquely designed expression cassette and Engineered Multiple Cloning Sites compatible with phagemid | Uniquely designed expression cassette and Engineered Multiple Cloning Sites compatible with phagemid | Uniquely designed expression cassette and Engineered Multiple Cloning Sites compatible with phagemid | Uniquely designed expression cassette and Engineered Multiple Cloning Sites compatible with phagemid |
| Featured an easy modification at DNA level without major alteration of backbone vector | Added feature to Improve transformation efficiency | Added feature to Improve transformation efficiency | Added feature to Improve transformation efficiency | Added feature to Improve transformation efficiency |

TABLE 1-continued

| Features of the present vectors | | | | |
|---|---|---|---|---|
| Phagemid of the present invention | Yeast vector - ScFv display of the present invention | Yeast Vector (Bi-Directional bi-cistronic) of the present invention | Yeast Vector (Uni-Directional bi-cistronic) of the present invention | Yeast vector - Mating Type of the present invention |
| Multiple tags to confirm expression | Maintains a conserved genetic element required for amplification in bacteria and compatible for future modifications. | Maintains a conserved genetic element required for amplification in bacteria and compatible for future modifications. | Maintains a conserved genetic element required for amplification in bacteria and compatible for future modifications. | Maintains a conserved genetic element required for amplification in bacteria and compatible for future modifications. |
| Improved purification of protein | Cleavable tag to purify antibody ScFv | Cleavable tag to purify antibody Fab | Cleavable tag to purify antibody Fab and ScFv | Cleavable tag to purify antibody Fab |
| Important part of a display system that can accommodate approximately or greater than$10^{11}$ clones. | Accommodates > $10^8$ clone diversity with compatible display system. | Accommodates > $10^8$ clone diversity with compatible display system. | Accommodates > $10^8$ clone diversity with compatible display system. | Accommodates > $10^8$ clone diversity with compatible display system. |
| No additional PCR based method required while generating or transferring clones | No additional PCR based method required while generating or transferring clones | No additional PCR based method while generating or transferring clones | No additional PCR based method while generating or transferring clones | No additional PCR based method while generating or transferring clones |
| High throughput assay compatibility | Compatible for in vitro assay. High-throughput assay compatible | Compatible for in vitro assay. High-throughput assay compatible | Compatible for in vitro assay. High-throughput assay compatible | Compatible for in vitro assay. High-throughput assay compatible |

The present disclosure is further described with reference to the following examples, which is only illustrative in nature and should not be construed to limit the scope of the present disclosure in any manner.

All the biological materials employed in the present disclosure/examples were obtained from outside India.

EXAMPLES

Materials Employed:

The following materials were employed to arrive at the present examples:

1 Kb Ladder (Invitrogen, USA); Agarose (SIGMA, USA); Gel elution Kit (Qiagen, USA); Mini prep Kit (Qiagen, USA); Taq Polymerase (NEB, USA); dATP (NEB. USA); T4 DNA ligase (NEB, USA); LB-Agar, dam−/dcm− (NEB, USA), Neb5alpha (NEB, USA); Ampicillin (MP Biomedicals, USA); NcoI-HF. (NEB, USA); XbaI, (NEB. USA); HindIII-HF, (NEB, USA); AscI (NEB, USA); HindIII-HF. (NEB, USA); AscI (NEB, USA); NotI (NEB, USA), SpeI-HF (NEB, USA), SacII (NEB, USA), XhoI (NEB, USA); TG1 cells (Lucigen, USA); T4 DNA ligase (NEB, USA); PCR purification Kit (Qiagen, USA); LB-Agar; Mini prep Kit (Qiagen, USA); LB-Broth; Ampicillin (MP Biomedicals, USA); Kanamycin (MP biomedicals, USA); Infusion HD (Clontech, USA); Glycerol (Fischer Scientific, USA); Dextrose (Merck. USA); Cas-amino acid (BD, USA); Yeast Nitrogen Base (SIGMA, USA); Di sodium hydrogen Phosphate (SIGMA, USA); Galactose (SIGMA, USA); YPD broth (SIGMA, USA); Ura Trp double drop out supplement (Clontech, USA).

Further, the following vector constructs/vector backbones were deposited with Microbial Type Culture Collection and Gene Bank (MTCC), India.

| S. No. | Taxonomic Designation | Identification Reference | MTCC Number Assigned | SEQ ID Nos. |
|---|---|---|---|---|
| 1. | *E. coli* | pZB001 | MTCC 25125 | 2 |
| 2. | *E. coli* | pZB002 | MTCC 25126 | 16 |
| 3. | *E. coli* | pZB003 | MTCC 25127 | 18 |
| 4. | *E. coli* | pZB004 | MTCC 25128 | 6 |

Example 1

General Vector Design Strategy:

The success of antibody libraries such as naïve or immune or synthetic libraries solely depends on the unique design which has to be diverse and on final library size which should be sufficiently large. Any antibody library size & diversity and antibody specificity & affinity are directly linked. Apart from the crucial design of variable light chain and heavy chain repertoire—synthetic or naïve; development of a system especially different expression vectors to accommodate the large repertoire is extremely important. In addition to the stated fact, aligning the usefulness of each vector strategically is the key feature to successful library generation and screening.

Current method involves the development of two unique Phagemid vectors in order to accommodate and express antibodies in Fab format with specific modifications designated towards kappa and lambda light chain constant regions along with heavy chain constant region, along with other features/modifications.

Developed vectors are used to accommodate antibody repertoire from natural source and synthetically designed source, interchangeably so. Post generation of naïve or synthetic phage libraries, these are used for screening against target antigens of various immune-oncology network.

The method involves the use of present phagemids and yeast expression plasmids in separate protein display technologies to express the proteins/antibody genes from naïve and/or synthetic library. Firstly, phage display technology is used to clone and screen potential antibody genes with high to moderate affinity towards specific antigen. These genes are then transferred to yeast display plasmids for further screening and identification of lead molecules. Combining these two complementary technologies result in screening of highly diverse antibody libraries and developing new/lead antibody molecules against specific antigens. The smooth transfer of clonal population from phage to yeast vectors is efficient since restriction enzymes used in MCS I and MCS II are identical with respect to the two expression systems. These carefully placed restriction enzyme sites allow transferring selected population of variable light chains from MCS I of Phagemid to MCS I of any yeast vector while heavy chains are relocated to MCS II of any yeast vectors. Apart from intersystem transfer, intra-system transfer i.e., altering display format from Fab to ScFv or vice versa, or same format but different expression vector such as transferring from mating type vectors to bi-cistronic vector is possible via respective set of MCS based restriction enzymes. The free transition across all possible systems and formats also provide a randomization of heavy and light chains which allows compensating the differences across two display systems.

Example 2

Generation of Phagemid Vector:

To obtain a highly efficient and functionally large protein/peptide library such as antibody library, the following important considerations were taken: 1) Efficient generation of functional and large antibody repertoire with either PCR amplified natural pool or in silico designed and synthetically developed pool of molecules in phagemid vectors; 2) Chosen antibody format and compatible cloning & expression vector, which would permit the rapid downstream analysis of selected clones as exemplified by compatibility with suitable screening method followed by transferring of selected clones for several subsequent characterization experiments.

In order to accommodate large number of molecules in Fab format, two step cloning method was adopted confirming the presence of both types of inserts i.e., light chain and heavy chain variable regions, at the construction level.

Herein, the Phagemid vectors are with bicistronic operon having specific human antibody constant regions attached for both light chains (Ck or CK & Cλ or CL) and heavy chains (human IgG1-CH1 domain). Other essential features such as ribosome binding site, PelB signal sequence, multiple cloning sites (MCS I for light chain repertoire and MCS II for Heavy chain repertoire), FLAG and c-Myc tags are present in the phagemid vectors. The tags are associated in continuation of CH1 domain and will be used for detection of Fab expression. IgG1-CH1 domain is linked with phage coat PIII protein, GeneIIIP. As a part of Fab display format, heavy chain is displayed on phage in an associated form through expressed GeneIIIP protein while the light chain is expressed as separate fragment, secreted into the periplasm, where it pairs with the heavy chain and completes the display configuration. An amber stop codon (TAG) is strategically placed between the antibody genes and phage GeneIIIP protein enabling the production of Fab fragments in a non-suppressor strain of *E. coli* as exemplified TG1 cells. Pool of light chain variable regions will be cloned into MCS I region consisting of NdeI, BglII, HindIII and AscI restriction sites while heavy chain variable regions was destined in MCS II which contains NcoI, XbaI, NheI and NotI sites. The design and employment of restriction enzymes was based on their low probability to cut within human variable heavy and light chain coding regions. Additionally, they produce overlaps of 4 nucleotides or more leading to optimal cloning efficiency. The enzymes do not depend on methylation and their efficiency in recommended double digestions is more that 90%. These restriction sites are maintained constant across multiple vectors in various expression systems such as yeast. To maintain the cloning sites throughout, there were several modifications that were made in Phagemid and subsequent vectors in yeast. As described above, these vectors are used to accommodate pool of nucleotide sequences of both naïve and synthetic origin, therefore several unique changes were incorporated to ease library generation process and subsequent transfer into yeast. These changes also diminished specific restriction sites or certain peptides without changing the amino acid compositions or frame of translation.

Some of the modifications carried out in the vector backbone and other individual elements/sequences are as follows:

1. NotI, EagI, SpeI, XmaI, SmaI, SfiI (SEQ ID No. 30, 2045 bp to 2106 bp) are few of the restriction enzymes that were removed from the pADL23c vector (FIG. 1).
2. EcoRI (SEQ ID No. 30, 2004 bp to 2009 bp) and BstXI (SEQ ID No. 30, 2116 bp to 2127 bp) enzyme sites from vector backbone are modified.
3. Specific regions (SEQ ID No. 30, 2108 bp to 2128 bp and SEQ ID No. 30, 2132 bp to 2161 bp) were removed from pADL23c vector backbone.
4. BamHI restriction site (SEQ ID No. 30, 2754 bp to 2760 bp) was modified from GeneIIIP protein.
5. BstEII, (SEQ ID No. 27, 2882 bp to 2888 bp) Bsu36I (SEQ ID No. 27, 2779 bp to 2786 bp) and BbeI (SEQ ID No. 27, 2733 bp to 2738 bp) enzyme sites were modified in the CH1 region.
6. HindIII site was modified from c-Myc tag (SEQ ID No. 2, 2958 bp to 2963 bp).
7. BlpI (SEQ ID No. 28, 2345 bp to 2351 bp) was removed from CK.

Figure 1:
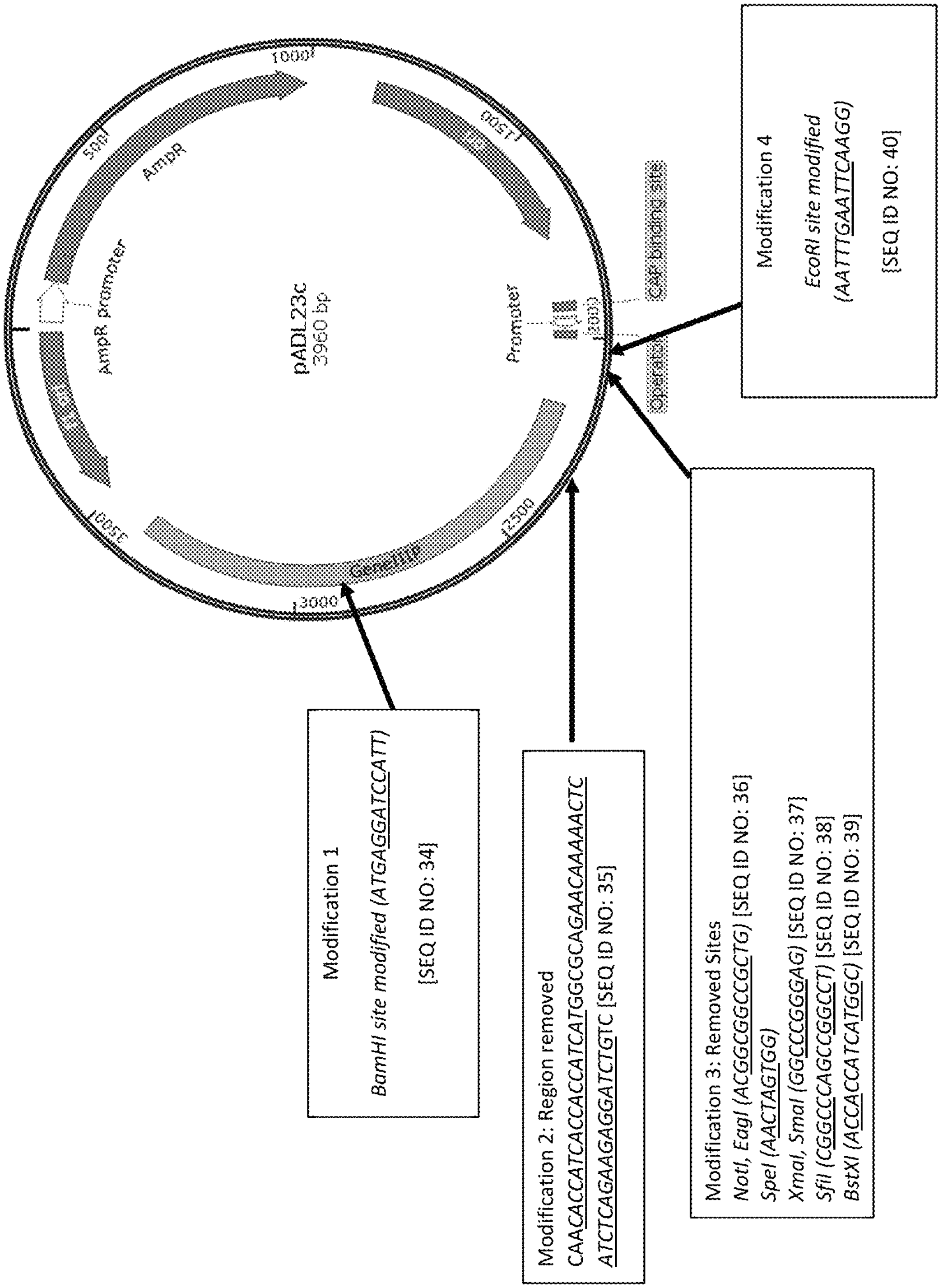
FIG. 1 illustrates modification of pADL23c vector. Multiple restriction sites and backbone sequences were modified, described as modification-1, modification-2, modification-3, modification-4, respectively.

Some of the aforesaid changes are also highlighted in FIG. 1 of the present disclosure.

As can be understood, phagemid vectors being the first step to generate and screen libraries (naive or synthetic antibody libraries) were designed with utmost attention considering various subsequent processes in mind. Taken together, this was the most efficient route for library construction and move along with the screening.

Considering all modifications and aim in mind, the insert/expression cassette was designed for kappa (FIG. 2A and SEQ ID No. 1) and Lambda (FIG. 3A and SEQ ID No. 3), and synthesized followed by incorporation of the insert/expression cassette into the commercially procured pADL23c vector backbone which was subsequently subjected to several modifications before linearization and cloning of the insert/expression cassette. pADL23c was used as a vector backbone towards the generation of two different Phagemid vectors. These Phagemid vectors will be majorly differentiated through the light chain constant regions i.e., kappa and lambda light chain constant regions. Homologous recombination based approach was adopted to clone the insert/expression cassette into the modified pADL23c backbone. Synthesized kappa-insert and lambda-insert constructs were transformed into dam−/dcm− cells and respective DNA were isolated in bulk quantity using midi prep kit from qiagen for further digestion. Strategies for cloning of kappa insert was slightly different in comparison to the cloning of lambda insert. About 10 μg of pADL23c was linearized using BamHI-HF and EcoRI-HF enzymes while about 5 μg of insert-kappa was digested with SfiI enzyme. On the other hand, about 5 μg of lambda-insert was first digested with PvuI at about 37° C. for about 2 hours followed by addition of SfiI at about 37° C. for about 2 hours which resulted three bands wherein the desired band size was ~2.3 kb. Linearized vector pADL23c and digested kappa-insert and Lambda-insert are gel eluted wherein excised gel is dissolved by mixing about 3 volumes of Buffer QX1 solution. About 30 μL of QIAEX II beads are added by vortexing for 30 seconds followed by incubation at about 50° C. for about 10 minutes. Series of washes are given to beads; first with about 500 μL of QX1 followed by 2 washes with about 500 μL of PE buffer. DNA is eluted with about 30 μL of nuclease-free water. Tables 2-4 below depicts the components/reagents used to linearize pADL23c vector and generation of kappa-insert and lambda-insert based phagemid vectors.

TABLE 2

| | |
|---|---|
| DNA (vector/pADL23c) | 5 μg |
| BamHI-HF (20 U/μL) | 2 μL |
| EcoRI (20 U/μL) | 2 μL |
| Cut smart Buffer | 5 μL |
| Water | respective volume of milli-Q water |
| Total | 50 μL |

TABLE 3

| | |
|---|---|
| DNA (Kappa_Insert) | 5 μg |
| SfiI (20 U/μL) | 2 μL |
| Cut smart Buffer | 5 μL |
| Water | respective volume of milli-Q water |
| Total | 50 μL |

TABLE 4

| | |
|---|---|
| DNA (Lambda_Insert) | 5 μg |
| PvuII (20 U/μL) | 1 μL |
| SfiI (20 U/μL) | 1 μL |
| Cut smart Buffer | 5 μL |
| Water | respective volume of milli-Q water |
| Total | 50 μL |

Infusion reaction was set up for vector and insert, kappa and lambda inserts (Table 5) followed by incubation at about 50° C. for about 15 minutes. Post incubation about 2.5 μl of the In-Fusion reaction mixture was added to the 50 μL Stellar competent cells. The reaction mixture was incubated for about 30 minutes on ice followed by addition about 500 μL SOC media for recovery of transformed cells. Cells were plated on LB agar plates with ampicillin followed by incubation for overnight at about 37° C. Colonies appeared on the following day and were inoculated in 5 mL LB-Amp and plasmid was isolated. The isolated plasmids were checked for restriction digestion analysis with BamHI/EcoRI and NcoI/HindIII and confirmed for the presence of kappa insert (FIGS. 2 B & C) whereas for lambda vector, the clones were tested for PvuII, NcoI/HindIII-HF, NcoI/PvuII and NdeI/PvuII alone or in respective combinations (FIGS. 3B & 3C). Positive clones were sent for sequencing and found to be error-free. Phagemid vectors were named as pZB001—phagemid with kappa insert (FIG. 2 D and SEQ ID No. 2) and pZB001.1 phagemid with lambda insert (FIG. 3 D and SEQ ID No. 4). Vector pZB001 has been submitted to MTCC under Budapest treaty with accession number being MTCC 25125 and named as pZB001. Further, the phagemid vector having light chain constant region (lambda insert—CL) can be prepared by a person average skilled in the art based on the aforementioned experimental procedure and the details of deposited phagemid vector (kappa insert).

TABLE 5

| | | | |
|---|---|---|---|
| DNA (Linearized vector) | 91.8 ng | DNA (Linearized vector) | 91.8 ng |
| Insert (Kappa) | 178.5 ng | Insert (Lambda) | 299 ng |
| 5X In-Fusion HD Enzyme Premix | 2 μL | 5X In-Fusion HD Enzyme Premix | 2 μL |
| Water | respective volume of milli-Q water | Water | respective volume of milli-Q water |
| Total | 10 μL | Total | 10 μL |

Sequence confirmed Phagemid vectors pZB001 and pZB001.1 were used for generation of naïve and synthetic phage library for screening/panning against target antigen. The size and diversity of the library was estimated by both peer group and next generation sequencing approaches. Sequencing results of panned molecule also confirmed that the diversity of the panned molecules is retained. Single stranded DNA was isolated from Panned molecules and to be transferred to yeast expression vectors.

Example 3

Generation of Yeast Expression Vectors:

Antibody display library represents a library of partial or complete antibodies expressed on cell surface linked to other cellular proteins. Phage display is the most accepted method due to ease of cloning, allowing for large library sizes, monovalent display and easy to determine various stability parameters. However, with phage display there are associated limitations on proper protein folding due to prokaryotic expression system and lack of post translational modifications of the displayed antibody fragments thereby. To overcome these limitations, yeast display platform, a robust, versatile, quantitative methodology for isolating and engineering antibody fragments is employed. Yeast, a eukaryotic display system is of choice as it is compatible with quantitative and real-time assessment employing fluorescence activated cell sorter (FACS)-sorting techniques.

In comparison with other in vitro display technologies, yeast display of naive/non-immune antibody libraries using the agglutinin adhesion receptor complex Aga1P and Aga2P has a significant number of advantages. For example, use of flow cytometry analysis allows rapid clone characterization including $K_D$ determination, $K_{off}$ measurement and epitope binding of mutually exclusive clones directly on the surface of yeast. This eliminates the need for purification of protein to perform these characterizations. The successful display of Fab antibody fragments on yeast suggests a simpler approach to large library construction. As Fab fragments are composed of heavy and light chains, therefore it is possible to encode the two polypeptides on different vectors in different yeast strains wherein two chains can be brought together in a single diploid yeast by mating, a highly efficient process. However, major challenge in case of yeast display is relatively smaller library size due to lower transformation efficiency in yeast, which is hereby overcome by the aspects provided by the instant disclosure, which employs a combination of phage and/or yeast display concept.

As can be understood from the aforementioned facts, phage panned molecules should be to be transferred to various Yeast expression vectors either combinatorially or non-combinatorially in various formats such as ScFv, Fab etc. In order to have a convenient transfer from phagemids to yeast vectors, multiple cloning sites were kept identical. Herein, the yeast expression vectors are with either bicistronic bidirectional or bicistronic unidirectional having specific human antibody constant regions attached for both light (Ck or CK & Cλ or CL) and heavy chains (human IgG1-CH1 domain). Other crucial features such as leader signal sequence (Mating type alpha factor for light chain; Aga2P leader peptide for heavy chain), multiple cloning sites (MCS I for light chain repertoire and MCS II for Heavy chain repertoire), tags (V5 epitope tag and 6×His tag for light chain; FLAG and c-Myc tags for heavy chain repertoire) are present in all kinds of yeast vectors. The tags are associated in continuation of constant domain and will be used for detection of Fab expression. The screening to obtain the yeast library by the surface display is carried out by employing competing antigenic epitopes, antibody paratope conformation, sequences and sequence motifs or any combination thereof to isolate Fab or ScFv molecule using protease cleavage sites selected from a group comprising Tobacco Etch Virus (TEV), Entero kinase (Ek) etc strategically placed after tags in heavy chain.

Approaches towards generation of yeast vectors that have been developed, are of three types: 1) Bi-cistronic bidirectional vector; 2) Bi cistronic unidirectional vector 3) ScFv vector and 4) mating type vectors.

(A) Generation of Yeast Bicistronic Bidirectional Vector: (pZB004 and pZB004.1)

To generate the yeast Bicistronic Bidirectional vector, pRS314vector (ATCC, USA) was used as backbone (FIG. 4). Some of the modifications carried out in the vector backbone and other individual elements/sequences are as follows:

1. SacI, SacII, EagI, NotI, SpeI, BamHI, XmaI, SmaI, PstI, EcoRI, EcoRV, SalI, XhoI, ApaI, are few of the restriction enzymes that were removed from the pRS314vector (SEQ ID No. 31, 1893 bp to 1989 bp, as shown in FIG. 4).
2. SpeI site (SEQ ID No. 29, 2600 bp to 2605 bp) was diminished from lambda light chain constant region (CL).

Further, inserts/expression cassettes for kappa (FIG. 5 A and SEQ ID No. 5) and lambda (FIG. 6 A and SEQ ID No. 7) was designed and synthesized comprising Gal1/10 promoter, alpha leader peptide, Aga2P leader peptide, MCS I & II, Tags (V5 and His-Tags for Light chains and FLAG, c-Myc for Heavy chain), respective constants regions attached for both light (Ck or Cλ) and heavy chains (human IgG1-CH1 domain). A SpeI restriction site has been removed from Cλ region.

As a part of Fab display format, heavy chain will be displayed on yeast in an associated form through expressed Aga2P protein while the light chain is expressed as separate fragment. During protein maturation process, it pairs with the heavy chain and completes the Fab display configuration. Separate terminator sequences were kept as exemplified by CYC1 terminator for heavy chain and alpha terminator for light chain. To aid the further screening process with soluble Fab, TEV protease cleavage site was fixed after the tags and before Aga2P protein sequence. There is a $(G4S)_3$ linker region strategically placed before the start of Aga2P protein in order to introduce flexibility in protein conformation.

About 10 μg of pRS314 vector and insert-kappa-yeast was digested with EcoRV and KpnI, respectively (Table 6) at about 37° C. for overnight followed by gel elution wherein excised gel is dissolved by mixing about 3 volumes of Buffer QX1 solution. About 30 μL of QIAEX II beads are added by vortexing for about 30 seconds followed by incubation at about 50° C. for about 10 minutes. Series of washes are given to beads, first with about 500 μL of QX1 followed by 2 washes with about 500 μL of PE buffer. DNA is eluted with about 30 μL of nuclease-free water. Digested and eluted, about 3 μg of pRS314 and insert-kappa-yeast were further cleaved with KpnI and EcoRV for overnight at about 37° C., respectively followed by gel elution and ligation set up.

TABLE 6a

| | | | |
|---|---|---|---|
| DNA (vector) | 10 μg | DNA (Kappa-insert-yeast) | 10 μg |
| EcoRV (20 U/μL) | 2 μL | KpnI (20 U/μL) | 2 μL |
| Cut smart Buffer | 10 μL | Cut smart Buffer | 10 μL |
| Water | respective volume of milli-Q water | Water | respective volume of milli-Q water |
| Total | 100 μL | Total | 100 μL |

TABLE 6b

| | | | |
|---|---|---|---|
| DNA (vector) | 3 μg | DNA (Kappa-insert-yeast) | 3 μg |
| KpnI (20 U/μL) | 2 μL | EcoRV (20 U/μL) | 2 μL |
| Cut smart Buffer | 10 μL | Cut smart Buffer | 10 μL |
| Water | respective volume of milli-Q water | Water | respective volume of milli-Q water |
| Total | 100 μL | Total | 100 μL |

TABLE 7

| | |
|---|---|
| DNA (Vector) | 35.8 ng |
| DNA (kappa-insert-yeast) | 76 ng |
| T4 DNA ligase | 2 μL |
| T4 DNA ligase buffer (10X) | 2 μL |
| Water | Respective volume of water |
| Total | 20 μL |

Ligation set up was done individually for kappa vectors at a ratio of 1:5 followed by transformation individually into TG1, highly competent cells. Individual colonies were picked up, inoculated followed by isolation plasmid DNA and restriction digestion set up using PvuII enzyme. Confirmed clones produce bands of ~4.3 Kb and ~2.9 Kb fragments (FIG. 5 B). Positive clones were further confirmed by restriction digestions with EcoRV/KpnI and NdeI/KpnI enzymes in respective combinations wherein former produces sizes of ~3.7 Kb & ~3.5 Kb while later produce ~5.5 Kb & ~1.8 Kb fragments (FIGS. 5 C & D). Confirmed clones were sent for sequencing and found to be error free (FIG. 5 E and SEQ ID No. 6). The confirmed yeast bidirectional vector containing kappa light chain constant region has been submitted to MTCC under Budapest treaty with accession number being MTCC 25128 and named as pZB004.

Further, the yeast bicistronic birectional vector having lambda light chain constant region is prepared by using said deposited vector yeast bicistronic birectional vector having kappa insert. The same is prepared wherein 10 μg of confirmed and deposited kappa vector (pZB004) and insert-lambda-yeast (SEQ ID No. 7) were digested with SpeI-HF/SacII (Table 8) followed by gel elution and ligation (Table 9) at about 4° C. for overnight. 25 ng of ligation mixture was transformed into TG1 competent cells. Individual colonies were inoculated and screened for insert release with PvuII, NdeI/NotI and NcoI/AscI enzymes (FIG. 6 B). Positive clones were sent for sequencing and found to be error-free (FIG. 6 C). The confirmed yeast bicistronic bi-directional vector containing lambda light chain constant region is named as pZB004.1 (SEQ ID No. 8).

TABLE 8

| | Vector | Insert |
|---|---|---|
| DNA | 10 μg | 10 μg |
| Cut smart Buffer (10X) | 10 μl | 10 μl |
| SpeI-HF (20 U/μl) | 1 μl | 1 μl |
| SacII (20 U/μl) | 1 μl | 1 μl |
| Water | Respective volume of water | Respective volume of water |
| Total volume | 100 μl | 100 μl |

TABLE 9

| | |
|---|---|
| DNA (Vector) | 51 ng |
| DNA (insert) | 74.6 ng |
| T4 DNA ligase | 1 μL |
| T4 DNA ligase buffer (10X) | 2 μL |
| Water | Respective volume of water |
| Total | 20 μL |

(B) Generation of Yeast Bicistronic Unidirectional Vectors (pZB004.2 and pZB004.3): Concept of Non-Combinatorial Transfer Yeast Bicistronic Unidirectional vector was designed to have an option of two separate promoters for expressing heavy chain and light chain in Fab format. Besides, unique configuration of this vector will allow for non-combinatorial transfer of Fab molecules from phage system to yeast system. This will in turn preserve a specific combination heavy chain and light chain to explore in eukaryotic system.

To generate the yeast Bicistronic unidirectional vector, the deposited yeast Bicistronic Bidirectional vector was used as backbone, wherein the insert for kappa (FIG. 7 A and SEQ ID No. 9) and lambda (FIG. 8 A and SEQ ID No. 11) were designed and synthesized comprising two Gal1/10 promoter (light and heavy chain), alpha leader peptide, Aga2P leader peptide, MCS I & II, Tags (V5 and His-Tags for Light chains and FLAG, c-Myc for Heavy chain), respective constants regions attached for both light (CK or CL) and heavy chains (human IgG1-CH1 domain). Confirmed yeast Bicistronic Bidirectional vectors kappa and lambda along with synthesized kappa and lambda insert were digested with SpeI-HF and SacII restriction enzymes at about 37° C. for about 3 hours (Table 10). Digested vectors (~4.8 Kb) and inserts (kappa and lambda, ~2.9 Kb) were gel eluted and ligation reaction (Table 11) was set up for overnight at about 4° C. followed by transformation in NEB 5-alpha Competent *E. coli* cells by heat shock method. Individual colonies were inoculated and screened for insert release with SpeI-HF/SacII enzymes (~2.9 Kb) and internal digestion with HindIII-HF enzyme (~1.7 Kb) (FIGS. 7 B and 8 B). Positive clones were sent for sequencing and found to be error-free (FIGS. 7 C & 8 C). The confirmed yeast uni-directional vectors containing kappa and lambda light chain constant regions are named as pZB004.2 (SEQ ID No. 10) and pZB004.3 (SEQ ID No. 12), respectively.

TABLE 10

| | |
|---|---|
| DNA (1 μg) | 3 μL |
| SpeI-HF | 1 μL |
| SacII | 1 μL |
| 10X Cut Smart | 2 μL |
| water | 13 μL |
| TOTAL VOLUME | 20 μL |

TABLE 11

| | Sample | Control |
|---|---|---|
| DNA (vector) ~50 ng | 1 μL | 1 μL |
| DNA (Insert) ~160 ng | 4 μL | 0 μL |
| 10X T4 DNA Ligase buffer | 1 μL | 1 μL |
| T4 DNA ligase | 1 μL | 1 μL |
| water | Respective volume | Respective volume |
| TOTAL VOLUME | 10 μL | 10 μL |

(C) Generation of Yeast ScFv Vector: pZB004.4

Another alternative vector which was generated for yeast display studies was compatible for ScFv molecules. The product of this construct is antibody molecules in ScFv format which is different from Fab format, wherein constant regions for both heavy chain and light chains are removed. This vector was based on a backbone of construct which was originated from pRS314 vector (ATCC, USA) (FIG. 9). Some of the modifications carried out in the vector backbone and other individual elements/sequences are as follows:

1. EagI, NotI, SpeI, BamHI, XmaI, SmaI, PstI, EcoR, EcoRV, SalI, XhoI are few of the restriction enzymes that were removed from the pRS314 vector (SEQ ID No. 31, 1904 bp to 1984 bp, and as shown in FIG. 9).

The gene in the vector backbone was replaced by the designed and synthesized insert/expression cassette (FIG. 10 A and SEQ ID. No. 13) between ApaI and SacII enzymes. The designed insert contains Gal1 promoter, nucleotide encoding Aga2P protein sequence, Aga2P leader sequence, Factor Xa site, HA tag, TEV cleavage site, MCS I (for Light chain variable region incorporation, NdeI, BglII, HindIII and AscI), linker region (G4S), MCS II (for heavy chain variable region incorporation, NcoI, XbaI, NheI and NotI), c-Myc tag, FLAG tag, alpha terminator.

As provided in Tables 12 and 13 below, about 10 μg of vector and insert were digested with ApaI at about 25° C. for overnight followed by addition of SacII enzyme at about 37° C. for about 3 hours. Digested material was gel eluted and ligated at about 4° C. for overnight. The 2 μL of the ligated mixture was transformed into NEB alpha competent cells. Individual colonies were inoculated and screened for internal digestion with EcoRV/XhoI enzyme (~2.9 Kb) (FIG. 10 B). Positive clones were sent for sequencing and found to be error-free (FIG. 10 C). The confirmed yeast ScFv vector containing heavy and light chain incorporation sites is named as pZB004.4 (SEQ ID No. 14).

TABLE 12

| | Vector | Insert |
|---|---|---|
| DNA | 10 μg | 10 μg |
| Cut smart Buffer (10X) | 10 μl | 10 μl |
| ApaI(20 U/μl) | 2 μl | 2 μl |
| SacII (20 U/μl) | 2 μl | 2 μl |
| Water | Respective volume of water | Respective volume of water |
| Total volume | 100 μl | 100 μl |

TABLE 13

| | |
|---|---|
| DNA (Vector) | 106.8 ng |
| DNA (insert) | 161.2 ng |
| T4 DNA ligase | 0.5 μL |
| T4 DNA ligase buffer (10X) | 2 μL |
| Water | Respective volume of water |
| Total | 20 μL |

(D) Construction of Yeast Mating Type Vectors (YMT Vectors):

Yeast surface display technology has constraint in the library size (typically $10^6$~$10^8$) compared with either phage ($10^9$ to $10^{11}$) or ribosome ($10^{11}$ to $10^{12}$) display technologies due to its limitations in yeast transformation efficiencies. Improved yeast transformation methods could overcome this limitation. However, various improved yeast transformation protocols are time-consuming and labor-intensive. So, yeast mating can be used as a powerful tool for generating a large antibody library. The yeast mating is achieved by cellular fusion between two haploid cells of opposite mating types through interaction with a-agglutinin of MATa cells and α-agglutinin of MATα cells. After mating, two distinct plasmids in each haploid cell are combined into one diploid cell, expressing simultaneously the encoded antibody fragment from each plasmid in the subsequent diploid cells. Fab antibody fragments comprise two chains; a heavy chain (HC) with VH and CH1 (the first domain of heavy chain constant regions) and a light chain (LC) with VL and CL (light chain constant domain). Thus, yeast mating is suitable for the construction of a combinatorial Fab library from two haploid cells of opposite mating types containing HC and LC libraries. The heterodimerization of secreted LC to yeast surface-anchored HC by formation of a disulfide bond between the two C-terminal Cys residues of CH1 and CL (light chain constant domain) facilitates the construction of the display Fab on the yeast cell surface.

(D.1) Construction of Mating Type Heavy Chain (HC) Expressing Vector (pZB002) in *Saccharomyces cerevisiae*

Mating type heavy chain expressing vector is designed to express HC chain (VH+CH1) on with tags and TEV cleavage site on yeast cell surface under the control of GAL1 promoter and CYC1 terminator. Aga2P signal sequence present in this vector facilitates HC chain to secretory pathway. Combination of various restriction sites is important to transfer to transfer phage panned molecules (VH) from phagemid to HC expressing vector. To achieve this, unique restriction sites (NcoI, BmtI, NheI, NotI) are kept between Aga2P signal sequence and CH1 open reading frame. Presence of myc and FLAG tags are provided to detect HC chain during flow cytometry screening. To cleave Fab fragment form yeast cell surface, highly sequence-specific cysteine protease Tobacco Etch Virus protease (TEV) and Enterokinase (EK) sites are incorporated in HC expressing vector.

For the construction of mating type heavy chain HC vector (pZB002), p414GAL1 and HC DNA cassette (SEQ ID No. 15) was used. p414 GAL1, a CEN-based shuttle vector with TRP1 marker from ATCC (Cat. No. ATCC® 87328™) was modified in order to accommodate HC DNA cassette. Said modifications are provided in FIG. 11 and are summarized below:

1) BamHI, SmaI, PstI, EcoR, BspDI, SalI, TspMI, ClaI, HincII and XmaI restriction sites were modified. To modify above mentioned restriction sites, nucleotides from 2208 bp to 2158 bp are removed from p414 GAL1 (SEQ ID No. 32 and FIG. 11).

HC DNA cassette (SEQ ID No. 15) is composed of unique AGA2P single sequence coding region, multi-cloning sites (NcoI, BmtI, NheI, NotI), heavy chain constant region1 (CH1) with Cysteine residue intact at the last position followed by tags (c-myc and FLAG), TEV cleavage site which is fused with c-terminally AGA2P open reading frame. HC DNA cassette is synthesized through Gene Art. HC DNA cassette (FIG. 12 A) and p414 GAL1 are digested with SpeI and XhoI at 37° C. and ligated (at 4° C.) further to create pZB002 (FIG. 12 B). The synthesized pZB002 HC expressing vector is deposited with MTCC under the accession number MTCC 25126. HC DNA cassette is under the control of GAL1 promoter and CYC1 terminator.

Unique NcoI, BmtI, NheI and NotI sites were kept after AGA2P signal sequence to clone VH region received from phage panned library in pZB002.

TABLE 14

| | |
|---|---|
| DNA p414 GAL1 or HC cassette | ~3 μg |
| SpeI | 3 μL |
| XhoI | 3 μL |
| 10X Cut Smart Buffer | 10 μL |
| Milli-Q water | respectively |
| Total volume | 100 μL |

TABLE 15

| | |
|---|---|
| DNA (Vector) | 1 μL |
| DNA (Insert) | 5 μL |
| T4 DNA ligase | 1 μL |
| T4 DNA ligase buffer (10X) | 1 μL |
| Milli-Q water | 2 μL |
| Total volume | 10 μL |

Below is the table which allows to understand the features of pZB002 (FIG. 12 C and SEQ ID No. 16).

TABLE 16

| Feature | Benefit |
|---|---|
| GAL1 promoter | Permits regulated expression of your recombinant protein |
| AGA2P signal sequence | Allows secretion of the heavy chain |
| Multiple cloning site (NcoI, BmtI, NheI, NotI) | Allows insertion of VH from phage panned library |
| CH1 with cysteine residue at the last position | Allows the formation of constant region of heavy chain and cysteine residue will make disulfide bond with light chain |
| FLAG and c-myc epitopes | Allows detection of the fusion protein with the Anti flag or anti myc antibodies |
| TEV cleavage site | Allows to cleave Fab format antibody from yeast cell surface |
| AGA2P coding sequence | Allows to attach heavy chain-Aga2p fusion protein on the yeast cell surface |

TABLE 16-continued

| Feature | Benefit |
|---|---|
| CYC1 terminator | Efficient transcription termination of mRNA |
| TRP1 gene | Allows selection of yeast transformants |
| CEN6/ARS | Allows stable, episomal replication and partitioning into daughter cells in yeast |
| Ampicillin resistance gene (β-lactamase) | Selection in *E. coli* |

(D.2) Construction of Mating Type Light Chain (LCλ) Expressing Vector (pZB003.1) in *Saccharomyces cerevisiae:*

Mating type light chain expressing vector is designed to express and secrete LC chain (VL+LCλ) with tags yeast cell surface under the control of GAL1 promoter and CYC1 terminator. mating alpha factor single sequence (pre region) present in this vector facilitates LC chain to secretory pathway. Combination of various restriction sites is important to transfer to transfer phage panned molecules (VL) from phagemid to HC expressing vector. To achieve this unique restriction sites (NdeI, BglII, HindIII and AscI) are kept between mating alpha factor single and LCλ open reading frame. Presence of V5 and His tags provide to detect LCλ chain during flow cytometry screening.

p416 GAL1 is a CEN-based shuttle vector with URA3 marker from ATCC (ATCC® 87332™) (FIG. 13). Which was used to generate several light chain constructs with different signal sequences. Said p416 GAL1 vector backbone was modified as provided in FIG. 13 and summarized below:

1) BamHI, SmaI, XmaI, TspMI, EcoRI, HindIII, BspDI, ClaI and SalI restriction sites were modified. To modify above mentioned restriction sites nucleotides from 2318 bp to 2268 bp are removed from p416 GAL1.

For the construction of the SS01 based secretion plasmid of LCλ, modified p416 GAL1 and LCλ DNA cassette (SEQ ID No. 19) was used. LCλ cassette is composed of alpha factor single sequence (SS01), unique multi-cloning sites (NdeI, BglII. HindIII and AscI), and light chain constant region (LCλ) with Cysteine residues intact at the last position followed by tags (V5 and His). LCλ DNA cassette (FIG. 14 A) is synthesized through Gene Art. Modified p416 GAL1 and LCλ are digested with SpeI and XhoI at 37° C. and ligated at 4° C. further to create pZB003.1 (Tables 18 and 19; FIG. 14 B). LCλ DNA cassette will be under the control of GAL1 promoter and CYC1 terminator in pZB003.1 vector. Unique NdeI, BglII, HindIII and AscI sites were kept after SS01 signal sequence to clone VL region from phage panned library in pZB003.1 vector (FIG. 14 C). The generated pZB003.1 vector is provided as SEQ ID No. 20.

TABLE 17

| | |
|---|---|
| DNA (p416 GAL1 or LCλ DNA) | ~3 μg |
| SpeI | 3 μL |
| XhoI | 3 μL |
| 10 X Cut Smart Buffer | 10 μL |
| Milli-Q water | respectively |
| Total volume | 100 μL |

TABLE 18

| | |
|---|---|
| DNA (Vector) | ~3 μg |
| DNA (Insert) | 3 μL |
| T4 DNA ligase | 3 μL |
| T4 DNA ligase buffer (10X) | 10 μL |
| Milli-Q water | respectively |
| Total volume | 100 μL |

Below is table 19 which allows one to understand the features of pZB003.1.

TABLE 19

| Feature | Benefit |
|---|---|
| GAL1 promoter | Permits regulated expression of your recombinant protein |
| Alpha mating factor 1 secretory signal sequence | Allows secretion of the light chain |
| Multiple cloning site (NdeI, BglII, HindIII and AscI) | Allows insertion of VL from phage panned library |
| LCλ with cysteine residue at the last position | Allows the formation of constant region of λ light chain and cysteine residue will make disulfide bond with heavy chain |
| V5 epitope and Polyhistidine epitope (6xHis tag) epitopes | Allows detection of the fusion protein with the Anti V5 or anti his antibodies |
| CYC1 terminator | Efficient transcription termination of mRNA |
| URA3gene | Allows selection of yeast transformants |
| CEN6/ARS | Allows stable, episomal replication and partitioning into daughter cells in yeast |
| Ampicillin resistance gene (β-lactamase) | Selection in *E. coli* |

(D.3) Construction of Mating Type Light Chain (LCκ) Expressing Vector (pZB003.2) Having SS01 Signal Sequence in *Saccharomyces cerevisiae:*

Mating type light chain expressing vector is designed to express and secrete LC chain (VL+LCκ) with tags yeast cell surface under the control of GAL1 promoter and CYC1 terminator. mating alpha factor single sequence (pre region) present in this vector facilitates LC chain to secretory pathway. Combination of various restriction sites is important to transfer to transfer phage panned molecules (VL) from phagemid to HC expressing vector. To achieve this, unique restriction sites (NdeI, BglII, HindIII and AscI) are kept between mating alpha factor single and LCκ open reading frame. Presence of V5 and His tags detect LCκ chain during flow cytometry screening.

For the construction of the SS01 based secretion plasmid of LCκ, modified p416 GAL1 and SS01-LCκ DNA (SEQ ID No. 21) cassette was used. p416 GAL1 is CEN-based shuttle vector with URA3 marker from ATCC (ATCC® 87332™). LCκ cassette is composed of mating alpha factor single sequence (SS01), unique multi-cloning sites (NdeI, BglII, HindIII and AscI), light chain constant region (LCκ) with Cysteine residues intact at the last position followed by tags (V5 and His). LCκ cassette (FIG. 15 A) is synthesized through Gene Art. p416 GAL1 and LCκ are digested with SpeI and XhoI at about 37° C. and ligated at about 4° C. further to create pZB003.2 vector (Tables 21 and 22; FIG. 15 B). LCκ DNA cassette will be under the control of GAL1 promoter and CYC1 terminator in pZB003.2. Unique NdeI, BglII, HindIII and AscI sites were kept after SS01 signal sequence to clone VL region from phage panned library in pZB003.2 vector (FIG. 15 C). The synthesized pZB003.2 vector is provided as SEQ ID No. 22.

TABLE 20

| | |
|---|---|
| DNA (p416 GAL1 or LCκ DNA) | ~3 μg |
| SpeI | 3 μL |
| XhoI | 3 μL |
| 10 X Cut Smart Buffer | 10 μL |
| Milli-Q water | respectively |
| Total volume | 100 μL |

TABLE 21

| | |
|---|---|
| DNA (Vector) | 1 μL |
| DNA (Insert) | 5 μL |
| T4 DNA ligase | 1 μL |
| T4 DNA ligase buffer (10X) | 1 μL |
| Milli-Q water | 2 μL |
| Total volume | 10 μL |

Below is the table which allows one to understand the features of pZB003.2.

TABLE 22

| Feature | Benefit |
|---|---|
| GAL1 promoter | Permits regulated expression of your recombinant protein |
| Alpha mating factor 1 secretory signal sequence | Allows secretion of the light chain |
| Multiple cloning site (NdeI, BglII, HindIII and AscI) | Allows insertion of VH from phage panned library |
| LCκ with cysteine residue at the last position | Allows the formation of constant region of κ light chain and cysteine residue will make disulfide bond with heavy chain |
| V5 epitope and Polyhistidine epitope (6xHis tag) epitopes | Allows detection of the fusion protein with the Anti V5 or anti his antibodies |
| CYC1 terminator | Efficient transcription termination of mRNA |
| URA3gene | Allows selection of yeast transformants |
| CEN6/ARS | Allows stable, episomal replication and partitioning into daughter cells in yeast |
| Ampicillin resistance gene (β-lactamase) | Selection in *E. coli* |

(D.4) Construction of Mating Type Light Chain LCκ Expressing Vectors in *Saccharomyces cerevisiae* Having SS02 Signal Sequence (pZB003):

To facilitate better secretion of LC chain, SS02 signal sequence is introduced in the place of mating factor alpha 1 signal sequence (pre region). SS02, is an engineered mating factor alpha factor 1 signal sequence including pre and pro region called as appS4. It was previously demonstrated that appS4 has 16 times better secretion ability than mating factor alpha 1 signal sequence including pre and pro region.

For the construction of SS02 based secretion plasmid of LCκ, pZB003.2 and SS02-LCκ cassette (FIG. 16 A) (SEQ ID No. 17) were used. SS02 DNA cassette contains engineered alpha factor single sequence (appS4) coding region. SS02 DNA cassette is synthesized through Gene Art. pZB003.2 and SS02-LCκ are digested at about 37° C. with SpeI and HindIII and ligated at about 4° C. further to create pZB003 (Tables 24 and 25; FIG. 16 B). The synthesized pZB003 vector (FIG. 16 C) is provided as SEQ ID No. 18 and deposited to MTCC with accession number MTCC 25127.

TABLE 23

| | |
|---|---|
| DNA (Derivative of pZB003.2 or SS02-LCκ cassette) | ~4 μg |
| HindIII | 4 μL |
| AscI | 4 μL |
| 10 X Cut Smart Buffer | 10 μL |
| Milli-Q water | respectively |
| Total volume | 100 μL |

TABLE 24

| | |
|---|---|
| DNA (Vector) | 1 μL |
| DNA (Insert) | 7 μL |
| T4 DNA ligase | 1 μL |
| T4 DNA ligase buffer (10X) | 1 μL |
| Milli-Q water | 0 μL |
| Total volume | 10 μL |

Below is the table which allows one to understand the features of pZB003.

TABLE 25

| Feature | Benefit |
|---|---|
| GAL1 promoter | Permits regulated expression of your recombinant protein |
| Engineered alpha factor single sequence (appS4) signal sequence | Allows efficient secretion of protein 16 times more than wild type alpha mating factor 1 |
| Multiple cloning site (NdeI, BglII, HindIII and AscI) | Allows insertion of VL from phage panned library |
| LCκ with cysteine residue at the last position | Allows the formation of constant region of κ light chain and cysteine residue will make disulfide bond with heavy chain |
| V5 epitope and Polyhistidine epitope (6xHis tag) epitopes | Allows detection of the fusion protein with the Anti V5 or anti his antibodies |
| CYC1 terminator | Efficient transcription termination of mRNA |
| URA3gene | Allows selection of yeast transformants |
| CEN6/ARS | Allows stable, episomal replication and partitioning into daughter cells in yeast |
| Ampicillin resistance gene (β-lactamase) | Selection in *E. coli* |

(D.5) Construction of Mating Type Light Chain LCκ Expressing Vectors in *Saccharomyces cerevisiae* Having SS03 Signal Sequence (pZB003.3):

To facilitate better secretion of LC chain. SS03 signal sequence is introduced in the place of mating factor alpha 1 signal sequence (Pre region). SS03, is an engineered mating factor alpha factor 1 signal sequence including pre and pro region called as app8. app8 has 16 times better secretion ability than mating factor alpha 1 signal sequence including pre and pro region.

For the construction of the SS03 based secretion plasmid of LCκ, pZB003.2 and SS03-LCκ DNA (SEQ ID No. 23) were used. SS03 DNA cassette contains engineered alpha factor single sequence (app8) coding region. pZB003.2 and SS03-LCκ DNA are digested with SpeI and HindIII at about 37° C. and ligated at about 4° C. further to create pZB003.3 (Tables 27 and 28; FIGS. 17 A & B). The synthesized pZB003.3 vector (FIG. 17 C) is provided as SEQ ID No. 24.

TABLE 26

| | |
|---|---|
| DNA (Derivative of pZB003.2 or SS03-LCκ DNA) | ~4 μg |
| HindIII | 4 μL |
| AscI | 4 μL |
| 10 X Cut Smart Buffer | 10 μL |
| Milli-Q water | respectively |
| Total volume | 100 μL |

TABLE 27

| | |
|---|---|
| DNA (Vector) | 1 μL |
| DNA (Insert) | 7 μL |
| T4 DNA ligase | 1 μL |
| T4 DNA ligase buffer (10X) | 1 μL |
| Milli-Q water | 0 μL |
| Total volume | 10 μL |

Below is the table which allows to understand the features of pZB003.3.

TABLE 28

| Feature | Benefit |
|---|---|
| GAL1 promoter | Permits regulated expression of your recombinant protein |
| Engineered alpha factor single sequence (app8) signal sequence | Allows efficient secretion of protein 16 times more than wild type alpha mating factor 1 |
| Multiple cloning site (NdeI, BglII, HindIII and AscI) | Allows insertion of VL from phage panned library |
| LCκ with cysteine residue at the last position | Allows the formation of constant region of κ light chain and cysteine residue will make disulfide bond with heavy chain |
| V5 epitope and Polyhistidine epitope (6xHis tag) epitopes | Allows detection of the fusion protein with the Anti V5 or anti his antibodies |
| CYC1 terminator | Efficient transcription termination of mRNA |
| URA3gene | Allows selection of yeast transformants |
| CEN6/ARS | Allows stable, episomal replication and partitioning into daughter cells in yeast |
| Ampicillin resistance gene (β-lactamase) | Selection in *E. coli* |

(D.6) Construction of Mating Type Light Chain LCκ Expressing Vectors in *Saccharomyces cerevisiae* Having SS04 Signal Sequence (pZB003.4):

To facilitate better secretion of LC chain, SS04 signal sequence is introduced in the place of mating factor alpha 1 signal sequence (pre region). SS04 is a Suc2p signal sequence which has secretion ability for various proteins in yeast.

For the construction of the SS04 based secretion plasmid of LCκ, pZB003.2 and SS04 DNA-LCκ cassette (SEQ ID No. 25) were used. SS04 DNA cassette contains Suc2p signal sequence coding region. pZB003.2 and SS04 DNA-LCκ are digested with SpeI and HindIII at about 37° C. and ligated at about 4° C. further to create pZB003.4 (Tables 30 and 31; FIGS. 18 A & B). The synthesized pZB003.4 vector (FIG. 18 C) is provided as SEQ ID No. 26.

TABLE 29

| | |
|---|---|
| DNA (Derivative of pZB003.2 or SS04 DNA-LCκ) | ~4 μg |
| HindIII | 4 μL |
| AscI | 4 μL |
| 10 × Cut Smart Buffer | 10 μL |
| Milli-Q water | respectively |
| Total volume | 100 μL |

TABLE 30

| | |
|---|---|
| DNA (Vector) | 1 μL |
| DNA (Vector) | 7 μL |
| T4 DNA ligase | 1 μL |
| T4 DNA ligase buffer (10X) | 1 μL |
| Milli-Q water | 0 μL |
| Total volume | 10 μL |

Below is the table which allows to understand the features of pZB003.4.

TABLE 31

| Feature | Benefit |
|---|---|
| GAL1 promoter | Permits regulated expression of your recombinant protein |
| Suc2p signal sequence | Allows efficient secretion of protein |
| Multiple cloning site (NdeI, BglII, HindIII and AscI) | Allows insertion of VL from phage panned library |
| LCκ with cysteine residue at the last position | Allows the formation of constant region of κ light chain and cysteine residue will make disulfide bond with heavy chain |
| V5 epitope and Polyhistidine epitope (6xHis tag) epitopes | Allows detection of the fusion protein with the Anti V5 or anti his antibodies |
| CYC1 terminator | Efficient transcription termination of mRNA |
| URA3gene | Allows selection of yeast transformants |
| CEN6/ARS | Allows stable, episomal replication and partitioning into daughter cells in yeast |
| Ampicillin resistance gene (β-lactamase) | Selection in *E. coli* |

Example 3

Generation of Antibody Library and Transfer of Library from Phagemid to Yeast Mating Vectors 5 μg of the kappa and lambda light chain from secondary PCR pool representing the naïve repertoire from healthy human donor along with phagemid vectors (kappa pZB001 and lambda pZB001.1, respectively) are digested with HindIII-HF and AscI at about 37° C. for overnight in a total volume of about 100 μL. The digested samples are gel eluted followed by ligation set up at about 4° C. for overnight. The 25-50 ng of ligation mixture is transformed into about 25 μL of TG1 cells through electroporation wherein 1.0 mm cuvette is used with an optimal setting of 1800 volts, 600 ohm and 10 μF. Post recovery in recovery media, about 200 μL of transformed cells are spread on 144 mm plates and incubated overnight at about 37° C. In total, there are about 6-8 plates from which colonies are scraped on following day and stocks are made with about 20% glycerol. Transformation efficiency is calculated by dilution plating and found to be in the range of about $10^8$ to about $10^{10}$, preferably at ~$10^8$.

The total numbers of cells are determined per vial of glycerol stocks through dilution plating and found to be $10^{12}$. Colonies are inoculated in about 5 mL LB-Amp and plasmid is isolated. The isolated plasmids are checked for restriction digestion analysis. The insert release of ~300 bp confirmed the presence of light chain, both kappa and lambda in the pool.

One vial of light chain pool (both kappa and lambda) are inoculated in about 100 mL of LB-Amp and grown for about 2-3 hours at about 37° C. shaker-incubator followed by plasmid isolation by qiagen midi prep kit as per manufacturer's protocol. The midi prepped DNA for both the light chains are confirmed with restriction digestion analysis before proceeding with incorporation of heavy chain into it. Few of the representative clones are used for plasmid isolation and confirmed by restriction digestion which indicated the ~100% presence of light chain insert. Separate Midi prep is done to isolate light chain library DNA, both kappa and lambda from the pool. Midi prep DNA is again confirmed through restriction digestion before using for further insertion of heavy chain pool.

About 5 μg of the kappa and lambda light chain library DNA along with secondary PCR pool of heavy chain are digested with NcoI and XbaI at about 37° C. for overnight in a total volume of about 100 μL. The digested samples are gel eluted followed by ligation set up at about 4° C. for overnight. The 25-50 ng of ligation mixture is transformed into 251 μL of TG1 cells through electroporation wherein 1.0 mm cuvette is used with an optimal setting of 1800 volts, 600 ohm and 10 μF. Post recovery in recovery media, about 200 μL of transformed cells are spread on 144 mm plates and incubated overnight at about 37° C. In total, there are about 6-8 plates from which colonies are scraped on following day and stocks are made with about 20% glycerol and stored in −80° C. freezer. Transformation efficiency is calculated by dilution plating and found to be in the range of about $10^8$ to about $10^{10}$, preferably at ~$10^8$.

The total numbers of cells are determined per vial of glycerol stocks through dilution plating and found to be $10^{12}$. Colonies are inoculated in 5 mL LB-Amp and plasmid is isolated. The isolated plasmids are checked for restriction digestion analysis with NcoI and XbaI for heavy chain and HindIII and AscI for Kappa & Lambda light chains. The insert release of ~400 bp confirmed the presence of heavy chain, in kappa pool (FIGS. 19 A & B) and lambda pool (FIGS. 20 A & B).

The heavy chain along with kappa and lambda light chain secondary PCR pool containing DNA library are digested individually with NcoI and XbaI followed by ligation and transformation individually into TG1, highly competent *E. coli* cells.

About 1 ml of kappa and lambda bacterial glycerol stock are grown into about 200 ml LB-AMP medium at about 37° C. until OD at 600 nm reaches 0.8. Further, M13KO7 helper phage at multiplicity of infection (MOI) of 10 to the bacteria is added and incubated at about 37° C. for another 30 minutes. Post infection, infected bacteria is centrifuged and the pellet is re-suspended into about 200 ml of LB with 100 μg/ml ampicillin and 25 μg/ml kanamycin followed by growth at about 30° C. for overnight at 250 rpm. Suspension is spun down at about 8000 rpm for about 15 minutes at about 4° C. followed by discarding the pellet. Separated supernatant is mixed with PEG/NaCl solution in volume of supernatant and the mixture is incubated on ice for about 1 hour. The mixture is centrifuged at 10000 g for about 15 minutes and the phage pellet is re-suspended into about 20 ml of PBS. Glycerol is added to a final concentration of 50% to the entire phage suspension and frozen in aliquots of about 1 ml at −80° C. as phage library stock.

Glycerol stocks of both kappa and lambda bacterial library are mixed, inoculated and used for phage library generation. With addition of helper phage, the phage particles displaying the diversity are precipitated and purified, and stored as glycerol stocks for future use. The estimated number of phage library that is derived from plaque forming assay, is found to be about $10^{10}$ to about $10^{11}$, preferably ~$10^{11}$ pfu/mL. Formation of plaque indicates the functionality of the Phagemid library displaying Fab fragment which will be screened against Her2 antigen. Panning experiments were performed to remove the non-binders from the naïve pool followed by plaque formation assay to estimate the number of binders. Estimation of binders was found to be ~$10^7$ which is four decades lower than the initial phage number indicating a successful panning.

The plan of the whole strategy is to transfer the specific binders from phage to yeast expression vectors in order to do the screening and sorting in yeast system. An affinity based method is employed using a compatible method i.e., FACS to further select and rank the best binders. The panned phage was amplified and ssDNA was isolated followed by PCR amplification to incorporate in yeast mating type vectors; for heavy chain and light chain incorporation. The Fab library is developed by exploiting the mating system wherein light chain library and heavy chain library is cloned in different yeast expression vectors. However, the kappa and lambda light chain PCR pool of panned molecules along with the in-house yeast expression vector (pZB003.1 & pZB003.2) exclusively designed and generated for light chains are digested with HindIII and AscI followed by ligation and transformation individually into TG1, highly competent cells. Likewise, HC chain pool and the respective vector (pZB002) are digested with NcoI and NotI followed by ligation and transformation into TG1, highly competent cells. Transformation efficiency obtained for both heavy and light chain panned library are >$10^7$ cfu. Obtained transformed colonies for both heavy and light chain libraries are checked for insert release using HindIII/AscI for light chain (FIG. 21 A) and NcoI/NotI for heavy chain (FIG. 21 B) before they are scraped for glycerol stock preparation. Insert release for both the chains confirmed the presence of panned molecules. Glycerol stocks are stored at −80° C. for future use.

Upon validation, the about 1 μg of each DNA is taken and transformed into yeast cells at ~$5\times10^6$-$2\times10^7$ cells/ml by electroporation method. Regarding the strains for transformation, EBY100 is used as a host for the cell surface display of the heavy chain library while YVH10 is used to express light chain library. Post transformation, the plates are incubated at about 30° C. for 2-4 days to allow for growth of transformants. Both heavy chain and light chain panned library are successfully transformed into yeast strains (EBY100-ura3Δ and YVH10) with an efficiency of >$10^6$.

In order to display Fab format of library on the surface, mating of the two grown haploid cells representing heavy chain and light chain libraries is performed by mixing equal numbers of haploid cells. The mating efficiency is calculated as the number of diploid colonies in the double-selective plates divided by the number of total colonies in the single selective plates wherein the calculated mating percentage is ~40%. Further, the diploid cells are enriched in double drop out media ($ura^-$, $Trp^-$) prior to any growth and expression analysis.

*Saccharomyces cerevisiae* 2N library having plasmids expressing heavy chain pool and light chain kappa pool are inoculated into 10 ml of SDCAA double drop out media and grown overnight at about 30° C. (16-20 hrs). The OD at 600 nm of the overnight grown culture is measured and inoculated accordingly in about 10 ml SDCAA double drop out glucose media (uninduced culture) and about 10 ml 2×SGCAA media (induced culture) such that the final OD at 600 nm becomes 0.2 to 0.3. Uninduced and induced cells are grown for different time points ranging from 24 to 48 hours at about 20° C.

The expression of light chain and heavy chain are observed in significant percentages. The light chain expression are probed by anti-His antibody and found to be >7% (FIG. 22 A) while heavy chain which is probed with anti-c-Myc antibody are found to be appearing in double positive quadrant with biotinylated Her2 at a percentage of 7.2 (FIG. 22 B). This result indicates the Fab formation and successful binding of the same with target antigen. This result indicates that the dual auxotrophic marker selected diploids express light chain associated with the heavy chain. Successful transfer of clones from phage to yeast system followed by expression of Fab and its binding to Her2 antigen validates the functionality and efficiency of phagemid and yeast vectors of the instant disclosure.

Similarly, the above approach can also be employed using variable light chain (kappa and lambda light chains) and heavy chain regions obtained from synthetic antibodies/repertoire.

Example 4

Generation of Antibody Library and Screening Using Yeast scFv Vector

Another yeast expression construct i.e., yeast ScFv expression construct (pZB004.4) was tested for expression of anti-Her2 ScFv gene sequence and binding with Her2 antigen. Anti-Her2 genes, $V_H$ and $V_L$ were cloned into pZB004.4 vector in to MCS I and II, respectively, between NdeI/AscI and NcoI/NotI, enzymes. Clones were transformed into yeast EBY100 followed by induction for expression and binding studies as described earlier. Flow cytometry analysis of induced yeast cells revealed interaction with Her2 antigen. Flow cytometry were carried out with biotinylated Her2 antigen, which is detected with streptavidin Alexa 633 conjugate. Additionally, anti c-myc antibody (alexa flour 488, conjugate) was used to detect expression of C-terminus c-myc tag. The result revealed distinct double positive fluorescence signal indicating expression of Anti Her2 ScFv molecules on yeast cell surface (FIG. 23).

Taken together, the present disclosure relates to the use of present phagemids and yeast expression plasmids in protein display technologies to express the proteins/antibody genes from naïve and/or synthetic library. Firstly, phage display technology is used to clone and screen potential antibody genes with high to moderate affinity towards specific antigen. These genes are then transferred to yeast display plasmids for further screening and identification of lead molecules. Combining these two complementary technologies result in screening of highly diverse antibody libraries and developing new/lead antibody molecules against specific antigens. The smooth transfer of clonal population from phage to yeast vectors is efficient since restriction enzymes used in MCS I and MCS II are identical with respect to the two expression systems. These carefully chosen restriction enzymes allow transferring selected population of variable light chains from MCS I of Phagemid to MCS I of any yeast vector while heavy chains are relocated to MCS II of any yeast vectors.

Further, the variable heavy chain and light chain repertoire from naïve and/or synthetic antibodies can also be directly cloned into the phagemid and yeast vectors of the present disclosure and desired results can be obtained.

Apart from intersystem transfer, intra-system transfer i.e., altering display format from Fab to ScFv or vice versa, or same format but different expression vector such as transferring from mating type vectors to bi-cistronic vector is possible via respective set of MCS enzymes. The free transition across all possible systems and formats also provide a randomization of heavy and light chains which allows compensating the differences across two display systems while availability of a system wherein specific combination is preserved across systems is definitely a benefit.

Accordingly, the present vectors provide numerous advantages in protein display technology, including but not limiting to:

- Intertransfer approach wherein the two complementary technologies (phage display and yeast display) result in screening of highly diverse antibody libraries and developing new/lead antibody molecules against specific antigens.
- Uniquely designed inserts/expression cassettes resulting in efficient and smooth transfer of clonal population from phage to yeast vectors, thus maintaining the diversity of the antibody molecules/fragments.
- Overcoming the drawbacks of yeast display technology which accommodates small library and the limitation of expressing/displaying eukaryotic proteins using prokaryotic display systems such as phage display.
- Intratransfer approach wherein display format can be altered from Fab to ScFv or vice versa, or the same format can be transferred from one yeast vector to another yeast vector, such as transferring from mating type vectors to bi-cistronic vector via respective set of MCS enzymes.

We claim:

1. A vector construct designed to receive a nucleic acid encoding an antibody or a fragment thereof from a phagemid comprising at least one cloning region or from a yeast vector comprising at least one cloning region, or, to transfer the nucleic acid encoding an antibody or a fragment thereof to a yeast vector comprising at least one cloning region, said vector construct containing an expression cassette which comprises:

at least one leader sequence;

at least one cloning region for receiving a gene encoding a peptide or a protein that selectively binds to a biologically active ligand;

at least one nucleotide sequence encoding a constant region immunoglobulin heavy chain or a fragment thereof, a constant region immunoglobulin light chain or a fragment thereof, or a combination of the constant region immunoglobulin heavy chain or the fragment thereof and the constant region immunoglobulin light chain or the fragment thereof, wherein the constant region immunoglobulin light chain or the fragment thereof, or the constant region immunoglobulin heavy chain or the fragment thereof comprises at least one change in the nucleotide sequence with respect to a corresponding constant region immunoglobulin light chain or a fragment thereof, or a corresponding constant region immunoglobulin heavy chain or a fragment thereof of a native immunoglobulin; and at least one recombinant tag sequence or a nucleic acid encoding a selection sequence;

wherein, the at least one cloning region of the expression cassette comprises (a) a multiple cloning site 1 (MCS I) and a multiple cloning site 2 (MCS II), (b) the MCS I alone, or (c) the MCS II alone, and wherein the MCS I comprises a first restriction site combination in a first sequential order of Ndel, BgJII, Hindlll, and Ascl, and the MCS II comprises a second restriction site combination in a second sequential order of Ncol, Xbal, Nhel, and Nod.

2. The vector construct as claimed in claim 1, wherein the at least one cloning region of the expression cassette, the phagemid and the yeast vector comprises (a) the MCS I and the MCS II, (b) the MCS I alone, or (c) the MCS II alone.

3. The vector construct as claimed in claim 1, wherein the expression cassette further comprises:

at least one sequence selected from the group consisting of:

(A) a terminator sequence;

(B) a terminator sequence, wherein an enzyme cleavage site fused with a nucleotide sequence encoding a product that enables display of a peptide or a protein on a surface of a protein expression system is disposed upstream of the terminator sequence; and (C) a nucleotide sequence encoding a phage coat protein disposed upstream of at least one ribosomal binding site.

4. The vector construct as claimed in claim 1, wherein the expression cassette contains one or more promoter sequence, the expression cassette contains or lacks an operator sequence, the vector construct is capable of expressing the antibody or the fragment thereof in a bacterial cell or a yeast cell, the promoter sequence is selected from the group consisting of Gal 1, Gal 1/10, and a combination thereof, the leader sequence is selected from the group consisting of pelB sequence, alpha leader sequence, Aga2P leader sequence, alpha mating factor 1 secretory signal sequence (SS01), engineered alpha factor (aapS4) signal sequence (SS02), engineered alpha factor (aap8) signal sequence (SS03), engineered alpha factor (aap8), signal sequence (SSO4), and combinations thereof, the recombinant tag sequence or the nucleic acid encoding the selection sequence is selected from the group consisting of FLAG, c-Myc, V5, His and combinations thereof, the terminator sequence is selected from the group consisting of alpha terminator, CYC1 terminator, and combinations thereof, the enzyme cleavage site is a TEV protease cleavage site;

the vector construct contains a nucleotide sequence encoding an Aga2P protein that enables display of a peptide or a protein on a surface of a protein expression system, and a phage coat protein is selected from the group consisting of pIII protein, G8P, and a combination thereof.

5. The vector construct as claimed in claim 1, wherein the nucleotide sequence encoding the constant region immunoglobulin heavy chain or the constant region immunoglobulin light chain comprising at least one change in the nucleotide sequence is selected from the group consisting of a first constant domain (CH1) of the immunoglobulin heavy chain or a fragment thereof, a kappa constant region (Ck) of the immunoglobulin light chain or a fragment thereof, and a lambda constant region (CL) of the immunoglobulin light chain or a fragment thereof, and wherein the gene received by the cloning region is selected from the group consisting of a kappa variable region (Vk) of the immunoglobulin light chain or a fragment thereof, a lambda variable region (VL) of the immunoglobulin light chain or a fragment thereof, and a variable region of the immunoglobulin heavy chain (VH) or a fragment thereof.

6. The vector construct as claimed in claim 1, wherein the vector construct is selected from the group consisting of a yeast bicistronic bidirectional vector, a yeast bicistronic unidirectional vector, a yeast mating type heavy chain expressing vector, a yeast mating-type light chain expressing vector, and the phagemid, and wherein the expression cassette is selected from the group consisting of expression cassettes having following configurations:

(a) sequentially, a promoter sequence;

a leader sequence;

a cloning region capable of receiving a gene encoding a variable region of an immunoglobulin heavy chain or a fragment thereof and comprising the MCS I, wherein the MCS I comprises the first restriction site combination in the first sequential order of Ndel, BgJII, Hindlll, and Ascl; and;

a nucleotide sequence encoding a first constant domain (CH1) of an IgG1 immunoglobulin heavy chain, wherein said first constant domain (CH1) of the IgG1 immunoglobulin heavy chain comprises at least one change in the nucleotide sequence with respect to a corresponding first constant domain (CH1) of native IgG1 immunoglobulin heavy chain;

a recombinant tag sequence or a nucleic acid encoding a selection sequence; and a terminator sequence wherein a protease cleavage site fused with a nucleotide sequence encoding Aga2P protein via a linker sequence is disposed upstream of the terminator sequence, (b) sequentially, a promoter sequence;

a leader sequence a cloning region capable of receiving a gene encoding the variable region of the immunoglobulin light chain or the fragment thereof and comprising the MCS I, wherein the MCS I comprises the first restriction site combination in the first sequential order of Ndel, BgJII, Hindlll, and Ascl;

a nucleotide sequence encoding a kappa constant region (Ck) of the immunoglobulin light chain or a lambda constant region (CL) of the immunoglobulin light chain, or fragments thereof, wherein said kappa constant region (Ck) of the immunoglobulin light chain or the lambda constant region (CL) of the immunoglobulin light chain, or the fragment thereof comprises at least one change in the nucleotide sequence with respect to a corresponding kappa constant region (Ck) of an immunoglobulin light chain or a corresponding lambda constant region (CL) of an immunoglobulin light chain or a fragment thereof of a native immunoglobulin;

a recombinant tag sequence or a nucleic acid encoding a selection sequence; and a terminator sequence, (c) sequentially, a first terminator sequence;

a first set of a recombinant tag sequence or a nucleic acid encoding a selection sequence;

a first nucleotide sequence encoding the kappa constant region (Ck) of the immunoglobulin light chain or the lambda constant region (CL) of the immunoglobulin light chain, or fragments thereof, wherein said kappa constant region (Ck) of the immunoglobulin light chain or the lambda constant region (CL) of the immunoglobulin light chain, or the fragments thereof comprises at least one change in the nucleotide sequence with respect to the corresponding kappa constant region (Ck) of the immunoglobulin light chain or the corresponding lambda constant region (CL) of the immunoglobulin light chain, or fragments thereof of a native immunoglobulin;

a first cloning region capable of receiving a gene encoding the variable region of the immunoglobulin light chain or a fragment thereof and comprising the MCS I, wherein the MCS I comprises the first restriction site combination in the first sequential order of Ndel, BgJII, Hindlll, and Ascl;

a first leader sequence a promoter sequence;

a second leader sequence;

a second cloning region capable of receiving a gene encoding the variable region of the immunoglobulin heavy chain or fragments thereof and comprising the MCS II, wherein the MCS II comprises the second restriction site combination in the second sequential order of Ncol, Xbal, Nhel, and Notl;

a second nucleotide sequence encoding a first constant domain (CM) of the IgG1 immunoglobulin heavy chain, wherein said constant region comprises at least one change in the nucleotide sequence with respect to a heavy chain constant region of a native immunoglobulin or a fragment thereof;

a second set of a recombinant tag sequence or a nucleic acid encoding a selection sequence; and a second terminator sequence wherein a protease cleavage site fused with a nucleotide sequence encoding Aga2P protein via a linker sequence is disposed upstream of the terminator sequence, (d) sequentially, a first promoter sequence;

a first leader sequence;

a first cloning region capable of receiving a gene encoding the variable region of the immunoglobulin light chain or the fragment thereof and comprising the MCS I, wherein the MCS I comprises the first restriction site combination in the first sequential order of Ndel, BgJII, Hindlll, and Ascl;

a first nucleotide sequence encoding the kappa constant region (Ck) of the immunoglobulin light chain or the lambda constant region (CL) of the immunoglobulin light chain, or the fragments thereof, wherein the kappa constant region (Ck) of the immunoglobulin light chain or a fragment thereof or the lambda constant region (CL) of the immunoglobulin light chain or the fragment thereof comprises at least one change in the nucleotide sequence with respect to the corresponding kappa constant region (Ck) of the immunoglobulin light chain or the fragment thereof or the corresponding lambda constant region (CL) of the immunoglobulin light chain or the fragment thereof of the native immunoglobulin;

a first set of a recombinant tag sequence or a nucleic acid encoding a selection sequence;

a first terminator sequence;

a second promoter sequence;

a second leader sequence;

a second cloning region capable of receiving a gene encoding the variable region of the immunoglobulin heavy chain or the fragment thereof and comprising the MCS II, wherein the MCS II comprises the second restriction site combination in the second sequential order of Ncol, Xbal, Nhel, and Notl;

a second nucleotide sequence encoding the first constant domain (CH1) of the IgG1 immunoglobulin heavy chain, wherein said constant domain comprises at least one change in the nucleotide sequence with respect to the heavy chain constant domain of the native immunoglobulin or a fragment thereof;

a second set of a recombinant tag sequence or a nucleic acid encoding a selection sequence; and a second terminator sequence wherein a protease cleavage site fused with a nucleotide sequence encoding Aga2P protein via a linker sequence is disposed upstream of the terminator sequence, and (e) sequentially, a promoter sequence;

an operator sequence;

a first ribosomal binding site;

a first leader sequence;

a first cloning region capable of receiving a gene encoding the variable region of the immunoglobulin light chain or the fragment thereof and comprising the MCS I, wherein the MCS I comprises the first restriction site combination in the first sequential order of Ndel, BgJII, Hindlll, and Ascl;

a first nucleotide sequence encoding the kappa constant region (Ck) of the immunoglobulin light chain or the fragment thereof or the lambda constant region (CL) of the immunoglobulin light chain, or the fragment thereof, wherein said kappa constant region (Ck) of the immunoglobulin light chain or the fragment thereof or the lambda constant region (CL) of the immunoglobulin light chain, or the fragment thereof comprises at least one change in the nucleotide sequence with respect to the corresponding kappa constant region (Ck) of the immunoglobulin light chain or the fragments thereof or the corresponding lambda constant region (CL) of the immunoglobulin light chain or the fragments thereof of the native immunoglobulin;

a second ribosomal binding site;

a second leader sequence;

a second cloning region capable of receiving a gene encoding the variable region of the immunoglobulin heavy chain or the fragment thereof and comprising the MCS II, wherein the MCS II comprises the second restriction site combination in the second sequential order of Ncol, Xbal, Nhel, and Notl;

a second nucleotide sequence encoding the first constant domain (CM) of the IgG1 immunoglobulin heavy chain, wherein said constant domain comprises at least one change in the nucleotide sequence with respect to the heavy chain constant domain of the native immunoglobulin or the fragment thereof;

a recombinant tag sequence or a nucleic acid selection sequence; and a nucleotide sequence encoding a phage coat protein.

7. A vector construct designed to clone an antibody or a fragment thereof, said vector construct containing an expression cassette which comprises:

a promoter sequence;

a leader sequence;

a nucleotide sequence encoding a product that enables display of a peptide or a protein on a surface of a protein expression system;

a first enzyme cleavage site;

a first recombinant tag sequence or a first nucleic acid encoding a selection sequence;

a first linker sequence;

a second enzyme cleavage site;

a first cloning region operably linked to a second cloning region and a second linker sequence, wherein the cloning regions are configured to receive a gene encoding a peptide or a protein that selectively binds to a biologically active ligand;

a second recombinant tag sequence or a second nucleic acid encoding a selection sequence; and a terminator sequence, wherein the first cloning region or the second cloning region of the expression cassette comprises a multiple cloning site 1 (MCS I) and a multiple cloning site 2 (MCS II), and wherein the MCS I comprises a first restriction site combination in a first sequential order of Ndel, BgJII, Hindlll, and Ascl, and the MCS II comprises a second restriction site combination in a second sequential order of Ncol, Xbal, Nhel, and Nod.

8. The vector construct as claimed in claim 7, wherein said vector construct is a scFv vector and is capable of expressing a single-chain variable fragment (scFv) or a fragment thereof in a yeast cell; and wherein the promoter sequence is Gal 1, the nucleotide sequence encodes an Aga2P protein that enables display of a peptide or a protein on the surface of the protein expression system, the enzyme cleavage sites are protease cleavage sites selected from the group consisting of a Factor Xa cleavage site, a TEV protease cleavage site and a combination thereof, the recombinant tag sequences or the nucleic acid encoding the selection sequences are selected from the group consisting of HA tag, c-Myc tag, FLAG, and combinations thereof, the first linker sequence or the second linker sequence is G4S sequence, a gene received by the first cloning region is selected from the group consisting of a kappa variable region (Vk) of an immunoglobulin light chain or a fragment thereof, a lambda variable region (VL) of an immunoglobulin light chain or a fragment thereof, and a combination thereof, a gene received by the second cloning region is a variable region of an immunoglobulin heavy chain (VH) or a fragment thereof, and the terminator sequence is selected from the group consisting of alpha terminator, CYC1 terminator, and a combination thereof.

9. The vector construct as claimed in claim 1, wherein the construct has a nucleic acid sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, and SEQ ID No. 26.

10. The vector construct as claimed in claim 1, wherein the vector construct further comprises regions selected from the group consisting of an origin of replication (Ori), an antibiotic resistant marker, an f1 origin of replication, a promoter, and combinations thereof; and wherein the vector construct is capable of expressing or displaying an antibody or a fragment thereof in a prokaryotic expression system, a yeast expression system, or a combination thereof.

11. The vector construct as claimed in claim 1, wherein the CH1 region has a nucleic acid sequence of SEQ ID No. 27, the Ck region has a nucleic acid sequence of SEQ ID No. 28, and the CL region has a nucleic acid sequence of SEQ ID No. 29.

12. A bacterial or yeast host cell, or a phage library or a yeast library therein comprising the vector construct as claimed in claim 1.

13. An expression cassette having a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, and SEQ ID No. 25.

* * * * *